(12) United States Patent
Cheng et al.

(10) Patent No.: US 9,040,547 B2
(45) Date of Patent: May 26, 2015

(54) PYRROLOPYRIMIDINE AND PURINE DERIVATIVES

(75) Inventors: Hengmiao Cheng, San Diego, CA (US); Theodore Otto Johnson, Jr., San Diego, CA (US); John Charles Kath, La Mesa, CA (US); Kevin Kun-Chin Liu, Shanghai (CN); Elizabeth Ann Lunney, San Diego, CA (US); Asako Nagata, San Diego, CA (US); Sajiv Krishnan Nair, Vista, CA (US); Simon Paul Planken, San Diego, CA (US); Scott Channing Sutton, San Diego, CA (US)

(73) Assignee: PFIZER INC., New York, NY (US)

( * ) Notice: Subject to any disclaimer, the term of this patent is extended or adjusted under 35 U.S.C. 154(b) by 187 days.

(21) Appl. No.: 13/617,035

(22) Filed: Sep. 14, 2012

(65) Prior Publication Data

US 2013/0079324 A1    Mar. 28, 2013

Related U.S. Application Data

(60) Provisional application No. 61/538,103, filed on Sep. 22, 2011, provisional application No. 61/639,639, filed on Apr. 27, 2012.

(51) Int. Cl.
| *A61K 31/519* | (2006.01) |
| *A61K 31/5377* | (2006.01) |
| *A61K 31/52* | (2006.01) |
| *C07D 473/16* | (2006.01) |
| *C07D 487/04* | (2006.01) |

(52) U.S. Cl.
CPC .................................. *C07D 487/04* (2013.01)

(58) Field of Classification Search
USPC .................. 514/265.1, 210.18, 263.2, 234.2; 544/117, 280
See application file for complete search history.

(56) References Cited

U.S. PATENT DOCUMENTS

| 2003/0036543 A1 | 2/2003 | Bebbington et al. |
| 2004/0110775 A1 | 6/2004 | Griffin et al. |
| 2005/0038023 A1 | 2/2005 | Bebbington et al. |
| 2005/0267089 A1 | 12/2005 | Wang et al. |
| 2006/0258658 A1 | 11/2006 | Bebbington et al. |
| 2007/0179130 A1 | 8/2007 | Bannen |
| 2008/0221060 A1 | 9/2008 | Pritchard et al. |
| 2008/0242683 A1 | 10/2008 | Fairhurst et al. |
| 2008/0306053 A1 | 12/2008 | Tachdjian et al. |
| 2008/0306093 A1 | 12/2008 | Servant et al. |
| 2009/0054425 A1 | 2/2009 | Song et al. |
| 2009/0209535 A1 | 8/2009 | Jensen et al. |
| 2010/0056494 A1 | 3/2010 | Winzeler et al. |
| 2010/0144705 A1 | 6/2010 | Miller |
| 2011/0224155 A1 | 9/2011 | Tachdjian et al. |
| 2011/0245156 A1 | 10/2011 | Sielecki-Dzurdz |
| 2012/0142647 A1 | 6/2012 | Dax et al. |
| 2012/0295911 A1 | 11/2012 | Mannion et al. |

FOREIGN PATENT DOCUMENTS

| WO | WO 98/05335 A1 | 2/1998 |
| WO | WO 00/44750 A1 | 8/2000 |
| WO | WO 02/50065 A2 | 6/2002 |
| WO | WO 02/50066 A2 | 6/2002 |
| WO | WO 02/057259 A2 | 7/2002 |
| WO | WO 02/059111 A2 | 8/2002 |
| WO | WO 02/059112 A2 | 8/2002 |
| WO | WO 02/062789 A1 | 8/2002 |
| WO | WO 02/066461 A1 | 8/2002 |
| WO | WO 02/068415 A1 | 9/2002 |
| WO | WO 2005/097135 A2 | 10/2005 |
| WO | WO 2008/075110 A1 | 6/2008 |
| WO | WO 2008/135785 A1 | 11/2008 |
| WO | WO 2010/034740 A1 | 4/2010 |
| WO | WO 2010/118367 A2 | 10/2010 |
| WO | WO 2010/129053 A2 | 11/2010 |
| WO | WO 2011/079231 A1 | 6/2011 |
| WO | WO 2011/140338 A1 | 11/2011 |
| WO | WO 2011/163424 A2 | 12/2011 |
| WO | WO 2012/009258 A2 | 1/2012 |
| WO | WO 2010/075282 A1 | 7/2012 |
| WO | WO 2014/140989 A2 | 9/2014 |

OTHER PUBLICATIONS

The International Search Report for International Application No. PCT/IB2012/054702 mailed on Dec. 5, 2012.
Zhou, W., et al., "Discovery of Selective Irreversible Inhibitors for EGFR-T790M," Bioorganic & Medicinal Chemistry Letters, 2011, 638-643, vol. 21, No. 2.

*Primary Examiner* — Sreeni Padmanabhan
*Assistant Examiner* — Sahar Javanmard
(74) *Attorney, Agent, or Firm* — Suzanne M. Bates; Stephen D. Prodnuk

(57) ABSTRACT

The present invention relates to compounds of formula (I)

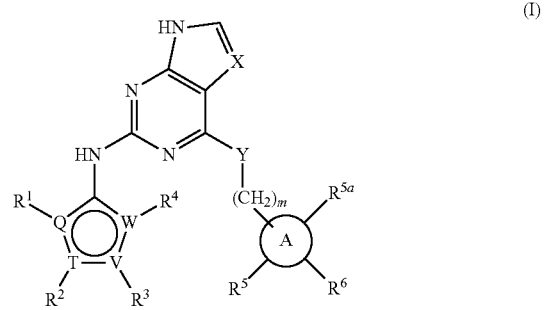

(I)

or pharmaceutically acceptable salts thereof, wherein Q, T, V, W, X, Y, Z, ring A, $R^1$, $R^2$, $R^3$, $R^4$, $R^5$, $R^{5a}$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and m are defined herein. There novel pyrrolopyrimidine and purine derivatives are useful in the treatment of abnormal cell growth, such as cancer, in mammals. Additional embodiments relate to pharmaceutical compositions containing the compounds and to methods of using the compounds and compositions in the treatment of abnormal cell growth in mammals.

41 Claims, No Drawings

PYRROLOPYRIMIDINE AND PURINE DERIVATIVES

CROSS-REFERENCE TO RELATED APPLICATIONS

This patent application claims the benefit of priority to U.S. Provisional Patent Application Ser. No. 61/538,103, filed Sep. 22, 2011, and U.S. Provisional Patent Application Ser. No. 61/639,639, filed Apr. 27, 2012, the contents of which are hereby incorporated by reference in their entireties.

FIELD OF THE INVENTION

The present invention relates to novel pyrrolopyrimidine and purine derivatives that are useful in the treatment of abnormal cell growth, such as cancer, in mammals. The present invention also relates to pharmaceutical compositions containing the compounds and to methods of using the compounds and compositions in the treatment of abnormal cell growth in mammals.

BACKGROUND

Lung cancer is the leading cause of cancer death worldwide, with an estimated 1.2 million new cases diagnosed each year. In lung adenocarcinoma, which is the most common form of lung cancer, patients harboring mutations in the epidermal growth factor receptor (EGFR) constitute between 10-30% of the overall population. It is this segment of patients for whom EGFR inhibitors such as erlotinib or gefitinib can be most effective (Paez et al. Science 2004; Lynch et al. NEJM 2004; Pao et al, PNAS 2004). The most common mutations associated with good response to these inhibitors are deletions within exon 19 (e.g. E740-A750) and point mutations in the activation loop (exon 21, in particular, L858R). Additional somatic mutations identified to date but to a lesser extent include point mutations: G719S, G719C, G719A, L861 and small insertions in Exon 20 (Shigematsu et al JNCI 2005; Fukuoka et al. JCO 2003; Kris et al JAMA 2003 and Shepherd et al NEJM 2004).

While these agents can be effective treatments for the EGFR mutant sub-population, the majority of patients who initially respond develop resistance. The primary mechanism of resistance, observed in approximately 50% of patients, is due to a second mutation (T790M) which occurs at the gatekeeper threonine residue (Kosaka et al CCR 2006; Balak et al CCR 2006 and Engelman et al Science 2007).

Thus, there is a need for compounds that inhibit EGFR T790M.

SUMMARY OF THE INVENTION

Each of the embodiments described below can be combined with any other embodiment described herein not inconsistent with the embodiment with which it is combined. Furthermore, each of the embodiments described herein envisions within its scope pharmaceutically acceptable salts of the compounds described herein. Accordingly, the phrase "or a pharmaceutically acceptable salt thereof" is implicit in the description of all compounds described herein.

Some embodiments described herein relate to a compound of formula (I):

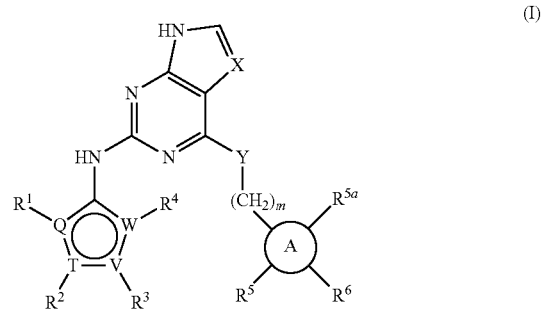

wherein
X is N or $CR^7$;
Y is absent, O, S or $NR^8$;
Q, T, V and W are each independently C or N, provided that at least two of Q, T, V and W are N and at least one of Q, T, V and W is C, and provided that when Q and T are N, at least one of $R^1$ and $R^2$ is absent, and further provided that when T and V are N, at least one of $R^2$ and $R^3$ is absent;
$R^1$ and $R^4$ are each independently absent, hydrogen, cyano, difluoromethyl, trifluoromethyl, $C_1$-$C_6$ alkyl, $C_2$-$C_6$ alkenyl, $C_2$-$C_6$ alkynyl, $C_1$-$C_6$ alkoxy, —N($R^9$)($R^{10}$), $C_3$-$C_5$ cycloalkyl or 4-6 membered heterocycloalkyl, wherein the $C_1$-$C_6$ alkyl may be optionally substituted by halogen, hydroxy, $C_1$-$C_6$ alkoxy or N($R^{11}$)($R^{12}$);
$R^2$ and $R^3$ are each independently absent, hydrogen, $C_1$-$C_6$ alkyl, $C_2$-$C_6$ alkynyl, $C_1$-$C_6$ alkoxy, $C_3$-$C_7$ cycloalkyl or 3-7 membered heterocycloalkyl, wherein the $C_1$-$C_6$ alkyl and $C_1$-$C_6$ alkoxy in $R^2$ and $R^3$ are each independently optionally substituted by one or more $R^{13}$ groups, and further wherein the $C_3$-$C_7$ cycloalkyl and the 3-7 membered heterocycloalkyl in $R^2$ and $R^3$ are each independently optionally substituted by one or more $R^{14}$ groups; or
$R^1$ and $R^2$ or $R^2$ and $R^3$ may combine to form a $C_5$-$C_7$ cycloalkyl ring or a 5-7 membered heterocycloalkyl ring, wherein the $C_5$-$C_7$ cycloalkyl ring and the 5-7 membered heterocycloalkyl ring are each independently optionally substituted by one or more $R^{13}$ groups;
ring A is absent, $C_3$-$C_{10}$ cycloalkyl, 3-10 membered heterocycloalkyl, $C_5$-$C_{10}$ aryl or 5-12 membered heteroaryl;
$R^5$ and $R^{5a}$ are each independently absent, halogen, cyano, hydroxy, difluoromethyl, trifluoromethyl, $C_1$-$C_3$ alkyl, $C_1$-$C_3$ alkoxy, $C_3$-$C_5$ cycloalkyl or 4-6 membered heteroaryl, wherein the $C_1$-$C_3$ alkyl is optionally substituted by hydroxy, difluoromethyl, trifluoromethyl, $C_1$-$C_3$ alkoxy or $C_3$-$C_5$ cycloalkyl;
$R^6$ is

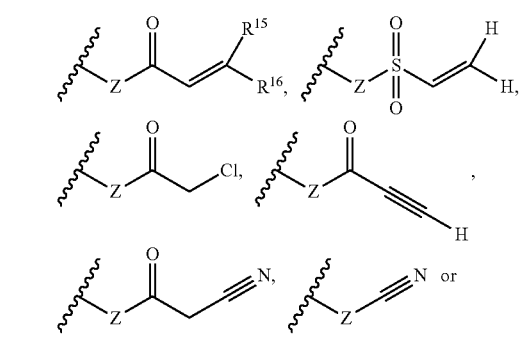

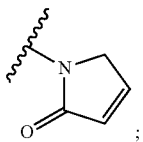

Z is absent when the attachment point of $R^6$ on ring A is a nitrogen atom, and Z is —$NR^{17}$— when ring A is absent or when the attachment point of $R^6$ on ring A is a carbon atom;

$R^7$ is hydrogen, halogen, cyano, $C_1$-$C_6$ alkyl, $C_2$-$C_6$ alkenyl, $C_2$-$C_6$ alkynyl or 4-6 membered heteroaryl, wherein the $C_1$-$C_6$ alkyl may be optionally substituted by hydroxy or $C_1$-$C_3$ alkoxy, and further wherein the 4-6 membered heteroaryl may be optionally substituted by $C_1$-$C_3$ alkyl;

$R^8$ is hydrogen or $C_1$-$C_3$ alkyl;

$R^9$ and $R^{10}$ are each independently hydrogen or $C_1$-$C_6$ alkyl; or $R^9$ and $R^{10}$ together with the nitrogen to which they are attached, may combine to form a 4-7 membered ring, when $R^9$ and $R^{10}$ are each $C_1$-$C_3$ alkyl, wherein the 4-7 membered ring is optionally substituted by one or more $R^{14}$ groups;

$R^{11}$ and $R^{12}$ are each independently hydrogen or $C_1$-$C_3$ alkyl;

each $R^{13}$ is independently halogen, cyano, hydroxy, $C_1$-$C_6$ alkoxy, —$N(R^9)(R^{10})$, —$CON(R^9)(R^{10})$ or 3-7 membered heterocycloalkyl, wherein the 3-7 membered heterocycloalkyl in $R^{13}$ is optionally substituted by one or more $R^{14}$ groups;

each $R^{14}$ is independently halogen, $C_1$-$C_3$ alkyl, hydroxy, $C_1$-$C_6$ alkoxy, —$NH_2$, —$NHCH_3$ or $N(CH_3)_2$;

$R^{15}$ and $R^{16}$ are each independently hydrogen or $C_1$-$C_6$ alkyl, wherein the $C_1$-$C_6$ alkyl of one of $R^{15}$ and $R^{16}$ is optionally substituted by —$N(R^9)(R^{10})$;

$R^{17}$ is hydrogen or $C_1$-$C_3$ alkyl; and m is 0, 1 or 2, provided that when ring A is absent, m is 2; or a pharmaceutically acceptable salt thereof.

Some embodiments relate to a compound of formula (I), or a pharmaceutically acceptable salt thereof, wherein X is $CR^7$.

More embodiments relate to a compound of formula (I), or a pharmaceutically acceptable salt thereof, wherein Y is O.

Some embodiments relate to a compound of formula (I), or a pharmaceutically acceptable salt thereof, wherein Y is $NR^8$.

Further embodiments relate to a compound of formula (I), or a pharmaceutically acceptable salt thereof, wherein X is $CR^7$ and Y is O.

Some embodiments relate to a compound of formula (I), or a pharmaceutically acceptable salt thereof, wherein $R^7$ is hydrogen, halogen, cyano or 4-6 membered heteroaryl.

Additional embodiments relate to a compound of formula (I), or a pharmaceutically acceptable salt thereof, wherein $R^7$ is hydrogen, halogen or cyano.

Some embodiments relate to a compound of formula (I), or a pharmaceutically acceptable salt thereof, wherein $R^7$ is hydrogen.

Some embodiments relate to a compound of formula (I), or a pharmaceutically acceptable salt thereof, wherein $R^7$ is halogen, and further wherein the halogen is fluorine.

More embodiments relate to a compound of formula (I), or a pharmaceutically acceptable salt thereof, wherein $R^7$ is halogen, and further wherein the halogen is chlorine.

Further embodiments relate to a compound of formula (I), or a pharmaceutically acceptable salt thereof, wherein $R^7$ is cyano.

Further embodiments relate to a compound of formula (I), or a pharmaceutically acceptable salt thereof, wherein $R^7$ is 4-6 membered heteroaryl optionally substituted by $C_1$-$C_3$ alkyl.

Additional embodiments relate to a compound of formula (I), or a pharmaceutically acceptable salt thereof, wherein m is 0.

Additional embodiments relate to a compound of formula (I), or a pharmaceutically acceptable salt thereof, wherein m is 1.

Some embodiments relate to a compound of formula (I), or a pharmaceutically acceptable salt thereof, wherein Q, T and V are N.

Additional embodiments relate to a compound of formula (I), or a pharmaceutically acceptable salt thereof, wherein Q, V and W are N.

Further embodiments relate to a compound of formula (I), or a pharmaceutically acceptable salt thereof, wherein Q and T are N.

More embodiments relate to a compound of formula (I), or a pharmaceutically acceptable salt thereof, wherein T and V are N.

Some embodiments relate to a compound of formula (I), or a pharmaceutically acceptable salt thereof, wherein $R^1$ is hydrogen or $C_1$-$C_3$ alkyl, wherein the $C_1$-$C_3$ alkyl may be optionally substituted by halogen or hydroxy.

Further embodiments relate to a compound of formula (I), or a pharmaceutically acceptable salt thereof, wherein $R^1$ is hydrogen.

Some embodiments relate to a compound of formula (I), or a pharmaceutically acceptable salt thereof, wherein $R^1$ is methyl or ethyl.

Some embodiments relate to a compound of formula (I), or a pharmaceutically acceptable salt thereof, wherein $R^1$ is methyl.

Some embodiments relate to a compound of formula (I), or a pharmaceutically acceptable salt thereof, wherein $R^1$ is $C_1$-$C_3$ alkoxy.

Some embodiments relate to a compound of formula (I), or a pharmaceutically acceptable salt thereof, wherein $R^1$ is —$CH_2F$ or —$C(CH_3)_2OH$.

More embodiments relate to a compound of formula (I), or a pharmaceutically acceptable salt thereof, wherein $R^2$ is absent.

More embodiments relate to a compound of formula (I), or a pharmaceutically acceptable salt thereof, wherein $R^2$ is $C_1$-$C_4$ alkyl or $C_3$-$C_4$ cycloalkyl.

Further embodiments relate to a compound of formula (I), or a pharmaceutically acceptable salt thereof, wherein $R^2$ is methyl.

Some embodiments relate to a compound of formula (I), or a pharmaceutically acceptable salt thereof, wherein $R^2$ is ethyl.

Additional embodiments relate to a compound of formula (I), or a pharmaceutically acceptable salt thereof, wherein $R^2$ is $C_1$-$C_6$ alkyl optionally substituted by hydroxy, —$N(R^9)(R^{10})$ or 3-7 membered heterocycloalkyl, and further wherein the 3-7 membered heterocycloalkyl is optionally substituted by $C_1$-$C_3$ alkyl.

Further embodiments relate to a compound of formula (I), or a pharmaceutically acceptable salt thereof, wherein $R^2$ is $C_1$-$C_3$ alkyl optionally substituted by —$N(CH_3)_2$ or morpholino, and further wherein the morpholino is optionally substituted by methyl.

Some embodiments relate to a compound of formula (I), or a pharmaceutically acceptable salt thereof, wherein $R^2$ is 3-7 membered heterocycloalkyl optionally substituted by one or more substituents selected from the group consisting of halogen, $C_1$-$C_3$ alkyl and hydroxy.

Some embodiments relate to a compound of formula (I), or a pharmaceutically acceptable salt thereof, wherein $R^2$ is tetrahydrofuran or tetrahydropyran.

More embodiments relate to a compound of formula (I), or a pharmaceutically acceptable salt thereof, wherein $R^2$ is pyrrolidine optionally substituted by one or more substituents selected from the group consisting of halogen, $C_1$-$C_3$ alkyl and hydroxy.

More embodiments relate to a compound of formula (I), or a pharmaceutically acceptable salt thereof, wherein $R^2$ is pyrrolidine optionally substituted by methyl.

Additional embodiments relate to a compound of formula (I), or a pharmaceutically acceptable salt thereof, wherein $R^3$ is hydrogen, $C_1$-$C_3$ alkyl or $C_3$-$C_7$ cycloalkyl, and further wherein the $C_1$-$C_3$ alkyl is optionally substituted by hydroxy, $C_1$-$C_6$ alkoxy or —N($R^9$)($R^{10}$).

Some embodiments relate to a compound of formula (I), or a pharmaceutically acceptable salt thereof, wherein $R^3$ is absent.

Some embodiments relate to a compound of formula (I), or a pharmaceutically acceptable salt thereof, wherein $R^3$ is methyl.

Further embodiments relate to a compound of formula (I), or a pharmaceutically acceptable salt thereof, wherein $R^4$ is hydrogen.

Some embodiments relate to a compound of formula (I), or a pharmaceutically acceptable salt thereof, wherein $R^4$ is $C_1$-$C_3$ alkyl.

Further embodiments relate to a compound of formula (I), or a pharmaceutically acceptable salt thereof, wherein $R^4$ is methyl.

Additional embodiments relate to a compound of formula (I), or a pharmaceutically acceptable salt thereof, wherein $R^5$ and $R^{5a}$ are each independently absent, halogen, cyano, trifluoromethyl, $C_1$-$C_3$ alkyl, $C_1$-$C_3$ alkoxy or $C_3$-$C_5$ cycloalkyl, wherein the $C_1$-$C_3$ alkyl is optionally substituted by hydroxy, difluoromethyl, trifluoromethyl or $C_3$-$C_5$ cycloalkyl.

Additional embodiments relate to a compound of formula (I), or a pharmaceutically acceptable salt thereof, wherein $R^{13}$ is independently halogen, hydroxy, $C_1$-$C_6$ alkoxy, —N($R^9$)($R^{10}$), —CON($R^9$)($R^{10}$) or 3-7 membered heterocycloalkyl, wherein the 3-7 membered heterocycloalkyl in $R^{13}$ is optionally substituted by one or more $R^{14}$ groups.

Further embodiments relate to a compound of formula (I), or a pharmaceutically acceptable salt thereof, wherein $R^5$ and $R^{5a}$ are each independently absent, halogen, cyano, trifluoromethyl, $C_1$-$C_3$ alkyl, $C_1$-$C_3$ alkoxy or $C_3$-$C_5$ cycloalkyl, wherein the $C_1$-$C_3$ alkyl is optionally substituted by hydroxy, difluoromethyl, trifluoromethyl or $C_3$-$C_5$ cycloalkyl; and wherein $R^{13}$ is independently halogen, hydroxy, $C_1$-$C_6$ alkoxy, —N($R^9$)($R^{10}$), —CON($R^9$)($R^{10}$) or 3-7 membered heterocycloalkyl, wherein the 3-7 membered heterocycloalkyl in $R^{13}$ is optionally substituted by one or more $R^{14}$ groups.

Some embodiments relate to a compound or a pharmaceutically acceptable salt of any of the embodiments of the compounds of formula (I), having formula (Ia):

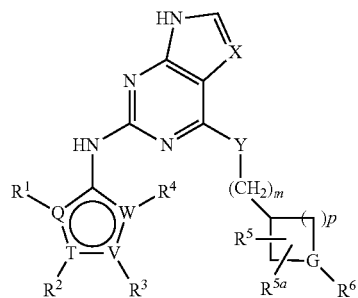

(Ia)

wherein
G is CH or N; and
p is 1 or 2.

Some embodiments relate to a compound of formula (Ia), or a pharmaceutically acceptable salt thereof, wherein G is CH.

Some embodiments relate to a compound of formula (Ia), or a pharmaceutically acceptable salt thereof, wherein G is N.

Further embodiments relate to a compound of formula (Ia), or a pharmaceutically acceptable salt thereof, wherein p is 1.

More embodiments relate to a compound of formula (Ia), or a pharmaceutically acceptable salt thereof, wherein p is 2.

Additional embodiments relate to a compound of formula (Ia), or a pharmaceutically acceptable salt thereof, wherein G is CH and p is 1.

Additional embodiments relate to a compound of formula (Ia), or a pharmaceutically acceptable salt thereof, wherein G is N and p is 2.

Some embodiments relate to a compound of formula (Ia), or a pharmaceutically acceptable salt thereof, wherein $R^5$ and $R^{5a}$ are each independently absent or methyl.

Further embodiments relate to a compound of formula (Ia), or a pharmaceutically acceptable salt thereof, wherein $R^5$ and $R^{5a}$ are each independently absent, halogen, trifluoromethyl, $C_1$-$C_3$ alkoxy or 4-6 membered heteroaryl.

More embodiments relate to a compound of formula (Ia), or a pharmaceutically acceptable salt thereof, wherein $R^5$ and $R^{5a}$ are each independently absent, difluoromethyl, trifluoromethyl, $C_1$-$C_3$ alkyl or $C_3$-$C_5$ cycloalkyl.

Additional embodiments relate to a compound of formula (Ia), or a pharmaceutically acceptable salt thereof, wherein $R^5$ and $R^{5a}$ are each independently absent, hydroxy, difluoromethyl, trifluoromethyl, $C_1$-$C_3$ alkyl, $C_1$-$C_3$ alkoxy or $C_3$-$C_5$ cycloalkyl.

Further embodiments relate to a compound of formula (Ia), or a pharmaceutically acceptable salt thereof, wherein $R^5$ and $R^{5a}$ are each independently absent, trifluoromethyl, $C_1$-$C_3$ alkyl, —($CH_2$)— trifluoromethyl or cyclopropyl.

Some embodiments relate to a compound of formula (Ia), or a pharmaceutically acceptable salt thereof, wherein $R^5$ is —$CH_2OH$, —$CH(CH_3)OH$ or —$C(CH_3)_2OH$.

Some embodiments relate to a compound or a pharmaceutically acceptable salt of any of the embodiments of the compounds of formula (I), wherein m is 1, having formula (Ib):

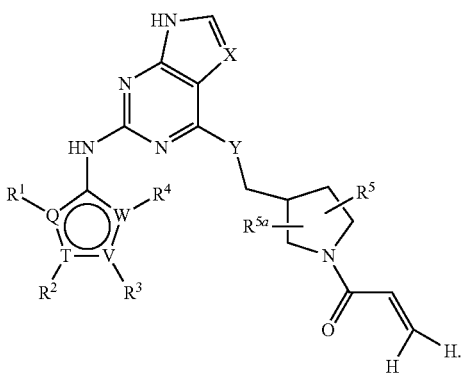

(Ib)

Additional embodiments relate to a compound of formula (Ib), or a pharmaceutically acceptable salt thereof, wherein $R^5$ and $R^{5a}$ are each independently absent, difluoromethyl, trifluoromethyl, $C_1$-$C_3$ alkyl, —($CH_2$)— trifluoromethyl or cyclopropyl.

Further embodiments relate to a compound of formula (Ib), or a pharmaceutically acceptable salt thereof, wherein $R^5$ and $R^{5a}$ are each independently absent, halogen, trifluoromethyl, $C_1$-$C_3$ alkoxy or 4-6 membered heteroaryl.

Some embodiments relate to a compound of formula (Ib), or a pharmaceutically acceptable salt thereof, wherein $R^5$ and $R^{5a}$ are each independently absent, hydroxy, difluoromethyl, trifluoromethyl, $C_1$-$C_3$ alkyl, $C_1$-$C_3$ alkoxy, cyclopropyl, —($CH_2$)—$OCH_3$ or —($CH_2$)-trifluoromethyl.

Further embodiments relate to a compound of formula (Ib), or a pharmaceutically acceptable salt thereof, wherein $R^5$ is —$CH_2OH$, —$CH(CH_3)OH$ or —$C(CH_3)_2OH$.

More embodiments relate to a compound of formula (Ib), or a pharmaceutically acceptable salt thereof, wherein $R^5$ and $R^{5a}$ are absent.

Additional embodiments relate to a compound of formula (Ib), or a pharmaceutically acceptable salt thereof, wherein $R^{5a}$ is absent.

Some embodiments relate to a compound or a pharmaceutically acceptable salt of any of the embodiments of the compounds of formula (I), wherein m is 0, having formula (Ic):

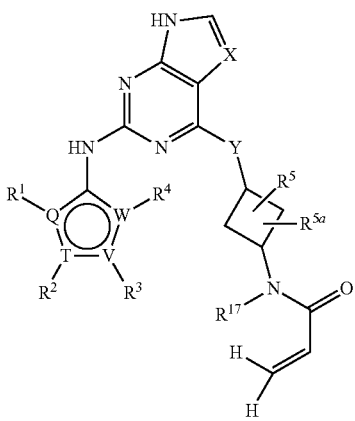

(Ic)

wherein
$R^5$ and $R^{5a}$ are each independently absent, trifluoromethyl, $C_1$-$C_3$ alkyl, or $C_3$-$C_5$ cycloalkyl.

Some embodiments relate to a compound of formula (Ic), or a pharmaceutically acceptable salt thereof, wherein $R^5$ is methyl.

More embodiments relate to a compound of formula (Ic), or a pharmaceutically acceptable salt thereof, wherein $R^{5a}$ is methyl.

More embodiments relate to a compound of formula (Ic), or a pharmaceutically acceptable salt thereof, wherein $R^5$ and $R^{5a}$ are absent.

Additional embodiments relate to a compound of formula (Ic), or a pharmaceutically acceptable salt thereof, wherein $R^{5a}$ is absent.

Additional embodiments relate to a compound of formula (Ic), or a pharmaceutically acceptable salt thereof, wherein $R^{17}$ is hydrogen.

Further embodiments relate to a compound of formula (Ic), or a pharmaceutically acceptable salt thereof, wherein $R^{17}$ is methyl.

Some embodiments relate to a compound or a pharmaceutically acceptable salt of any of the embodiments of the compounds of formula (I), wherein m is 0, having formula (Id):

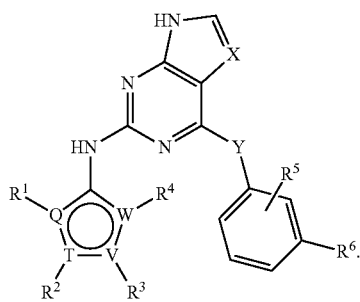

(Id)

Additional embodiments relate to a compound of formula (Id), or a pharmaceutically acceptable salt thereof, wherein $R^5$ is fluorine.

Further embodiments relate to a compound of formula (Id), or a pharmaceutically acceptable salt thereof, wherein $R^6$ is

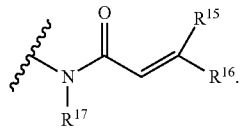

Some embodiments relate to a compound or a pharmaceutically acceptable salt of any of the embodiments of the compounds of formula (I), wherein m is 0, having formula (Ie):

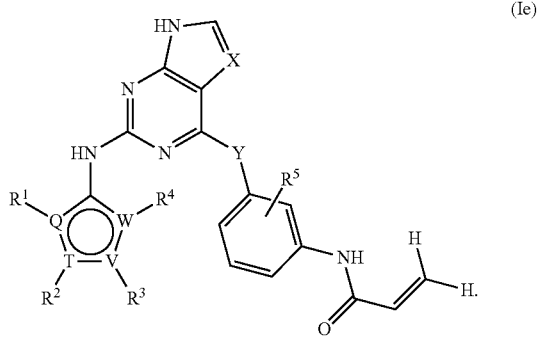

(Ie)

Some embodiments relate to a compound of formula (Ie), or a pharmaceutically acceptable salt thereof, wherein $R^5$ is fluorine.

Some embodiments relate to a compound or a pharmaceutically acceptable salt of any of the embodiments of the compounds of formula (I), having formula (If):

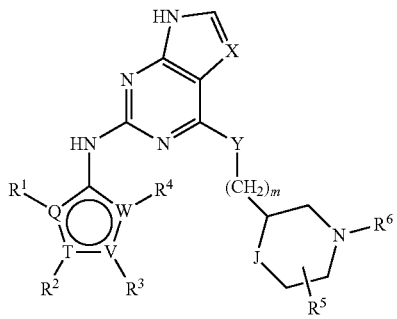

(If)

wherein
J is $CH_2$, $NR^{18}$ or O, provided that when J is $NR^{18}$ or O, m is not 0; and
$R^{18}$ is hydrogen or $C_1$-$C_3$ alkyl.

Further embodiments relate to a compound of formula (If), or a pharmaceutically acceptable salt thereof, wherein $R^6$ is

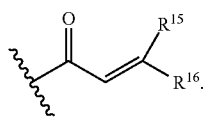

Some embodiments relate to a compound or a pharmaceutically acceptable salt of any of the embodiments of the compounds of formula (I), wherein Y is absent and m is 0, having formula (Ig):

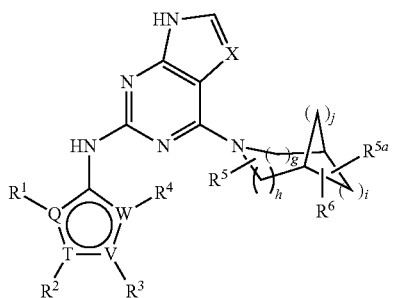

(Ig)

wherein
g is 0, 1 or 2;
h is 0, 1 or 2;
i is 1 or 2; and
j is 0, 1 or 2.

Further embodiments relate to a compound of formula (Ig), or a pharmaceutically acceptable salt thereof, wherein $R^5$ and $R^{5a}$ are each independently absent, fluorine, hydroxy, $C_1$-$C_3$ alkyl or $C_1$-$C_3$ alkoxy, wherein the $C_1$-$C_3$ alkyl is optionally substituted by hydroxy or $C_1$-$C_3$ alkoxy.

Some embodiments relate to a compound of formula (Ig), or a pharmaceutically acceptable salt thereof, wherein $R^6$ is

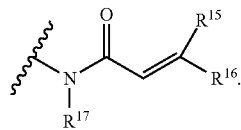

Some embodiments relate to a compound or a pharmaceutically acceptable salt of any of the embodiments of the compounds of formula (I), wherein Y is absent and m is 0, having formula (Ih):

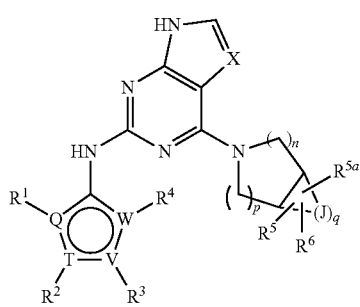

(Ih)

wherein
each J is independently CH or N, provided that at least one J is CH, and further provided that no more than one J is N;
n is 0, 1 or 2;
p is 0, 1 or 2; and
q is 1, 2, 3 or 4.

More embodiments relate to a compound of formula (Ih), or a pharmaceutically acceptable salt thereof, wherein $R^5$ and $R^{5a}$ are each independently absent, fluorine, hydroxy, $C_1$-$C_3$ alkyl or $C_1$-$C_3$ alkoxy, wherein the $C_1$-$C_3$ alkyl is optionally substituted by hydroxy or $C_1$-$C_3$ alkoxy.

Additional embodiments relate to a compound or a pharmaceutically acceptable salt of any of the embodiments of the compounds of formula (I), wherein Y is absent and m is 0, having formula (Ii):

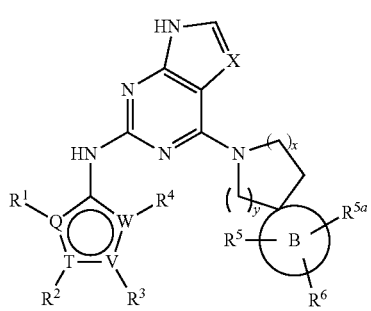

(Ii)

wherein
ring B is 3-6 membered monocyclic cycloalkyl or 3-6 membered monocyclic heterocycloalkyl; and
x is 0, 1, 2 or 3; and
y is 0 or 1.

Additional embodiments relate to a compound or a pharmaceutically acceptable salt of any of the embodiments of the compounds of formula (II), wherein $R^5$ and $R^{5a}$ are each independently absent, fluorine, hydroxy, $C_1$-$C_3$ alkyl or $C_1$-$C_3$ alkoxy, wherein the $C_1$-$C_3$ alkyl is optionally substituted by hydroxy or $C_1$-$C_3$ alkoxy.

Some embodiments described herein relate to a compound of formula (II):

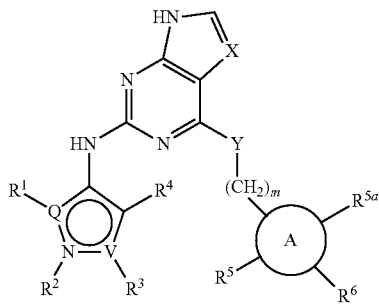

(II)

wherein

X is N or $CR^7$;

Y is absent, O, S or $NR^8$;

Q and V are each independently C or N, provided that at least one of Q and V is N, and further provided that when Q is N, at least one of $R^1$ and $R^2$ is absent;

$R^1$ and $R^4$ are each independently absent, hydrogen, cyano, difluoromethyl, trifluoromethyl, $C_1$-$C_6$ alkyl, $C_2$-$C_6$ alkenyl, $C_2$-$C_6$ alkynyl, $C_1$-$C_6$ alkoxy, $-N(R^9)(R^{10})$, $C_3$-$C_5$ cycloalkyl or 4-6 membered heterocycloalkyl, wherein the $C_1$-$C_6$ alkyl may be optionally substituted by halogen, hydroxy, $C_1$-$C_6$ alkoxy or $N(R^{11})(R^{12})$;

$R^2$ and $R^3$ are each independently absent, hydrogen, $C_1$-$C_6$ alkyl, $C_2$-$C_6$ alkynyl, $C_1$-$C_6$ alkoxy, $C_3$-$C_7$ cycloalkyl or 3-7 membered heterocycloalkyl, wherein the $C_1$-$C_6$ alkyl and $C_1$-$C_6$ alkoxy in $R^2$ and $R^3$ are each independently optionally substituted by one or more $R^{13}$ groups, and further wherein the $C_3$-$C_7$ cycloalkyl and the 3-7 membered heterocycloalkyl in $R^2$ and $R^3$ are each independently optionally substituted by one or more $R^{14}$ groups; or $R^1$ and $R^2$ or $R^2$ and $R^3$ may combine to form a $C_5$-$C_7$ cycloalkyl ring or a 5-7 membered heterocycloalkyl ring, wherein the $C_5$-$C_7$ cycloalkyl ring and the 5-7 membered heterocycloalkyl ring are each independently optionally substituted by one or more $R^{13}$ groups;

ring A is absent, $C_3$-$C_{10}$ cycloalkyl, 3-10 membered heterocycloalkyl, $C_5$-$C_{10}$ aryl or 5-12 membered heteroaryl;

$R^5$ and $R^{5a}$ are each independently absent, halogen, cyano, hydroxy, difluoromethyl, trifluoromethyl, $C_1$-$C_3$ alkyl, $C_1$-$C_3$ alkoxy, $C_3$-$C_5$ cycloalkyl or 4-6 membered heteroaryl, wherein the $C_1$-$C_3$ alkyl is optionally substituted by hydroxy, difluoromethyl, trifluoromethyl, $C_1$-$C_3$ alkoxy or $C_3$-$C_5$ cycloalkyl;

$R^6$ is

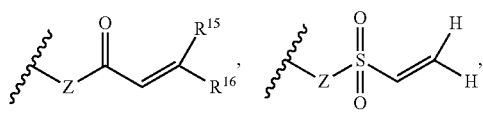

-continued

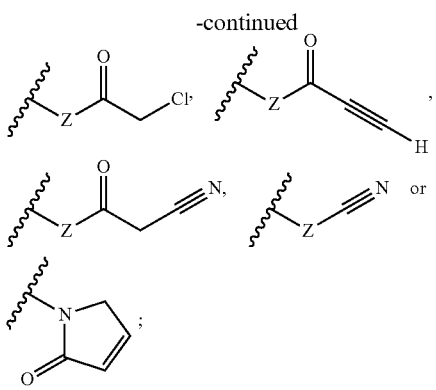

Z is absent when the attachment point of $R^6$ on ring A is a nitrogen atom, and Z is $-NR^{17}-$ when ring A is absent or when the attachment point of $R^6$ on ring A is a carbon atom;

$R^7$ is hydrogen, halogen, cyano, $C_1$-$C_6$ alkyl, $C_2$-$C_6$ alkenyl, $C_2$-$C_6$ alkynyl or 4-6 membered heteroaryl, wherein the $C_1$-$C_6$ alkyl may be optionally substituted by hydroxy or $C_1$-$C_3$ alkoxy, and further wherein the 4-6 membered heteroaryl may be optionally substituted by $C_1$-$C_3$ alkyl;

$R^8$ is hydrogen or $C_1$-$C_3$ alkyl;

$R^9$ and $R^{10}$ are each independently hydrogen or $C_1$-$C_6$ alkyl; or $R^9$ and $R^{10}$ together with the nitrogen to which they are attached, may combine to form a 4-7 membered ring, when $R^9$ and $R^{10}$ are each $C_1$-$C_3$ alkyl, wherein the 4-7 membered ring is optionally substituted by one or more $R^{14}$ groups;

$R^{11}$ and $R^{12}$ are each independently hydrogen or $C_1$-$C_3$ alkyl;

each $R^{13}$ is independently halogen, cyano, hydroxy, $C_1$-$C_6$ alkoxy, $-N(R^9)(R^{10})$, $-CON(R^9)(R^{10})$ or 3-7 membered heterocycloalkyl, wherein the 3-7 membered heterocycloalkyl in $R^{13}$ is optionally substituted by one or more $R^{14}$ groups;

each $R^{14}$ is independently halogen, $C_1$-$C_3$ alkyl, hydroxy, $C_1$-$C_6$ alkoxy, $-NH_2$, $-NHCH_3$, or $N(CH_3)_2$;

$R^{15}$ and $R^{16}$ are each independently hydrogen or $C_1$-$C_6$ alkyl, wherein the $C_1$-$C_6$ alkyl of one of $R^{15}$ and $R^{16}$ is optionally substituted by $-N(R^9)(R^{10})$;

$R^{17}$ is hydrogen or $C_1$-$C_3$ alkyl; and m is 0, 1 or 2, provided that when ring A is absent, m is 2; or a pharmaceutically acceptable salt thereof.

More embodiments relate to a compound of formula (II), or a pharmaceutically acceptable salt thereof, wherein X is $CR^7$.

Some embodiments relate to a compound of formula (II), or a pharmaceutically acceptable salt thereof, wherein Y is O.

Some embodiments relate to a compound of formula (II), or a pharmaceutically acceptable salt thereof, wherein Y is $NR^8$.

Additional embodiments relate to a compound of formula (II), or a pharmaceutically acceptable salt thereof, wherein X is $CR^7$ and Y is O.

Some embodiments relate to a compound of formula (II), or a pharmaceutically acceptable salt thereof, wherein $R^7$ is hydrogen, halogen, cyano or 4-6 membered heteroaryl.

Further embodiments relate to a compound of formula (II), or a pharmaceutically acceptable salt thereof, wherein $R^7$ is hydrogen, halogen or cyano.

More embodiments relate to a compound of formula (II), or a pharmaceutically acceptable salt thereof, wherein $R^7$ is hydrogen.

Some embodiments relate to a compound of formula (II), or a pharmaceutically acceptable salt thereof, wherein $R^7$ is halogen, and further wherein the halogen is fluorine.

Some embodiments relate to a compound of formula (II), or a pharmaceutically acceptable salt thereof, wherein $R^7$ is halogen, and further wherein the halogen is chlorine.

Further embodiments relate to a compound of formula (II), or a pharmaceutically acceptable salt thereof, wherein $R^7$ is cyano.

Further embodiments relate to a compound of formula (II), or a pharmaceutically acceptable salt thereof, wherein $R^7$ is 4-6 membered heteroaryl optionally substituted by $C_1$-$C_3$ alkyl.

Additional embodiments relate to a compound of formula (II), or a pharmaceutically acceptable salt thereof, wherein m is 0.

More embodiments relate to a compound of formula (II), or a pharmaceutically acceptable salt thereof, wherein m is 1.

More embodiments relate to a compound of formula (II), or a pharmaceutically acceptable salt thereof, wherein Q and V are N.

Some embodiments relate to a compound of formula (II), or a pharmaceutically acceptable salt thereof, wherein Q is N.

Some embodiments relate to a compound of formula (II), or a pharmaceutically acceptable salt thereof, wherein V is N.

Some embodiments relate to a compound of formula (II), or a pharmaceutically acceptable salt thereof, wherein $R^1$ is hydrogen or $C_1$-$C_3$ alkyl, wherein the $C_1$-$C_3$ alkyl may be optionally substituted by halogen or hydroxy.

More embodiments relate to a compound of formula (II), or a pharmaceutically acceptable salt thereof, wherein $R^1$ is hydrogen.

More embodiments relate to a compound of formula (II), or a pharmaceutically acceptable salt thereof, wherein $R^1$ is methyl or ethyl.

More embodiments relate to a compound of formula (II), or a pharmaceutically acceptable salt thereof, wherein $R^1$ is methyl.

Some embodiments relate to a compound of formula (II), or a pharmaceutically acceptable salt thereof, wherein $R^1$ is $C_1$-$C_3$ alkoxy.

Further embodiments relate to a compound of formula (II), or a pharmaceutically acceptable salt thereof, wherein $R^1$ is —$CH_2F$ or —$C(CH_3)_2OH$.

More embodiments relate to a compound of formula (II), or a pharmaceutically acceptable salt thereof, wherein $R^2$ is absent.

Additional embodiments relate to a compound of formula (II), or a pharmaceutically acceptable salt thereof, wherein $R^2$ is $C_1$-$C_4$ alkyl or $C_3$-$C_4$ cycloalkyl.

More embodiments relate to a compound of formula (II), or a pharmaceutically acceptable salt thereof, wherein $R^2$ is methyl.

More embodiments relate to a compound of formula (II), or a pharmaceutically acceptable salt thereof, wherein $R^2$ is ethyl.

Additional embodiments relate to a compound of formula (II), or a pharmaceutically acceptable salt thereof, wherein $R^2$ is $C_1$-$C_6$ alkyl optionally substituted by hydroxy, —N($R^9$)($R^{10}$) or 3-7 membered heterocycloalkyl, and further wherein the 3-7 membered heterocycloalkyl is optionally substituted by $C_1$-$C_3$ alkyl.

Some embodiments relate to a compound of formula (II), or a pharmaceutically acceptable salt thereof, wherein $R^2$ is $C_1$-$C_3$ alkyl optionally substituted by —N($CH_3$)$_2$ or morpholino, and further wherein the morpholino is optionally substituted by methyl.

Some embodiments relate to a compound of formula (II), or a pharmaceutically acceptable salt thereof, wherein $R^2$ is 3-7 membered heterocycloalkyl optionally substituted by one or more substituents selected from the group consisting of halogen, $C_1$-$C_3$ alkyl and hydroxy.

Some embodiments relate to a compound of formula (II), or a pharmaceutically acceptable salt thereof, wherein $R^2$ is tetrahydrofuran or tetrahydropyran.

More embodiments relate to a compound of formula (II), or a pharmaceutically acceptable salt thereof, wherein $R^2$ is pyrrolidine optionally substituted by one or more substituents selected from the group consisting of halogen, $C_1$-$C_3$ alkyl and hydroxy.

More embodiments relate to a compound of formula (II), or a pharmaceutically acceptable salt thereof, wherein $R^2$ is pyrrolidine optionally substituted by methyl.

Additional embodiments relate to a compound of formula (II), or a pharmaceutically acceptable salt thereof, wherein $R^3$ is hydrogen, $C_1$-$C_3$ alkyl or $C_3$-$C_7$ cycloalkyl, and further wherein the $C_1$-$C_3$ alkyl is optionally substituted by hydroxy, $C_1$-$C_6$ alkoxy or —N($R^9$)($R^{10}$).

More embodiments relate to a compound of formula (II), or a pharmaceutically acceptable salt thereof, wherein $R^3$ is absent.

More embodiments relate to a compound of formula (II), or a pharmaceutically acceptable salt thereof, wherein $R^3$ is methyl.

Some embodiments relate to a compound of formula (II), or a pharmaceutically acceptable salt thereof, wherein $R^4$ is hydrogen.

Further embodiments relate to a compound of formula (II), or a pharmaceutically acceptable salt thereof, wherein $R^4$ is $C_1$-$C_3$ alkyl.

More embodiments relate to a compound of formula (II), or a pharmaceutically acceptable salt thereof, wherein $R^4$ is methyl.

Additional embodiments relate to a compound of formula (II), or a pharmaceutically acceptable salt thereof, wherein $R^5$ and $R^{5a}$ are each independently absent, halogen, cyano, trifluoromethyl, $C_1$-$C_3$ alkyl, $C_1$-$C_3$ alkoxy or $C_3$-$C_5$ cycloalkyl, wherein the $C_1$-$C_3$ alkyl is optionally substituted by hydroxy, difluoromethyl, trifluoromethyl or $C_3$-$C_5$ cycloalkyl.

Additional embodiments relate to a compound of formula (II), or a pharmaceutically acceptable salt thereof, wherein $R^{13}$ is independently halogen, hydroxy, $C_1$-$C_6$ alkoxy, —N($R^9$)($R^{10}$), —CON($R^9$)($R^{10}$) or 3-7 membered heterocycloalkyl, wherein the 3-7 membered heterocycloalkyl in $R^{13}$ is optionally substituted by one or more $R^{14}$ groups.

Further embodiments relate to a compound of formula (II), or a pharmaceutically acceptable salt thereof, wherein $R^5$ and $R^{5a}$ are each independently absent, halogen, cyano, trifluoromethyl, $C_1$-$C_3$ alkyl, $C_1$-$C_3$ alkoxy or $C_3$-$C_5$ cycloalkyl, wherein the $C_1$-$C_3$ alkyl is optionally substituted by hydroxy, difluoromethyl, trifluoromethyl or $C_3$-$C_5$ cycloalkyl; and wherein $R^{13}$ is independently halogen, hydroxy, $C_1$-$C_6$ alkoxy, —N($R^9$)($R^{10}$), —CON($R^9$)($R^{10}$) or 3-7 membered heterocycloalkyl, wherein the 3-7 membered heterocycloalkyl in $R^{13}$ is optionally substituted by one or more $R^{14}$ groups.

Some embodiments relate to a compound or a pharmaceutically acceptable salt of any of the embodiments of the compounds of formula (II), having formula (IIa):

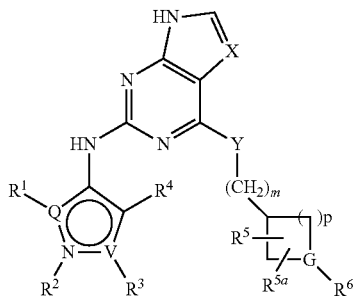

(IIa)

wherein
G is CH or N; and
p is 1 or 2.

Some embodiments relate to a compound of formula (IIa), or a pharmaceutically acceptable salt thereof, wherein G is CH.

Some embodiments relate to a compound of formula (IIa), or a pharmaceutically acceptable salt thereof, wherein G is N.

More embodiments relate to a compound of formula (IIa), or a pharmaceutically acceptable salt thereof, wherein p is 1.

More embodiments relate to a compound of formula (IIa), or a pharmaceutically acceptable salt thereof, wherein p is 2.

Further embodiments relate to a compound of formula (IIa), or a pharmaceutically acceptable salt thereof, wherein G is CH and p is 1.

Additional embodiments relate to a compound of formula (IIa), or a pharmaceutically acceptable salt thereof, wherein G is N and p is 2.

Further embodiments relate to a compound of formula (IIa), or a pharmaceutically acceptable salt thereof, wherein $R^5$ and $R^{5a}$ are each independently absent or methyl.

Further embodiments relate to a compound of formula (IIa), or a pharmaceutically acceptable salt thereof, wherein $R^5$ and $R^{5a}$ are each independently absent, halogen, trifluoromethyl, $C_1$-$C_3$ alkoxy or 4-6 membered heteroaryl.

Additional embodiments relate to a compound of formula (IIa), or a pharmaceutically acceptable salt thereof, wherein $R^5$ and $R^{5a}$ are each independently absent, difluoromethyl, trifluoromethyl, $C_1$-$C_3$ alkyl or $C_3$-$C_5$ cycloalkyl.

More embodiments relate to a compound of formula (IIa), or a pharmaceutically acceptable salt thereof, wherein $R^5$ and $R^{5a}$ are each independently absent, hydroxy, difluoromethyl, trifluoromethyl, $C_1$-$C_3$ alkyl, $C_1$-$C_3$ alkoxy or $C_3$-$C_5$ cycloalkyl.

Some embodiments relate to a compound of formula (IIa), or a pharmaceutically acceptable salt thereof, wherein $R^5$ and $R^{5a}$ are each independently absent, trifluoromethyl, $C_1$-$C_3$ alkyl, —(CH$_2$)— trifluoromethyl or cyclopropyl.

More embodiments relate to a compound of formula (IIa), or a pharmaceutically acceptable salt thereof, wherein $R^5$ and $R^{5a}$ are each independently absent, trifluoromethyl, $C_1$-$C_3$ alkyl, cyclopropyl, —(CH$_2$)-trifluoromethyl or —(CH$_2$)—OCH$_3$.

Further embodiments relate to a compound of formula (IIa), or a pharmaceutically acceptable salt thereof, wherein $R^5$ is —CH$_2$OH, —CH(CH$_3$)OH or —C(CH$_3$)$_2$OH.

Some embodiments relate to a compound or a pharmaceutically acceptable salt of any of the embodiments of the compounds of formula (II), wherein m is 1, having formula (IIb):

(IIb)

Further embodiments relate to a compound of formula (IIb), or a pharmaceutically acceptable salt thereof, wherein $R^5$ and $R^{5a}$ are each independently absent, difluoromethyl, trifluoromethyl, $C_1$-$C_3$ alkyl, —(CH$_2$)— trifluoromethyl or cyclopropyl.

Some embodiments relate to a compound of formula (IIb), or a pharmaceutically acceptable salt thereof, wherein $R^5$ and $R^{5a}$ are each independently absent, hydroxy, difluoromethyl, trifluoromethyl, $C_1$-$C_3$ alkyl, $C_1$-$C_3$ alkoxy, cyclopropyl, —(CH$_2$)—OCH$_3$ or —(CH$_2$)-trifluoromethyl.

Further embodiments relate to a compound of formula (IIb), or a pharmaceutically acceptable salt thereof, wherein $R^5$ and $R^{5a}$ are each independently absent, halogen, trifluoromethyl, $C_1$-$C_3$ alkoxy or 4-6 membered heteroaryl.

Further embodiments relate to a compound of formula (IIb), or a pharmaceutically acceptable salt thereof, wherein $R^5$ is —CH$_2$OH, —CH(CH$_3$)OH or —C(CH$_3$)$_2$OH.

Some embodiments relate to a compound of formula (IIb), or a pharmaceutically acceptable salt thereof, wherein $R^5$ and $R^{5a}$ are absent.

More embodiments relate to a compound of formula (IIb), or a pharmaceutically acceptable salt thereof, wherein $R^5$ is absent.

Some embodiments relate to a compound or a pharmaceutically acceptable salt of any of the embodiments of the compounds of formula (II), wherein m is 0, having formula (IIc):

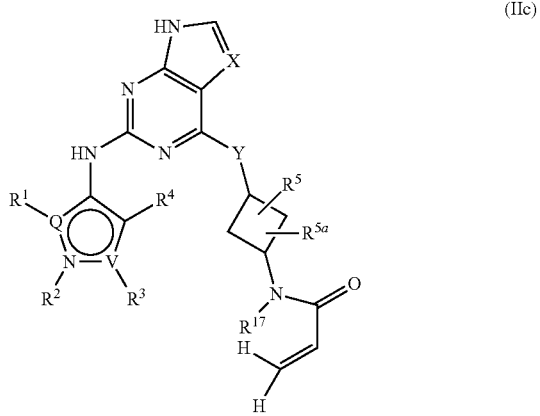

(IIc)

wherein
$R^5$ and $R^{5a}$ are each independently absent, trifluoromethyl, $C_1$-$C_3$ alkyl, or $C_3$-$C_5$ cycloalkyl.

Some embodiments relate to a compound of formula (IIc), or a pharmaceutically acceptable salt thereof, wherein $R^5$ is methyl.

Some embodiments relate to a compound of formula (IIc), or a pharmaceutically acceptable salt thereof, wherein $R^{5a}$ is methyl.

Some embodiments relate to a compound of formula (IIc), or a pharmaceutically acceptable salt thereof, wherein $R^5$ and $R^{5a}$ are absent.

More embodiments relate to a compound of formula (IIc), or a pharmaceutically acceptable salt thereof, wherein $R^5$ is absent.

More embodiments relate to a compound of formula (IIc), or a pharmaceutically acceptable salt thereof, wherein $R^{17}$ is hydrogen.

Further embodiments relate to a compound of formula (IIc), or a pharmaceutically acceptable salt thereof, wherein $R^{17}$ is methyl.

Some embodiments relate to a compound or a pharmaceutically acceptable salt of any of the embodiments of the compounds of formula (II), wherein m is 0, having formula (IId):

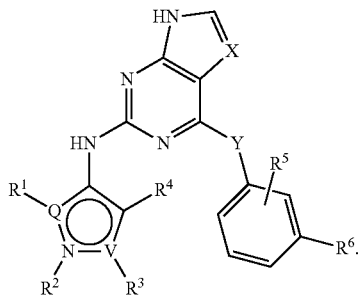

(IId)

Additional embodiments relate to a compound of formula (IId), or a pharmaceutically acceptable salt thereof, wherein $R^5$ is fluorine.

Further embodiments relate to a compound of formula (IId), or a pharmaceutically acceptable salt thereof, wherein $R^6$ is

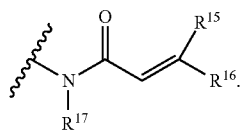

Some embodiments relate to a compound or a pharmaceutically acceptable salt of any of the embodiments of the compounds of formula (II), wherein m is 0, having formula (IIe):

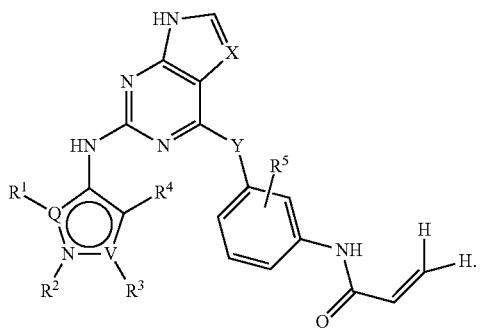

(IIe)

Some embodiments relate to a compound of formula (IIe), or a pharmaceutically acceptable salt thereof, wherein $R^5$ is fluorine.

Some embodiments relate to a compound or a pharmaceutically acceptable salt of any of the embodiments of the compounds of formula (II), having formula (IIf):

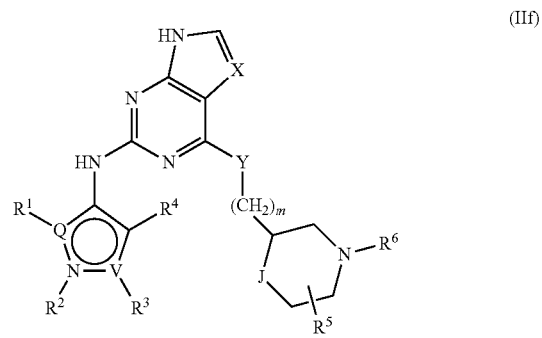

(IIf)

wherein
J is $CH_2$, $NR^{18}$ or O, provided that when J is $NR^{18}$ or O, m is not 0; and
$R^{18}$ is hydrogen or $C_1$-$C_3$ alkyl.

Some embodiments relate to a compound of formula (IIf), or a pharmaceutically acceptable salt thereof, wherein $R^6$ is

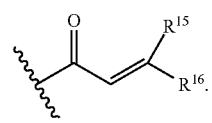

Some embodiments relate to a compound or a pharmaceutically acceptable salt of any of the embodiments of the compounds of formula (II), wherein Y is absent and m is 0, having formula (IIg):

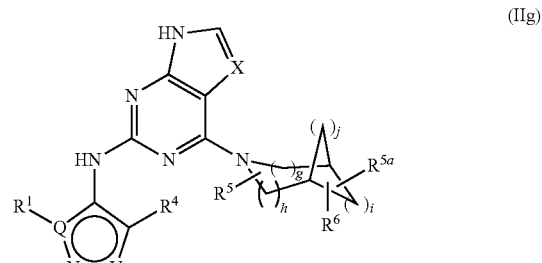

(IIg)

wherein
g is 0, 1 or 2;
h is 0, 1 or 2;
i is 1 or 2; and
j is 0, 1 or 2.

Some embodiments relate to a compound of formula (IIg), or a pharmaceutically acceptable salt thereof, wherein $R^5$ and $R^{5a}$ are each independently absent, fluorine, hydroxy, $C_1$-$C_3$ alkyl or $C_1$-$C_3$ alkoxy, wherein the $C_1$-$C_3$ alkyl is optionally substituted by hydroxy or $C_1$-$C_3$ alkoxy.

More embodiments relate to a compound of formula (IIg), or a pharmaceutically acceptable salt thereof, wherein $R^6$ is

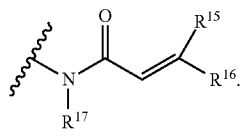

Some embodiments relate to a compound or a pharmaceutically acceptable salt of any of the embodiments of the compounds of formula (II), wherein Y is absent and m is 0, having formula (IIh):

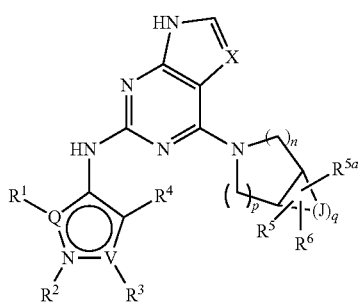

(IIh)

wherein
each J is independently CH or N, provided that at least one J is CH, and further provided that no more than one J is N;
n is 0, 1 or 2;
p is 0, 1 or 2; and
q is 1, 2, 3 or 4.

More embodiments relate to a compound of formula (IIh), or a pharmaceutically acceptable salt thereof, wherein $R^5$ and $R^{5a}$ are each independently absent, fluorine, hydroxy, $C_1$-$C_3$ alkyl or $C_1$-$C_3$ alkoxy, wherein the $C_1$-$C_3$ alkyl is optionally substituted by hydroxy or $C_1$-$C_3$ alkoxy.

Some embodiments relate to a compound or a pharmaceutically acceptable salt of any of the embodiments of the compounds of formula (II), wherein Y is absent and m is 0, having formula (IIi):

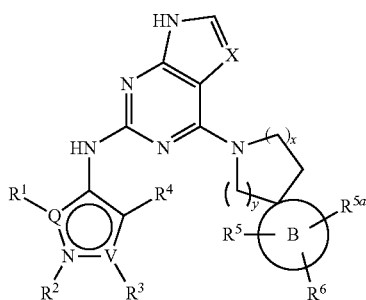

(IIi)

wherein
ring B is 3-6 membered monocyclic cycloalkyl or 3-6 membered monocyclic heterocycloalkyl; and
x is 0, 1, 2 or 3; and
y is 0 or 1.

More embodiments relate to a compound of formula (IIi), or a pharmaceutically acceptable salt thereof, wherein $R^5$ and $R^{5a}$ are each independently absent, fluorine, hydroxy, $C_1$-$C_3$ alkyl or $C_1$-$C_3$ alkoxy, wherein the $C_1$-$C_3$ alkyl is optionally substituted by hydroxy or $C_1$-$C_3$ alkoxy.

Some embodiments described herein relate to a compound of formula (III):

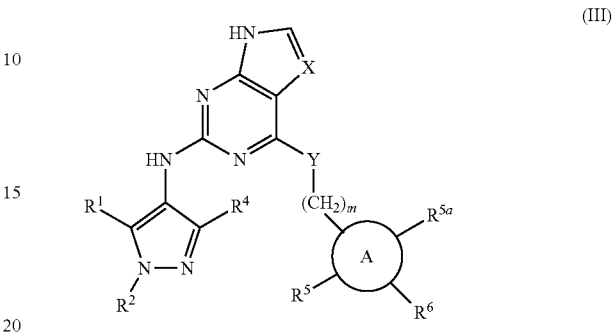

(III)

wherein
X is N or $CR^7$;
Y is absent, O, S or $NR^8$;
$R^1$ and $R^4$ are each independently hydrogen, cyano, difluoromethyl, trifluoromethyl, $C_1$-$C_6$ alkyl, $C_2$-$C_6$ alkenyl, $C_2$-$C_6$ alkynyl, $C_1$-$C_6$ alkoxy, —N($R^9$)($R^{10}$), $C_3$-$C_5$ cycloalkyl or 4-6 membered heterocycloalkyl, wherein the $C_1$-$C_6$ alkyl may be optionally substituted by halogen, hydroxy, $C_1$-$C_6$ alkoxy or N($R^{11}$)($R^{12}$);
$R^2$ is $C_1$-$C_6$ alkyl, $C_2$-$C_6$ alkynyl, $C_1$-$C_6$ alkoxy, $C_3$-$C_7$ cycloalkyl or 3-7 membered heterocycloalkyl, wherein the $C_1$-$C_6$ alkyl and $C_1$-$C_6$ alkoxy in $R^2$ is optionally substituted by one or more $R^{13}$ groups, and further wherein the $C_3$-$C_7$ cycloalkyl and the 3-7 membered heterocycloalkyl in $R^2$ is optionally substituted by one or more $R^{14}$ groups; or
$R^1$ and $R^2$ may combine to form a $C_5$-$C_7$ cycloalkyl ring or a 5-7 membered heterocycloalkyl ring, wherein the $C_5$-$C_7$ cycloalkyl ring and the 5-7 membered heterocycloalkyl ring are optionally substituted by one or more $R^{13}$ groups;
ring A is absent, $C_3$-$C_{10}$ cycloalkyl, 3-10 membered heterocycloalkyl, $C_5$-$C_{10}$ aryl or 5-12 membered heteroaryl;
$R^5$ and $R^{5a}$ are each independently absent, halogen, cyano, hydroxy, difluoromethyl, trifluoromethyl, $C_1$-$C_3$ alkyl, $C_1$-$C_3$ alkoxy, $C_3$-$C_5$ cycloalkyl or 4-6 membered heteroaryl, wherein the $C_1$-$C_3$ alkyl is optionally substituted by hydroxy, difluoromethyl, trifluoromethyl, $C_1$-$C_3$ alkoxy or $C_3$-$C_5$ cycloalkyl;
$R^6$ is

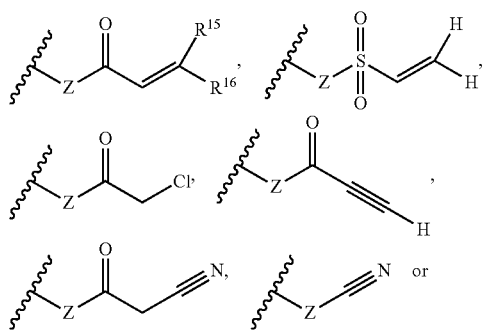

-continued

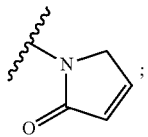

Z is absent when the attachment point of $R^6$ on ring A is a nitrogen atom, and Z is —$NR^{17}$— when ring A is absent or when the attachment point of $R^6$ on ring A is a carbon atom;

$R^7$ is hydrogen, halogen, cyano, $C_1$-$C_6$ alkyl, $C_2$-$C_6$ alkenyl, $C_2$-$C_6$ alkynyl or 4-6 membered heteroaryl, wherein the $C_1$-$C_6$ alkyl may be optionally substituted by hydroxy or $C_1$-$C_3$ alkoxy, and further wherein the 4-6 membered heteroaryl may be optionally substituted by $C_1$-$C_3$ alkyl;

$R^8$ is hydrogen or $C_1$-$C_3$ alkyl;

$R^9$ and $R^{10}$ are each independently hydrogen or $C_1$-$C_6$ alkyl; or $R^9$ and $R^{10}$ together with the nitrogen to which they are attached, may combine to form a 4-7 membered ring, when $R^9$ and $R^{10}$ are each $C_1$-$C_3$ alkyl, wherein the 4-7 membered ring is optionally substituted by one or more $R^{14}$ groups;

$R^{11}$ and $R^{12}$ are each independently hydrogen or $C_1$-$C_3$ alkyl;

each $R^{13}$ is independently halogen, cyano, hydroxy, $C_1$-$C_6$ alkoxy, —$N(R^9)(R^{10})$, —$CON(R^9)(R^{10})$ or 3-7 membered heterocycloalkyl, wherein the 3-7 membered heterocycloalkyl in $R^{13}$ is optionally substituted by one or more $R^{14}$ groups;

each $R^{14}$ is independently halogen, $C_1$-$C_3$ alkyl, hydroxy, $C_1$-$C_6$ alkoxy, —$NH_2$, —$NHCH_3$ or $N(CH_3)_2$;

$R^{15}$ and $R^{16}$ are each independently hydrogen or $C_1$-$C_6$ alkyl, wherein the $C_1$-$C_6$ alkyl of one of $R^{15}$ and $R^{16}$ is optionally substituted by —$N(R^9)(R^{10})$;

$R^{17}$ is hydrogen or $C_1$-$C_6$ alkyl; and m is 0, 1 or 2, provided that when ring A is absent, m is 2;

or a pharmaceutically acceptable salt thereof.

Some embodiments relate to a compound of formula (III), or a pharmaceutically acceptable salt thereof, wherein X is $CR^7$.

Some embodiments relate to a compound of formula (III), or a pharmaceutically acceptable salt thereof, wherein Y is O.

More embodiments relate to a compound of formula (III), or a pharmaceutically acceptable salt thereof, wherein Y is $NR^8$.

Further embodiments relate to a compound of formula (III), or a pharmaceutically acceptable salt thereof, wherein X is $CR^7$ and Y is O.

Some embodiments relate to a compound of formula (III), or a pharmaceutically acceptable salt thereof, wherein $R^7$ is hydrogen, halogen, cyano or 4-6 membered heteroaryl.

Additional embodiments relate to a compound of formula (III), or a pharmaceutically acceptable salt thereof, wherein $R^7$ is hydrogen, halogen or cyano.

Additional embodiments relate to a compound of formula (III), or a pharmaceutically acceptable salt thereof, wherein $R^7$ is hydrogen.

More embodiments relate to a compound of formula (III), or a pharmaceutically acceptable salt thereof, wherein $R^7$ is halogen, and further wherein the halogen is fluorine.

Some embodiments relate to a compound of formula (III), or a pharmaceutically acceptable salt thereof, wherein $R^7$ is halogen, and further wherein the halogen is chlorine.

Additional embodiments relate to a compound of formula (III), or a pharmaceutically acceptable salt thereof, wherein $R^7$ is cyano.

Further embodiments relate to a compound of formula (III), or a pharmaceutically acceptable salt thereof, wherein $R^7$ is 4-6 membered heteroaryl optionally substituted by $C_1$-$C_3$ alkyl.

Further embodiments relate to a compound of formula (III), or a pharmaceutically acceptable salt thereof, wherein m is 0.

Some embodiments relate to a compound of formula (III), or a pharmaceutically acceptable salt thereof, wherein m is 1.

Further embodiments relate to a compound of formula (III), or a pharmaceutically acceptable salt thereof, wherein $R^1$ is hydrogen or $C_1$-$C_3$ alkyl, wherein the $C_1$-$C_3$ alkyl may be optionally substituted by halogen or hydroxy.

More embodiments relate to a compound of formula (III), or a pharmaceutically acceptable salt thereof, wherein $R^1$ is hydrogen.

More embodiments relate to a compound of formula (III), or a pharmaceutically acceptable salt thereof, wherein $R^1$ is methyl or ethyl.

More embodiments relate to a compound of formula (III), or a pharmaceutically acceptable salt thereof, wherein $R^1$ is methyl.

Some embodiments relate to a compound of formula (III), or a pharmaceutically acceptable salt thereof, wherein $R^1$ is $C_1$-$C_3$ alkoxy.

Additional embodiments relate to a compound of formula (III), or a pharmaceutically acceptable salt thereof, wherein $R^1$ is —$CH_2F$ or —$C(CH_3)_2OH$.

Some embodiments relate to a compound of formula (III), or a pharmaceutically acceptable salt thereof, wherein $R^2$ is absent.

Some embodiments relate to a compound of formula (III), or a pharmaceutically acceptable salt thereof, wherein $R^2$ is $C_1$-$C_4$ alkyl or $C_3$-$C_4$ cycloalkyl.

Some embodiments relate to a compound of formula (III), or a pharmaceutically acceptable salt thereof, wherein $R^2$ is methyl.

More embodiments relate to a compound of formula (III), or a pharmaceutically acceptable salt thereof, wherein $R^2$ is ethyl.

Some embodiments relate to a compound of formula (III), or a pharmaceutically acceptable salt thereof, wherein $R^2$ is $C_1$-$C_6$ alkyl optionally substituted by hydroxy, —$N(R^9)(R^{10})$ or 3-7 membered heterocycloalkyl, and further wherein the 3-7 membered heterocycloalkyl is optionally substituted by $C_1$-$C_3$ alkyl.

More embodiments relate to a compound of formula (III), or a pharmaceutically acceptable salt thereof, wherein $R^2$ is $C_1$-$C_3$ alkyl optionally substituted by —$N(CH_3)_2$ or morpholino, and further wherein the morpholino is optionally substituted by methyl.

More embodiments relate to a compound of formula (III), or a pharmaceutically acceptable salt thereof, wherein $R^2$ is 3-7 membered heterocycloalkyl optionally substituted by one or more substituents selected from the group consisting of halogen, $C_1$-$C_3$ alkyl and hydroxy.

Additional embodiments relate to a compound of formula (III), or a pharmaceutically acceptable salt thereof, wherein $R^2$ is tetrahydrofuran or tetrahydropyran.

Additional embodiments relate to a compound of formula (III), or a pharmaceutically acceptable salt thereof, wherein $R^2$ is pyrrolidine optionally substituted by one or more substituents selected from the group consisting of halogen, $C_1$-$C_3$ alkyl and hydroxy.

Further embodiments relate to a compound of formula (III), or a pharmaceutically acceptable salt thereof, wherein $R^2$ is pyrrolidine optionally substituted by methyl.

More embodiments relate to a compound of formula (III), or a pharmaceutically acceptable salt thereof, wherein $R^4$ is hydrogen.

Some embodiments relate to a compound of formula (III), or a pharmaceutically acceptable salt thereof, wherein $R^4$ is $C_1$-$C_3$ alkyl.

Some embodiments relate to a compound of formula (III), or a pharmaceutically acceptable salt thereof, wherein $R^4$ is methyl.

Additional embodiments relate to a compound of formula (III), or a pharmaceutically acceptable salt thereof, wherein $R^5$ and $R^{5a}$ are each independently absent, halogen, cyano, trifluoromethyl, $C_1$-$C_3$ alkyl, $C_1$-$C_3$ alkoxy or $C_3$-$C_5$ cycloalkyl, wherein the $C_1$-$C_3$ alkyl is optionally substituted by hydroxy, difluoromethyl, trifluoromethyl or $C_3$-$C_5$ cycloalkyl.

Additional embodiments relate to a compound of formula (III), or a pharmaceutically acceptable salt thereof, wherein $R^{13}$ is independently halogen, hydroxy, $C_1$-$C_6$ alkoxy, —N($R^9$)($R^{10}$), —CON($R^9$)($R^{10}$) or 3-7 membered heterocycloalkyl, wherein the 3-7 membered heterocycloalkyl in $R^{13}$ is optionally substituted by one or more $R^{14}$ groups.

Further embodiments relate to a compound of formula (III), or a pharmaceutically acceptable salt thereof, wherein $R^5$ and $R^{5a}$ are each independently absent, halogen, cyano, trifluoromethyl, $C_1$-$C_3$ alkyl, $C_1$-$C_3$ alkoxy or $C_3$-$C_5$ cycloalkyl, wherein the $C_1$-$C_3$ alkyl is optionally substituted by hydroxy, difluoromethyl, trifluoromethyl or $C_3$-$C_5$ cycloalkyl; and, wherein $R^{13}$ is independently halogen, hydroxy, $C_1$-$C_6$ alkoxy, —N($R^9$)($R^{10}$), —CON($R^9$)($R^{10}$) or 3-7 membered heterocycloalkyl, wherein the 3-7 membered heterocycloalkyl in $R^{13}$ is optionally substituted by one or more $R^{14}$ groups.

Some embodiments relate to a compound or a pharmaceutically acceptable salt of any of the embodiments of the compounds of formula (III), having formula (IIIa):

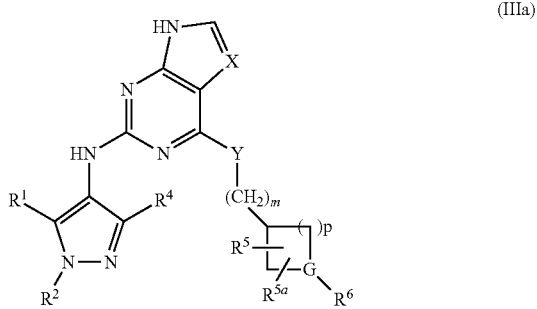

(IIIa)

wherein
G is CH or N; and
p is 1 or 2.

More embodiments relate to a compound of formula (IIIa), or a pharmaceutically acceptable salt thereof, wherein G is CH.

More embodiments relate to a compound of formula (IIIa), or a pharmaceutically acceptable salt thereof, wherein G is N.

Some embodiments relate to a compound of formula (IIIa), or a pharmaceutically acceptable salt thereof, wherein p is 1.

Some embodiments relate to a compound of formula (IIIa), or a pharmaceutically acceptable salt thereof, wherein p is 2.

Additional embodiments relate to a compound of formula (IIIa), or a pharmaceutically acceptable salt thereof, wherein G is CH and p is 1.

Further embodiments relate to a compound of formula (IIIa), or a pharmaceutically acceptable salt thereof, wherein G is N and p is 2.

Additional embodiments relate to a compound of formula (IIIa), or a pharmaceutically acceptable salt thereof, wherein $R^5$ and $R^{5a}$ are each independently absent or methyl.

Further embodiments relate to a compound of formula (IIIa), or a pharmaceutically acceptable salt thereof, wherein $R^5$ and $R^{5a}$ are each independently absent, halogen, trifluoromethyl, $C_1$-$C_3$ alkoxy or 4-6 membered heteroaryl.

Further embodiments relate to a compound of formula (IIIa), or a pharmaceutically acceptable salt thereof, wherein $R^5$ and $R^{5a}$ are each independently absent, difluoromethyl, trifluoromethyl, $C_1$-$C_3$ alkyl or $C_3$-$C_5$ cycloalkyl.

Further embodiments relate to a compound of formula (IIIa), or a pharmaceutically acceptable salt thereof, wherein $R^5$ and $R^{5a}$ are each independently absent, hydroxy, difluoromethyl, trifluoromethyl, $C_1$-$C_3$ alkyl, $C_1$-$C_3$ alkoxy or $C_3$-$C_5$ cycloalkyl.

More embodiments relate to a compound of formula (IIIa), or a pharmaceutically acceptable salt thereof, wherein $R^5$ and $R^{5a}$ are each independently absent, trifluoromethyl, $C_1$-$C_3$ alkyl, —($CH_2$)— trifluoromethyl or cyclopropyl.

More embodiments relate to a compound of formula (IIIa), or a pharmaceutically acceptable salt thereof, wherein $R^5$ and $R^{5a}$ are each independently absent, trifluoromethyl, $C_1$-$C_3$ alkyl, cyclopropyl, —($CH_2$)— trifluoromethyl or —($CH_2$)— $OCH_3$.

Some embodiments relate to a compound of formula (IIIa), or a pharmaceutically acceptable salt thereof, wherein $R^5$ is —$CH_2OH$, —$CH(CH_3)OH$ or —$C(CH_3)_2OH$.

Some embodiments relate to a compound or a pharmaceutically acceptable salt of any of the embodiments of the compounds of formula (III), wherein m is 1, having formula (IIIb):

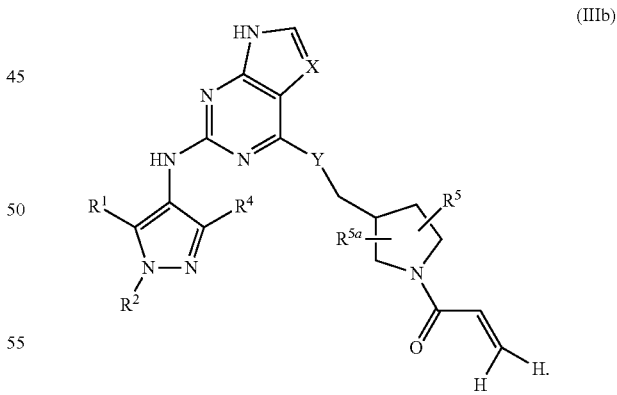

(IIIb)

More embodiments relate to a compound of formula (IIIb), or a pharmaceutically acceptable salt thereof, wherein $R^5$ and $R^{5a}$ are each independently absent, difluoromethyl, trifluoromethyl, $C_1$-$C_3$ alkyl, —($CH_2$)— trifluoromethyl or cyclopropyl.

Further embodiments relate to a compound of formula (IIIb), or a pharmaceutically acceptable salt thereof, wherein $R^5$ and $R^{5a}$ are each independently absent, halogen, trifluoromethyl, $C_1$-$C_3$ alkoxy or 4-6 membered heteroaryl.

More embodiments relate to a compound of formula (IIIb), or a pharmaceutically acceptable salt thereof, wherein $R^5$ and $R^{5a}$ are each independently absent, hydroxy, difluoromethyl, trifluoromethyl, $C_1$-$C_3$ alkyl, $C_1$-$C_3$ alkoxy, cyclopropyl, —($CH_2$)—$OCH_3$ or —($CH_2$)-trifluoromethyl.

Some embodiments relate to a compound of formula (IIIb), or a pharmaceutically acceptable salt thereof, wherein $R^5$ is —$CH_2OH$, —$CH(CH_3)OH$ or —$C(CH_3)_2OH$.

More embodiments relate to a compound of formula (IIIb), or a pharmaceutically acceptable salt thereof, wherein $R^5$ and $R^{5a}$ are absent.

Further embodiments relate to a compound of formula (IIIb), or a pharmaceutically acceptable salt thereof, wherein $R^{5a}$ is absent.

Some embodiments relate to a compound or a pharmaceutically acceptable salt of any of the embodiments of the compounds of formula (III), wherein m is 0, having formula (IIIc):

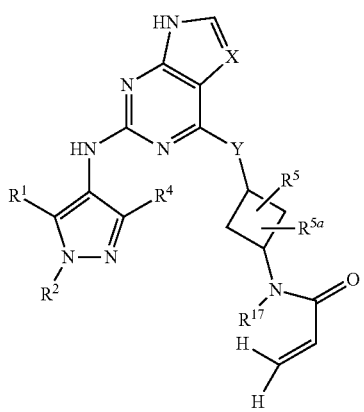

(IIIc)

wherein $R^5$ and $R^{5a}$ are each independently absent, trifluoromethyl, $C_1$-$C_3$ alkyl, or $C_3$-$C_5$ cycloalkyl.

Some embodiments relate to a compound of formula (IIIc), or a pharmaceutically acceptable salt thereof, wherein $R^5$ is methyl.

More embodiments relate to a compound of formula (IIIc), or a pharmaceutically acceptable salt thereof, wherein $R^{5a}$ is methyl.

More embodiments relate to a compound of formula (IIIc), or a pharmaceutically acceptable salt thereof, wherein $R^5$ and $R^{5a}$ are absent.

Further embodiments relate to a compound of formula (IIIc), or a pharmaceutically acceptable salt thereof, wherein $R^{5a}$ is absent.

Further embodiments relate to a compound of formula (IIIc), or a pharmaceutically acceptable salt thereof, wherein $R^{17}$ is hydrogen.

Additional embodiments relate to a compound of formula (IIIc), or a pharmaceutically acceptable salt thereof, wherein $R^{17}$ is methyl.

Some embodiments relate to a compound or a pharmaceutically acceptable salt of any of the embodiments of the compounds of formula (III), wherein m is 0, having formula (IIId):

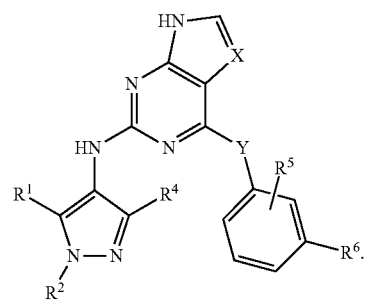

(IIId)

Additional embodiments relate to a compound of formula (IIId), or a pharmaceutically acceptable salt thereof, wherein $R^5$ is fluorine.

Further embodiments relate to a compound of formula (IIId), or a pharmaceutically acceptable salt thereof, wherein $R^6$ is

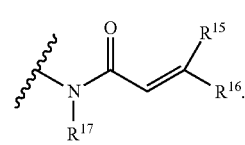

Some embodiments relate to a compound or a pharmaceutically acceptable salt of any of the embodiments of the compounds of formula (III), wherein m is 0, having formula (IIIe):

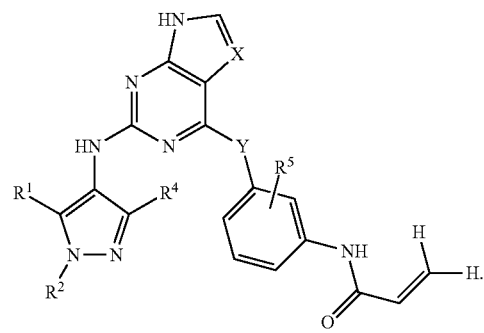

(IIIe)

More embodiments relate to a compound of formula (IIIe), or a pharmaceutically acceptable salt thereof, wherein $R^5$ is fluorine.

Some embodiments relate to a compound or a pharmaceutically acceptable salt of any of the embodiments of the compounds of formula (III), having formula (IIIf):

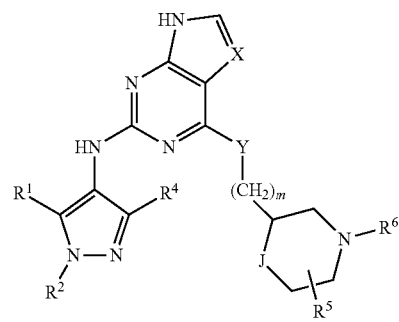

(IIIf)

wherein

J is $CH_2$, $NR^{18}$ or O, provided that when J is $NR^{18}$ or O, m is not 0; and $R^{18}$ is hydrogen or $C_1$-$C_3$ alkyl.

More embodiments relate to a compound of formula (IIIf), or a pharmaceutically acceptable salt thereof, wherein $R^6$ is

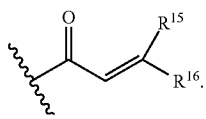

Some embodiments relate to a compound or a pharmaceutically acceptable salt of any of the embodiments of the compounds of formula (III), wherein Y is absent and m is 0, having formula (IIIg):

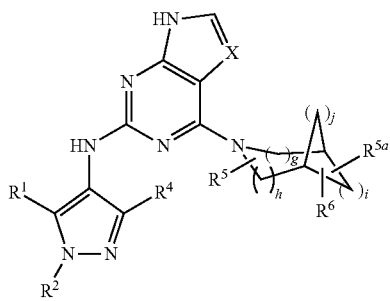

(IIIg)

wherein g is 0, 1 or 2;

h is 0, 1 or 2;

i is 1 or 2; and j is 0, 1 or 2.

More embodiments relate to a compound of formula (IIIg), or a pharmaceutically acceptable salt thereof, wherein $R^5$ and $R^{5a}$ are each independently absent, fluorine, hydroxy, $C_1$-$C_3$ alkyl or $C_1$-$C_3$ alkoxy, wherein the $C_1$-$C_3$ alkyl is optionally substituted by hydroxy or $C_1$-$C_3$ alkoxy.

Some embodiments relate to a compound of formula (IIIg), or a pharmaceutically acceptable salt thereof, wherein $R^6$ is

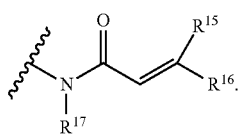

Further embodiments relate to a compound or a pharmaceutically acceptable salt of any of the embodiments of the compounds of formula (III), wherein Y is absent and m is 0, having formula (IIIh):

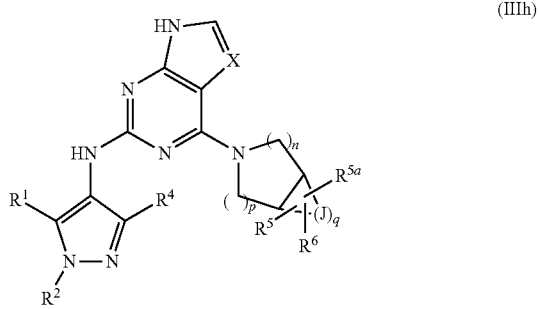

(IIIh)

wherein each J is independently CH or N, provided that at least one J is CH, and further provided that no more than one J is N;

n is 0, 1 or 2;

p is 0, 1 or 2; and q is 1, 2, 3 or 4.

Some embodiments relate to a compound of formula (IIIh), or a pharmaceutically acceptable salt thereof, wherein $R^5$ and $R^{5a}$ are each independently absent, fluorine, hydroxy, $C_1$-$C_3$ alkyl or $C_1$-$C_3$ alkoxy, wherein the $C_1$-$C_3$ alkyl is optionally substituted by hydroxy or $C_1$-$C_3$ alkoxy.

Further embodiments relate to a compound or a pharmaceutically acceptable salt of any of the embodiments of the compounds of formula (III), wherein Y is absent and m is 0, having formula (IIIi):

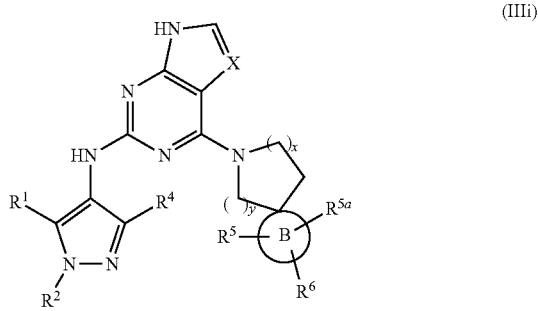

(IIIi)

wherein ring B is 3-6 membered monocyclic cycloalkyl or 3-6 membered monocyclic heterocycloalkyl; and x is 0, 1, 2 or 3; and y is 0 or 1.

Some embodiments relate to a compound of formula (IIIi), or a pharmaceutically acceptable salt thereof, wherein $R^5$ and $R^{5a}$ are each independently absent, fluorine, hydroxy, $C_1$-$C_3$ alkyl or $C_1$-$C_3$ alkoxy, wherein the $C_1$-$C_3$ alkyl is optionally substituted by hydroxy or $C_1$-$C_3$ alkoxy.

Some embodiments described herein relate to a compound of formula (IV):

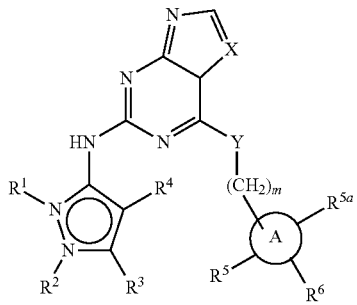

wherein:

X is N or $CR^7$;

Y is absent, O, S or $NR^8$;

$R^1$ is absent, hydrogen or $C_1$-$C_3$ alkyl;

$R^2$ is absent, hydrogen, $C_1$-$C_6$ alkyl, $C_2$-$C_6$ alkynyl, $C_1$-$C_6$ alkoxy, $C_3$-$C_7$ cycloalkyl or 3-7 membered heterocycloalkyl, wherein the $C_1$-$C_6$ alkyl and $C_1$-$C_6$ alkoxy in $R^2$ are optionally substituted by one or more $R^{13}$ groups, and further wherein the $C_3$-$C_7$ cycloalkyl and the 3-7 membered heterocycloalkyl in $R^2$ are optionally substituted by one or more $R^{14}$ groups;

provided that at least one of $R^1$ or $R^2$ is absent;

$R^3$ is absent, hydrogen, $C_1$-$C_6$ alkyl, $C_1$-$C_6$ alkoxy or $C_3$-$C_7$ cycloalkyl, wherein the $C_1$-$C_6$ alkyl and the $C_1$-$C_6$ alkoxy in $R^3$ are optionally substituted by one or more $R^{13}$ groups;

$R^4$ is hydrogen, cyano or $C_1$-$C_3$ alkyl;

ring A is absent, $C_3$-$C_{10}$ cycloalkyl, 3-10 membered heterocycloalkyl, $C_5$-$C_{10}$ aryl or 5-12 membered heteroaryl;

$R^5$ and $R^{5a}$ are each independently absent, halogen, cyano, hydroxy, difluoromethyl, trifluoromethyl, $C_1$-$C_3$ alkyl, $C_1$-$C_3$ alkoxy, $C_3$-$C_5$ cycloalkyl or 4-6 membered heteroaryl, wherein the $C_1$-$C_3$ alkyl is optionally substituted by hydroxy, difluoromethyl, trifluoromethyl, $C_1$-$C_3$ alkoxy or $C_3$-$C_5$ cycloalkyl;

$R^6$ is

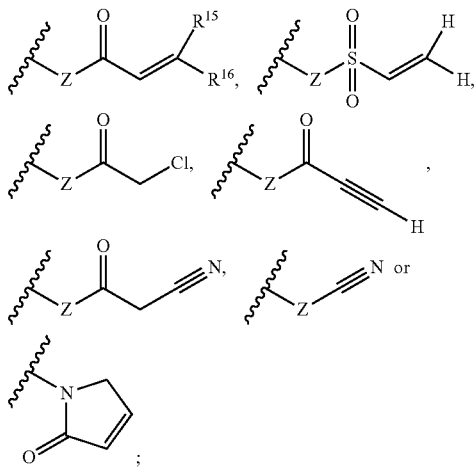

Z is absent when the attachment point of $R^6$ on ring A is a nitrogen atom, and Z is —$NR^{17}$— when ring A is absent or when the attachment point of $R^6$ on ring A is a carbon atom;

$R^7$ is hydrogen, halogen, cyano, $C_1$-$C_6$ alkyl, $C_2$-$C_6$ alkenyl, $C_2$-$C_6$ alkynyl or 4-6 membered heteroaryl, wherein the $C_1$-$C_6$ alkyl may be optionally substituted by hydroxy or $C_1$-$C_3$ alkoxy, and further wherein the 4-6 membered heteroaryl may be optionally substituted by $C_1$-$C_3$ alkyl;

$R^8$ is hydrogen or $C_1$-$C_3$ alkyl;

$R^9$ and $R^{10}$ are each independently hydrogen or $C_1$-$C_6$ alkyl; or $R^9$ and $R^{10}$ together with the nitrogen to which they are attached, may combine to form a 4-7 membered ring, when $R^9$ and $R^{10}$ are each $C_1$-$C_3$ alkyl, wherein the 4-7 membered ring is optionally substituted by one or more $R^{14}$ groups;

$R^{11}$ and $R^{12}$ are each independently hydrogen or $C_1$-$C_3$ alkyl;

each $R^{13}$ is independently halogen, cyano, hydroxy, $C_1$-$C_6$ alkoxy, —$N(R^9)(R^{10})$, —$CON(R^9)(R^{10})$ or 3-7 membered heterocycloalkyl, wherein the 3-7 membered heterocycloalkyl in $R^{13}$ is optionally substituted by one or more $R^{14}$ groups;

each $R^{14}$ is independently halogen, $C_1$-$C_3$ alkyl, hydroxy, $C_1$-$C_6$ alkoxy, —$NH_2$, —$NHCH_3$, or $N(CH_3)_2$;

$R^{15}$ and $R^{16}$ are each independently hydrogen or $C_1$-$C_6$ alkyl, wherein the $C_1$-$C_6$ alkyl of one of $R^{15}$ and $R^{16}$ is optionally substituted by —$N(R^9)(R^{10})$;

$R^{17}$ is hydrogen or $C_1$-$C_3$ alkyl; and m is 0, 1 or 2, provided that when ring A is absent, m is 2; or a pharmaceutically acceptable salt thereof.

Some embodiments relate to a compound of formula (IV), or a pharmaceutically acceptable salt thereof, wherein X is $CR^7$.

More embodiments relate to a compound of formula (IV), or a pharmaceutically acceptable salt thereof, wherein Y is O.

More embodiments relate to a compound of formula (IV), or a pharmaceutically acceptable salt thereof, wherein Y is $NR^8$.

Further embodiments relate to a compound of formula (IV), or a pharmaceutically acceptable salt thereof, wherein X is $CR^7$ and Y is O.

Some embodiments relate to a compound of formula (IV), or a pharmaceutically acceptable salt thereof, wherein $R^7$ is hydrogen, halogen, cyano or 4-6 membered heteroaryl.

Further embodiments relate to a compound of formula (IV), or a pharmaceutically acceptable salt thereof, wherein $R^7$ is hydrogen, halogen or cyano.

More embodiments relate to a compound of formula (IV), or a pharmaceutically acceptable salt thereof, wherein $R^7$ is hydrogen.

Additional embodiments relate to a compound of formula (IV), or a pharmaceutically acceptable salt thereof, wherein $R^7$ is halogen, and further wherein the halogen is fluorine.

Some embodiments relate to a compound of formula (IV), or a pharmaceutically acceptable salt thereof, wherein $R^7$ is halogen, and further wherein the halogen is chlorine.

More embodiments relate to a compound of formula (IV), or a pharmaceutically acceptable salt thereof, wherein $R^7$ is cyano.

Further embodiments relate to a compound of formula (IV), or a pharmaceutically acceptable salt thereof, wherein $R^7$ is 4-6 membered heteroaryl optionally substituted by $C_1$-$C_3$ alkyl.

Some embodiments relate to a compound of formula (IV), or a pharmaceutically acceptable salt thereof, wherein m is 0.

Further embodiments relate to a compound of formula (IV), or a pharmaceutically acceptable salt thereof, wherein m is 1.

Additional embodiments relate to a compound of formula (IV), or a pharmaceutically acceptable salt thereof, wherein $R^5$ and $R^{5a}$ are each independently absent, halogen, cyano, trifluoromethyl, $C_1$-$C_3$ alkyl, $C_1$-$C_3$ alkoxy or $C_3$-$C_5$ cycloalkyl, wherein the $C_1$-$C_3$ alkyl is optionally substituted by hydroxy, difluoromethyl, trifluoromethyl or $C_3$-$C_5$ cycloalkyl.

Additional embodiments relate to a compound of formula (IV), or a pharmaceutically acceptable salt thereof, wherein $R^{13}$ is independently halogen, hydroxy, $C_1$-$C_6$ alkoxy, —N($R^9$)($R^{10}$), —CON($R^9$)($R^{10}$) or 3-7 membered heterocycloalkyl, wherein the 3-7 membered heterocycloalkyl in $R^{13}$ is optionally substituted by one or more $R^{14}$ groups.

Further embodiments relate to a compound of formula (IV), or a pharmaceutically acceptable salt thereof, wherein $R^5$ and $R^{5a}$ are each independently absent, halogen, cyano, trifluoromethyl, $C_1$-$C_3$ alkyl, $C_1$-$C_3$ alkoxy or $C_3$-$C_5$ cycloalkyl, wherein the $C_1$-$C_3$ alkyl is optionally substituted by hydroxy, difluoromethyl, trifluoromethyl or $C_3$-$C_5$ cycloalkyl; and, wherein $R^{13}$ is independently halogen, hydroxy, $C_1$-$C_6$ alkoxy, —N($R^9$)($R^{19}$), —CON($R^9$)($R^{10}$) or 3-7 membered heterocycloalkyl, wherein the 3-7 membered heterocycloalkyl in $R^{13}$ is optionally substituted by one or more $R^{14}$ groups.

Some embodiments relate to a compound or a pharmaceutically acceptable salt of any of the embodiments of the compounds of formula (IV), having formula (IVa):

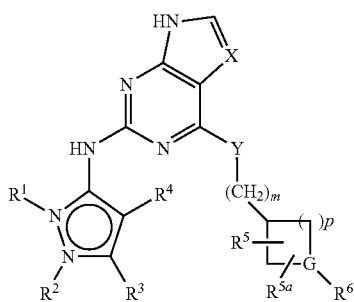

(IVa)

wherein
G is CH or N; and
p is 1 or 2.

Some embodiments relate to a compound of formula (IVa), or a pharmaceutically acceptable salt thereof, wherein G is CH.

More embodiments relate to a compound of formula (IVa), or a pharmaceutically acceptable salt thereof, wherein G is N.

More embodiments relate to a compound of formula (IVa), or a pharmaceutically acceptable salt thereof, wherein p is 1.

Additional embodiments relate to a compound of formula (IVa), or a pharmaceutically acceptable salt thereof, wherein p is 2.

Further embodiments relate to a compound of formula (IVa), or a pharmaceutically acceptable salt thereof, wherein G is CH and p is 1.

Further embodiments relate to a compound of formula (IVa), wherein G is N and p is 2.

Some embodiments relate to a compound of formula (IVa), wherein $R^5$ and $R^{5a}$ are each independently absent or methyl.

Further embodiments relate to a compound of formula (IVa), or a pharmaceutically acceptable salt thereof, wherein $R^5$ and $R^{5a}$ are each independently absent, halogen, trifluoromethyl, $C_1$-$C_3$ alkoxy or 4-6 membered heteroaryl.

Some embodiments relate to a compound of formula (IVa), wherein $R^5$ and $R^{5a}$ are each independently absent, difluoromethyl, trifluoromethyl, $C_1$-$C_3$ alkyl or $C_3$-$C_5$ cycloalkyl.

Some embodiments relate to a compound of formula (IVa), wherein $R^5$ and $R^{5a}$ are each independently absent, hydroxy, difluoromethyl, trifluoromethyl, $C_1$-$C_3$ alkyl, $C_1$-$C_3$ alkoxy or $C_3$-$C_5$ cycloalkyl.

Additional embodiments relate to a compound of formula (IVa), wherein $R^5$ and $R^{5a}$ are each independently absent, trifluoromethyl, $C_1$-$C_3$ alkyl, —(CH$_2$)— trifluoromethyl or cyclopropyl.

Additional embodiments relate to a compound of formula (IVa), wherein $R^5$ and $R^{5a}$ are each independently absent, trifluoromethyl, $C_1$-$C_3$ alkyl, cyclopropyl, —(CH$_2$)— trifluoromethyl or —(CH$_2$)—OCH$_3$.

Further embodiments relate to a compound of formula (IVa), wherein $R^5$ is —CH$_2$OH, —CH(CH$_3$)OH or —C(CH$_3$)$_2$ OH.

Some embodiments relate to a compound or a pharmaceutically acceptable salt of any of the embodiments of the compounds of formula (IV), wherein m is 1, having formula (IVb):

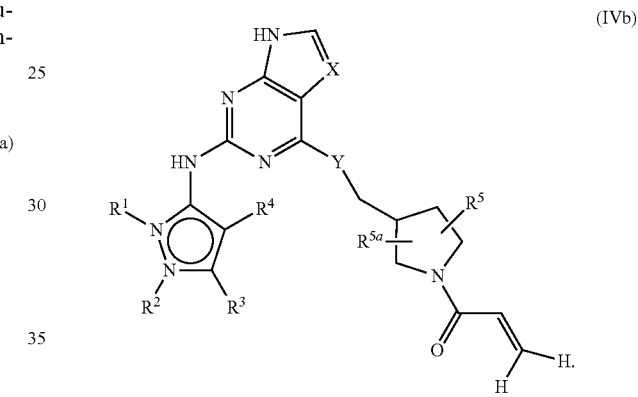

(IVb)

More embodiments relate to a compound of formula (IVb), or a pharmaceutically acceptable salt thereof, wherein $R^5$ and $R^{5a}$ are each independently absent, $C_1$-$C_3$ alkyl, difluoromethyl, trifluoromethyl, —(CH$_2$)— trifluoromethyl or cyclopropyl.

Further embodiments relate to a compound of formula (Ia), or a pharmaceutically acceptable salt thereof, wherein $R^5$ and $R^{5a}$ are each independently absent, halogen, trifluoromethyl, $C_1$-$C_3$ alkoxy or 4-6 membered heteroaryl.

Some embodiments relate to a compound of formula (IVb), or a pharmaceutically acceptable salt thereof, wherein $R^5$ and $R^{5a}$ are each independently absent, hydroxy, difluoromethyl, trifluoromethyl, $C_1$-$C_3$ alkyl, $C_1$-$C_3$ alkoxy, cyclopropyl, —(CH$_2$)—OCH$_3$ or —(CH$_2$)-trifluoromethyl.

Additional embodiments relate to a compound of formula (IVb), or a pharmaceutically acceptable salt thereof, wherein $R^5$ is —CH$_2$OH, —CH(CH$_3$)OH or —C(CH$_3$)$_2$OH.

Additional embodiments relate to a compound of formula (IVb), or a pharmaceutically acceptable salt thereof, wherein $R^5$ and $R^{5a}$ are absent.

Additional embodiments relate to a compound of formula (IVb), or a pharmaceutically acceptable salt thereof, wherein $R^{5a}$ is absent.

Some embodiments relate to a compound or a pharmaceutically acceptable salt of any of the embodiments of the compounds of formula (IV), wherein m is 0, having formula (IVc):

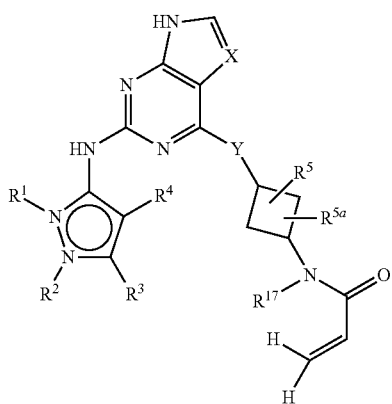
(IVc)

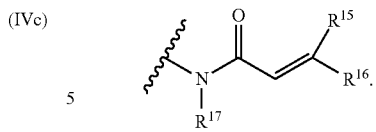
(IVc)

Some embodiments relate to a compound or a pharmaceutically acceptable salt of any of the embodiments of the compounds of formula (IV), wherein m is 0, having formula (IVe):

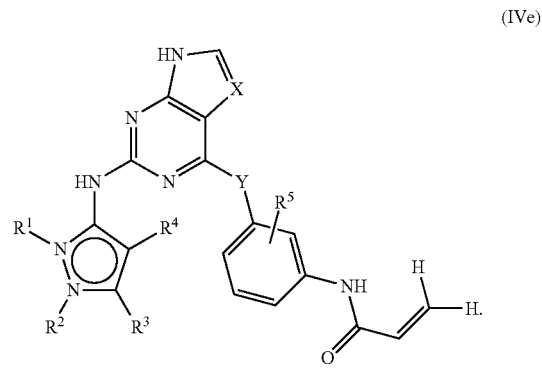
(IVe)

wherein $R^5$ and $R^{5a}$ are each independently absent, trifluoromethyl, $C_1$-$C_3$ alkyl, or $C_3$-$C_5$ cycloalkyl.

Some embodiments relate to a compound of formula (IVc), or a pharmaceutically acceptable salt thereof, wherein $R^5$ is methyl.

More embodiments relate to a compound of formula (IVc), or a pharmaceutically acceptable salt thereof, wherein $R^{5a}$ is methyl.

Additional embodiments relate to a compound of formula (IVc), or a pharmaceutically acceptable salt thereof, wherein $R^5$ and $R^{5a}$ are absent.

Additional embodiments relate to a compound of formula (IVc), or a pharmaceutically acceptable salt thereof, wherein $R^{5a}$ is absent.

Some embodiments relate to a compound of formula (IVc), or a pharmaceutically acceptable salt thereof, wherein $R^{17}$ is hydrogen.

Further embodiments relate to a compound of formula (IVc), or a pharmaceutically acceptable salt thereof, wherein $R^{17}$ is methyl.

Some embodiments relate to a compound or a pharmaceutically acceptable salt of any of the embodiments of the compounds of formula (IV), wherein m is 0, having formula (IVd):

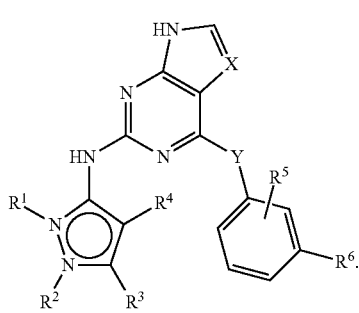
(IVd)

Additional embodiments relate to a compound of formula (IVd), or a pharmaceutically acceptable salt thereof, wherein $R^5$ is fluorine.

Further embodiments relate to a compound of formula (IVd), or a pharmaceutically acceptable salt thereof, wherein $R^6$ is Some embodiments relate to a compound of formula (IVe), or a pharmaceutically acceptable salt thereof, wherein $R^5$ is fluorine.

Some embodiments relate to a compound or a pharmaceutically acceptable salt of any of the embodiments of the compounds of formula (IV), having formula (IVf):

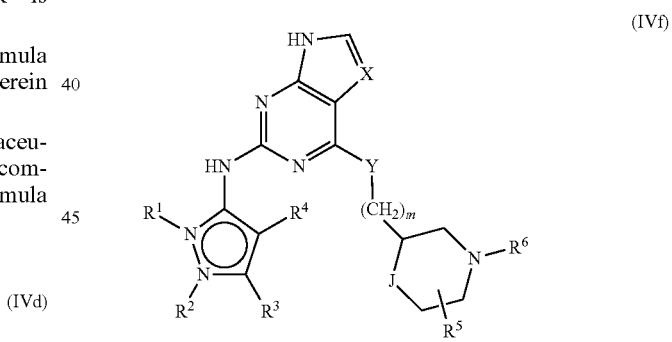
(IVf)

wherein

J is $CH_2$, $NR^{18}$ or O, provided that when J is $NR^{18}$ or O, m is not 0; and $R^{18}$ is hydrogen or $C_1$-$C_3$ alkyl.

Further embodiments relate to a compound of formula (IVf), or a pharmaceutically acceptable salt thereof, wherein $R^6$ is

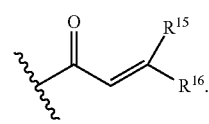

Further embodiments relate to a compound or a pharmaceutically acceptable salt of any of the embodiments of the compounds of formula (IV), wherein Y is absent and m is 0, having formula (IVg):

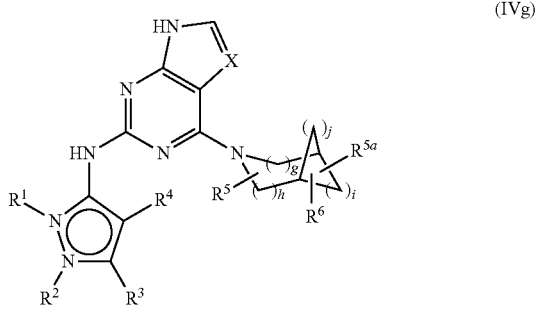

(IVg)

wherein
g is 0, 1 or 2;
h is 0, 1 or 2;
i is 1 or 2; and
j is 0, 1 or 2.

Some embodiments relate to a compound of formula (IVg), or a pharmaceutically acceptable salt thereof, wherein $R^5$ and $R^{5a}$ are each independently absent, fluorine, hydroxy, $C_1$-$C_3$ alkyl or $C_1$-$C_3$ alkoxy, wherein the $C_1$-$C_3$ alkyl is optionally substituted by hydroxy or $C_1$-$C_3$ alkoxy.

Some embodiments relate to a compound of formula (IVg), or a pharmaceutically acceptable salt thereof, wherein, wherein $R^6$ is

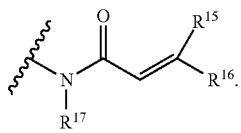

Further embodiments relate to a compound or a pharmaceutically acceptable salt of any of the embodiments of the compounds of formula (IV), wherein Y is absent and m is 0, having formula (IVh):

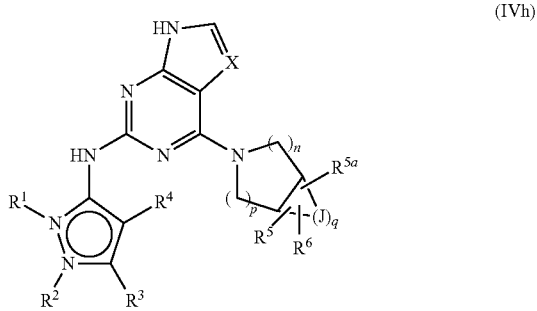

(IVh)

wherein
each J is independently CH or N, provided that at least one J is CH, and further provided that no more than one J is N;
n is 0, 1 or 2;
p is 0, 1 or 2; and
q is 1, 2, 3 or 4.

Some embodiments relate to a compound of formula (IVh), or a pharmaceutically acceptable salt thereof, wherein, wherein $R^5$ and $R^{5a}$ are each independently absent, fluorine, hydroxy, $C_1$-$C_3$ alkyl or $C_1$-$C_3$ alkoxy, wherein the $C_1$-$C_3$ alkyl is optionally substituted by hydroxy or $C_1$-$C_3$ alkoxy.

Further embodiments relate to a compound or a pharmaceutically acceptable salt of any of the embodiments of the compounds of formula (IV), wherein Y is absent and m is 0, having formula (IVi):

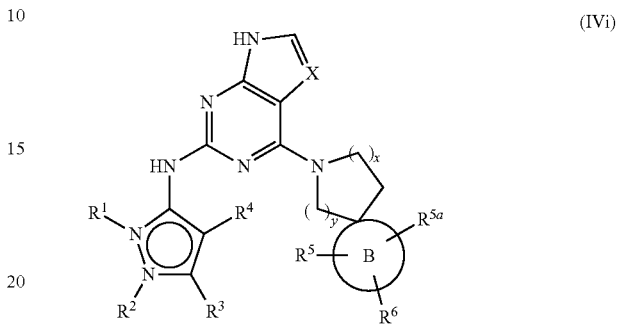

(IVi)

wherein
ring B is 3-6 membered monocyclic cycloalkyl or 3-6 membered monocyclic heterocycloalkyl; and
x is 0, 1, 2 or 3; and
y is 0 or 1.

Some embodiments relate to a compound of formula (IVi), or a pharmaceutically acceptable salt thereof, wherein, wherein $R^5$ and $R^{5a}$ are each independently absent, fluorine, hydroxy, $C_1$-$C_3$ alkyl or $C_1$-$C_3$ alkoxy, wherein the $C_1$-$C_3$ alkyl is optionally substituted by hydroxy or $C_1$-$C_3$ alkoxy.

In some embodiments, the compound is selected from:
N-[3-({5-fluoro-2-[(1-methyl-1H-pyrazol-3-yl)amino]-7H-pyrrolo[2,3-d]pyrimidin-4-yl}oxy)phenyl]prop-2-enamide;
N-(3-{[2-({1-[2-(dimethylamino)ethyl]-1H-pyrazol-4-yl}amino)-7H-pyrrolo[2,3-d]pyrimidin-4-yl]oxy}phenyl)prop-2-enamide;
1-{(3S,4S)-3-methyl-4-[({2-[(1-methyl-1H-pyrazol-4-yl)amino]-7H-pyrrolo[2,3-d]pyrimidin-4-yl}oxy)methyl]pyrrolidin-1-yl}prop-2-en-1-one;
1-{(3R,4R)-3-methyl-4-[({2-[(1-methyl-1H-pyrazol-4-yl)amino]-7H-pyrrolo[2,3-d]pyrimidin-4-yl}oxy)methyl]pyrrolidin-1-yl}prop-2-en-1-one;
N-[cis-3-({5-cyano-2-[(1-methyl-1H-pyrazol-4-yl)amino]-7H-pyrrolo[2,3-d]pyrimidin-4-yl}oxy)cyclobutyl]prop-2-enamide;
N-[trans-3-({2-[(1-methyl-1H-pyrazol-4-yl)amino]-7H-pyrrolo[2,3-d]pyrimidin-4-yl}amino)cyclobutyl]prop-2-enamide;
N-{3-[(2-{[1-(1-methylpyrrolidin-3-yl)-1H-pyrazol-4-yl]amino}-9H-purin-6-yl)oxy]phenyl}prop-2-enamide;
N-[3-({2-[(1-methyl-1H-pyrazol-4-yl)amino]-5-(pyridin-3-yl)-7H-pyrrolo[2,3-d]pyrimidin-4-yl}oxy)phenyl]prop-2-enamide;
1-{(3R,4R)-3-[({5-chloro-2-[(1-methyl-1H-pyrazol-4-yl)amino]-7H-pyrrolo[2,3-d]pyrimidin-4-yl}oxy)methyl]-4-methoxypyrrolidin-1-yl}prop-2-en-1-one;
1-{(3R,4R)-3-[({5-chloro-2-[(1-methyl-1H-pyrazol-4-yl)amino]-7H-pyrrolo[2,3-d]pyrimidin-4-yl}oxy)methyl]-4-[(1S)-1-hydroxyethyl]pyrrolidin-1-yl}prop-2-en-1-one;
N-[(3R)-1-{5-chloro-2-[(1-methyl-1H-pyrazol-4-yl)amino]-7H-pyrrolo[2,3-d]pyrimidin-4-yl}piperidin-3-yl]prop-2-enamide;

N-[trans-3-({2-[(1-methyl-1H-pyrazol-4-yl)amino]-5-(pyridin-2-yl)-7H-pyrrolo[2,3-d]pyrimidin-4-yl}oxy)cyclobutyl]prop-2-enamide;

N-methyl-N-[trans-3-({2-[(1-methyl-1H-pyrazol-4-yl)amino]-5-(pyridin-3-yl)-7H-pyrrolo[2,3-d]pyrimidin-4-yl}oxy)cyclobutyl]prop-2-enamide;

N-[trans-3-({5-cyano-2-[(1-methyl-1H-pyrazol-4-yl)amino]-7H-pyrrolo[2,3-d]pyrimidin-4-yl}oxy)cyclobutyl]prop-2-enamide;

1-{trans-3-ethyl-4-[({2-[(1-methyl-1H-pyrazol-4-yl)amino]-7H-pyrrolo[2,3-d]pyrimidin-4-yl}oxy)methyl]pyrrolidin-1-yl}prop-2-en-1-one;

1-{3-[({2-[(1-methyl-1H-pyrazol-4-yl)amino]-7H-pyrrolo[2,3-d]pyrimidin-4-yl}oxy)methyl]azetidin-1-yl}prop-2-en-1-one;

1-{(2R)-2-[({2-[(1-methyl-1H-pyrazol-4-yl)amino]-7H-pyrrolo[2,3-d]pyrimidin-4-yl}oxy)methyl]morpholin-4-yl}prop-2-en-1-one;

1-{(2S)-2-[({2-[(1-methyl-1H-pyrazol-4-yl)amino]-7H-pyrrolo[2,3-d]pyrimidin-4-yl}oxy)methyl]morpholin-4-yl}prop-2-en-1-one;

1-[(3S,4S)-3-[({2-[(1-methyl-1H-pyrazol-4-yl)amino]-7H-pyrrolo[2,3-d]pyrimidin-4-yl}oxy)methyl]-4-(trifluoromethyl)pyrrolidin-1-yl]prop-2-en-1-one;

4-{[(3R)-1-acryloylpyrrolidin-3-yl]oxy}-2-[(1-methyl-1H-pyrazol-4-yl)amino]-7H-pyrrolo[2,3-d]pyrimidine-5-carbonitrile;

N-[3-({5-chloro-2-[(1-methyl-1H-pyrazol-3-yl)amino]-7H-pyrrolo[2,3-d]pyrimidin-4-yl}oxy)phenyl]prop-2-enamide;

N-[3-({2-[(1-ethyl-1H-pyrazol-3-yl)amino]-7H-pyrrolo[2,3-d]pyrimidin-4-yl}oxy)phenyl]prop-2-enamide;

1-[(3R,4R)-3-[({2-[(1-methyl-1H-pyrazol-4-yl)amino]-7H-pyrrolo[2,3-d]pyrimidin-4-yl}oxy)methyl]-4-(trifluoromethyl)pyrrolidin-1-yl]prop-2-en-1-one;

N-[3-({2-[(1,5-dimethyl-1H-pyrazol-4-yl)amino]-7H-pyrrolo[2,3-d]pyrimidin-4-yl}oxy)phenyl]prop-2-enamide;

N-{3-[(2-{[1-(2-hydroxy-2-methylpropyl)-1H-pyrazol-4-yl]amino}-7H-pyrrolo[2,3-d]pyrimidin-4-yl)oxy]phenyl}prop-2-enamide;

N-[3-({2-[(1,3-dimethyl-1H-pyrazol-5-yl)amino]-7H-pyrrolo[2,3-d]pyrimidin-4-yl}oxy)phenyl]prop-2-enamide;

N-(3-{[2-(1H-pyrazol-3-ylamino)-7H-pyrrolo[2,3-d]pyrimidin-4-yl]oxy}phenyl)prop-2-enamide;

N-[3-({2-[(1-methyl-1H-pyrazol-3-yl)amino]-7H-pyrrolo[2,3-d]pyrimidin-4-yl}oxy)phenyl]prop-2-enamide;

1-[4-({2-[(1-methyl-1H-pyrazol-3-yl)amino]-7H-pyrrolo[2,3-d]pyrimidin-4-yl}oxy)-2,3-dihydro-1H-indol-1-yl]prop-2-en-1-one;

N-[3-({2-[(1,3-dimethyl-1H-pyrazol-4-yl)amino]-7H-pyrrolo[2,3-d]pyrimidin-4-yl}oxy)phenyl]prop-2-enamide;

N-{3-[(2-{[1-(propan-2-yl)-1H-pyrazol-4-yl]amino}-7H-pyrrolo[2,3-d]pyrimidin-4-yl)oxy]phenyl}prop-2-enamide;

N-{3-[(2-{[1-methyl-3-(trifluoromethyl)-1H-pyrazol-4-yl]amino}-7H-pyrrolo[2,3-d]pyrimidin-4-yl)oxy]phenyl}prop-2-enamide;

N-{3-[(2-{[1-(1-methylpiperidin-4-yl)-1H-pyrazol-4-yl]amino}-7H-pyrrolo[2,3-d]pyrimidin-4-yl)oxy]phenyl}prop-2-enamide;

N-{3-[(2-{[1-(1-methylpyrrolidin-3-yl)-1H-pyrazol-4-yl]amino}-7H-pyrrolo[2,3-d]pyrimidin-4-yl)oxy]phenyl}prop-2-enamide;

N-[3-({2-[(1-methyl-1H-pyrazol-4-yl)amino]-7H-pyrrolo[2,3-d]pyrimidin-4-yl}oxy)phenyl]prop-2-enamide;

N-[3-({5-cyano-2-[(1-methyl-1H-pyrazol-3-yl)amino]-7H-pyrrolo[2,3-d]pyrimidin-4-yl}oxy)phenyl]prop-2-enamide;

4-[(1-acryloyl-2,3-dihydro-1H-indol-4-yl)oxy]-2-[(1-methyl-1H-pyrazol-4-yl)amino]-7H-pyrrolo[2,3-d]pyrimidine-5-carbonitrile;

1-[4-({2-[(1-methyl-1H-pyrazol-4-yl)amino]-7H-pyrrolo[2,3-d]pyrimidin-4-yl}oxy)-2,3-dihydro-1H-indol-1-yl]prop-2-en-1-one;

N-{3-[(2-{[1-(tetrahydrofuran-3-yl)-1H-pyrazol-4-yl]amino}-7H-pyrrolo[2,3-d]pyrimidin-4-yl)oxy]phenyl}prop-2-enamide;

N-[3-({2-[(2-methyl-2H-1,2,3-triazol-4-yl)amino]-7H-pyrrolo[2,3-d]pyrimidin-4-yl}oxy)phenyl}prop-2-enamide;

4-{[trans-1-acryloyl-4-cyclopropylpyrrolidin-3-yl]methoxy}-2-[(1-methyl-1H-pyrazol-4-yl)amino]-7H-pyrrolo[2,3-d]pyrimidine-5-carbonitrile;

4-{[trans-1-acryloyl-4-(2,2,2-trifluoroethyl)pyrrolidin-3-yl]methoxy}-2-[(1-methyl-1H-pyrazol-4-yl)amino]-7H-pyrrolo[2,3-d]pyrimidine-5-carbonitrile;

N-{3-[({2-[(1-methyl-1H-pyrazol-4-yl)amino]-7H-pyrrolo[2,3-d]pyrimidin-4-yl}oxy)methyl]phenyl}prop-2-enamide;

4-{[1-(ethenylsulfonyl)-2,3-dihydro-1H-indol-4-yl]oxy}-N-(1-methyl-1H-pyrazol-4-yl)-7H-pyrrolo[2,3-d]pyrimidin-2-amine;

N-{3-[(2-{[3-(methoxymethyl)-1-methyl-1H-pyrazol-5-yl]amino}-7H-pyrrolo[2,3-d]pyrimidin-4-yl)oxy]phenyl}prop-2-enamide;

N-[3-({2-[(3-cyclopropyl-1-methyl-1H-pyrazol-5-yl)amino]-7H-pyrrolo[2,3-d]pyrimidin-4-yl}oxy)phenyl]prop-2-enamide;

N-[3-({2-[(3-ethyl-1-methyl-1H-pyrazol-5-yl)amino]-7H-pyrrolo[2,3-d]pyrimidin-4-yl}oxy)phenyl]prop-2-enamide;

N-[3-({2-[(1-methyl-1H-pyrazol-3-yl)amino]-7H-pyrrolo[2,3-d]pyrimidin-4-yl}oxy)phenyl]prop-2-enamide;

N-[3-fluoro-5-({2-[(1-methyl-1H-pyrazol-3-yl)amino]-7H-pyrrolo[2,3-d]pyrimidin-4-yl}oxy)phenyl]prop-2-enamide;

N-{3-[(2-{[1-(1-methylpiperidin-4-yl)-1H-pyrazol-4-yl]amino}-9H-purin-6-yl)oxy]phenyl}prop-2-enamide;

N-(3-{[2-({1-[2-(dimethylamino)ethyl]-1H-pyrazol-3-yl}amino)-7H-pyrrolo[2,3-d]pyrimidin-4-yl]oxy}phenyl)prop-2-enamide;

N-{3-[(2-{[1-(2-hydroxy-2-methylpropyl)-1H-pyrazol-4-yl]amino}-9H-purin-6-yl)oxy]phenyl}prop-2-enamide;

N-(3-{[2-({1-[2-(dimethylamino)ethyl]-1H-pyrazol-4-yl}amino)-9H-purin-6-yl]oxy}phenyl)prop-2-enamide;

N-[3-({2-[(1-methyl-1H-pyrazol-4-yl)amino]-9H-purin-6-yl}oxy)phenyl]prop-2-enamide;

N-[(cis)-3-({2-[(1-methyl-1H-pyrazol-4-yl)amino]-9H-purin-6-yl}oxy)cyclobutyl]prop-2-enamide;

N-[(trans)3-({2-[(1-methyl-1H-pyrazol-4-yl)amino]-9H-purin-6-yl}oxy)cyclobutyl]prop-2-enamide;

N-[3-({5-cyano-2-[(1-methyl-1H-pyrazol-4-yl)amino]-7H-pyrrolo[2,3-d]pyrimidin-4-yl}oxy)phenyl]prop-2-enamide;

N-(3-{[2-({1-[2-(dimethylamino)-2-oxoethyl]-1H-pyrazol-4-yl}amino)-7H-pyrrolo[2,3-d]pyrimidin-4-yl]oxy}phenyl)prop-2-enamide;

N-[2-fluoro-3-({2-[(1-methyl-1H-pyrazol-3-yl)amino]-7H-pyrrolo[2,3-d]pyrimidin-4-yl}oxy)phenyl]prop-2-enamide;

N-[3-({5-(1-methyl-1H-pyrazol-4-yl)-2-[(1-methyl-1H-pyrazol-4-yl)amino]-7H-pyrrolo[2,3-d]pyrimidin-4-yl}oxy)phenyl]prop-2-enamide;

N-[3-({5-cyano-2-[(1-methyl-1H-pyrazol-4-yl)amino]-7H-pyrrolo[2,3-d]pyrimidin-4-yl}oxy)cyclobutyl]-N-methylprop-2-enamide;

N-[trans-3-({5-chloro-2-[(1,3-dimethyl-1H-pyrazol-4-yl)amino]-7H-pyrrolo[2,3-d]pyrimidin-4-yl}oxy)cyclobutyl]-N-methylprop-2-enamide;

N-[trans-3-({5-chloro-2-[(1-methyl-1H-pyrazol-4-yl)amino]-7H-pyrrolo[2,3-d]pyrimidin-4-yl}oxy)cyclobutyl]prop-2-enamide;

1-{(3R)-3-[({5-chloro-2-[(1-methyl-1H-pyrazol-4-yl)amino]-7H-pyrrolo[2,3-d]pyrimidin-4-yl}oxy)methyl]pyrrolidin-1-yl}prop-2-en-1-one;

1-[(3R)-3-({5-chloro-2-[(1-methyl-1H-pyrazol-4-yl)amino]-7H-pyrrolo[2,3-d]pyrimidin-4-yl}oxy)pyrrolidin-1-yl]prop-2-en-1-one;

1-[(1R,5S,6s)-6-({5-chloro-2-[(1-methyl-1H-pyrazol-4-yl)amino]-7H-pyrrolo[2,3-d]pyrimidin-4-yl}oxy)-3-azabicyclo[3.1.0]hex-3-yl]prop-2-en-1-one;

1-{(3R,4R)-3-[({5-chloro-2-[(2-ethyl-2H-1,2,3-triazol-4-yl)amino]-7H-pyrrolo[2,3-d]pyrimidin-4-yl}oxy)methyl]-4-methoxypyrrolidin-1-yl}prop-2-en-1-one;

1-{(3R,4R)-3-[({2-[(3-ethyl-1-methyl-1H-pyrazol-4-yl)amino]-5-fluoro-7H-pyrrolo[2,3-d]pyrimidin-4-yl}oxy)methyl]-4-methoxypyrrolidin-1-yl}prop-2-en-1-one;

N-[cis-3-({5-chloro-2-[(1-methyl-1H-pyrazol-4-yl)amino]-7H-pyrrolo[2,3-d]pyrimidin-4-yl}oxy)-3-methylcyclobutyl]prop-2-enamide;

1-{(3R,4R)-3-[({5-chloro-2-[(3-methoxy-1-methyl-1H-pyrazol-4-yl)amino]-7H-pyrrolo[2,3-d]pyrimidin-4-yl}oxy)methyl]-4-methoxypyrrolidin-1-yl}prop-2-en-1-one;

1-[(3aR,6aS)-5-{5-chloro-2-[(1-methyl-1H-pyrazol-4-yl)amino]-7H-pyrrolo[2,3-d]pyrimidin-4-yl}hexahydropyrrolo[3,4-c]pyrrol-2(1H)-yl]prop-2-en-1-one;

1-[(3R,4R)-3-({[5-chloro-2-({1-[(3R)-tetrahydrofuran-3-yl]-1H-pyrazol-4-yl}amino)-7H-pyrrolo[2,3-d]pyrimidin-4-yl]oxy}methyl)-4-methoxypyrrolidin-1-yl]prop-2-en-1-one;

1-{(3R,4R)-3-[({5-chloro-2-[(1-methyl-1H-pyrazol-4-yl)amino]-7H-pyrrolo[2,3-d]pyrimidin-4-yl}oxy)methyl]-4-hydroxypyrrolidin-1-yl}prop-2-en-1-one;

1-[(3R,4R)-3-[({5-chloro-2-[(1-methyl-1H-pyrazol-4-yl)amino]-7H-pyrrolo[2,3-d]pyrimidin-4-yl}oxy)methyl]-4-(methoxymethyl)pyrrolidin-1-yl]prop-2-en-1-one;

N-(trans-3-{[5-chloro-2-({1-[3-(dimethylamino)-2-hydroxypropyl]-1H-pyrazol-4-yl}amino)-7H-pyrrolo[2,3-d]pyrimidin-4-yl]oxy}cyclobutyl)-N-methylprop-2-enamide;

1-(2-{5-chloro-2-[(1-methyl-1H-pyrazol-4-yl)amino]-7H-pyrrolo[2,3-d]pyrimidin-4-yl}-6-oxa-2,9-diazaspiro[4.5]dec-9-yl)prop-2-en-1-one;

N-[(1S,3R)-3-({5-chloro-2-[(1-methyl-1H-pyrazol-4-yl)amino]-7H-pyrrolo[2,3-d]pyrimidin-4-yl}oxy)cyclopentyl]prop-2-enamide;

4-{[(3R)-1-acryloylpyrrolidin-3-yl]amino}-2-[(1-methyl-1H-pyrazol-4-yl)amino]-7H-pyrrolo[2,3-d]pyrimidine-5-carbonitrile;

1-[3-({5-chloro-2-[(1-methyl-1H-pyrazol-4-yl)amino]-7H-pyrrolo[2,3-d]pyrimidin-4-yl}amino)azetidin-1-yl]prop-2-en-1-one;

N-[trans-3-({5-chloro-2-[(3-cyano-1-methyl-1H-pyrazol-4-yl)amino]-7H-pyrrolo[2,3-d]pyrimidin-4-yl}oxy)cyclobutyl]-N-methylprop-2-enamide;

N-[trans-3-({2-[(1,3-dimethyl-1H-pyrazol-4-yl)amino]-5-(pyridin-2-yl)-7H-pyrrolo[2,3-d]pyrimidin-4-yl}oxy)cyclobutyl]-N-methylprop-2-enamide;

1-[(3S,4R)-3-({5-chloro-2-[(1-methyl-1H-pyrazol-4-yl)amino]-7H-pyrrolo[2,3-d]pyrimidin-4-yl}amino)-4-(1H-1,2,3-triazol-1-yl)pyrrolidin-1-yl]prop-2-en-1-one;

1-[trans)-3-({5-chloro-2-[(1-methyl-1H-pyrazol-4-yl)amino]-7H-pyrrolo[2,3-d]pyrimidin-4-yl}amino)-4-fluoropyrrolidin-1-yl]prop-2-en-1-one;

1-[(3aS,6aS)-5-{5-chloro-2-[(1-methyl-1H-pyrazol-4-yl)amino]-7H-pyrrolo[2,3-d]pyrimidin-4-yl}-3a-hydroxyhexahydropyrrolo[3,4-c]pyrrol-2(1H)-yl]prop-2-en-1-one;

1-[(3R,4S)-3-({5-chloro-2-[(1-methyl-1H-pyrazol-4-yl)amino]-7H-pyrrolo[2,3-d]pyrimidin-4-yl}amino)-4-(difluoromethyl)pyrrolidin-1-yl]prop-2-en-1-one;

N-methyl-N-[trans-3-({5-(1-methyl-1H-pyrazol-3-yl)-2-[(1-methyl-1H-pyrazol-4-yl)amino]-7H-pyrrolo[2,3-d]pyrimidin-4-yl}oxy)cyclobutyl]prop-2-enamide;

1-[(3R,4S)-3-({5-chloro-2-[(1-methyl-1H-pyrazol-4-yl)amino]-7H-pyrrolo[2,3-d]pyrimidin-4-yl}amino)-4-(trifluoromethyl)pyrrolidin-1-yl]prop-2-en-1-one;

1-[5-{5-chloro-2-[(1-methyl-1H-pyrazol-4-yl)amino]-7H-pyrrolo[2,3-d]pyrimidin-4-yl}-3a-methoxyhexahydropyrrolo[3,4-c]pyrrol-2(1H)-yl]prop-2-en-1-one;

N-methyl-N-[trans-3-({2-[(1-methyl-1H-pyrazol-4-yl)amino]-5-(pyridin-2-yl)-7H-pyrrolo[2,3-d]pyrimidin-4-yl}oxy)cyclobutyl]prop-2-enamide;

1-{(3R,4R)-3-[({5-chloro-2-[(1-methyl-1H-pyrazol-4-yl)amino]-7H-pyrrolo[2,3-d]pyrimidin-4-yl}oxy)methyl]-4-fluoropyrrolidin-1-yl}prop-2-en-1-one;

1-{(3S,4S)-3-[({5-chloro-2-[(1-methyl-1H-pyrazol-4-yl)amino]-7H-pyrrolo[2,3-d]pyrimidin-4-yl}oxy)methyl]-4-fluoropyrrolidin-1-yl}prop-2-en-1-one;

N-(trans-3-{[5-chloro-2-(1H-pyrazol-4-ylamino)-7H-pyrrolo[2,3-d]pyrimidin-4-yl]oxy}cyclobutyl)-N-methylprop-2-enamide;

{4-[(4-{[(3R,4R)-1-acryloyl-4-methoxypyrrolidin-3-yl]methoxy}-5-chloro-7H-pyrrolo[2,3-d]pyrimidin-2-yl)amino]-1H-pyrazol-1-yl}acetonitrile;

N-[(3R)-1-{5-chloro-2-[(1-methyl-1H-pyrazol-4-yl)amino]-7H-pyrrolo[2,3-d]pyrimidin-4-yl}piperidin-3-yl]-N-methylprop-2-enamide;

N-methyl-N-[trans-3-({5-(1-methyl-1H-pyrazol-4-yl)-2-[(1-methyl-1H-pyrazol-4-yl)amino]-7H-pyrrolo[2,3-d]pyrimidin-4-yl}oxy)cyclobutyl]prop-2-enamide;

1-[(3R)-3-({5-chloro-2-[(1-methyl-1H-pyrazol-4-yl)amino]-7H-pyrrolo[2,3-d]pyrimidin-4-yl}amino)pyrrolidin-1-yl]prop-2-en-1-one;

1-[(3S)-3-({5-chloro-2-[(1-methyl-1H-pyrazol-4-yl)amino]-7H-pyrrolo[2,3-d]pyrimidin-4-yl}amino)pyrrolidin-1-yl]prop-2-en-1-one;

N-[trans-3-({5-chloro-2-[(1,3-dimethyl-1H-pyrazol-4-yl)amino]-7H-pyrrolo[2,3-d]pyrimidin-4-yl}amino)cyclobutyl]-N-methylprop-2-enamide;

1-[(3aR,6aS)-5-{5-chloro-2-[(3-methoxy-1-methyl-1H-pyrazol-4-yl)amino]-7H-pyrrolo[2,3-d]pyrimidin-4-yl}hexahydropyrrolo[3,4-c]pyrrol-2(1H)-yl]prop-2-en-1-one;

1-[(3R,4R)-3-{[(5-chloro-2-{[1-(2-hydroxypropyl)-1H-pyrazol-4-yl]amino}-7H-pyrrolo[2,3-d]pyrimidin-4-yl)oxy]methyl}-4-methoxypyrrolidin-1-yl]prop-2-en-1-one;

1-[(3R,4R)-3-{[(5-chloro-2-{[1-(2-hydroxyethyl)-1H-pyrazol-4-yl]amino}-7H-pyrrolo[2,3-d]pyrimidin-4-yl)oxy]methyl}-4-methoxypyrrolidin-1-yl]prop-2-en-1-one;

1-[(3R,4R)-3-({[5-chloro-2-({1-[(3S)-tetrahydrofuran-3-yl]-1H-pyrazol-4-yl}amino)-7H-pyrrolo[2,3-d]pyrimidin-4-yl]oxy}methyl)-4-methoxypyrrolidin-1-yl]prop-2-en-1-one;

1-[(3R,4R)-3-({[5-chloro-2-({1-[(3R)-tetrahydrofuran-3-yl]-1H-pyrazol-4-yl}amino)-7H-pyrrolo[2,3-d]pyrimidin-4-yl]oxy}methyl)-4-methoxypyrrolidin-1-yl]prop-2-en-1-one;

N-(3-{[2-({3-[2-(dimethylamino)ethoxy]-1-methyl-1H-pyrazol-5-yl}amino)-7H-pyrrolo[2,3-d]pyrimidin-4-yl]oxy}-2-fluorophenyl)prop-2-enamide;

1-[3-({5-chloro-2-[(1-methyl-1H-pyrazol-4-yl)amino]-7H-pyrrolo[2,3-d]pyrimidin-4-yl}oxy)azetidin-1-yl]prop-2-en-1-one;

N-(2-fluoro-3-{[2-({1-[(3S)-1-methylpyrrolidin-3-yl]-1H-pyrazol-4-yl}amino)-7H-pyrrolo[2,3-d]pyrimidin-4-yl]oxy}phenyl)prop-2-enamide;

N-(3-fluoro-5-{[2-({1-[(3R)-1-methylpyrrolidin-3-yl]-1H-pyrazol-4-yl}amino)-7H-pyrrolo[2,3-d]pyrimidin-4-yl]oxy}phenyl)prop-2-enamide;

N-[trans-3-({5-chloro-2-[(1-methyl-1H-pyrazol-4-yl)amino]-7H-pyrrolo[2,3-d]pyrimidin-4-yl}oxy)cyclobutyl]-N-methylprop-2-enamide;

N-[cis-3-({2-[(1-methyl-1H-pyrazol-4-yl)amino]-5-(pyridin-3-yl)-7H-pyrrolo[2,3-d]pyrimidin-4-yl}oxy)cyclobutyl]prop-2-enamide;

1-[(3R,4R)-3-[({5-chloro-2-[(1-methyl-1H-pyrazol-4-yl)amino]-7H-pyrrolo[2,3-d]pyrimidin-4-yl}oxy)methyl]-4-(trifluoromethyl)pyrrolidin-1-yl]prop-2-en-1-one;

1-{(3R,4R)-3-[({5-chloro-2-[(1-methyl-1H-pyrazol-3-yl)amino]-7H-pyrrolo[2,3-d]pyrimidin-4-yl}oxy)methyl]-4-methoxypyrrolidin-1-yl}prop-2-en-1-one;

1-(2-{5-chloro-2-[(1-methyl-1H-pyrazol-4-yl)amino]-7H-pyrrolo[2,3-d]pyrimidin-4-yl}-6-oxa-2,9-diazaspiro[4.5]dec-9-yl)prop-2-en-1-one;

N-[trans-3-({5-chloro-2-[(1-methyl-1H-pyrazol-4-yl)amino]-7H-pyrrolo[2,3-d]pyrimidin-4-yl}oxy)-1-methylcyclobutyl]prop-2-enamide;

N-[cis-3-({5-chloro-2-[(1-methyl-1H-pyrazol-4-yl)amino]-7H-pyrrolo[2,3-d]pyrimidin-4-yl}oxy)-1-methylcyclobutyl]prop-2-enamide;

{4-[(4-{[(3R,4R)-1-acryloyl-4-methoxypyrrolidin-3-yl]methoxy}-5-chloro-7H-pyrrolo[2,3-d]pyrimidin-2-yl)amino]-3-methyl-1H-pyrazol-1-yl}acetonitrile;

N-{trans-3-[(5-chloro-2-{[1-(cyanomethyl)-1H-pyrazol-4-yl]amino}-7H-pyrrolo[2,3-d]pyrimidin-4-yl)oxy]cyclobutyl}-N-methylprop-2-enamide; and 1-{(3R,4R)-3-methoxy-4-[({2-[(1-methyl-1H-pyrazol-4-yl)amino]-5-(pyridin-2-yl)-7H-pyrrolo[2,3-d]pyrimidin-4-yl}oxy)methyl]pyrrolidin-1-yl}prop-2-en-1-one, or a pharmaceutically acceptable salt thereof.

In additional embodiments, the compound is selected from:

1-{(3R,4R)-3-[({5-chloro-2-[(1-methyl-1H-pyrazol-4-yl)amino]-7H-pyrrolo[2,3-d]pyrimidin-4-yl}oxy)methyl]-4-methoxypyrrolidin-1-yl}prop-2-en-1-one;

N-[3-({5-(1-methyl-1H-pyrazol-4-yl)-2-[(1-methyl-1H-pyrazol-4-yl)amino]-7H-pyrrolo[2,3-d]pyrimidin-4-yl}oxy)phenyl]prop-2-enamide;

N-[trans-3-({2-[(1,3-dimethyl-1H-pyrazol-4-yl)amino]-5-(pyridin-2-yl)-7H-pyrrolo[2,3-d]pyrimidin-4-yl}oxy)cyclobutyl]-N-methylprop-2-enamide;

1-[(3S,4R)-3-({5-chloro-2-[(1-methyl-1H-pyrazol-4-yl)amino]-7H-pyrrolo[2,3-d]pyrimidin-4-yl}amino)-4-(1H-1,2,3-triazol-1-yl)pyrrolidin-1-yl]prop-2-en-1-one;

1-[(3R,4S)-3-({5-chloro-2-[(1-methyl-1H-pyrazol-4-yl)amino]-7H-pyrrolo[2,3-d]pyrimidin-4-yl}amino)-4-(trifluoromethyl)pyrrolidin-1-yl]prop-2-en-1-one;

N-methyl-N-[trans-3-({2-[(1-methyl-1H-pyrazol-4-yl)amino]-5-(pyridin-2-yl)-7H-pyrrolo[2,3-d]pyrimidin-4-yl}oxy)cyclobutyl]prop-2-enamide;

1-{(3R,4R)-3-[({5-chloro-2-[(1-methyl-1H-pyrazol-4-yl)amino]-7H-pyrrolo[2,3-d]pyrimidin-4-yl}oxy)methyl]-4-fluoropyrrolidin-1-yl}prop-2-en-1-one; and 1-{(3R,4R)-3-methoxy-4-[({2-[(1-methyl-1H-pyrazol-4-yl)amino]-5-(pyridin-2-yl)-7H-pyrrolo[2,3-d]pyrimidin-4-yl}oxy)methyl]pyrrolidin-1-yl}prop-2-en-1-one, or a pharmaceutically acceptable salt thereof.

Some embodiments relate to a pharmaceutical composition comprising a compound of any of the embodiments of the compounds of formula (I), formula (II), formula (III) or formula (IV), or a pharmaceutically acceptable salt thereof, and a pharmaceutically acceptable carrier or diluent.

More embodiments relate to a method of treating abnormal cell growth in a mammal comprising administering to the mammal an amount of a composition of any of the embodiments of the compounds of formula (I), formula (II), formula (III) or formula (IV), or a pharmaceutically acceptable salt thereof, that is effective in treating abnormal cell growth.

Further embodiments relate to a method of treating abnormal cell growth in a mammal comprising administering to the mammal an amount of a compound of any of the embodiments of the compounds of formula (I), formula (II), formula (III) or formula (IV), or a pharmaceutically acceptable salt thereof, that is effective in treating abnormal cell growth.

Additional embodiments relate to the method of treating abnormal cell growth, wherein the abnormal cell growth is cancer.

Further embodiments relate to the method of treating cancer, wherein the cancer is selected from the group consisting of basal cell cancer, medulloblastoma cancer, liver cancer, rhabdomyosarcoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system, primary central nervous system lymphoma, spinal axis tumors, brain stem glioma and pituitary adenoma, or a combination of one or more of the foregoing cancers.

Further embodiments relate to the method of treating lung cancer, wherein the lung cancer is non-small cell lung cancer.

DETAILED DESCRIPTION OF THE INVENTION

The following abbreviations may be used herein: Ac (acetyl); APCI (atomic pressure chemical ionization); Boc (tert-butoxycarbonyl); Boc$_2$O (di-tert-butyl dicarbonate); BrettPhos Palladacycle (chloro[2-(dicyclohexylphosphino)-3,6-dimethoxy-2',4',6'-triisopropyl-1,1'-biphenyl][2-(2-aminoethyl)phenyl]palladium(II)); DCC (1,3-dicyclohexylcarbodiimide); DCM (dichloromethane); Deoxo-Fluor® (bis(2-methoxyethyl)aminosulfur trifluoride); DIAD (diisopropyl azodicarboxylate); DIEA (diisopropylethylamine); DIPEA (N,N-diisopropylethylamine); DMAP (4-dimethylaminopyridine); DMEM (Dulbecco's modified Eagle's medium); DMF (dimethylformamide); DMSO (dimethylsulphoxide); DPPA (diphenyl phosphorazidate); eq (equivalent); Et (ethyl); EtOH (ethanol); EtOAc (ethyl acetate); Et$_2$O (diethyl ether); FBS (fetal bovine serum); HATU (2-(7-aza-1H-benzotriazole-1-yl)-1,1,3,3-tetramethyluronium hexafluorophosphate); HMDS (bis(trimethylsilyl)amine, which is also known as hexamethyldisilazane or hexamethyldisiloxane); HOAc (acetic acid); HPLC (high-performance liquid chromatography); iPr (isopropyl); iPrMgCl (isopropylmagnesium chloride); iPrOH (isopropyl alcohol); KHMDS (potassium bis(trimethylsilyl)amide); LAH (lithium aluminum hydride); LCMS (liquid chromatography-mass spectrometry); LiHMDS (lithium bis(trimethylsilyl)amide); Me (methyl); MeOH (methanol); MeCN (acetonitrile); N (normal); N/A (not available); NaHMDS (sodium bis(trimethylsilyl)amide); N/D (not determined); NIS (N-iodosuccinimide); NMM (N-methylmorpholine); NMR (nuclear magnetic resonance); $Pd_2(dba)_3$ (tris(dibenzylideneacetone)dipalladium (0)); PG (protecting group); Ph (phenyl); $PhI(OAc)_2$ (iodobenzene diacetate); psi (pounds per square inch); Rf (retention factor); RPMI (Roswell Park Memorial Institute); rt (room temperature); sat. (saturated); SCX (strong cation exchange); SEM (2-(trimethylsilyl)ethoxymethyl); SEM-Cl (2-(trimethylsilyl)ethoxymethyl chloride); SFC (supercritical fluid chromatography); TBAF (tetrabutylammonium fluoride); TBDPS (tert-butyldiphenylsilyl); TBS (tert-butyldimethylsilyl); t-BuXPhos Palladacycle (chloro[2-(di-tert-butylphosphino)-2',4',6'-triisopropyl-1,1'-biphenyl][2-(2-aminoethyl)phenyl)]palladium(II); TFA (trifluoroacetate); THF (tetrahydrofuran); TLC (thin layer chromatography); toluene (methylbenzene); tosyl (p-toluenesulfonyl); and Xantphos (4,5-bis(diphenylphosphino)-9,9-dimethylxanthene).

The term "halogen", as used herein, refers to a fluorine, chlorine, bromine, or iodine atom or fluoro, chloro, bromo, or iodo. Additionally, the term "halogen" refers to F, Cl, Br, or I. The terms fluorine, fluoro and F, for example, are understood to be equivalent herein.

The term "alkyl", as used herein, refers to saturated monovalent hydrocarbon radicals containing, in certain embodiments, from one to six, or from one to three carbon atoms, having straight or branched moieties. The term "$C_1$-$C_6$ alkyl" refers to an alkyl radical containing from one to six carbon atoms, having straight or branched moieties. The term "$C_1$-$C_6$ alkyl" includes within its definition the terms "$C_1$-$C_3$ alkyl" and "$C_1$-$C_4$ alkyl". Examples of alkyl groups include, but are not limited to, methyl, ethyl, propyl, isopropyl, butyl, isobutyl, sec-butyl, tert-butyl, pentyl, 2-pentyl, 3-pentyl, iso-pentyl, neopentyl, (R)-2-methylbutyl, (S)-2-methylbutyl, 3-methylbutyl, 2,3-dimethylpropyl, 2,3-dimethylbutyl, hexyl, and the like.

The term "alkenyl", as used herein, refers to saturated monovalent hydrocarbon radicals containing, in certain embodiments, from two to six carbon atoms having at least one carbon-carbon double bond. Alkenyl radicals include both straight and branched moieties. The term "$C_2$-$C_6$ alkenyl", refers to an alkenyl radical containing from two to six carbon atoms, having straight or branched moieties. The double bond may or may not be the point of attachment to another group. Alkenyl groups include, but are not limited to, ethenyl, 1-propenyl, 2-propenyl, 2-methyl-2-propenyl, butenyl, pentenyl, 3-hexenyl, and the like.

The term "alkynyl", as used herein, refers to saturated monovalent hydrocarbon radicals containing, in certain embodiments, from two to six carbon atoms having at least one carbon-carbon triple bond. Alkynyl radicals include both straight and branched moieties. The term "$C_2$-$C_6$ alkynyl", refers to an alkynyl radical containing from two to six carbon atoms, having straight or branched moieties. The triple bond may or may not be the point of attachment to another group. Alkynyl groups include, but are not limited to, ethynyl, 1-propynyl, 2-propynyl, 2-methyl-2-propynyl, butynyl, pentynyl, 3-hexynyl, and the like.

The term "alkoxy", as used herein, refers to an alkyl radical that is single bonded to an oxygen atom. The attachment point of an alkoxy radical to a molecule is through the oxygen atom. An alkoxy radical may be depicted as alkyl-O—. The term "$C_1$-$C_6$ alkoxy", refers to an alkoxy radical containing from one to six carbon atoms, having straight or branched moieties. Alkoxy groups, include, but are not limited to, methoxy, ethoxy, propoxy, isopropoxy, butoxy, hexyloxy, and the like.

The term "cycloalkyl", as used herein, refers to a mono, fused or bridged bicyclic or tricyclic carbocyclic rings containing, in certain embodiments, from three to ten carbon atoms. As used herein, a cycloalkyl group rings may optionally contain one or two double bonds. The term "cycloalkyl" also includes spiro cycloalkyl groups, including multi-ring systems joined by a single atom. The terms "$C_3$-$C_{10}$ cycloalkyl", "$C_3$-$C_7$ cycloalkyl", "$C_3$-$C_4$ cycloalkyl", "$C_3$-$C_5$ cycloalkyl", and "$C_5$-$C_7$ cycloalkyl" contain from three to ten, from three to seven, from three to four, from three to five, and from five to seven carbon atoms, respectively. Cycloalkyl groups include, but are not limited to, cyclopropyl, cyclobutyl, cyclopentyl, cyclohexyl, cycloheptyl, cyclopentenyl, cyclohexenyl, bicyclo[2.2.1]heptanyl, bicyclo[3.2.1]octanyl, bicyclo[5.2.0]nonanyl, adamantanyl, and the like.

The term "heterocycloalkyl", as used herein, refers to a non-aromatic, monocyclic, fused or bridged bicyclic or tricyclic or spirocyclic ring group containing, in certain embodiments, a total of three to ten ring atoms, in which one to four ring atoms are heteroatoms independently selected from nitrogen, oxygen, and sulfur, and wherein the sulfur atom may be optionally oxidized with one or two oxygen atoms, the remaining ring atoms being carbon, with the proviso that such ring systems may not contain two adjacent oxygen atoms or two adjacent sulfur atoms. The heterocycloalkyl ring may also be substituted by an oxo (=O) group at any available carbon atom. The rings may also have one or more double bonds. Furthermore, such groups may be bonded to the remainder of the compounds of embodiments disclosed herein through either a carbon atom or a heteroatom, if possible. The terms "3-10 membered heterocycloalkyl", "3-7 membered heterocycloalkyl", and "4-6 membered heterocycloalkyl" contain from three to ten, from three to seven, and from three to six carbon atoms, respectively. Examples of saturated heterocycloalkyl groups include, but are not limited to:

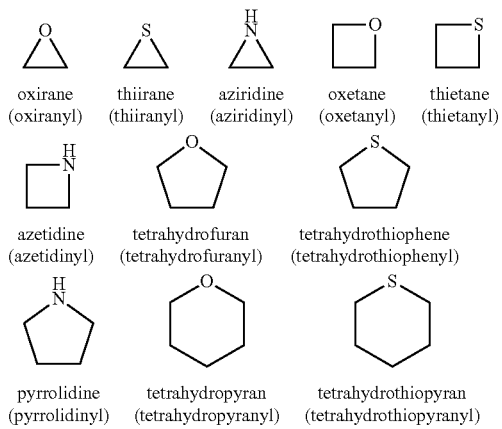

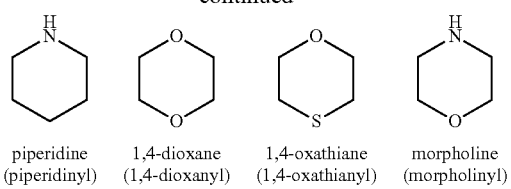

piperidine (piperidinyl)   1,4-dioxane (1,4-dioxanyl)   1,4-oxathiane (1,4-oxathianyl)   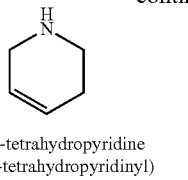

morpholine (morpholinyl)

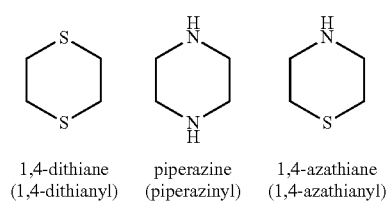

1,4-dithiane (1,4-dithianyl)   piperazine (piperazinyl)   1,4-azathiane (1,4-azathianyl)

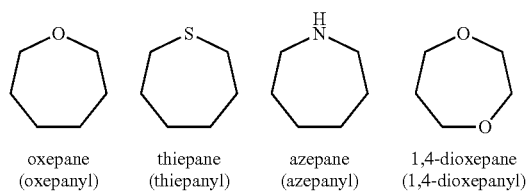

oxepane (oxepanyl)   thiepane (thiepanyl)   azepane (azepanyl)   1,4-dioxepane (1,4-dioxepanyl)

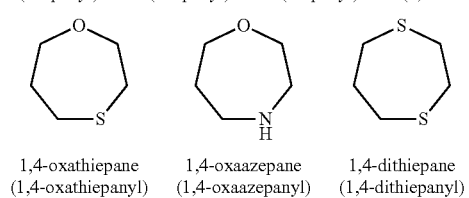

1,4-oxathiepane (1,4-oxathiepanyl)   1,4-oxaazepane (1,4-oxaazepanyl)   1,4-dithiepane (1,4-dithiepanyl)

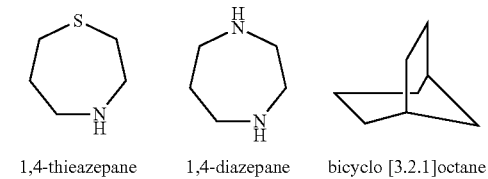

1,4-thieazepane (1,4-thieazepanyl)   1,4-diazepane (1,4-diazepanyl)   bicyclo [3.2.1]octane

bicyclo[2.2.1]heptane

Examples of suitable partially unsaturated heterocloalkyl groups include, but are not limited to:

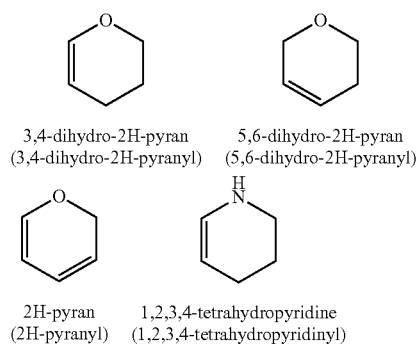

3,4-dihydro-2H-pyran (3,4-dihydro-2H-pyranyl)   5,6-dihydro-2H-pyran (5,6-dihydro-2H-pyranyl)

2H-pyran (2H-pyranyl)   1,2,3,4-tetrahydropyridine (1,2,3,4-tetrahydropyridinyl)

1,2,5,6-tetrahydropyridine (1,2,5,6-tetrahydropyridinyl)

The term "aryl", as used herein, refers to a group derived from an aromatic hydrocarbon containing in certain embodiments, from five to ten carbon atoms. The term "$C_5$-$C_{10}$ aryl" contains from five to ten carbon atoms. Examples of such groups include, but are not limited to, phenyl and naphthyl. The term "aryl" also includes fused polycyclic aromatic ring systems in which an aromatic ring is fused to one or more rings. Examples include, but are not limited to, 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heteroaryl, as used herein, refers to an aromatic monocyclic or bicyclic heterocyclic group having a total of from 5 to 12 atoms in its ring, and containing from 2 to 9 carbon atoms and from one to four heteroatoms each independently selected from nitrogen, oxygen, and sulfur, with the proviso that the ring of said group does not contain two adjacent oxygen atoms or two adjacent sulfur atoms. The terms "5-12 membered heteroaryl" and "4-6 membered heteroaryl" contain from five to twelve and from four to six ring atoms, respectively. The heteroaryl groups include benzo-fused ring systems. Examples of heteroaryl groups include, but are not limited to, pyrrolyl, furyl, thienyl, imidazolyl, pyrazolyl, oxazolyl, isoxazolyl, isothiazolyl, triazolyl, oxadiazolyl, furazanyl, thiadiazolyl, thiazolyl, tetrazolyl, pyridinyl, pyrazinyl, pyrimidinyl, pyridazinyl, triazinyl, indolyl, isoindolyl, indolizinyl, benzofuranyl, benzothiophenyl, indazolyl, benzimidazolyl, benzoxazolyl, furo[3,2-b]pyridinyl, benzothiazolyl, benzofurazanyl, purinyl, quinolinyl, isoquinolinyl, quinazolinyl, quinoxalinyl, naphthyridinyl, cinnolinyl, phthalazinyl, pyrido[3,4-d]pyrimidinyl, pteridinyl, and the like.

Also included within the scope of the term "5-12 membered heteroaryl", as used herein, are benzo-fused unsaturated nitrogen heterocycles, which refer to a heterocyclic group in which a heteroatomic ring is fused to one or more aromatic rings. Examples include, but are not limited to, indolinyl, isoindolinyl, tetrahydroquinolinyl, tetrahydroisoquinolinyl, and the like.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

As used herein, an "effective" amount refers to an amount of a substance, agent, compound, or composition that is of sufficient quantity to result in a decrease in severity of disease symptoms, an increase in frequency and duration of disease symptom-free periods, or a prevention of impairment or disability due to the disease affliction—either as a single dose or according to a multiple dose regimen, alone or in combination with other agents or substances. One of ordinary skill in the art would be able to determine such amounts based on such factors as the subject's size, the severity of the subject's symptoms, and the particular composition or route of administration selected. The subject may be a human or non-human mammal (e.g., rabbit, rat, mouse, monkey or other lower-order primate).

Embodiments disclosed herein include isotopically-labeled compounds, which are identical to those recited in formula (I), formula (II), formula (III) or formula (IV), but for the fact that one or more atoms are replaced by an atom having an atomic mass or mass number different from the atomic mass or mass number usually found in nature. Examples of isotopes that can be incorporated into compounds of the embodiments disclosed herein include isotopes of hydrogen, carbon, nitrogen, oxygen, phosphorous, sulfur, fluorine and chlorine, such as, but not limited to, $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein and pharmaceutically acceptable salts of said compounds which contain the aforementioned isotopes and/or other isotopes of other atoms are within the scope of the present embodiments. Certain isotopically-labeled compounds of the embodiments disclosed herein, for example, those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example, increased in vivo half-life or reduced dosage requirements and, hence, may be preferred in some circumstances. Isotopically-labeled compounds of embodiments disclosed herein can generally be prepared by carrying out the procedures disclosed in the Schemes and/or in the Examples and Preparations below, by substituting a readily available isotopically-labeled reagent for a non-isotopically-labeled reagent.

Some embodiments relate to the pharmaceutically acceptable salts of the compounds described herein. Pharmaceutically acceptable salts of the compounds described herein include the acid addition and base addition salts thereof.

Some embodiments also relate to the pharmaceutically acceptable acid addition salts of the compounds described herein. Suitable acid addition salts are formed from acids which form non-toxic salts. Non-limiting examples of suitable acid addition salts, i.e., salts containing pharmacologically acceptable anions, include, but are not limited to, the acetate, acid citrate, adipate, aspartate, benzoate, besylate, bicarbonate/carbonate, bisulphate/sulphate, bitartrate, borate, camsylate, citrate, cyclamate, edisylate, esylate, ethanesulfonate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methanesulfonate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, p-toluenesulfonate, tosylate, trifluoroacetate and xinofoate salts.

Additional embodiments relate to base addition salts of the compounds described herein. Suitable base addition salts are formed from bases which form non-toxic salts. Non-limiting examples of suitable base salts include the aluminium, arginine, benzathine, calcium, choline, diethylamine, diolamine, glycine, lysine, magnesium, meglumine, olamine, potassium, sodium, tromethamine and zinc salts.

The compounds described herein that are basic in nature are capable of forming a wide variety of salts with various inorganic and organic acids. The acids that may be used to prepare pharmaceutically acceptable acid addition salts of such basic compounds described herein are those that form non-toxic acid addition salts, e.g., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds described herein that include a basic moiety, such as an amino group, may form pharmaceutically acceptable salts with various amino acids, in addition to the acids mentioned above.

The chemical bases that may be used as reagents to prepare pharmaceutically acceptable base salts of those compounds of the compounds described herein that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of the embodiments described herein include all stereoisomers (e.g., cis and trans isomers) and all optical isomers of compounds described herein (e.g., R and S enantiomers), as well as racemic, diastereomeric and other mixtures of such isomers. While all stereoisomers are encompassed within the scope of our claims, one skilled in the art will recognize that particular stereoisomers may be preferred.

In some embodiments, the compounds described herein can exist in several tautomeric forms, including the enol and imine form, and the keto and enamine form and geometric isomers and mixtures thereof. All such tautomeric forms are included within the scope of the present embodiments. Tautomers exist as mixtures of a tautomeric set in solution. In solid form, usually one tautomer predominates. Even though one tautomer may be described, the present embodiments includes all tautomers of the present compounds.

The present embodiments also include atropisomers of the compounds described herein. Atropisomers refer to compounds that can be separated into rotationally restricted isomers.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds described herein are known to one of skill in the art.

The term "solvate" is used herein to describe a molecular complex comprising a compound described herein and one or more pharmaceutically acceptable solvent molecules, for example, ethanol.

The compounds described herein may also exist in unsolvated and solvated forms. Accordingly, some embodiments relate to the hydrates and solvates of the compounds described herein.

Compounds described herein containing one or more asymmetric carbon atoms can exist as two or more stereoisomers. Where a compound described herein contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds described herein containing, for example, an imino, keto, or oxime group, or so-called valence tautomerism in compounds which contain an aromatic moiety. A single compound may exhibit more than one type of isomerism.

Included within the scope of the present embodiments are all stereoisomers, geometric isomers and tautomeric forms of the compounds described herein, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where a compound described herein contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

Further embodiments relate to methods of treating abnormal cell growth in a mammal. Additional embodiments relate to a method of treating abnormal cell growth in a mammal comprising administering to the mammal an amount of a compound described herein that is effective in treating abnormal cell growth.

In other embodiments, the abnormal cell growth is cancer.

In some embodiments, the cancer is selected from the group consisting of lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of two or more of the foregoing cancers.

Additional embodiments relate to methods of treating cancer solid tumors in a mammal. Some embodiments relate to the treatment of cancer solid tumor in a mammal comprising administering to the mammal an amount of a compound described herein that is effective in treating said cancer solid tumor.

In other embodiments, the cancer solid tumor is breast, lung, colon, brain, prostate, stomach, pancreatic, ovarian, skin (melanoma), endocrine, uterine, testicular, or bladder.

Further embodiments relate to methods of treating abnormal cell growth in a mammal which comprises administering to said mammal an amount of a compound described herein that is effective in treating abnormal cell growth in combination with an anti-tumor agent selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

More embodiments relate to pharmaceutical compositions for treating abnormal cell growth in a mammal comprising an amount of a compound described herein that is effective in treating abnormal cell growth, and a pharmaceutically acceptable carrier.

Additional embodiments relate to a method of treating abnormal cell growth in a mammal, including a human, comprising administering to the mammal an amount of a compound described herein, or a pharmaceutically acceptable salt, solvate, hydrate or prodrug thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In one embodiment the method comprises comprising administering to a mammal an amount of a compound described herein that is effective in treating said cancer solid tumor. In one preferred embodiment the solid tumor is breast, lung, colon, brain, prostate, stomach, pancreatic, ovarian, skin (melanoma), endocrine, uterine, testicular, and bladder cancer.

In another embodiment of said method, said abnormal cell growth is a benign proliferative disease, including, but not limited to, psoriasis, benign prostatic hypertrophy or restinosis.

Some embodiments relate to a method of treating abnormal cell growth in a mammal which comprises administering to said mammal an amount of a compound described herein, or a pharmaceutically acceptable salt, solvate, hydrate or prodrug thereof, that is effective in treating abnormal cell growth in combination with an anti-tumor agent selected from the group consisting of mitotic inhibitors, alkylating agents, antimetabolites, intercalating antibiotics, growth factor inhibitors, cell cycle inhibitors, enzymes, topoisomerase inhibitors, biological response modifiers, antibodies, cytotoxics, antihormones, and anti-androgens.

Additional embodiments relate to a pharmaceutical composition for treating abnormal cell growth in a mammal, including a human, comprising an amount of a compound described herein, or a pharmaceutically acceptable salt, solvate, hydrate or prodrug thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

Further embodiments relate to a method of treating abnormal cell growth in a mammal which comprises administering to said mammal an amount of a compound described herein, or a pharmaceutically acceptable salt, solvate, or hydrate thereof, that is effective in treating abnormal cell growth in combination with another anti-tumor agent selected from the group consisting of mitotic inhibitors, alkylating agents, antimetabolites, intercalating antibiotics, growth factor inhibitors, cell cycle inhibitors, enzymes, topoisomerase inhibitors, biological response modifiers, antibodies, cytotoxics, antihormones, and anti-androgens. Some embodiments contemplate a pharmaceutical composition for treating abnormal cell growth wherein the composition includes a compound described herein, or a pharmaceutically acceptable salt, solvate, or hydrate thereof, that is effective in treating abnormal cell growth, and another anti-tumor agent selected from the group consisting of mitotic inhibitors, alkylating agents, antimetabolites, intercalating antibiotics, growth factor inhibitors, cell cycle inhibitors, enzymes, topoisomerase inhibitors, biological response modifiers, antibodies, cytotoxics, antihormones, and anti-androgens.

Yet more embodiments relate to a method of treating a disorder associated with angiogenesis in a mammal, including a human, comprising administering to said mammal an amount of a compound described above, or a pharmaceutically acceptable salt, solvate, hydrate or prodrug thereof, that is effective in treating said disorder in combination with one or more anti-tumor agents listed above. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi*, *Yersinia* spp., *Bordetella pertussis*, and group A *Streptococcus*.

Some embodiments relate to a method of (and to a pharmaceutical composition for) treating abnormal cell growth in a mammal which comprise an amount of a compound described herein, or a pharmaceutically acceptable salt, solvate, or hydrate thereof, in combination with an amount of one or more substances selected from anti-angiogenesis agents, signal transduction inhibitors inhibitor (e.g., inhibiting the means by which regulatory molecules that govern the fundamental processes of cell growth, differentiation, and survival communicated within the cell), and antiproliferative agents, which amounts are together effective in treating said abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound described herein in the methods and pharmaceutical compositions described herein. Examples of useful COX-II inhibitors include CELEBREX™ (celecoxib), Bextra (valdecoxib), paracoxib, Vioxx (rofecoxib), and Arcoxia (etoricoxib). Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds described herein are AG-3340, RO 32-3555, RS 13-0830, and the following compounds:
3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R,3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

3-[4-(4-chloro-phenoxy)-benzenesulfonylamino]-tetrahydro-pyran-3-carboxylic acid hydroxyamide;

(2R,3R)1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and 3-[4-(4-fluoro-phenoxy)-benzenesulfonylamino]-tetrahydro-furan-3-carboxylic acid hydroxyamide;

and pharmaceutically acceptable salts and solvates of said compounds.

VEGF inhibitors, for example, sutent and axitinib, can also be combined with a compound described herein. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); Avastin, an anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound described herein. Such erbB2 inhibitors include Herceptin, 2C4, and pertuzumab. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the embodiments described herein are also described in U.S. Provisional Application No. 60/117,341, filed Jan. 27, 1999, and in U.S. Provisional Application No. 60/117,346, filed Jan. 27, 1999, both of which are herein incorporated by reference in their entirety. Other erbb2 receptor inhibitors include TAK-165 (Takeda) and GW-572016 (Glaxo-Wellcome).

Various other compounds, such as styrene derivatives, have also been shown to possess tyrosine kinase inhibitory properties, and some of tyrosine kinase inhibitors have been identified as erbB2 receptor inhibitors. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. Other patent applications that refer to anti-cancer compounds are World Patent Application WO00/44728 (published Aug. 3, 2000), EP 1029853A1 (published Aug. 23, 2000), and WO01/98277 (published Dec. 12, 2001) all of which are incorporated herein by reference in their entirety.

Epidermal growth factor receptor (EGFR) inhibitors may be administered in combination with a compound of the presentation invention. Such EGFR inhibitors include gefinitib, erlotinib, icotinib, afatinib and dacomitinib. Monoclonal antibody inhibitors of EGFR, such as cetuximab, may also be combined with a compound of the present invention.

c-Met inhibitors may be administered in combination with a compound of the presentation invention. Such c-Met inhibitors include crizotinib and ARQ-197. Monoclonal antibody inhibitors of c-Met, such as METMab, may also be combined with a compound of the present invention.

Other antiproliferative agents that may be used with the compounds described herein include inhibitors of the enzyme farnesyl protein transferase and inhibitors of the receptor tyrosine kinase PDGFr, including the compounds disclosed and claimed in the following U.S. patent applications: Ser. No. 09/221,946 (filed Dec. 28, 1998); Ser. No. 09/454,058 (filed Dec. 2, 1999); Ser. No. 09/501,163 (filed Feb. 9, 2000); Ser. No. 09/539,930 (filed Mar. 31, 2000); Ser. No. 09/202,796 (filed May 22, 1997); Ser. No. 09/384,339 (filed Aug. 26, 1999); and Ser. No. 09/383,755 (filed Aug. 26, 1999); and the compounds disclosed and claimed in the following U.S. provisional patent applications: 60/168,207 (filed Nov. 30, 1999); 60/170,119 (filed Dec. 10, 1999); 60/177,718 (filed Jan. 21, 2000); 60/168,217 (filed Nov. 30, 1999), and 60/200, 834 (filed May 1, 2000). Each of the foregoing patent applications and provisional patent applications is herein incorporated by reference in their entirety.

A compound described herein may also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present embodiments include those described in U.S. Provisional Application 60/113,647 (filed Dec. 23, 1998) which is herein incorporated by reference in its entirety.

A compound described herein may be applied as a sole therapy or may involve one or more other anti-tumor substances, for example those selected from, for example, mitotic inhibitors, for example vinblastine; alkylating agents, for example cis-platin, oxaliplatin, carboplatin and cyclophosphamide; anti-metabolites, for example 5-fluorouracil, capecitabine, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex (tamoxifen) or, for example anti-androgens such as Casodex (4'-cyano-3-(4-fluorophenylsulphonyl)-2-hydroxy-2-methyl-3'-(trifluoromethyl)propionanilide).

The compounds described herein may be used alone or in combination with one or more of a variety of anti-cancer agents or supportive care agents. For example, the compounds described herein may be used with cytotoxic agents, e.g., one or more selected from the group consisting of a camptothecin, irinotecan HCl (Camptosar), edotecarin, SU-11248, epirubicin (Ellence), docetaxel (Taxotere), paclitaxel, rituximab (Rituxan) bevacizumab (Avastin), imatinib mesylate (Gleevac), Erbitux, gefitinib (Iressa), and combinations thereof. Some embodiments also contemplate the use of the compounds described herein together with hormonal therapy, e.g., exemestane (Aromasin), Lupron, anastrozole (Arimidex), tamoxifen citrate (Nolvadex), Trelstar, and combinations thereof. Further, some embodiments provide a compound described herein alone or in combination with one or more supportive care products, e.g., a product selected from the group consisting of Filgrastim (Neupogen), ondansetron (Zofran), Fragmin, Procrit, Aloxi, Emend, or combinations thereof. Such conjoint treatment may be achieved by way of the simultaneous, sequential or separate dosing of the individual components of the treatment.

The compounds described herein may be used with anti-tumor agents, alkylating agents, antimetabolites, antibiotics, plant-derived antitumor agents, camptothecin derivatives, tyrosine kinase inhibitors, antibodies, interferons, and/or biological response modifiers. In this regard, the following is a non-limiting list of examples of secondary agents that may be used with the compounds described herein.

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, carboplatin, eptaplatin, lobaplatin, nedaplatin, oxaliplatin or satrplatin.

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, gemcitabine, fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred anti-metabolites disclosed in European Patent Application No. 239362 such as N-(5[N-(3,4-dihydro-2-methyl-4-oxoquinazolin-6-ylmethyl)-N-methylamino]-2-thenoyl)-L-glutamic acid.

Antibiotics include but are not limited to: aclarubicin, actinomycin D, amrubicin, annamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin or zinostatin.

Hormonal therapy agents, e.g., exemestane (Aromasin), Lupron, anastrozole (Arimidex), doxercalciferol, fadrozole, formestane, anti-estrogens such as tamoxifen citrate (Nolvadex) and fulvestrant, Trelstar, toremifene, raloxifene, lasofoxifene, letrozole (Femara), or anti-androgens such as bicalutamide, flutamide, mifepristone, nilutamide, Casodex® (4'-cyano-3-(4-fluorophenylsulphonyl)-2-hydroxy-2-methyl-3'-(trifluoromethyl)propionanilide) and combinations thereof.

Plant derived anti-tumor substances include for example those selected from mitotic inhibitors, for example vinblastine, docetaxel (Taxotere) and paclitaxel.

Cytotoxic topoisomerase inhibiting agents include one or more agents selected from the group consisting of aclarubicn, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, and topotecan, and combinations thereof.

Immunologicals include interferons and numerous other immune enhancing agents. Interferons include interferon alpha, interferon alpha-2a, interferon, alpha-2b, interferon beta, interferon gamma-1a or interferon gamma-n1. Other agents include PF3512676, filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoVAX-CL, sargramostim, tasonermin, tecleukin, thymalasin, tositumomab, Virulizin, Z-100, epratuzumab, mitumomab, oregovomab, pemtumomab, Provenge.

Biological response modifiers are agents that modify defense mechanisms of living organisms or biological responses, such as survival, growth, or differentiation of tissue cells to direct them to have anti-tumor activity. Such agents include krestin, lentinan, sizofuran, picibanil, or ubenimex.

Other anticancer agents include alitretinoin, ampligen, atrasentan bexarotene, bortezomib. Bosentan, calcitriol, exisulind, finasteride, fotemustine, ibandronic acid, miltefosine, mitoxantrone, 1-asparaginase, procarbazine, dacarbazine, hydroxycarbamide, pegaspargase, pentostatin, tazarotne, TLK-286, Velcade, Tarceva, or tretinoin.

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain and Vitaxin.

Platinum-coordinated compounds include but are not limited to, cisplatin, carboplatin, nedaplatin, or oxaliplatin.

Camptothecin derivatives include but are not limited to camptothecin, 10-hydroxycamptothecin, 9-aminocamptothecin, irinotecan, SN-38, edotecarin, and topotecan.

Tyrosine kinase inhibitors include, for example, Iressa and SU5416.

Antibodies include, for example, Herceptin, Erbitux, Avastin, and Rituximab.

Interferons include, for example, interferon alpha, interferon alpha-2a, interferon, alpha-2b, interferon beta, interferon gamma-1a and interferon gamma-n1.

Biological response modifiers include agents that modify defense mechanisms of living organisms or biological responses, such as survival, growth, or differentiation of tissue cells to direct them to have anti-tumor activity. Such agents include, for example, krestin, lentinan, sizofuran, picibanil, and ubenimex.

Other antitumor agents include, for example, mitoxantrone, 1-asparaginase, procarbazine, dacarbazine, hydroxycarbamide, pentostatin, and tretinoin. Additionally, PI3K inhibitors and RAS-targeted cancer treatments may be combined with the compounds described herein.

Some embodiments also relate to a pharmaceutical composition comprising a compound of formula I, formula II, formula III, or formula IV, or a pharmaceutically acceptable salt or solvate thereof, as hereinbefore defined in association with a pharmaceutically acceptable adjuvant, diluent or carrier.

Further embodiments relate to a pharmaceutical composition which comprises mixing a compound of formula I, formula II, formula III, or formula IV, or a pharmaceutically acceptable salt or solvate thereof, as hereinbefore defined with a pharmaceutically acceptable adjuvant, diluent or carrier.

For the above-mentioned therapeutic uses the dosage administered will, of course, vary with the compound employed, the mode of administration, the treatment desired and the disorder indicated. The daily dosage of the compound of formula I, formula II, formula III, or formula IV, or pharmaceutically acceptable salt thereof, may be in the range from 1 mg to 1 gram, preferably 1 mg to 250 mg, more preferably 10 mg to 100 mg.

The present embodiments also encompass sustained release compositions.

Administration of the compounds described herein (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The active compound may be applied as a sole therapy or may involve one or more other anti-tumor substances, for example those selected from, for example, mitotic inhibitors, for example vinblastine; alkylating agents, for example cisplatin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex® (tamoxifen) or, for example anti-androgens such as Casodex® (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound described herein as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The examples and preparations provided below further illustrate and exemplify the compounds described herein and methods of preparing such compounds. The scope of the embodiments described herein is not limited in any way by the following examples and preparations. In the following examples, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

In the examples shown, salt forms were occasionally isolated as a consequence of the mobile phase additives during HPLC based chromatographic purification. In these cases, salts such as formate, trifluorooacetate and acetate were isolated and tested without further processing. It will be recognized that one of ordinary skill in the art will be able to realize the free base form by standard methodology (such as using ion exchange columns, or performing simple basic extractions using a mild aqueous base).

In general, the compounds described herein may be prepared by processes known in the chemical arts, particularly in light of the description contained herein. Certain processes for the manufacture of the compounds described herein are provided as further features of the embodiments and are illustrated in the reaction schemes provided below and in the experimental section.

Unless stated otherwise, the variables in Schemes A-J have the same meanings as defined herein.
Scheme A:
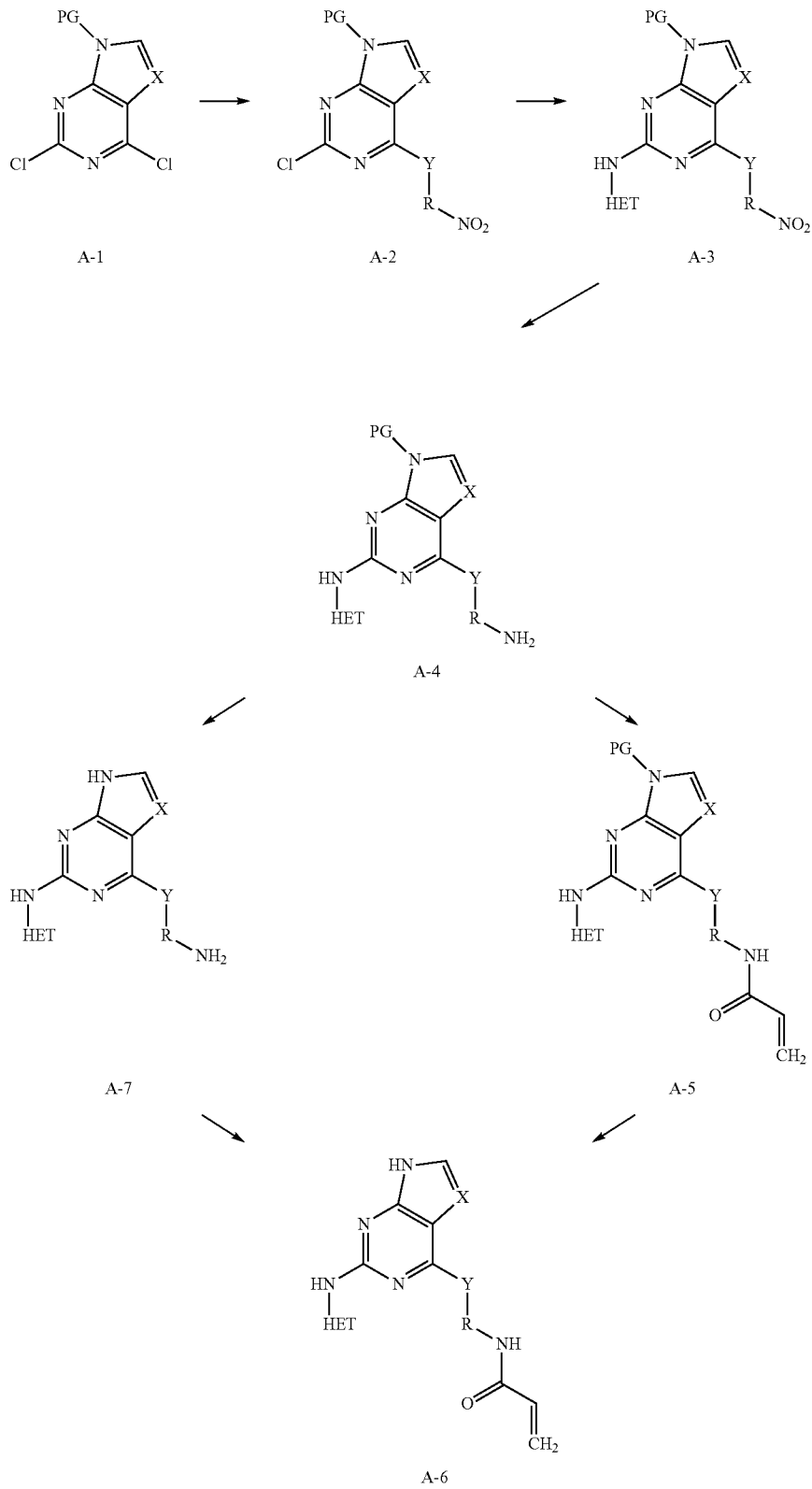

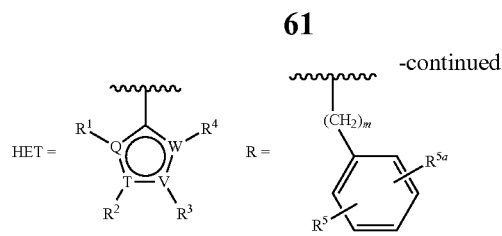

As exemplified in Scheme A, the core A-1, which is suitably protected under standard conditions known in the art, such as by using a SEM protecting group, is subjected to selective chlorine displacement with an alkoxide, phenoxide or amine (using parent alcohol, phenol or amine derivatives in the presence of a suitable base {NaH, NaHMDS, KHMDS, K₂CO₃ or DIPEA, respectively}) in a suitable solvent (such as iPrOH, MeCN, THF or DMF) to afford A-2. A-2 is then treated under Buchwald amination conditions known in the literature with an amino-heterocycle to yield A-3. Nitro reduction under standard conditions known in the art yields aniline A-4 that is acylated with acryloyl chloride or subjected to amide formation using a suitable amide coupling agent (such as HATU) and an appropriate carboxylic acid to give A-5. Subsequent deprotection under standard conditions known in the art affords A-6. Alternatively, the aniline species A-4 is globally deprotected first to A-7 and is then acylated as previously detailed to afford A-6.

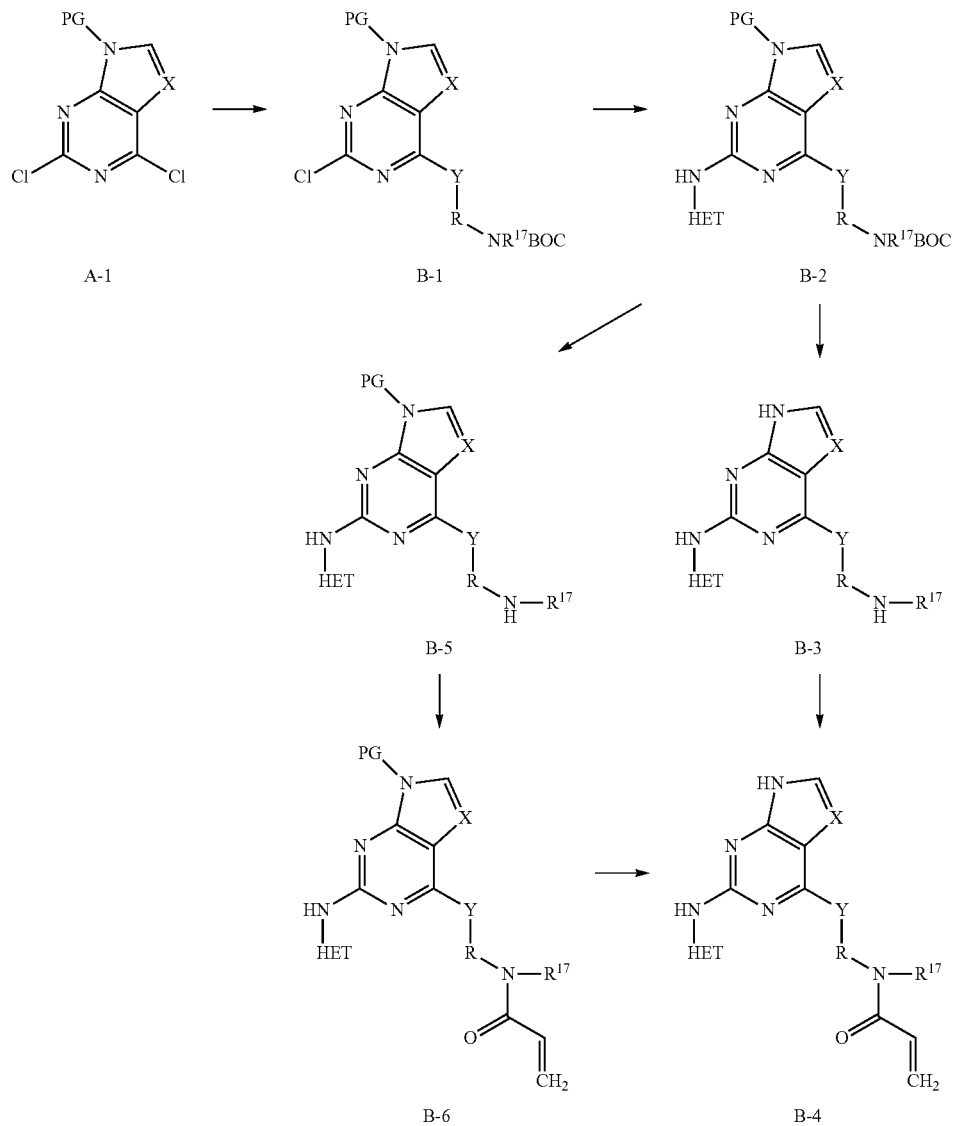

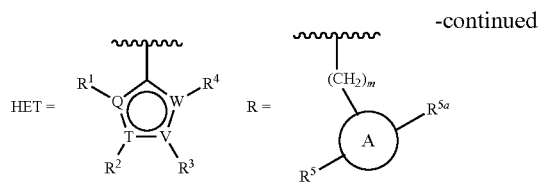

As exemplified in Scheme B, the suitably protected core A-1 is treated with an alkoxide, phenoxide or amine (using parent alcohol, phenol or amine derivatives in the presence of a suitable base {NaH, NaHMDS, KHDMS, $K_2CO_3$ or DIPEA, respectively}) in a suitable solvent (such as iPrOH, MeCN, THF or DMF) to afford the protected intermediate B-1. Subsequent Buchwald amination under conditions known in the literature with an amino-heterocycle affords B-2, which is globally deprotected under standard conditions known in the art to B-3. Acylation affords B-4.

Alternatively, selective deprotection of B-2 affords the suitably protected intermediate B-5, which is acylated to B-6. Subsequent removal of the protecting group yields B-4.

Scheme B illustrates a general methodology to afford primary amine derived acrylamides. It will be understood by one of skill in the art that this methodology may be utilized to afford secondary amine derived analogues, where a nitrogen atom in ring A serves as the attachment point of the acrylamide.

Scheme C:

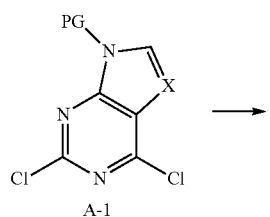
A-1

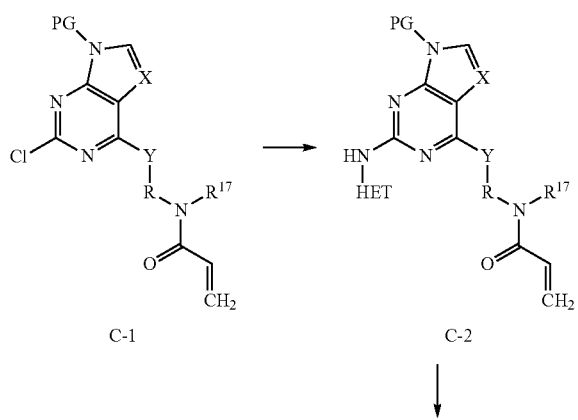
C-1    C-2

-continued

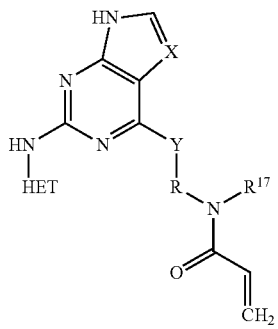
C-3

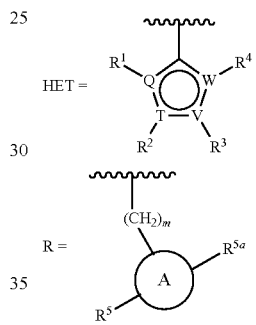

As exemplified in Scheme C, the suitably protected core A-1 is treated with a functionalized alkoxide or phenoxide (using parent alcohol or phenol derivatives in the presence of a suitable base {NaH or $K_2CO_3$, respectively}) in a suitable solvent (such as DMF) to yield intermediate C-1. Buchwald amination with a suitable amino-heterocycle yields C-2, which is followed by deprotection under standard conditions known in the art to afford C-3.

Scheme C illustrates a general methodology to afford primary amine derived acrylamides. It will be understood by one of skill in the art that this methodology may be utilized to afford secondary amine derived analogues, where a nitrogen atom in ring A serves as the attachment point of the acrylamide.

Scheme D:

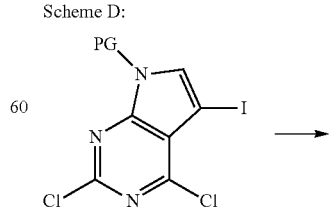
D-1

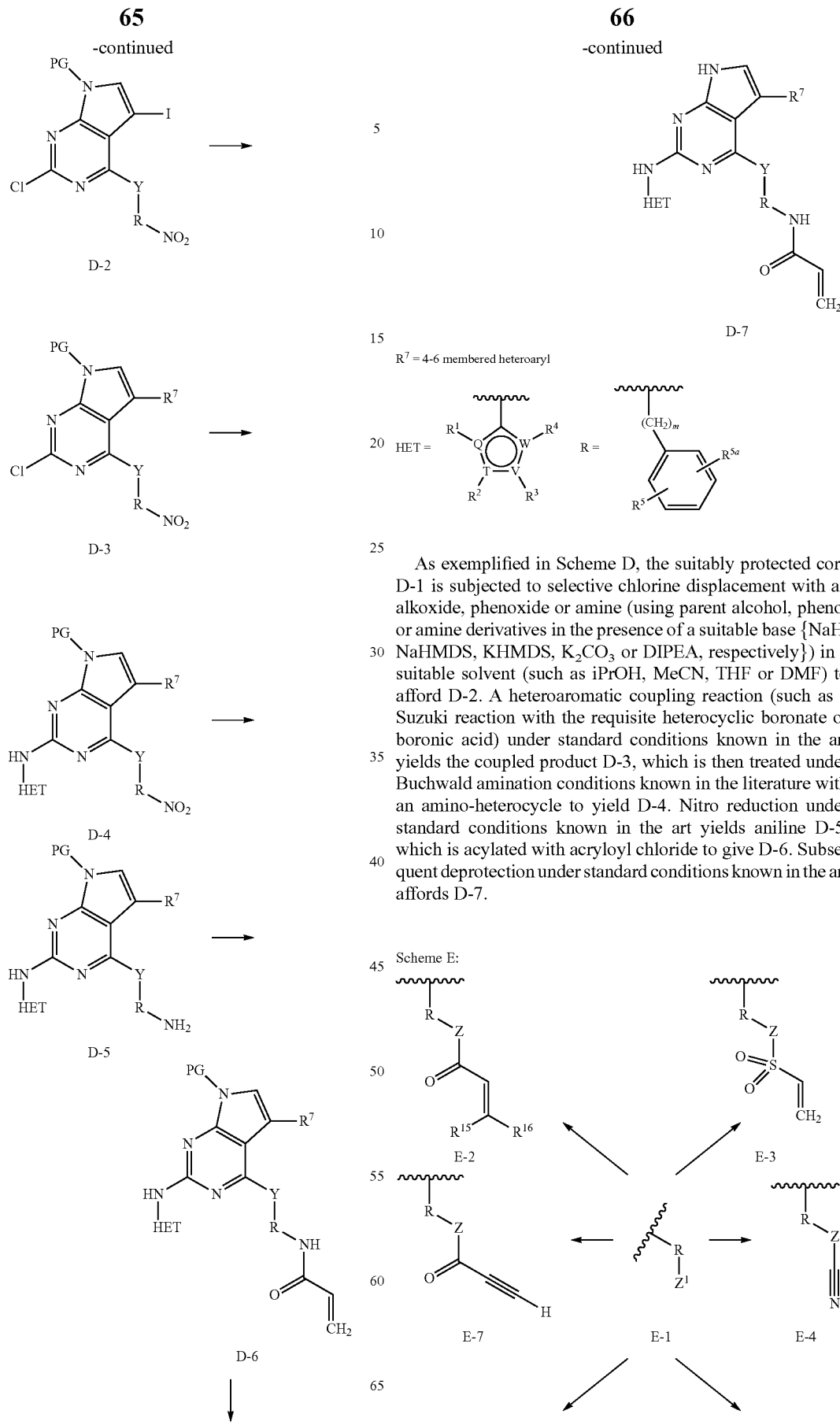

As exemplified in Scheme D, the suitably protected core D-1 is subjected to selective chlorine displacement with an alkoxide, phenoxide or amine (using parent alcohol, phenol or amine derivatives in the presence of a suitable base {NaH, NaHMDS, KHMDS, $K_2CO_3$ or DIPEA, respectively}) in a suitable solvent (such as iPrOH, MeCN, THF or DMF) to afford D-2. A heteroaromatic coupling reaction (such as a Suzuki reaction with the requisite heterocyclic boronate or boronic acid) under standard conditions known in the art yields the coupled product D-3, which is then treated under Buchwald amination conditions known in the literature with an amino-heterocycle to yield D-4. Nitro reduction under standard conditions known in the art yields aniline D-5, which is acylated with acryloyl chloride to give D-6. Subsequent deprotection under standard conditions known in the art affords D-7.

Scheme E:

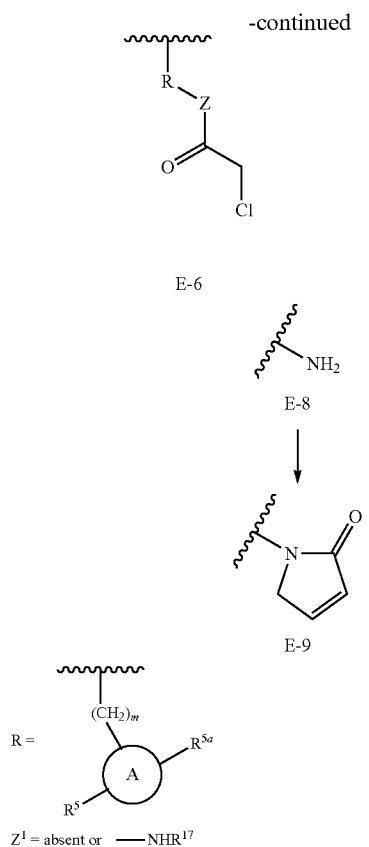

Electrophiles of the present invention may be synthesized as described in Scheme E. Amide E-2 is prepared via acylation methodology, such as acylating with acyl chlorides in the presence of a suitable base (such as Hunig's base or triethylamine). Alternatively, amide E-2 is prepared via amide coupling with a suitable carboxylic acid under standard conditions known in the art, such as HATU or DCC in the presence of a suitable base such as triethylamine. Sulphonamide E-3 is synthesized by reacting the amine or aniline E-1 with chloroethanesulphonyl chloride in the presence of a suitable base to afford the unsaturated sulphonamide E-3 directly (see, for example, Org. Lett., 10 (14), 2951-2954, 2008). Reaction of amine or aniline E-1 with cyanogen bromide in the presence of base affords the cyanamide E-4 (see, for example, J. Med. Chem., 32 (8), 1754, 1989). Coupling of the amine or aniline E-1 with cyanoacetic acid using standard amide coupling conditions (for example, HATU in the presence of Hunig's base) affords cyanoacetamide E-5 (see, for example, Bioorganic & Medicinal Chemistry Letters, 16(5), 1126-1129, 2006). Haloamide E-6 can be synthesized by reacting amine or aniline E-1 with chloroacetyl chloride or fluoroacetyl chloride (see, for example, Journal of Medicinal Chemistry, 47(22), 5451-5466; 2004). Alternatively, coupling amine or aniline E-1 with a suitable carboxylic acid affords haloamide E-6 (see Bioorganic & Medicinal Chemistry Letters, 19(22), 6424-6428, 2009). Preparation of the alkyne E-7 is accomplished by amide coupling of amine or aniline E-1 with a propargylic acid derivative under standard conditions known in the art (see, for example, Tett. Letts, 48(36), 6397-6400, 2007). Lactam E-9 is synthesized through ring closing metathesis (see, for example, Bioorganic & Medicinal Chemistry Letters, 20(6), 1924-1927, 2010) or alternatively, through condensation with 2,5-dihydro-2,5-dimethoxyfuran (see, for example, Journal of the Brazilian Chemical Society, 18(4), 855-859, 2007).

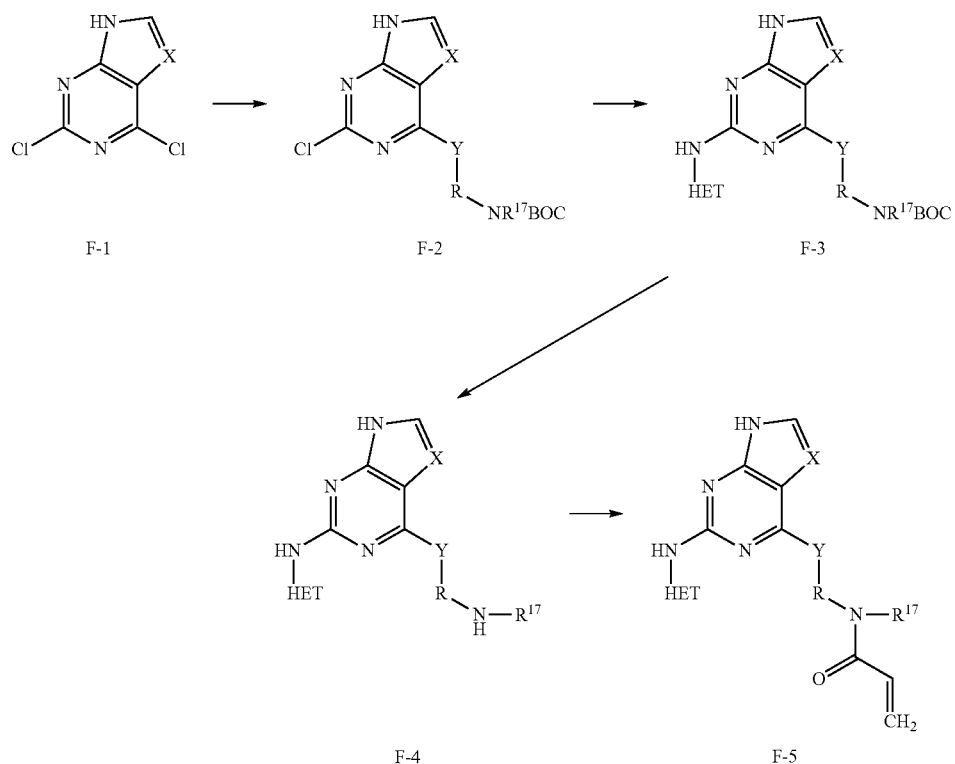

Scheme F:

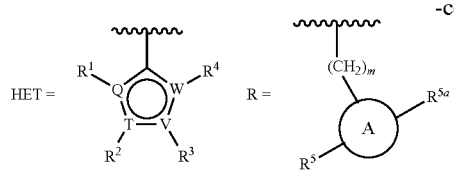

As exemplified in Scheme F, the core F-1 is treated with an alkoxide, phenoxide or amine (using parent alcohol, phenol or amine derivatives in the presence of a suitable base {potassium tert-pentoxide, NaH, NaHMDS, KHMDS, potassium carbonate or DIPEA}) in a suitable solvent (such as 1,4-dioxane, iPrOH, THF or DMF) to afford the protected intermediate F-2. Subsequent Buchwald amination using a preformed palladacycle (see Biscoe, M. R., et al., *J. Am. Chem. Soc.*, 130:6686 (2008)) with an amino-heterocycle affords the coupled intermediate F-3, which is deprotected under standard conditions known in the art to F-4. Acylation affords F-5.

Scheme F illustrates a general methodology to afford primary amine derived acrylamides. It will be understood by one of skill in the art that this methodology may be utilized to afford secondary amine derived analogues, where a nitrogen atom in ring A serves as the attachment point of the acrylamide.

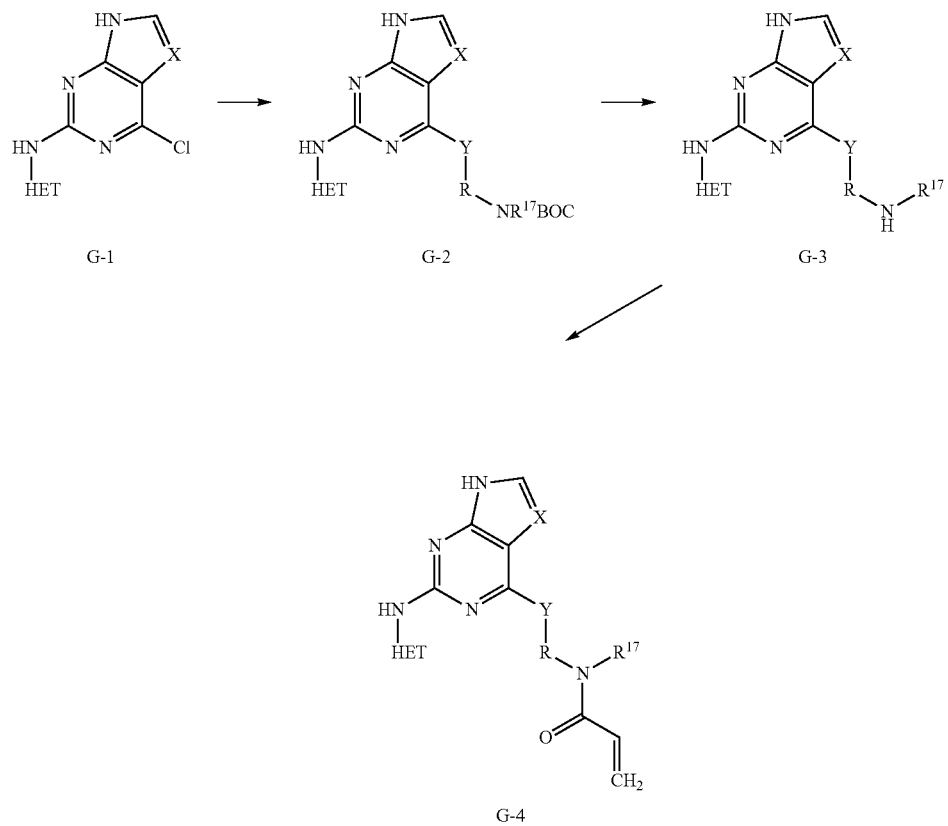

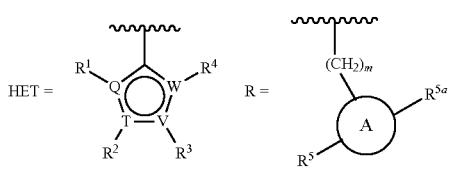

As exemplified in Scheme G, the core G-1 is treated with an alkoxide, phenoxide or amine (using parent alcohol, phenol or amine derivatives in the presence of a suitable base {potassium tert-pentoxide, NaH, NaHMDS, KHMDS, potassium carbonate or DIPEA}) in a suitable solvent (such as DMSO, 1,4-dioxane, iPrOH, THF or DMF) to afford the protected intermediate G-2. Subsequent deprotection under standard conditions known in the art affords the amine G-3. Acylation affords G-4.

Scheme G illustrates a general methodology to afford primary amine derived acrylamides. It will be understood by one of skill in the art that this methodology may be utilized to afford secondary amine derived analogues, where a nitrogen atom in ring A serves as the attachment point of the acrylamide.

Scheme H:

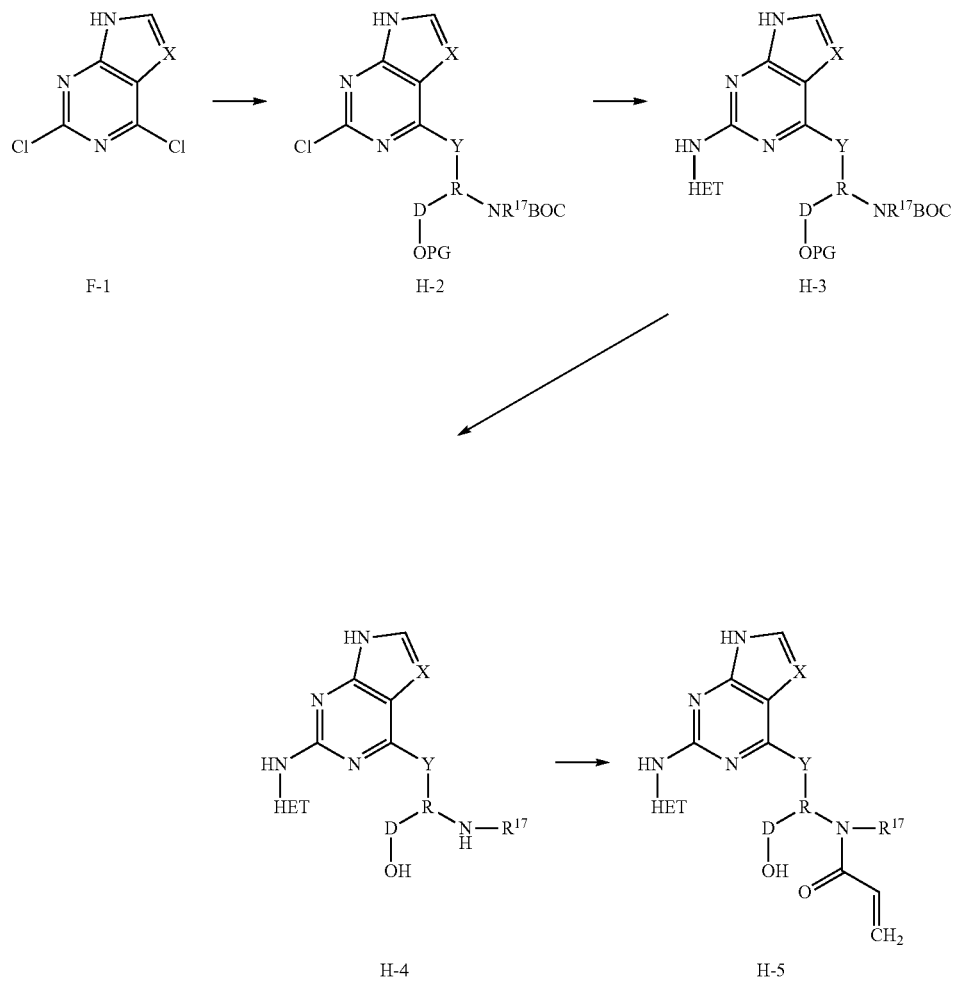

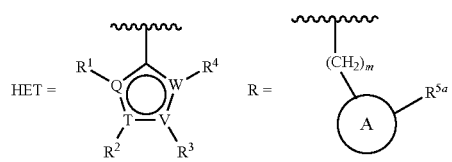

As exemplified in Scheme H, the core F-1 is treated with a bis-protected (i.e., a pendant hydroxy group is protected with a suitable protecting group such as TBS or TBDPS) alkoxide, phenoxide or amine (using parent alcohol, phenol or amine derivatives in the presence of a suitable base {potassium tert-pentoxide, NaH, NaHMDS, KHMDS, potassium carbonate or DIPEA}) in a suitable solvent (such as 1,4-dioxane, iPrOH, THF or DMF) to afford the protected intermediate H-2. Subsequent Buchwald amination using a preformed palladacycle (see Biscoe, M. R., et al., *J. Am. Chem. Soc.*, 130: 6686 (2008)) with an amino-heterocycle affords the coupled intermediate H-3, which is deprotected either globally or sequentially under standard conditions known in the art to H-4. Acylation afforded H-5.

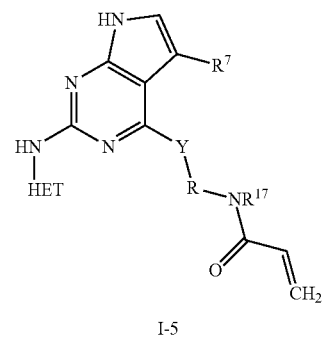

I-5

Scheme I:

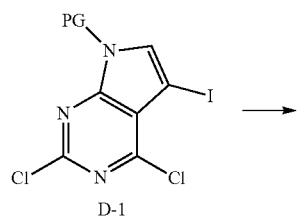

D-1

$R^7$ = 4-6 membered heteroaryl

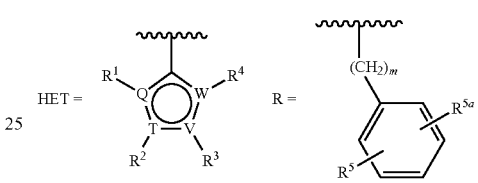

As exemplified in Scheme I, the suitably protected core D-1 is subjected to Suzuki or Negishi aryl coupling conditions known in the art with an appropriate boronic acid (or ester) or zincate, respectively, to afford I-1, I-1 is treated with an alkoxide, phenoxide or amine (using parent alcohol, phenol or amine derivatives, respectively, in the presence of a suitable base {potassium tert-pentoxide, NaH, NaHMDS, KHMDS, potassium carbonate or DIPEA}) in a suitable solvent (such as 1,4-dioxane, iPrOH, THF or DMF) to afford the protected intermediate I-2. Subsequent Buchwald amination under standard conditions known in the art with an amino-heterocycle affords the coupled intermediate I-3, which is then globally deprotected under standard conditions known in the art to I-4. Acylation affords product I-5.

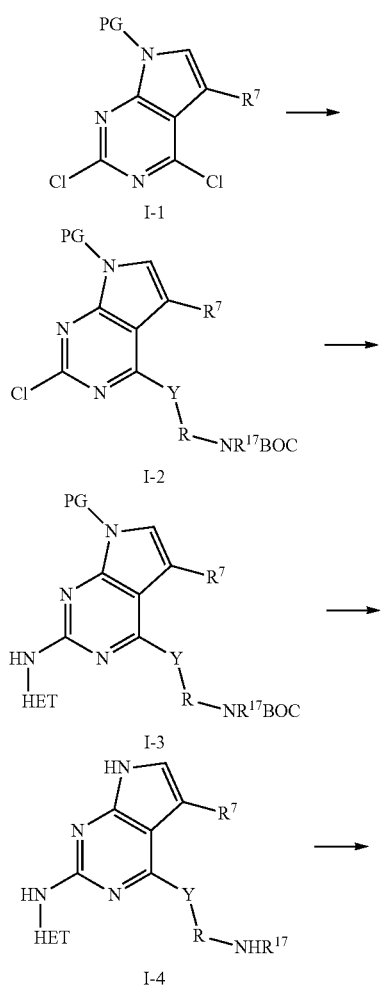

Scheme J:

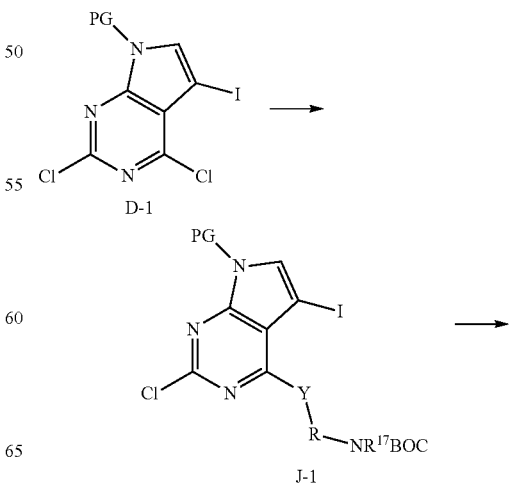

-continued

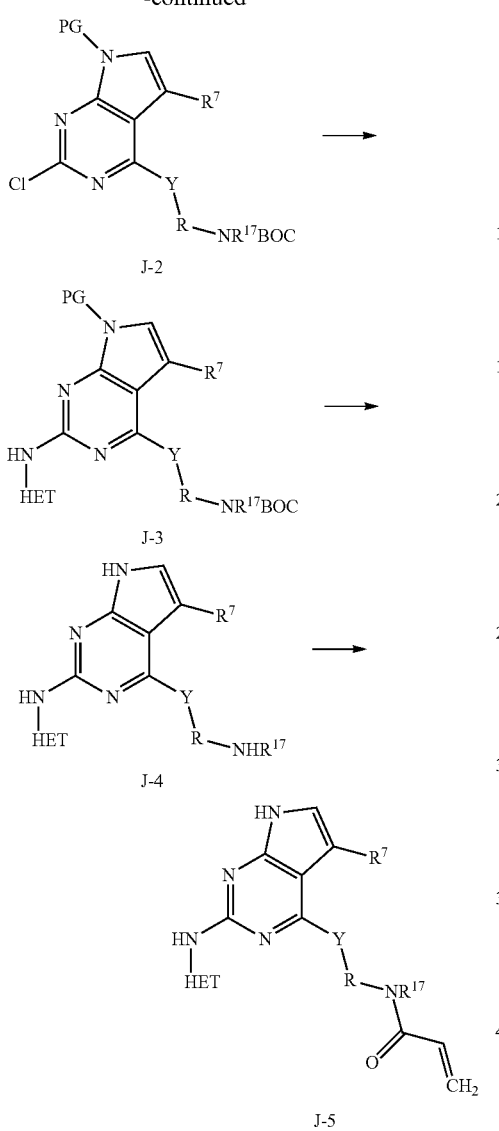

$R^7$ = 4-6 membered heteroaryl

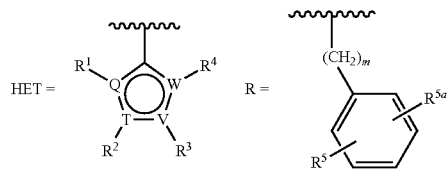

As exemplified in Scheme J, the suitably protected core D-1 is treated with either an alkoxide, phenoxide or amine (using parent alcohol, phenol or amine derivatives, respectively, in the presence of a suitable base {potassium tert-pentoxide, NaH, NaHMDS, KHMDS, potassium carbonate or DIPEA}) in a suitable solvent (such as 1,4-dioxane, iPrOH, THF or DMF) to afford the protected intermediate J-1. Subsequent Suzuki or Negishi aryl coupling conditions known in the art with an appropriate boronic acid (or ester) or zincate, respectively, affords J-2. Buchwald amination under standard conditions known in the art with an amino-heterocycle affords the coupled intermediate J-3, which is then globally deprotected under standard conditions known in the art to J-4. Acylation affords product J-5.

EXAMPLES

Example 1

(Scheme A): Preparation of N-[3-({5-fluoro-2-[(1-methyl-1H-pyrazol-3-yl)amino]-7H-pyrrolo[2,3-d]pyrimidin-4-yl}oxy)phenyl]prop-2-enamide

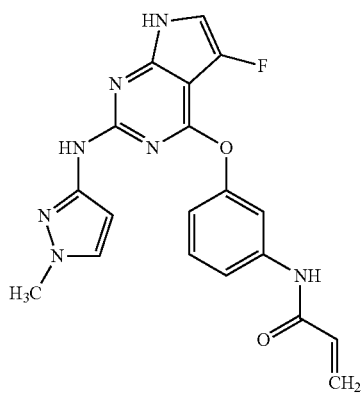 [SMILES: C=CC(=O)Nc1cccc(Oc2nc(Nc3ccn(C)n3)nc3[nH]cc(F)c23)c1]

Step 1: Preparation of 2,4-dichloro-5-fluoro-7-((2-(trimethylsilyl)ethoxy)methyl)-7H-pyrrolo[2,3-d]pyrimidine

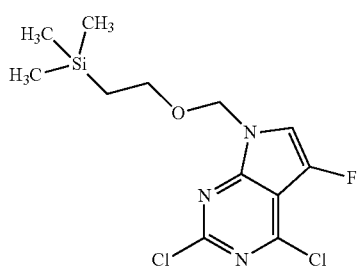 [SMILES: C[Si](C)(C)CCOCn1cc(F)c2c(Cl)nc(Cl)nc21]

2,4-Dichloro-5-fluoro-7H-pyrrolo[2,3-d]pyrimidine (see Seela, et al., *Helvetica Chimica Acta*, 91(6):1083-1105 (2008)) (654 mg, 3.2 mmol) was dissolved in DMF (6.5 mL). After cooling to 0° C., NaH (254 mg, 6.35 mmol, 60% in mineral oil) was added. After complete addition, the mixture was warmed to rt and allowed to stir for 30 min. A solution of (2-(chloromethoxy)ethyl)trimethylsilane (529 mg, 3.2 mmol) in DMF (2 mL) was added dropwise to the mixture and stirring was continued for 3 hrs. The reaction was quenched by pouring the mixture over ice water (75 mL). The resulting aqueous layer was then extracted with Et$_2$O (three×50 mL). The combined organics were washed with water (two times), brine (two times) and dried over MgSO$_4$. After concentrating, the brown solid was purified via flash chromatography eluting with a gradient of 1%-10% EtOAc in heptanes to afford the title compound (0.45 g, 42% yield) as a white, low melting solid. $^1$H NMR (400 MHz, chloroform-d) δ ppm-0.03 (s, 9H), 0.87-0.97 (m, 2H), 3.48-3.58 (m, 2H), 5.57 (s, 2H), 7.14 (d, J=2.78 Hz, 1H). APCI (MH+). m/z (APCI+) for $C_{12}H_{16}Cl_2FN_3OSi$ 336.2 (M+H)+.

Step 2: Preparation of 2-chloro-5-fluoro-4-(3-nitrophenoxy)-7-{[2-(trimethylsilyl)ethoxy]methyl}-7H-pyrrolo[2,3-d]pyrimidine

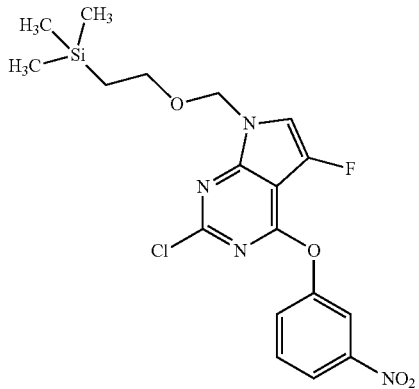 [SMILES: C[Si](C)(C)CCOCn1cc(F)c2c(Oc3cccc([N+](=O)[O-])c3)nc(Cl)nc21]

To a vial containing 2,4-dichloro-5-fluoro-7-((2-(trimethylsilyl)ethoxy)methyl)-7H-pyrrolo[2,3-d]pyrimidine (389.5 mg, 1.2 mmol) was added m-nitrophenol (161 mg, 1.2 mmol), DMF (5 mL) and $K_2CO_3$ (320 mg, 2.3 mmol). The reaction mixture was heated at 60° C. for 1 hr. The reaction was diluted with EtOAc (120 mL) and water (30 mL). The organic layer was separated, washed with water (20 mL) and brine (20 mL), dried over $Na_2SO_4$ and evaporated to give an oil. The oil was purified via flash chromatography eluting with 100% heptanes. The solvent was removed to afford the title compound (505 mg, 99% yield) as a white solid. $^1$H NMR (400 MHz, DMSO-d6) δ ppm 8.34 (t, J=2.27 Hz, 1H) 8.22-8.28 (m, 1H) 7.90-7.96 (m, 1H) 7.86 (d, J=8.31 Hz, 1H) 7.78-7.84 (m, 1H) 5.59 (s, 2H) 3.54-3.66 (m, 2H) 0.84-0.99 (m, 2H) 0.00 (s, 9H). m/z (APCI+) for $C_{18}H_{20}ClFN_4O_4Si$ 439.1 (M+H)+.

Step 3: Preparation of 5-fluoro-N-(1-methyl-1H-pyrazol-3-yl)-4-(3-nitrophenoxy)-7-((2-(trimethylsilyl)ethoxy)methyl)-7H-pyrrolo[2,3-d]pyrimidin-2-amine

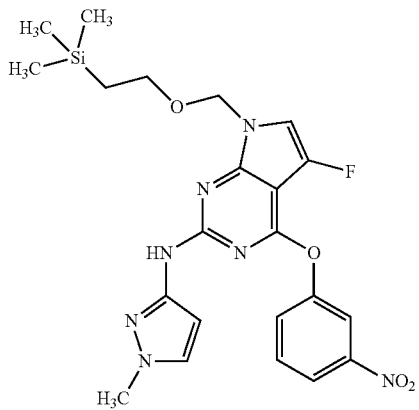

To a solution of 2-chloro-5-fluoro-4-(3-nitrophenoxy)-7-{[2-(trimethylsilyl)ethoxy]methyl}-7H-pyrrolo[2,3-d]pyrimidine (483 mg, 1.1 mmol), in 1,4-dioxane (12 mL) was added 1-methyl-1H-pyrazol-3-amine (128 mg, 1.32 mmol), $Cs_2CO_3$ (717 mg, 2.2 mmol), Xantphos (66 mg, 0.11 mmol) and $Pd_2(dba)_3$ (101 mg, 0.11 mmol). The reaction vial was flushed with nitrogen, capped, stirred and heated at 140° C. in a microwave reactor for 45 min. After removing the reaction solvent, the residue was partitioned in EtOAc (120 mL) and water (20 mL). The organic layer was separated, washed with water (20 mL) and brine (10 mL), dried over $Na_2SO_4$ and evaporated. Purification via flash chromatography with a gradient of 0%-50% EtOAc in heptanes afforded the title compound (523 mg, 95% yield) as a thick oil. $^1$H NMR (400 MHz, DMSO-d6) δ ppm 9.62 (s, 1H) 8.28-8.32 (m, 1H) 8.26 (d, J=8.06 Hz, 1H) 7.90-7.95 (m, 1H) 7.81-7.88 (m, 1H) 7.45 (br. s., 1H) 7.32 (d, J=2.27 Hz, 1H) 5.52 (s, 2H) 3.74 (s, 3H) 3.55-3.66 (m, 2H) 0.94 (t, J=8.18 Hz, 2H) 0.00 (s, 9H). m/z (APCI+) for $C_{22}H_{26}FN_7O_4Si$ 500.1 (M+H)+.

Step 4: Preparation of 4-(3-aminophenoxy)-5-fluoro-N-(1-methyl-1H-pyrazol-3-yl)-7-((2-(trimethylsilyl)ethoxy)methyl)-7H-pyrrolo[2,3-d]pyrimidin-2-amine

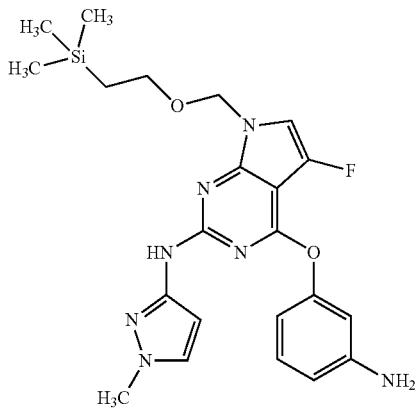 [SMILES: Cn1ccc(Nc2nc(Oc3cccc([N+](=O)[O-])c3)c3c(F)cn(COCC[Si](C)(C)C)c3n2)n1]

A reaction vial was charged with 5-fluoro-N-(1-methyl-1H-pyrazol-3-yl)-4-(3-nitrophenoxy)-7-((2-(trimethylsilyl)ethoxy)methyl)-7H-pyrrolo[2,3-d]pyrimidin-2-amine (520 mg, 1.04 mmol), zinc dust (340 mg, 5.2 mmol), ammonium chloride (279 mg, 5.2 mmol), water (4 mL) and EtOAc (20 mL). The reaction mixture was capped and stirred at rt for 20 hrs. The reaction was diluted with EtOAc (100 mL) and saturated aqueous $NaHCO_3$ (15 mL). The insoluble material was removed by filtration through Celite. The filtrate was separated, and the organic layer was washed with brine (10 mL), dried over $Na_2SO_4$ and evaporated to afford the title compound (394 mg, 81% yield) as a foam. $^1$H NMR (400 MHz, DMSO-d6) δ ppm 9.52 (s, 1H) 7.45 (s, 1H) 7.26 (d, J=2.27 Hz, 1H) 7.14 (t, J=7.93 Hz, 1H) 6.49-6.59 (m, 2H) 6.46 (dd, J=7.93, 1.38 Hz, 1H) 6.30-6.43 (m, 1H) 5.50 (s, 2H) 5.32 (s, 2H) 3.75 (s, 3H) 3.56-3.67 (m, 2H) 0.89-0.98 (m, 2H) 0.00 (s, 9H). m/z (APCI+) for $C_{22}H_{28}FN_7O_2Si$ 470.1 (M+H)+.

Step 5: Preparation of N-{3-[(5-fluoro-2-[(1-methyl-1H-pyrazol-3-yl)amino]-7-{[2-(trimethylsilyl)ethoxy]methyl}-7H-pyrrolo[2,3-d]pyrimidin-4-yl)oxy]phenyl}prop-2-enamide

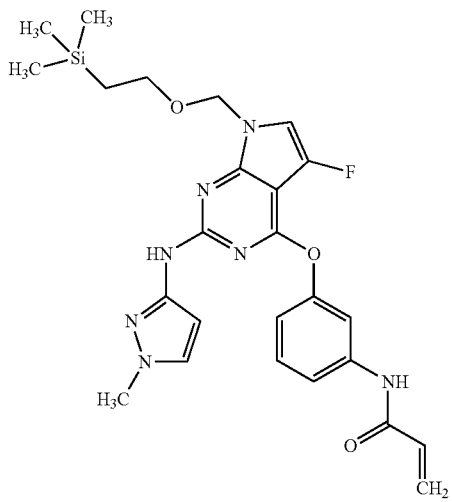 [SMILES: C=CC(=O)Nc1cccc(Oc2nc(Nc3ccn(C)n3)nc3c2c(F)cn3COCC[Si](C)(C)C)c1]

To a solution of 4-(3-aminophenoxy)-5-fluoro-N-(1-methyl-1H-pyrazol-3-yl)-7-((2-(trimethylsilyl)ethoxy)methyl)-7H-pyrrolo[2,3-d]pyrimidin-2-amine (197 mg, 0.42 mmol) in DCM (20 mL) was added acryloyl chloride (34 μL, 0.42 mmol) and the reaction was stirred at rt for 45 min. Additional acryloyl chloride (34 μL, 0.42 mmol) was added and after another 2 hrs a final charge of acryloyl chloride (34 μL, 0.42 mmol) was added. After 30 min, the reaction was complete and was partitioned between DCM (30 mL) and saturated aqueous NaHCO$_3$ (10 mL). The organic layer was separated, dried over Na$_2$SO$_4$ and evaporated to dryness. Purification via flash chromatography eluting with a gradient of 0%-80% EtOAc in heptane afforded the title compound (123 mg, 56 yield) as a solid. $^1$H NMR (400 MHz, methanol-d4) δ ppm 7.64 (s, 1H) 7.57 (d, J=8.81 Hz, 1H) 7.41 (t, J=8.18 Hz, 1H) 7.27 (d, J=1.76 Hz, 1H) 7.01 (dd, J=8.18, 2.14 Hz, 1H) 6.89 (d, J=2.27 Hz, 1H) 6.30-6.48 (m, 3H) 5.76 (dd, J=9.44, 2.14 Hz, 1H) 5.48 (s, 2H) 3.71 (s, 3H) 3.58 (t, J=8.06 Hz, 2H) 0.90 (t, J=8.06 Hz, 2H) −0.08 (s, 9H). m/z (APCI+) for C$_{25}$H$_{30}$FN$_7$O$_3$Si 524.2 (M+H)$^+$.

Step 6: Preparation of N-[3-({5-fluoro-2-[(1-methyl-1H-pyrazol-3-yl)amino]-7H-pyrrolo[2,3-d]pyrimidin-4-yl}oxy)phenyl]prop-2-enamide

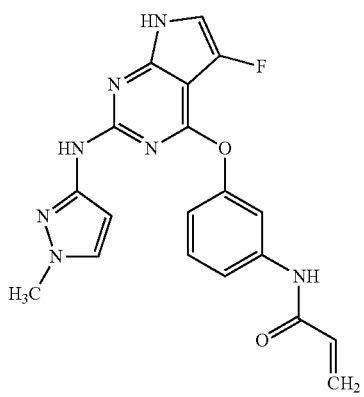 [SMILES: C=CC(=O)Nc1cccc(Oc2nc(Nc3ccn(C)n3)nc3[nH]cc(F)c23)c1]

To a solution N-{3-[(5-fluoro-2-[(1-methyl-1H-pyrazol-3-yl)amino]-7-{[2-(trimethylsilyl)ethoxy]methyl}-7H-pyrrolo[2,3-d]pyrimidin-4-yl)oxy]phenyl}prop-2-enamide (120 mg, 0.23 mmol) in DCM (10 mL) was added TFA (0.7 mL, 6.7 mmol). The reaction solution was stirred at rt for 4 hrs. The reaction was evaporated to dryness and EtOH (5 mL), water (1 mL), and K$_2$CO$_3$ (158 mg, 1.1 mmol) were added. The reaction mixture was stirred at rt for 2 hrs and concentrated to dryness, suspended in EtOAc and filtered. The filtrate was concentrated to dryness and then suspended in EtOAc (20 mL) and heated to 70° C. with stirring for 30 min. The mixture was then cooled to rt with stirring overnight. A light yellow solid precipitated over this time and was collected by filtration, washed with EtOAc (5 mL) and dried to afford the title compound (50.2 mg, 56% yield) as a pale yellow solid. $^1$H NMR (400 MHz, DMSO-d6) δ ppm 11.25 (br. s., 1H) 10.27 (s, 1H) 9.25 (s, 1H) 7.64 (s, 1H) 7.53-7.60 (m, 1H) 7.41 (t, J=8.06 Hz, 1H) 7.28 (d, J=1.26 Hz, 1H) 7.02 (dd, J=7.93, 1.89 Hz, 1H) 6.99 (s, 1H) 6.38-6.48 (m, 1H) 6.05 (br. s., 1H) 5.77 (dd, J=10.07, 1.51 Hz, 1H) 3.65 (s, 4H). m/z (APCI+) for C$_{19}$H$_{16}$FN$_7$O$_2$ 394.1 (M+H)$^+$.

Example 2

(Scheme B): Preparation of N-(3-{[2-({1-[2-(dimethylamino)ethyl]-1H-pyrazol-4-yl}amino)-7H-pyrrolo[2,3-d]pyrimidin-4-yl]oxy}phenyl)prop-2-enamide

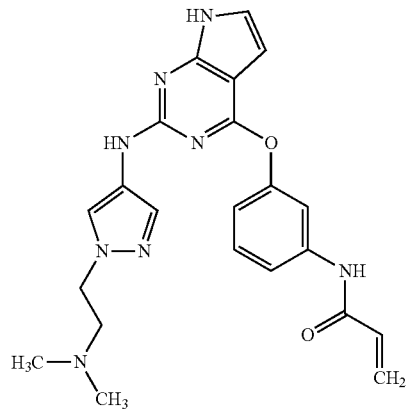 [SMILES: C=CC(=O)Nc1cccc(Oc2nc(Nc3cnn(CCN(C)C)c3)nc3[nH]ccc23)c1]

Step 1: Preparation of 2,4-dichloro-7-{[2-(trimethylsilyl)ethoxy]methyl}-7H-pyrrolo[2,3-d]pyrimidine

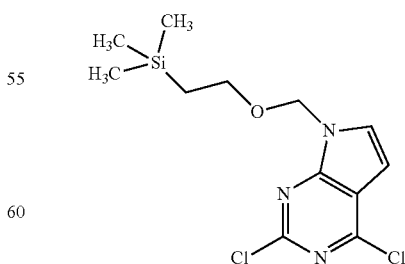

In a 1000 mL flask, LiHMDS (140 mL, 140 mmol) was diluted in dry THF (100 mL) and cooled to −78° C. The 2,4-dichloro-7H-pyrrolo[2,3-d]pyrimidine (25.0 g, 133 mmol) was suspended in THF (200 mL) using gentle warm ing and sonication. This suspension was added dropwise to the base solution over 30 min. 50 mL more THF was used to dissolve any residue and this suspension was also added dropwise. After complete addition, the mixture was allowed to stir at −78° C. for 30 min. SEM-Cl (25 mL, 140 mmol) was added dropwise to the mixture and stirring was continued at −78° C. for 30 min. Then, the ice bath was allowed to slowly warm to rt overnight. The reaction was quenched by the addition of cold water (150 mL). EtOAc (200 mL) was added and the layers separated. The resulting aqueous layer was then extracted with EtOAc (two×200 mL). The combined organics were washed with brine (two times) and dried over MgSO$_4$, filtered and concentrated. The orange oil was purified via gravity "plug" chromatography eluting with 80% heptanes/20% DCM eluant to afford the title compound (33.4 g, 79% yield) as an orange oil which solidified upon standing. $^1$H NMR (400 MHz, chloroform-D) δ ppm-0.03 (s, 9H), 0.85-0.99 (m, 2H), 3.50-3.59 (m, 2H), 5.61 (s, 2H), 6.67 (d, J=3.53 Hz, 5H), 7.38 (d, J=3.78 Hz, 1H). m/z (APCI+) for $C_{12}H_{17}Cl_2N_3OSi$ 318.00/320.05 (M+H)$^+$ for Cl isotopes.

Step 2: Preparation of tert-butyl {3-[(2-chloro-7-{[2-(trimethylsilyl)ethoxy]methyl}-7H-pyrrolo[2,3-d]pyrimidin-4-yl)oxy]phenyl}carbamate

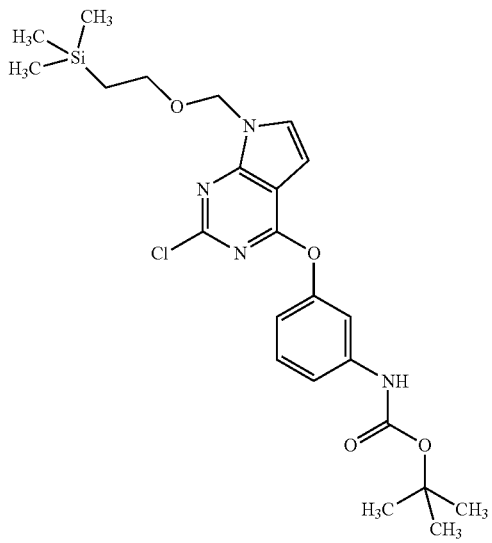 [SMILES: CC(C)(C)OC(=O)Nc1cccc(Oc2nc(Cl)nc3c2ccn3COCC[Si](C)(C)C)c1]

To a solution of 2,4-dichloro-7-{[2-(trimethylsilyl)ethoxy]methyl}-7H-pyrrolo[2,3-d]pyrimidine (1470 mg, 4.62 mmol) in acetonitrile (10 mL) was added tert-butyl (3-hydroxyphenyl)carbamate (966 mg, 4.62 mmol) and K$_2$CO$_3$ (1280 mg, 9.24 mmol) and the mixture heated at 80° C. with stirring overnight. The reaction was then cooled to rt, EtOAc (20 mL) added, washed with water (50 mL), the aqueous layer extracted with EtOAc (three×20 mL), dried with MgSO$_4$, filtered and stripped to a light oil. Upon standing, the light oil solidified to give the title compound (2052 mg, 90% yield) as a tan solid. $^1$H NMR (400 MHz, DMSO-d6) δ ppm 9.38-9.83 (m, 1H) 7.73 (d, J=3.78 Hz, 1H) 7.41-7.46 (m, 2H) 7.51 (s, 1H) 6.97 (dt, J=5.98, 2.68 Hz, 1H) 6.58 (d, J=3.78 Hz, 1H) 5.64 (s, 2H) 3.54-3.67 (m, 2H) 1.54 (s, 9H) 0.91-0.96 (m, 2H) 0.00 (s, 9H). LCMS (ESI, pos): m/z (ESI+) for $C_{23}H_{31}ClN_4O_4Si$ 491.20 (M+H)$^+$.

Step 3: Preparation of tert-butyl(3-{[2-({1-[2-(dimethylamino)ethyl]-1H-pyrazol-4-yl}amino)-7-{[2-(trimethylsilyl)ethoxy]methyl}-7H-pyrrolo[2,3-d]pyrimidin-4-yl]oxy}phenyl)carbamate

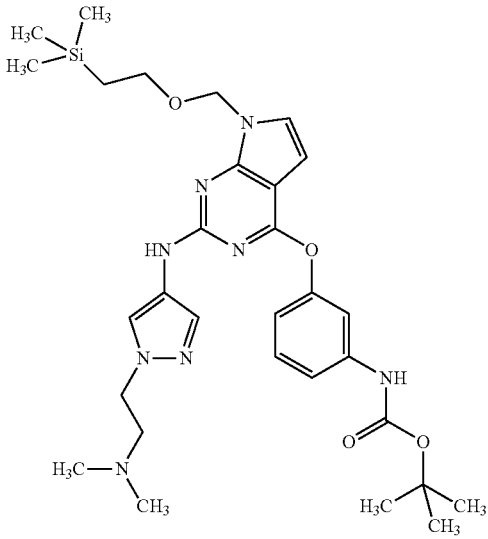 [SMILES: CN(C)CCn1cc(Nc2nc(Oc3cccc(NC(=O)OC(C)(C)C)c3)c3ccn(COCC[Si](C)(C)C)c3n2)cn1]

To a solution of tert-butyl {3-[(2-chloro-7-{[2-(trimethylsilyl)ethoxy]methyl}-7H-pyrrolo[2,3-d]pyrimidin-4-yl)oxy]phenyl}carbamate (300 mg, 0.61 mmol) in 1,4-dioxane (4 mL) in a microwave vial was added 1-[2-(dimethylamino)ethyl]-1H-pyrazol-4-amine (94.1 mg, 0.61 mmol) followed by Cs$_2$CO$_3$ (298 mg, 0.915 mmol), Pd$_2$(dba)$_3$ (8.2 mg, 0.009 mmol) and Xantphos (5.4 mg, 0.009 mmol) and the mixture heated in the microwave to 140° C. for 45 min. The reaction was cooled to rt and brine (20 mL) was added and the mixture was extracted with EtOAc (three×10 mL). The combined extracts were dried over MgSO$_4$, filtered and stripped to give the title compound as a dark oil that was taken on to the next step with no purification. m/z (ESI+) for $C_{30}H_{44}N_8O_4Si$ 609.25 (M+H)$^+$.

Step 4: Preparation of [4-(3-aminophenoxy)-2-({1-[2-(dimethylamino)ethyl]-1H-pyrazol-4-yl}amino)-7H-pyrrolo[2,3-d]pyrimidin-7-yl]methanol

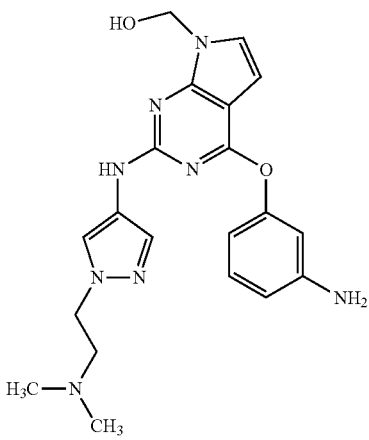 [SMILES: CN(C)CCn1cc(Nc2nc(Oc3cccc(N)c3)c3ccn(CO)c3n2)cn1]

To a solution of tert-butyl (3-{[2-({1-[2-(dimethylamino)ethyl]-1H-pyrazol-4-yl}amino)-7-{[2-(trimethylsilyl)ethoxy]methyl}-7H-pyrrolo[2,3-d]pyrimidin-4-yl]oxy}phenyl)carbamate in DCM (5 mL) was added TFA (3 mL) and stirred at rt for 4 hrs. This was concentrated down to give the title compound as a dark oil that was taken on to the next step with no purification. m/z (ESI+) for $O_{20}H_{24}N_8O_2$ 409.1 (M+H)$^+$.

Step 5: Preparation of 4-(3-aminophenoxy)-N-{1-[2-(dimethylamino)ethyl]-1H-pyrazol-4-yl}-7H-pyrrolo[2,3-d]pyrimidin-2-amine

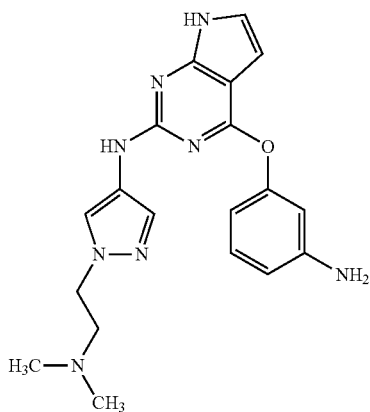 [SMILES: CN(C)CCn1cc(Nc2nc(Oc3cccc(N)c3)c3cc[nH]c3n2)cn1]

To a solution of [4-(3-aminophenoxy)-2-({1-[2-(dimethylamino)ethyl]-1H-pyrazol-4-yl}amino)-7H-pyrrolo[2,3-d]pyrimidin-7-yl]methanol in MeOH (10 mL) and water (2 mL) was added $K_2CO_3$ until the pH of the reaction mixture was about 12. The reaction mixture was then stirred at rt for 2 hrs. Water was added and extracted with EtOAc (three×20 mL), dried with $MgSO_4$, filtered and stripped to a dark oil to give the title compound as a dark oil that was taken on to the next step with no purification. m/z (ESI+) for $C_{19}H_{22}N_8O$ 379.15 (M+H)$^+$.

Step 6: Preparation of N-(3-{[2-({1-[2-(dimethylamino)ethyl]-1H-pyrazol-4-yl}amino)-7H-pyrrolo[2,3-d]pyrimidin-4-yl]oxy}phenyl)prop-2-enamide

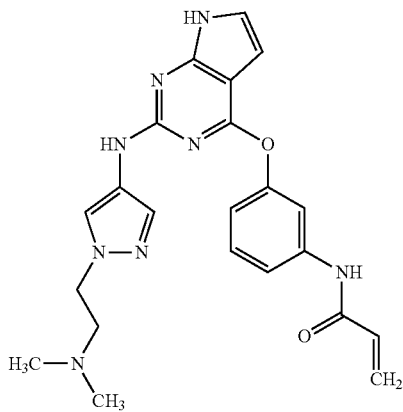 [SMILES: C=CC(=O)Nc1cccc(Oc2nc(Nc3cnn(CCN(C)C)c3)nc3[nH]ccc23)c1]

To a solution of 4-(3-aminophenoxy)-N-{1-[2-(dimethylamino)ethyl]-1H-pyrazol-4-yl}-7H-pyrrolo[2,3-d]pyrimidin-2-amine in THF (5 mL) which was cooled to 10° C. was added prop-2-enoyl chloride (47.8 mg, 0.528 mmol) and stirred at 10° C. for 3 hrs. The volatiles were removed in vacuo and the residue purified by HPLC (Phenominex Gemini C18, 21.2×100 mm, 5 μm column using the water/acetonitrile with 10 mM ammonium acetate, with the flow rate 40 mL/min with gradient 55%-67% acetonitrile in 6 min) which was then lyophilized to afford the title compound (28.5 mg, 11% yield) as a tan solid. $^1$H NMR (600 MHz, DMSO-D6) δ ppm 11.06-11.23 (m, 1H) 9.96-10.08 (m, 1H) 8.56-8.64 (m, 1H) 7.56-7.66 (m, 2H) 7.39-7.47 (m, 2H) 7.30-7.36 (m, 1H) 6.94-7.02 (m, 2H) 6.37-6.47 (m, 1H) 6.18-6.30 (m, 2H) 5.68-5.80 (m, 1H) 3.89-4.04 (m, 2H) 2.57-2.64 (m, 2H) 2.18 (s, 6H). m/z (ESI+) for $C_{22}H_{24}N_8O_2$ 433.2 (M+H)$^+$.

Examples 3 and 4

(Scheme B): Preparation of 1-{(3S,4S)-3-methyl-4-[({2-[1-methyl-1H-pyrazol-4-yl)amino]-7H-pyrrolo[2,3-d]pyrimidin-4-yl}oxy)methyl]pyrrolidin-1-yl}prop-2-en-1-one and 1-{(3R,4R)-3-methyl-4-[({2-[(1-methyl-1H-pyrazol-4-yl)amino]-7H-pyrrolo[2,3-d]pyrimidin-4-yl}oxy)methyl]pyrrolidin-1-yl}prop-2-en-1-one

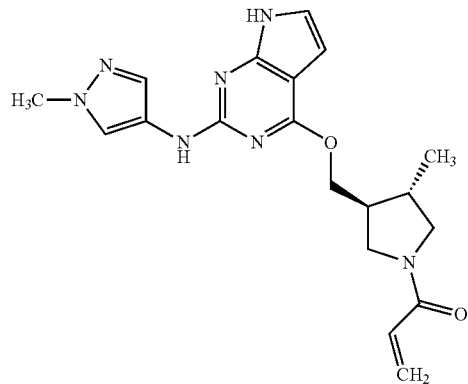

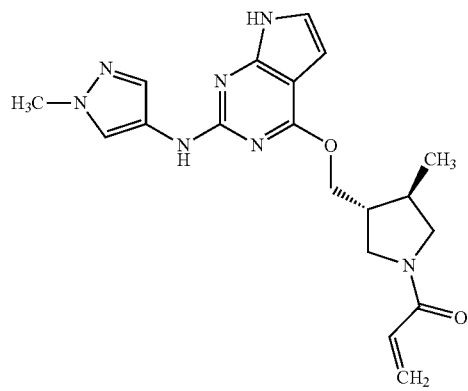

Step 1: Preparation of tert-butyl trans-3-{[(2-chloro-7-{[2-(trimethylsilyl)ethoxy]methyl}-7H-pyrrolo[2,3-d]pyrimidin-4-yl)oxy]methyl}-4-methylpyrrolidine-1-carboxylate

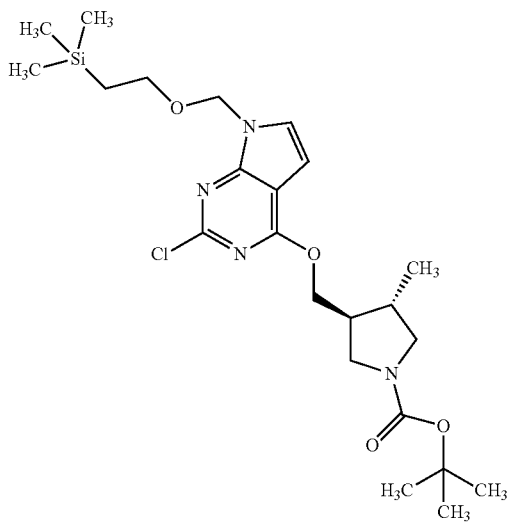 [SMILES: C[C@@H]1CN(C(=O)OC(C)(C)C)C[C@H]1COc1nc(Cl)nc2c1ccn2COCC[Si](C)(C)C]

To a stirred solution of tert-butyl trans-3-(hydroxymethyl)-4-methylpyrrolidine-1-carboxylate (0.58 g, 2.7 mmol) in DMF (15 mL) was added NaH (60% in oil, 162 mg, 4.05 mmol) at 0° C. After stirring at rt for 30 min, 2,4-dichloro-7-{[2-(trimethylsilyl)ethoxy]methyl}-7H-pyrrolo[2,3-d]pyrimidine (0.85 g, 2.7 mmol) was added to the mixture. The resulting mixture was stirred at rt for 1 hr. TLC (petroleum ether/EtOAc=5:1) showed the reaction was complete. The reaction mixture was quenched by water (10 mL) and extracted with EtOAc (two×20 mL). The combined organic layers were washed with brine (four×20 mL), dried over $Na_2SO_4$ and concentrated to yield the title compound (1.34 g, 100% yield) as a brown oil.

Step 2: Preparation of tert-butyl trans-3-methyl-4-{[(2-[(1-methyl-1H-pyrazol-4-yl)amino]-7-{[2-(trimethylsilyl)ethoxy]methyl}-7H-pyrrolo[2,3-d]pyrimidin-4-yl)oxy]methyl}pyrrolidine-1-carboxylate

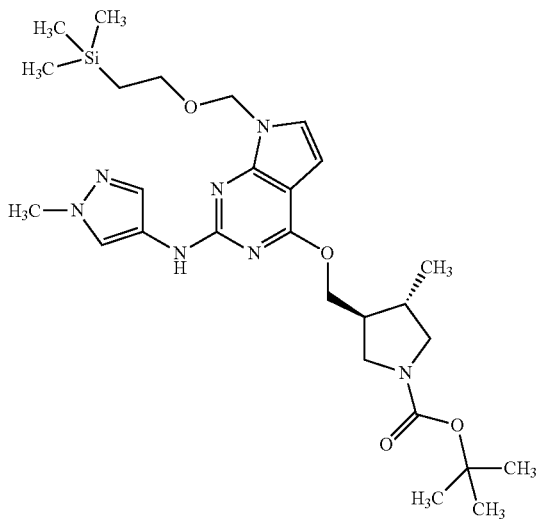 [SMILES: C[C@@H]1CN(C(=O)OC(C)(C)C)C[C@H]1COc1nc(Nc2cnn(C)c2)nc2c1ccn2COCC[Si](C)(C)C]

To a mixture of tert-butyl trans-3-{[(2-chloro-7-{[2-(trimethylsilyl)ethoxy]methyl}-7H-pyrrolo[2,3-d]pyrimidin-4-yl)oxy]methyl}-4-methylpyrrolidine-1-carboxylate (1.34 g, 2.7 mmol), 1-methyl-1H-pyrazol-4-amine (0.397 g, 4.05 mmol), $Cs_2CO_3$ (2.7 g, 8.4 mmol) and Xantphos (138 mg, 0.27 mmol) in 1,4-dioxane (30 mL) was added $Pd_2(dba)_3$ (247 mg, 0.27 mmol). The reaction was irradiated at 140° C. in three microwave tubes for 1 hr. TLC (petroleum ether/EtOAc=5:1) showed the reaction was complete. The mixture was concentrated and diluted with water (20 mL), then extracted with EtOAc (two×20 mL). The combined organic layers were washed with brine (four×20 mL), dried over $Na_2SO_4$ and concentrated. The residue was purified by Biotage flash chromatography (petroleum ether/EtOAc=1:1, Rf: 0.3) to yield the title compound (0.9 g, 59% yield) as a brown oil. m/z (APCI+) for $C_{27}H_{43}N_7O_4Si$ 558.3 $(M+H)^+$.

Step 3: Preparation of N-(1-methyl-1H-pyrazol-4-yl)-4-{[[trans-4-methylpyrrolidin-3-yl]methoxy}-7-{[2-(trimethylsilyl)ethoxy]methyl}-7H-pyrrolo[2,3-d]pyrimidin-2-amine

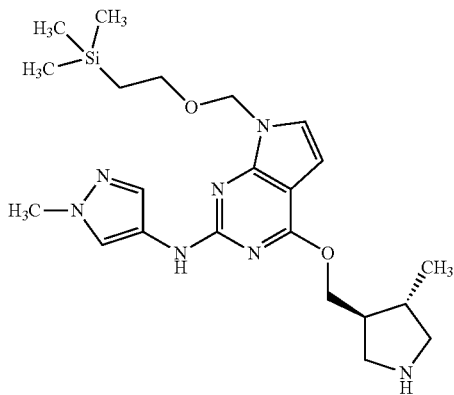 [SMILES: C[C@@H]1CNC[C@H]1COc1nc(Nc2cnn(C)c2)nc2c1ccn2COCC[Si](C)(C)C]

To a solution of tert-butyl trans-3-methyl-4-{[(2-[(1-methyl-1H-pyrazol-4-yl)amino]-7-{[2-(trimethylsilyl)ethoxy]methyl}-7H-pyrrolo[2,3-d]pyrimidin-4-yl)oxy]methyl}pyrrolidine-1-carboxylate (0.9 g, 1.61 mmol) in DCM (20 mL) was added TFA (1.0 mL) dropwise at rt. The mixture was stirred at rt for 12 hrs. TLC (petroleum ether/EtOAc=1:1) showed the reaction was not complete. So TFA (1.0 mL) was added dropwise to the mixture at rt. The mixture was stirred at rt for 2 hrs. TLC (petroleum ether/EtOAc=1:1) showed the reaction was complete. The mixture was concentrated to afford the TFA salt of the title compound (0.9 g, 100% yield) as a brown syrup. m/z (APCI+) for $C_{22}H_{35}N_7O_2Si$ 458.1 $(M+H)^+$.

Step 4: Preparation of 1-[trans-3-methyl-4-{[(2-[(1-methyl-1H-pyrazol-4-yl)amino]-7-{[2-(trimethylsilyl)ethoxy]methyl}-7H-pyrrolo[2,3-d]pyrimidin-4-yl)oxy]methyl}pyrrolidin-1-yl]prop-2-en-1-one

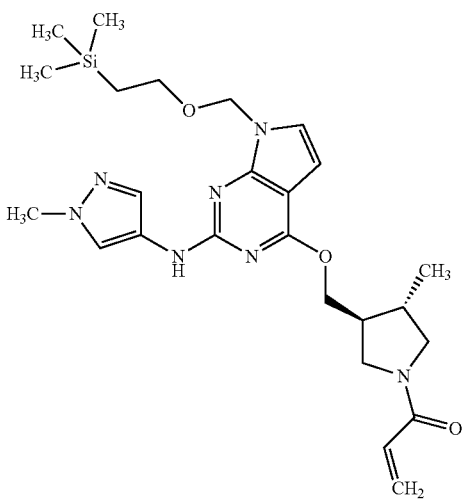 [SMILES: C=CC(=O)N1C[C@@H](COc2nc(Nc3cnn(C)c3)nc3c2ccn3COCC[Si](C)(C)C)[C@H](C)C1]

To a solution of the TFA salt of N-(1-methyl-1H-pyrazol-4-yl)-4-{[trans-4-methylpyrrolidin-3-yl]methoxy}-7-{[2-(trimethylsilyl)ethoxy]methyl}-7H-pyrrolo[2,3-d]pyrimidin-2-amine (0.9 g, 1.61 mmol) in dry DCM (20 mL) were added DIPEA (1.25 g, 9.7 mmol) and acryloyl chloride (144.9 mg, 1.61 mmol) at rt. After the addition, the reaction mixture was stirred at rt for 1 hr. TLC(CH$_2$Cl$_2$/MeOH=10:1) showed the reaction was complete. The reaction mixture was diluted with DCM (10 mL), washed with water (10 mL), brine (10 mL), dried over Na$_2$SO$_4$ and concentrated to yield the title compound (0.82 g, 100% yield) as a brown solid.

Step 5: Preparation of 1-{trans-3-[({7-(hydroxymethyl)-2-[(1-methyl-1H-pyrazol-4-yl)amino-1-7H-pyrrolo[2,3-d]pyrimidin-4-yl}oxy)methyl]-4-methyl pyrrolidin-1-yl}prop-2-en-1-one

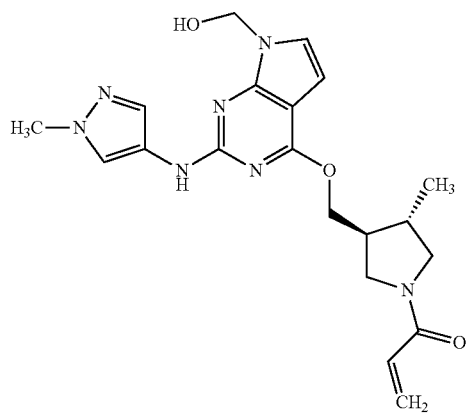 [SMILES: C=CC(=O)N1C[C@@H](COc2nc(Nc3cnn(C)c3)nc3c2ccn3CO)[C@H](C)C1]

To a mixture of 1-[trans-3-methyl-4-{[(2-[(1-methyl-1H-pyrazol-4-yl)amino]-7-{[2-(trimethylsilyl)ethoxy]methyl}-7H-pyrrolo[2,3-d]pyrimidin-4-yl)oxy]methyl}pyrrolidin-1-yl]prop-2-en-1-one (0.82 g, 1.61 mmol) in dry DCM (20 mL) were added BF$_3$.Et$_2$O (2 mL) dropwise at 0° C. After the addition, the reaction mixture was stirred at rt for 1.5 hrs. TLC (petroleum ether/EtOAc=1:1) showed the reaction was complete. The reaction mixture was washed with saturated NaHCO$_3$ (10 mL), brine (10 mL), dried over Na$_2$SO$_4$ and concentrated to yield crude title compound (0.66 g, 100% yield) as a yellow solid. m/z (APCI+) for C$_{20}$H$_{25}$N$_7$O$_3$ 433.9 (M+H)$^+$.

Step 6: Preparation of 1-{(3S,4S)-3-methyl-4-[({2-[(1-methyl-1H-pyrazol-4-yl)amino]-7H-pyrrolo[2,3-d]pyrimidin-4-yl}oxy)methyl]pyrrolidin-1-yl}prop-2-en-1-one and 1-{(3R,4R)-3-methyl-4-[({2-[(1-methyl-1H-pyrazol-4-yl)amino]-7H-pyrrolo[2,3-d]pyrimidin-4-yl}oxy)methyl]pyrrolidin-1-yl}prop-2-en-1-one

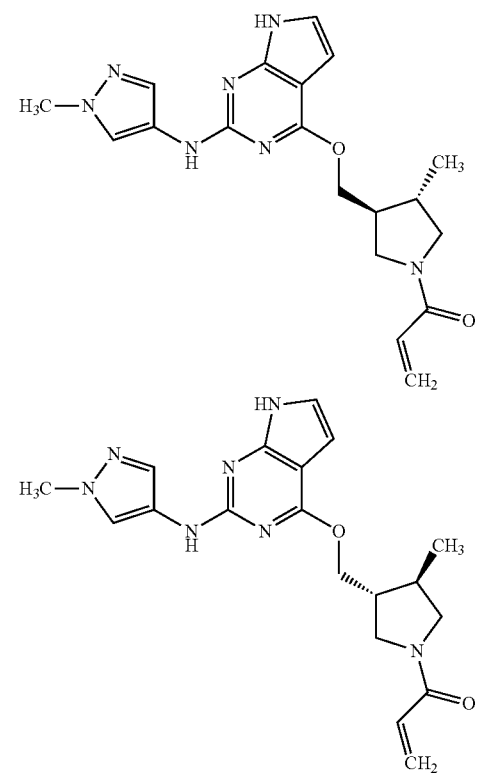

A mixture of 1-{trans-3-[({7-(hydroxymethyl)-2-[(1-methyl-1H-pyrazol-4-yl)amino]-7H-pyrrolo[2,3-d]pyrimidin-4-yl}oxy)methyl]-4-methylpyrrolidin-1-yl}prop-2-en-1-one (0.66 g, 1.61 mmol) and KOH (1 g, 16.1 mmol) in THF (10 mL) and water (1 mL) was stirred at rt overnight. LCMS showed the reaction was almost complete. The mixture was concentrated and DCM (20 mL) was added. The mixture was washed with water (20 mL), brine (20 mL), dried over Na$_2$SO$_4$ and concentrated. The residue was purified by chiral preparative HPLC to give a clean mix of isomers as formic acid salts (200 mg, 32.6% yield) as a yellow solid. Secondary chiral preparative HPLC isomer separation yielded trans single isomers:

Isomer 1: 1-{(3S,4S)-3-methyl-4-[({2-[(1-methyl-1H-pyrazol-4-yl)amino]-7H-pyrrolo[2,3-d]pyrimidin-4-yl}oxy)methyl]pyrrolidin-1-yl}prop-2-en-1-one $^1$H NMR (400 MHz, DMSO-D6): δ ppm 11.32 (brs, 1H), 8.91 (s, 1H), 7.89 (s, 1H), 7.53 (s, 1H), 6.93-6.92 (s, 1H), 6.61-6.55 (m, 1H), 6.28-6.11 (m, 2H), 5.69-5.65 (m, 1H), 4.56-4.44 (m, 2H), 3.91-3.77 (m, 2H), 3.87 (s, 3H), 3.28-3.18 (m, 2H), 2.40-2.10 (m, 2H), 1.12-1.11 (d, 3H). m/z (APCI+) for $C_{19}H_{23}N_7O_2$ 404.0 (M+Na)$^+$.

Isomer 2: 1-{(3R,4R)-3-methyl-4-[({2-[(1-methyl-1H-pyrazol-4-yl)amino]-7H-pyrrolo[2,3-d]pyrimidin-4-yl}oxy)methyl]pyrrolidin-1-yl}prop-2-en-1-one $^1$H NMR (400 MHz, DMSO-D6): δ ppm 11.32 (brs, 1H), 8.91 (s, 1H), 7.89 (s, 1H), 7.53 (s, 1H), 6.93-6.92 (s, 1H), 6.61-6.55 (m, 1H), 6.28-6.11 (m, 2H), 5.69-5.65 (m, 1H), 4.56-4.44 (m, 2H), 3.91-3.77 (m, 2H), 3.87 (s, 3H), 3.28-3.18 (m, 2H), 2.40-2.10 (m, 2H), 1.12-1.11 (d, 3H). m/z (APCI+) for $C_{19}H_{23}N_7O_2$ 404.0 (M+Na)$^+$.

Example 5

(Scheme B): Preparation of N-[cis-3-({5-cyano-2-[(1-methyl-1H-pyrazol-4-yl)amino]-7H-pyrrolo[2,3-d]pyrimidin-4-yl}oxy)cyclobutyl]prop-2-enamide

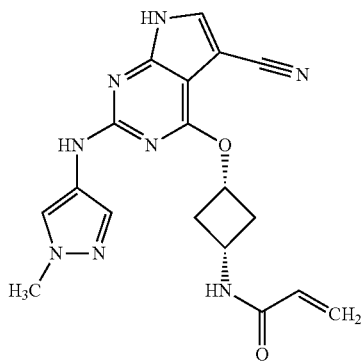 [SMILES: C=CC(=O)N[C@H]1C[C@@H](Oc2nc(Nc3cnn(C)c3)nc3[nH]cc(C#N)c23)C1]

Step 1: Preparation of 2,4-dichloro-5-iodo-7-{[2-(trimethylsilyl)ethoxy]methyl}-7H-pyrrolo[2,3-d]pyrimidine

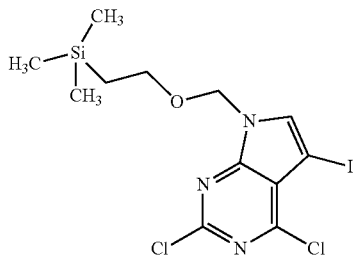 [SMILES: C[Si](C)(C)CCOCn1cc(I)c2c(Cl)nc(Cl)nc21]

To a reaction vial was added 2,4-dichloro-7-{[2-(trimethylsilyl)ethoxy]methyl}-7H-pyrrolo[2,3-d]pyrimidine (2.55 g, 8.0 mmol), NIS (2.2 g, 9.6 mmol, 1.2 mol eq) and DMF (14 mL), as prepared in Example 2, step 1. The resulting solution was stirred and heated to 80° C. (block temperature) for 6 hrs. The volatiles were removed to give a residue. The residue was partitioned between saturated aqueous NaHCO$_3$ (30 mL) and EtOAc (200 mL) and the organic layer was separated, washed with water (20 mL) and brine (20 mL), dried over Na$_2$SO$_4$ and evaporated to give a dark residue (3.9 g). Water (30 mL) was added and the resulting suspension was stirred at rt for 16 hrs. The light pink solid was collected by filtration, washed with water (30 mL) and dried to give the title compound (3.33 g, 94% yield) as light pink solid. $^1$H NMR (400 MHz, DMSO-d6) δ ppm 8.22 (s, 1H) 5.62 (s, 2H) 3.56-3.64 (m, 2H) 0.86-0.96 (m, 2H) 0.00 (s, 9H). m/z (APCI+) for $C_{12}H_{16}Cl_2IN_3OSi$ 443.9 (M+H)$^+$.

Step 2: Preparation of 2,4-dichloro-7-{[2-(trimethylsilyl)ethoxy]methyl}-7H-pyrrolo[2,3-d]pyrimidine-5-carbonitrile

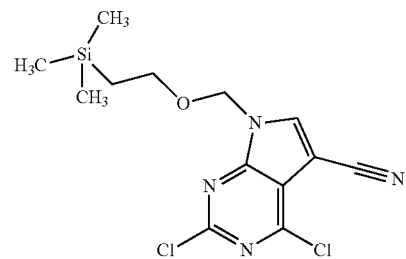 [SMILES: C[Si](C)(C)CCOCn1cc(C#N)c2c(Cl)nc(Cl)nc21]

To a solution of LiCl (dry, 5.3 g, 126 mmol) in THF (150 mL) was added iPrMgCl (63 mL of 2 M in THF, 126 mmol). After stirring for 15 min, the mixture was cooled to −78° C. and 2,4-dichloro-5-iodo-7-{[2-(trimethylsilyl)ethoxy]methyl}-7H-pyrrolo[2,3-d]pyrimidine (31 g, 4.5 mmol) was added dropwise as a solution in THF (50 mL). After stirring for 20 min, a solution of tosyl cyanide (19.8 g, 100 mmol) in THF (50 mL) was added dropwise. The mixture was stirred at −78° C. for 30 min. The reaction was quenched with HOAc (20 mL) and after stirring at −78° C. for 15 min, water (200 mL) and EtOAc (200 mL) were added. The organic layer was separated, and the aqueous layer was further extracted with EtOAc (two×150 mL). The combined organic extracts were washed with brine, dried over MgSO$_4$ and concentrated in vacuo to give the crude product. After sitting as a concentrate in EtOAc overnight, crystals formed which were collected to afford 3.8 grams 90% purity by $^1$H NMR. The filtrate was purified via flash chromatography to afford the title compound (12 g). The combined yield was 15.8 grams (66% yield) as a white solid. $^1$H NMR (400 MHz, chloroform-d) 0.00 (s, 9H), 0.91-1.01 (m, 2H), 3.53-3.66 (m, 2H), 5.65 (s, 2H), 7.94 (s, 1H).

Step 3: Preparation of tert-butyl {3-[(2-chloro-5-cyano-7-{[2-(trimethylsilyl)ethoxy]methyl}-7H-pyrrolo[2,3-d]pyrimidin-4-yl)oxy]cyclobutyl}carbamate

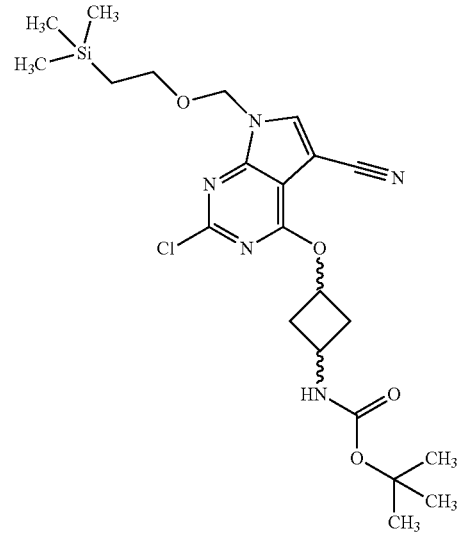 [SMILES: CC(C)(C)OC(=O)NC1CC(Oc2nc(Cl)nc3c2c(C#N)cn3COCC[Si](C)(C)C)C1]

To a solution of 2,4-dichloro-7-{[2-(trimethylsilyl)ethoxy]methyl}-7H-pyrrolo[2,3-d]pyrimidine-5-carbonitrile (481 mg, 1.4 mmol) in THF (12 mL) was added a 1:1 cis:trans mixture of tert-butyl (3-hydroxycyclobutyl)carbamate (see Radchenko et al., *Journal of Organic Chemistry*, 75(17): 5941-5952 (2010)) (288 mg, 1.54 mmol) and KHMDS (419 mg, 2.1 mmol). The reaction solution was stirred at rt for 1 hr. The reaction was quenched with brine (5 mL), then partitioned between EtOAc (120 mL) and water (30 mL). The organic layer was separated, washed with brine (20 mL), dried over $Na_2SO_4$ and evaporated to give a light yellow gum. The gum was purified using flash chromatography eluting with a gradient of 0%-40% EtOAc in heptanes. The product fractions were combined and evaporated to afford the title compound (508 mg, 73 yield) as a solid. $^1$H NMR (400 MHz, DMSO-d6) δ ppm 8.64 (s, 1H) 7.27-7.52 (m, 1H) 5.63 (s, 2H) 5.04-5.60 (m, 1H) 3.73-4.32 (m, 1H) 3.53-3.69 (m, 2H) 2.88 (m, J=9.35, 6.91, 6.91, 3.02 Hz, 1H) 2.50-2.56 (m, 2H) 2.13-2.28 (m, 1H) 1.46 (d, J=4.78 Hz, 9H) 0.92 (t, J=8.06 Hz, 2H) 0.00 (d, J=1.51 Hz, 9H). m/z (APCI+) for $C_{22}H_{32}ClN_5O_4Si$ 440.0 (M−$^t$Bu+H)+.

Step 4: Preparation of tert-butyl {3-[(5-cyano-2-[(1-methyl-1H-pyrazol-4-yl)amino]-7-{[2-(trimethylsilyl)ethoxy]methyl}-7H-pyrrolo[2,3-d]pyrimidin-4-yl)oxy]cyclobutyl}carbamate

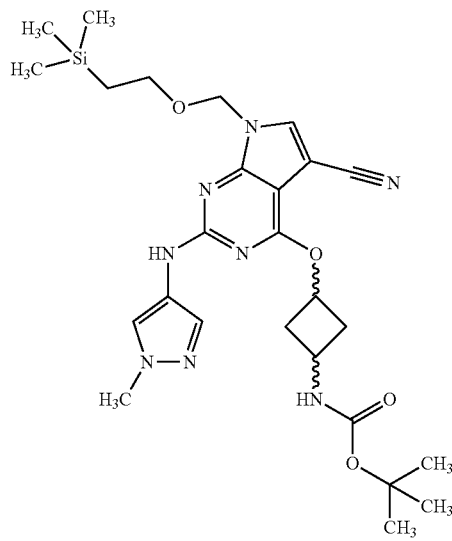 [SMILES: Cn1cc(Nc2nc(OC3CC(NC(=O)OC(C)(C)C)C3)c3c(C#N)cn(COCC[Si](C)(C)C)c3n2)cn1]

To a microwave reaction vial was added tert-butyl {3-[(2-chloro-5-cyano-7-{[2-(trimethylsilyl)ethoxy]methyl}-7H-pyrrolo[2,3-d]pyrimidin-4-yl)oxy]cyclobutyl}carbamate (508 mg, 1.0 mmol), 1-methyl-1H-pyrazol-4-amine (110 mg, 1.1 mmol), 1,4-dioxane (10 mL), $Cs_2CO_3$ (670 mg, 2.1 mmol, 2 mol eq), Xantphos (62 mg, 0.1 mmol) and $Pd_2(dba)_3$ (94 mg, 0.1 mmol). The reaction vial was flushed with nitrogen, capped, stirred and heated to 140° C. in a Biotage microwave reactor for 1 hr and 45 min. The reaction was diluted with EtOAc (120 mL) and water (20 mL). The organic layer was separated, washed with water (20 mL), brine (10 mL), and dried over $Na_2SO_4$. After concentrating the extract to dryness, the product was purified via flash chromatography eluting with a gradient of 0%-60% EtOAc in heptanes to afford the title compound (480 mg, 84 yield) as a light yellow solid. 1:1 cis:trans mixture: $^1$H NMR (400 MHz, DMSO-d6) δ ppm 9.42 (s, 1H) 8.11 (s, 1H) 7.96 (br. s., 1H) 7.49-7.60 (m, 1H) 7.20-7.46 (m, 1H) 5.53 (br. s., 2H) 4.11-5.13 (m, 1H) 3.82 (s, 3H) 3.56 (t, J=7.55 Hz, 2H) 2.83 (d, J=6.80 Hz, 1H) 2.39-2.48 (m, 2H) 2.02-2.16 (m, 1H) 1.39 (d, J=5.54 Hz, 9H) 0.84 (t, J=8.06 Hz, 2H) −0.12 (br. s., 9H). m/z (APCI+) for $C_{26}H_{38}N_8O_4Si$ 555.1 (M+H)+.

Step 5: Preparation of 4-[(3-aminocyclobutyl)oxy]-2-[(1-methyl-1H-pyrazol-4-yl)amino]-7-{[2-(trimethylsilyl)ethoxy]methyl}-7H-pyrrolo[2,3-d]pyrimidine-5-carbonitrile

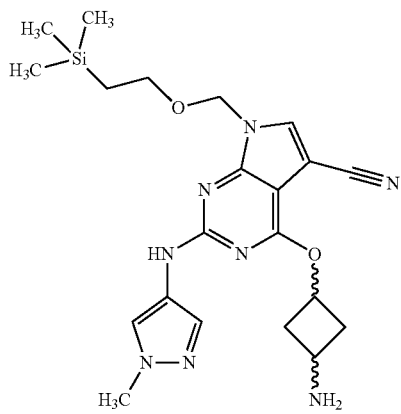 [SMILES: Cn1cc(Nc2nc(OC3CC(N)C3)c3c(C#N)cn(COCC[Si](C)(C)C)c3n2)cn1]

To a solution of tert-butyl {3-[(5-cyano-2-[(1-methyl-1H-pyrazol-4-yl)amino]-7-{[2-(trimethylsilyl)ethoxy]methyl}-7H-pyrrolo[2,3-d]pyrimidin-4-yl)oxy]cyclobutyl}carbamate (cis:trans (1:1), 470 mg, 0.85 mmol) in DCM (20 mL) was added HCl (0.85 mL of 4 M in 1,4-dioxane, 3.4 mmol). After 20 hrs, the volatiles were removed and the reaction mixture was partitioned between DCM (50 mL) and saturated aqueous $NaHCO_3$ (20 mL). The organic layer was separated, dried over $Na_2SO_4$ and evaporated to give the title compound (380 mg, 99% yield) as a 1:1 cis:trans isomeric mixture. $^1$H NMR (400 MHz, DMSO-d6) δ ppm 9.41 (d, J=12.59 Hz, 1H) 8.10 (s, 1H) 7.96 (br. s., 1H) 7.55 (s, 1H) 5.53 (br. s., 2H) 3.82 (s, 3H) 3.61-3.73 (m, 1H) 3.52-3.60 (m, 4H) 3.04 (br. s., 1H) 2.71-2.85 (m, 1H) 2.15-2.40 (m, 2H) 1.76-1.92 (m, 1H) 0.76-0.91 (m, 1H) −0.12 (br. s., 9H). m/z (APCI+) for $C_{21}H_{30}N_8O_2Si$ 455.1 (M+H)+.

Step 6: Preparation of N-{3-[(5-cyano-2-[(1-methyl-1H-pyrazol-4-yl)amino]-7-{[2-(trimethylsilyl)ethoxy]methyl}-7H-pyrrolo[2,3-d]pyrimidin-4-yl)oxy]cyclobutyl}prop-2-enamide

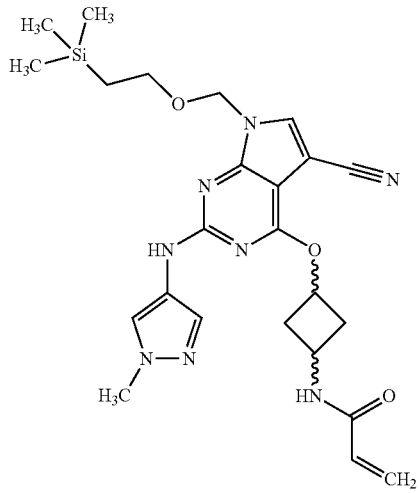 [SMILES: C=CC(=O)NC1CC(Oc2nc(Nc3cnn(C)c3)nc3c2c(C#N)cn3COCC[Si](C)(C)C)C1]

To a solution of 4-[(3-aminocyclobutyl)oxy]-2-[(1-methyl-1H-pyrazol-4-yl)amino]-7-{[2-(trimethylsilyl)ethoxy]methyl}-7H-pyrrolo[2,3-d]pyrimidine-5-carbonitrile (cis:trans 1:1) (380 mg, 0.84 mmol) in DCM (10 mL) was added acryloyl chloride (68 µL, 0.84 mmol) and DIPEA (146 µL, 0.84 mmol). The reaction solution was stirred at rt for 10 min. The reaction mixture was partitioned between DCM (50 mL) and saturated aqueous NaHCO$_3$ (20 mL). The organic layer was separated, dried over Na$_2$SO$_4$ and evaporated. The product was purified via flash chromatography eluting with a gradient of 0%-100% EtOAc in heptanes to give the title compound (317 mg, 75% yield) as a 1:1 cis:trans isomeric mixture. $^1$H NMR (400 MHz, DMSO-d6) δ ppm 9.43 (s, 1H) 8.42-8.63 (m, 1H) 8.11 (s, 1H) 7.96 (br. s., 1H) 7.43-7.62 (m, 1H) 6.00-6.31 (m, 2H) 5.61 (ddd, J=9.69, 7.05, 2.64 Hz, 3H) 4.07-5.26 (m, 2H) 3.81 (d, J=5.79 Hz, 3H) 3.56 (t, J=7.93 Hz, 2H) 2.84-2.99 (m, 1H) 2.51-2.58 (m, 2H) 2.08-2.20 (m, 1H) 0.84 (t, J=8.06 Hz, 2H) −0.12 (br. s., 9H). m/z (APCI+) for C$_{24}$H$_{32}$N$_8$O$_3$Si 509.1 (M+H)$^+$.

Step 7: Preparation of N-[cis-3-({5-cyano-2-[(1-methyl-1H-pyrazol-4-yl)amino]-7H-pyrrolo[2,3-d]pyrimidin-4-yl}oxy)cyclobutyl]prop-2-enamide

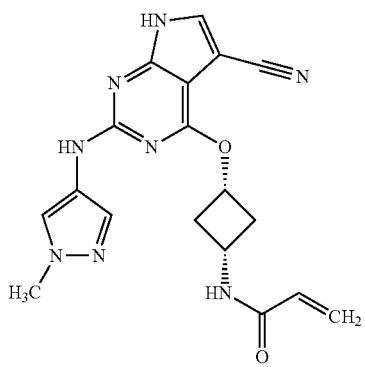 [SMILES: C=CC(=O)N[C@H]1C[C@@H](Oc2nc(Nc3cnn(C)c3)nc3[nH]cc(C#N)c23)C1]

To a solution of a 1:1 isomeric mixture of cis:trans N-{3-[(5-cyano-2-[(1-methyl-1H-pyrazol-4-yl)amino]-7-{[2-(trimethylsilyl)ethoxy]methyl}-7H-pyrrolo[2,3-d]pyrimidin-4-yl)oxy]cyclobutyl}prop-2-enamide in DCM (10 mL) was added TFA (1.9 mL). The solution was stirred at rt for 5 hrs and the solvents were removed. EtOH (20 mL), water (5 mL), and K$_2$CO$_3$ (424 mg) were added and the reaction mixture was stirred at rt for 30 min. The volatiles were removed to give a pale yellow solid. Water (20 mL) was added and the solid that precipitated out was collected by filtration, washed with water (5 mL) and dried to afford (185.6 mg, 80% yield) of N-[3-({5-cyano-2-[(1-methyl-1H-pyrazol-4-yl)amino]-7H-pyrrolo[2,3-d]pyrimidin-4-yl}oxy)cyclobutyl]prop-2-enamide as a pale yellow solid (cis:trans mixture 1:1). $^1$H NMR (400 MHz, DMSO-d6) δ ppm 8.66-9.47 (m, 1H) 8.58 (br. s., 1H) 7.84-8.08 (m, 1H) 7.74 (d, J=6.29 Hz, 1H) 7.48 (d, J=11.58 Hz, 1H) 5.99-6.34 (m, 2H) 5.40-5.71 (m, 2H) 4.06-5.20 (m, 2H) 3.71-3.90 (m, 3H) 2.90 (br. s., 1H) 2.12 (br. s., 1H). m/z (APCI+) for C$_{18}$H$_{18}$N$_8$O$_2$ 379.1 (M+H)$^+$. The cis/trans mixture (148 mg, 0.39 mmol) was subjected to further purification using supercritical fluid chromatography to separate the isomers: 64 mg of peak 1 and 60 mg of peak 2 was recovered from this separation. $^1$H NMR analysis of both peaks revealed that peak 1 corresponded to the cis isomer: $^1$H NMR (400 MHz, DMSO-d6) δ ppm 12.29 (br. s., 1H) 9.16 (s, 1H) 8.50 (d, J=7.81 Hz, 1H) 7.90 (s, 1H) 7.86 (s, 1H) 7.54 (s, 1H) 6.01-6.27 (m, 2H) 5.53-5.70 (m, 1H) 5.13 (quin, J=6.92 Hz, 1H) 4.13 (sxt, J=7.76 Hz, 1H) 3.82 (s, 3H) 2.82-2.99 (m, 2H) 2.04-2.21 (m, 2H). m/z (APCI+) for C$_{18}$H$_{18}$N$_8$O$_2$ 379.1 (M+H)$^+$.

Example 6

(Scheme B): Preparation of N-[trans-3-({2-[(1-methyl-1H-pyrazol-4-yl)amino]-7H-pyrrolo[2,3-d]pyrimidin-4-yl}amino)cyclobutyl]prop-2-enamide

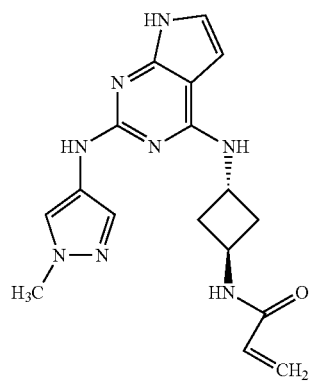 [SMILES: C=CC(=O)N[C@H]1C[C@H](Nc2nc(Nc3cnn(C)c3)nc3[nH]ccc23)C1]

Step 1: Preparation of tert-butyl((trans)-3-((2-chloro-7-((2-(trimethylsilyl)ethoxy)methyl)-7H-pyrrolo[2,3-d]pyrimidin-4-yl)amino)cyclobutyl)carbamate

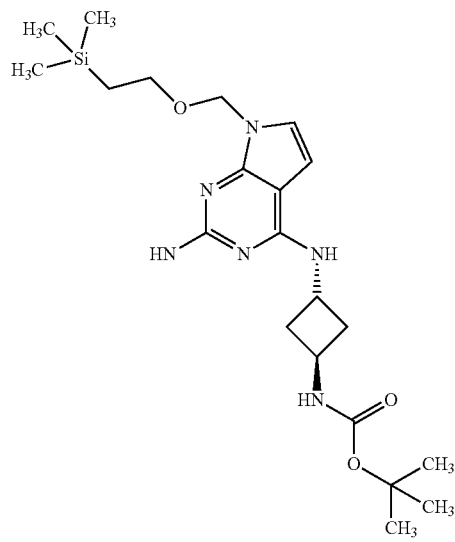

To a mixture of 2,4-dichloro-7-((2-(trimethylsilyl)ethoxy)methyl)-7H-pyrrolo[2,3-d]pyrimidine (342 mg, 1.07 mmol), as prepared in Example 2, step 1, and tert-butyl((trans)-3-aminocyclobutyl)carbamate (200 mg, 1.07 mmol) in iPrOH (4 mL) was added DIPEA (0.5 mL). A stir bar was added to the reaction vessel and it was capped and heated in a reaction block at 70° C. for 2 hrs. The solvent was removed and the product was purified via flash chromatography eluting with a gradient of 12%-100% EtOAc in heptanes to afford the title compound (260 mg, 52% yield) as a pink solid.

Step 2: Preparation of tert-butyl((trans)-3-((2-((1-methyl-1H-pyrazol-4-yl)amino)-7-((2-(trimethylsilyl)ethoxy)methyl)-7H-pyrrolo[2,3-d]pyrimidin-4-yl)amino)cyclobutyl)carbamate

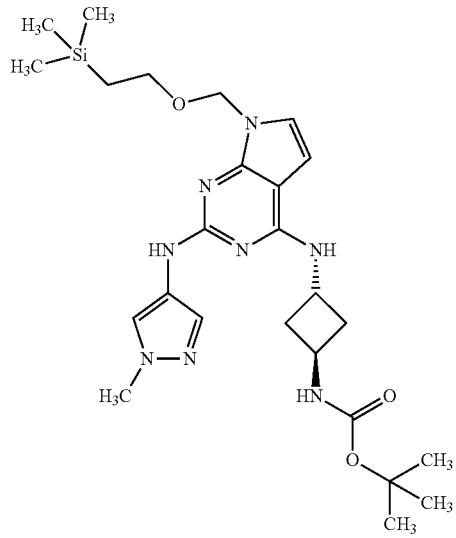

A microwave tube fitted with a stir bar was charged with tert-butyl((trans)-3-((2-chloro-7-((2-(trimethylsilyl)ethoxy)methyl)-7H-pyrrolo[2,3-d]pyrimidin-4-yl)amino)cyclobutyl)carbamate (260 mg, 0.55 mmol), 1,4-dioxane (3 mL), $Cs_2CO_3$ (452 mg, 1.4 mmol), $Pd_2(dba)_3$ (16 mg, 0.03 mmol), Xantphos (34 mg, 0.056 mmol) and 1-methyl-1H-pyrazol-4-amine (60 mg, 0.58 mmol). The tube was flushed with nitrogen gas and heated at 140° C. in a Biotage microwave reactor for 40 min. The product was purified via flash chromatography eluting with a gradient of 30%-100% EtOAc in heptanes to afford the title compound (115 mg, 39% yield) as an orange foam.

Step 3: Preparation of $N^4$-((trans)-3-aminocyclobutyl)-$N^2$-(1-methyl-1H-pyrazol-4-yl)-7-((2-(trimethylsilyl)ethoxy)methyl)-7H-pyrrolo[2,3-d]pyrimidine-2,4-diamine

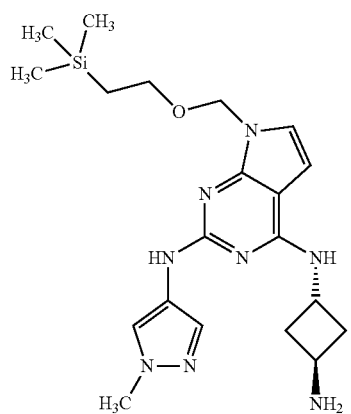

To tert-butyl((trans)-3-((2-((1-methyl-1H-pyrazol-4-yl)amino)-7-((2-(trimethylsilyl)ethoxy)methyl)-7H-pyrrolo[2,3-d]pyrimidin-4-yl)amino)cyclobutyl)carbamate (115 mg, 0.218 mmol) in DCM (5 mL) was added 4 N HCl in 1,4-dioxane (0.3 mL, 1.2 mmol). The reaction was allowed to stir at rt for 3.5 hrs and then quenched with saturated aqueous $NaHCO_3$ (2 mL). DCM (10 mL) was added and the DCM extract was dried over $MgSO_4$, filtered and concentrated to afford the title compound (87 mg, 93% yield) as a tan foam.

Step 4: Preparation of N-{trans-3-[(2-[(1-methyl-1H-pyrazol-4-yl)amino]-7-{[2-(trimethylsilyl)ethoxy]methyl}-7H-pyrrolo[2,3-d]pyrimidin-4-yl)amino]cyclobutyl}prop-2-enamide

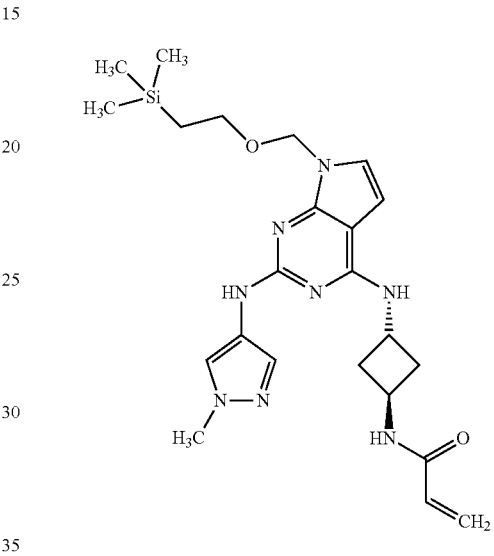

$N^4$-((trans)-3-aminocyclobutyl)-$N^2$-(1-methyl-1H-pyrazol-4-yl)-7-((2-(trimethylsilyl)ethoxy)methyl)-7H-pyrrolo[2,3-d]pyrimidine-2,4-diamine (87 mg, 0.2 mmol) was dissolved in DCM (5 mL). DIPEA (53 µL, 0.3 mmol) was added and the reaction was cooled to 0° C. Acryloyl chloride (16 µL, 0.2 mmol) was added via a 10 µL syringe and the reaction was allowed to stir at 0° C. for 1 hr. The reaction was concentrated and purified via flash chromatography eluting with a gradient of 1%-20% EtOH in DCM. The fractions containing the product were pooled and dried down to afford the title compound as a tan solid (confirmed to be product by LCMS). This tan solid was taken directly to the final step.

Step 5: Preparation of N-[trans-3-({2-[(1-methyl-1H-pyrazol-4-yl)amino]-7H-pyrrolo[2,3-d]pyrimidin-4-yl}amino)cyclobutyl]prop-2-enamide

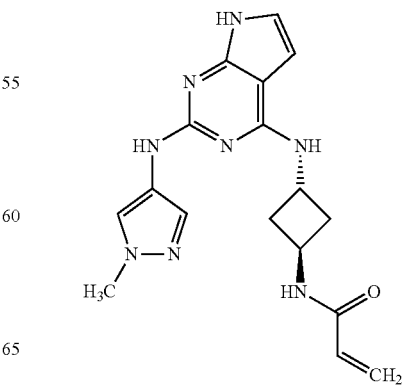

N-{trans-3-[(2-[(1-methyl-1H-pyrazol-4-yl)amino]-7-{[2-(trimethylsilyl)ethoxy]methyl}-7H-pyrrolo[2,3-d]pyrimidin-4-yl)amino]cyclobutyl}prop-2-enamide (18 mmol) was dissolved in DCM (5 mL) and TFA (0.5 mL) was added. After stirring for 3 hrs, the solvents were removed and chromatography eluting with a gradient of 2%-20% EtOH in DCM to afford N-[trans-3-({7-(hydroxymethyl)-2-[(1-methyl-1H-pyrazol-4-yl)amino]-7H-pyrrolo[2,3-d]pyrimidin-4-yl}amino)cyclobutyl]prop-2-enamide. To this N-hydroxymethyl intermediate, was added EtOH (5 mL) and $K_2CO_3$ (100 mg) dissolved in water (2.5 mL). The reaction was allowed to stir for 6 hrs and the solvents were removed. Water (3 mL) was added and the product was extracted into 2-methyl-THF (four×3 mL). After drying the organic extract over $MgSO_4$, filtering, and concentrating, the white residue was carefully precipitated from DCM/MeOH/heptane (1:1:1) to afford the title compound (16 mg, 26% yield). $^1$H NMR (400 MHz, DMSO-d6) δ ppm 10.8 (br. s., 1H), 8.52 (d, J=6.80 Hz, 1H), 8.32 (s, 1H), 7.86 (s, 1H), 7.45 (s, 1H), 6.87 (s, 1H), 6.72 (br. s., 1H), 6.64 (s, 1H), 6.18-6.29 (m, 1H), 6.12 (d, J=1.76 Hz, 1H), 5.60 (dd, J=10.07, 2.01 Hz, 1H), 4.68 (d, J=6.29 Hz, 1H), 4.40 (d, J=6.55 Hz, 1H), 2.37 (br. s., 3H), 2.18 (s, 2H). m/z (APCI+) for $C_{17}H_{20}N_8O$ 353.1 (M+H)$^+$.

Example 7

(Scheme C): Preparation of N-{3-[(2-{[1-(1-methylpyrrolidin-3-yl)-1H-pyrazol-4-yl]amino}-9H-purin-6-yl)oxy]phenyl}prop-2-enamide

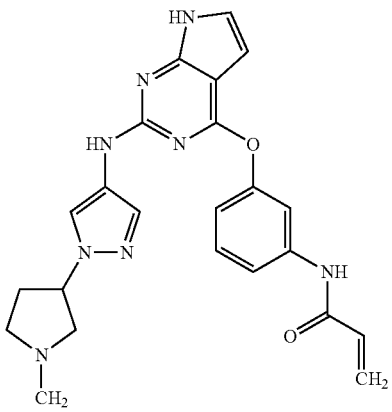 [SMILES: C=CC(=O)Nc1cccc(Oc2nc(Nc3cnn(C4CCN(C)C4)c3)nc3[nH]ccc23)c1]

Step 1: Preparation of 2,6-dichloro-9-{[2-(trimethylsilyl)ethoxy]methyl}-9H-purine

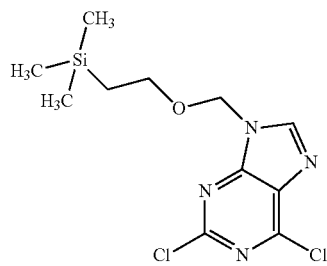 [SMILES: C[Si](C)(C)CCOCn1cnc2c(Cl)nc(Cl)nc21]

A solution of 2,6-dichloropurine (4.0 g, 21 mmol) in DMF (100 mL) was cooled to 0° C. NaH (1.69 g, 42.3 mmol, 60% dispersion in mineral oil) was added, and the mixture was stirred at rt for 30 min. The reaction was again cooled to 0° C., and SEM-Cl (5.29 g, 31.7 mmol) was added. The reaction was stirred at rt for 1 hr, at which point LCMS showed complete consumption of starting material. Water was added slowly, and the mixture was extracted with EtOAc (three times). The combined organics were washed with water (three times) and brine, dried over $Mg_2SO_4$, and filtered. The filtrate was concentrated, and the crude material was purified by flash chromatography on a Biotage 40M column; eluted with 0%-20% EtOAc/heptane to afford the title compound (3.82 g, 57% yield) as a pale yellow oil. $^1$H NMR (400 MHz, chloroform-d) δ ppm 8.26 (s, 1H) 5.64 (s, 2H) 3.61-3.67 (m, 2H) 0.92-1.00 (m, 2H) −0.01 (s, 9H).

Step 2: Preparation of N-{3-[(2-chloro-9-{[2-(trimethylsilyl)ethoxy]methyl}-9H-purin-6-yl)oxy]phenyl}prop-2-enamide

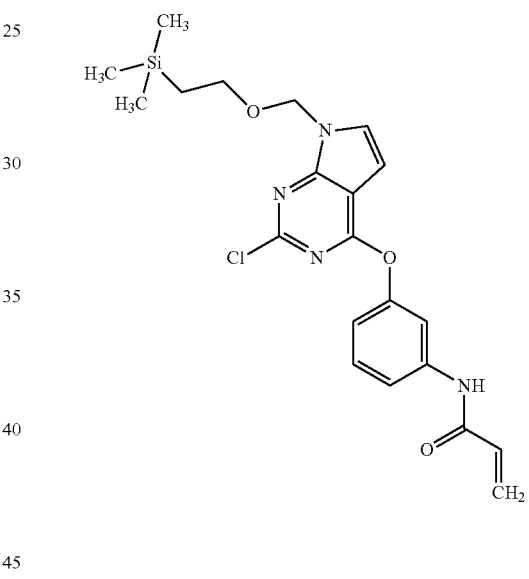

To a solution of 2,6-dichloro-9-{[2-(trimethylsilyl)ethoxy]methyl}-9H-purine (1.78 g, 5.58 mmol) and N-(3-hydroxyphenyl)prop-2-enamide (1.00 g, 6.13 mmol) in DMF (28 mL) was added $K_2CO_3$ (2.34 g, 16.7 mmol). The reaction was heated to 60° C. for 30 min, at which point LCMS showed consumption of starting material. The mixture was cooled to rt and partitioned between water and EtOAc. The layers were separated, and the aqueous layer was extracted with EtOAc twice more. The combined organics were washed with water (three times) and brine, dried over $Mg_2SO_4$, and filtered. The filtrate was concentrated, and the crude material was purified by flash chromatography on a Biotage 40M column; product was eluted with 0%-40% EtOAc/heptane to yield the title compound (2.10 g, 85% yield) as a white solid. $^1$H NMR (400 MHz, DMSO-d6) δ ppm 10.35 (s, 1H) 8.69 (s, 1H) 7.74 (t, J=2.02 Hz, 1H) 7.50-7.56 (m, 1H) 7.41-7.48 (m, 1H) 7.05 (ddd, J=7.96, 2.27, 0.88 Hz, 1H) 6.39-6.50 (m, 1H) 6.22-6.32 (m, 1H) 5.75-5.81 (m, 1H) 5.62 (s, 2H) 3.57-3.66 (m, 2H)

0.84-0.91 (m, 2H) −0.05 (s, 9H). m/z (APCI+) for C$_{20}$H$_{24}$ClN$_5$O$_3$Si 446.00 (M+H)$^+$.

Step 3: Preparation of 1-(1-methylpyrrolidin-3-yl)-1H-pyrazol-4-amine

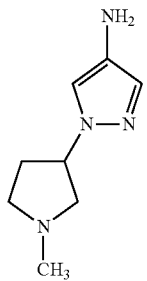

A reaction flask containing a suspension of LAH (499 mg, 13.2 mmol) in THF (22 mL) was evacuated and back-filled with nitrogen three times. A solution of tert-butyl 3-(4-amino-1H-pyrazol-1-yl)pyrrolidine-1-carboxylate (830 mg, 3.3 mmol) in THF (11 mL) was added dropwise, via an addition funnel and the reaction mixture was stirred at rt under nitrogen overnight. The reaction was quenched sequentially with water (1 mL), 1N NaOH (1 mL), and water (3 mL) to afford a suspension. The precipitate was filtered off and washed with ethyl acetate. The combined filtrates were diluted with a small amount of water and transferred to a separatory funnel. The layers were separated, and the aqueous layer was extracted with ethyl acetate. The organics were combined and concentrated to give crude material (137 mg). To recover product in the aqueous layer, the aqueous extraces were lyophilized to give a solid residue. This was suspended in EtOAc and filtered. The filtrate was evaporated to give additional crude material (287 mg). The combined crude was purified via Biotage flash chromatography (25S column, eluting with 7 N NH$_3$/MeOH in DCM (1%-4%)) to give the title compound (279 mg, 51% yield). m/z (APCI+) for C$_8$H$_{14}$N$_4$ 167.2 (M+H)$^+$. $^1$H NMR (400 MHz, DMSO-d6) δ ppm 1.89-2.00 (m, 1H) 2.20-2.31 (m, 1H) 2.26 (s, 3H) 2.42 (td, J=8.40, 6.19 Hz, 1H) 2.60 (dd, J=9.60, 4.80 Hz, 1H) 2.64-2.77 (m, 2H) 3.79 (br. s., 2H) 4.67 (m, J=9.44, 7.23, 4.67, 4.67 Hz, 1H) 6.87 (s, 1H) 7.07 (s, 1H).

Step 4: Preparation of N-{3-[(2-{[1-(1-methylpyrrolidin-3-yl)-1H-pyrazol-4-yl]amino}-9-{[2-(trimethylsilyl)ethoxy]methyl}-9H-purin-6-yl)oxy]phenyl}prop-2-enamide

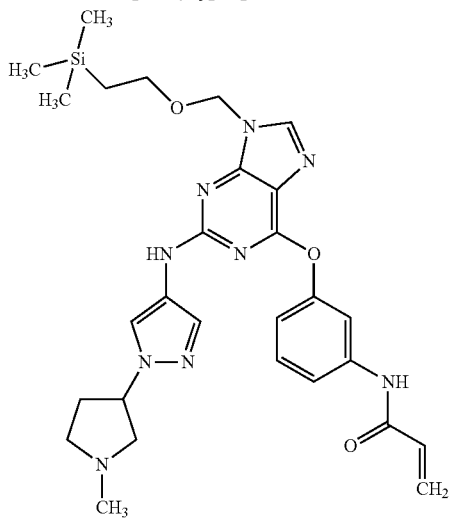

To a mixture of N-{3-[(2-chloro-9-{[2-(trimethylsilyl)ethoxy]methyl}-9H-purin-6-yl)oxy]phenyl}prop-2-enamide (210 mg, 0.471 mmol) and 1-(1-methylpyrrolidin-3-yl)-1H-pyrazol-4-amine (93.9 mg, 0.565 mmol) in 1,4-dioxane (7.85 mL) were added Pd$_2$(dba)$_3$ (43.0 mg, 10 mol %), Xantphos (27.2 mg, 10 mol %), and cesium carbonate (460 mg, 1.41 mmol). The reaction vial was sealed, then evacuated and back-filled with nitrogen three times. The mixture was subjected to microwave irradiation at 140° C. for 1 hr at normal absorption. After cooling to rt the reaction was diluted with EtOAc and filtered through a glass fiber filter set. The filtrate was concentrated and dried to give the title compound, which was carried forward without further purification, assuming quantitative yield. m/z (APCI+) for C$_{28}$H$_{37}$N$_9$O$_3$Si 576.20 (M+H)$^+$.

Step 5: Preparation of N-{3-[(2-{[1-(1-methylpyrrolidin-3-yl)-1H-pyrazol-4-yl]amino}-9H-purin-6-yl)oxy]phenyl}prop-2-enamide

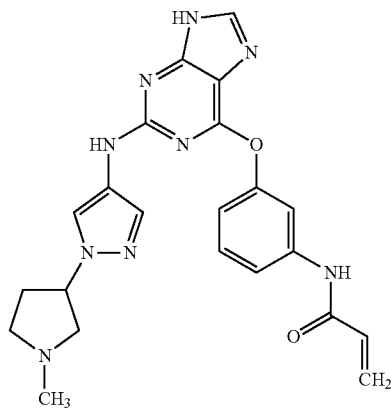 [SMILES: C=CC(=O)Nc1cccc(Oc2nc(Nc3cnn(C4CCN(C)C4)c3)nc3[nH]cnc23)c1]

To a mixture of N-{3-[(2-{[1-(1-methylpyrrolidin-3-yl)-1H-pyrazol-4-yl]amino}-9-{[2-(trimethylsilyl)ethoxy]methyl}-9H-purin-6-yl)oxy]phenyl}prop-2-enamide (271 mg, 0.471 mmol) in DCM (5.89 mL) was added TFA (1.81 mL, 23.6 mmol). The resulting solution was stirred at rt overnight, then concentrated and dried under vacuum. The resulting residue was taken up in water and neutralized with NaHCO$_3$ to get a slightly sticky suspension. The solid was filtered off, washed with water, dried, and collected to give the crude product, which was purified by SFC to afford the title compound (21 mg, 10 yield) as a lyophilized solid. $^1$H NMR (400 MHz, DMSO-d6) δ ppm 12.80 (br. s., 1H) 10.37 (br. s., 1H) 9.20 (br. s., 1H) 8.01-8.11 (m, 1H) 7.61-7.78 (m, 1H) 7.48 (br. s., 1H) 7.37 (d, J=6.32 Hz, 1H) 7.03 (d, J=7.33 Hz, 2H) 6.36-6.59 (m, 1H) 6.20-6.34 (m, 1H) 5.77 (dd, J=10.23, 1.89 Hz, 1H) 4.57 (br. s., 1H) 3.99-4.27 (m, 1H) 3.65-3.94 (m, 3H) 3.00 (br. s., 2H) 2.79 (m, J=15.66 Hz, 1H) 2.00 (br. s., 1H) 1.23 (s, 1H). m/z (APCI+) for C$_{22}$H$_{23}$N$_9$O$_2$ 446.05 (M+H)$^+$.

Example 8

(Scheme D): Preparation of N-[3-({2-[(1-methyl-1H-pyrazol-4-yl)amino]-5-(pyridin-3-yl)-7H-pyrrolo[2,3-d]pyrimidin-4-yl}oxy)phenyl]prop-2-enamide

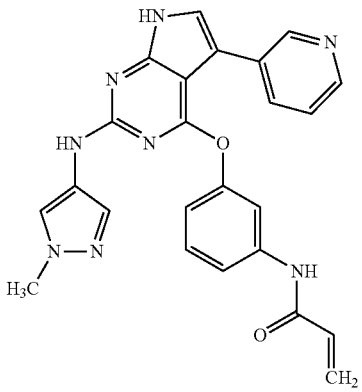 [SMILES: C=CC(=O)Nc1cccc(Oc2nc(Nc3cnn(C)c3)nc3[nH]cc(-c4cccnc4)c23)c1]

Step 1: Preparation of 2-chloro-5-iodo-4-(3-nitrophenoxy)-7-{[2(trimethylsilyl)ethoxy]methyl}-7H-pyrrolo[2,3-d]pyrimidine

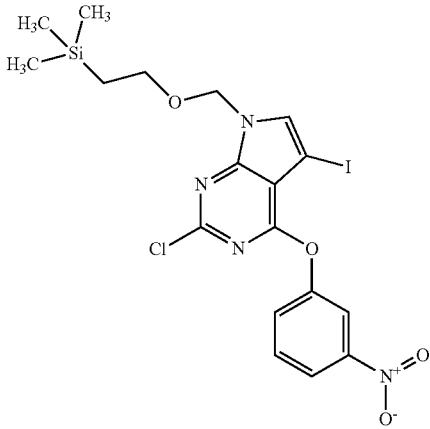 [SMILES: C[Si](C)(C)CCOCn1cc(I)c2c(Oc3cccc([N+](=O)[O-])c3)nc(Cl)nc21]

To a reaction vial was added 2,4-dichloro-5-iodo-7-{[2-(trimethylsilyl)ethoxy]methyl}-7H-pyrrolo[2,3-d]pyrimidine (3.50 g, 7.9 mmol), as prepared in Example 5, step 1, 3-nitrophenol (1.1 g, 7.9 mmol), DMF (26 mL) and K$_2$CO$_3$ (2.18 g, 16 mmol, 2 mol eq). The reaction mixture was stirred and heated to 60° C. (block temperature) for 1 hr. The volatiles were removed and water (30 mL) was added. Ethyl acetate (120 mL) was added and the organic layer was separated, washed with water (20 mL), brine (20 mL), dried over Na$_2$SO$_4$ and evaporated to give crude product (TLC: Rf 0.6 (major) and 0.4 (minor) in 20% ethyl acetate-80% heptane). The product was purified on silica to give a light yellow oil, which solidified to a light yellow solid (3.65 g, 85% yield). $^1$H NMR (400 MHz, DMSO-d6) δ ppm 8.28-8.31 (m, 1H) 8.26 (d, J=8.06 Hz, 1H) 8.02 (s, 1H) 7.90-7.94 (m, 1H) 7.83-7.89 (m, 1H) 5.60 (s, 2H) 3.53-3.67 (m, 2H) 0.84-0.99 (m, 2H) 0.00 (s, 9H). m/z (APCI+) for C$_{18}$H$_{20}$ClIN$_4$O$_4$Si 547.0 (M+H)$^+$.

Step 2: Preparation of 2-chloro-4-(3-nitrophenoxy)-5-(pyridin-3-yl)-7-{[2(trimethylsilyl)ethoxy]methyl}-7H-pyrrolo[2,3-d]pyrimidine

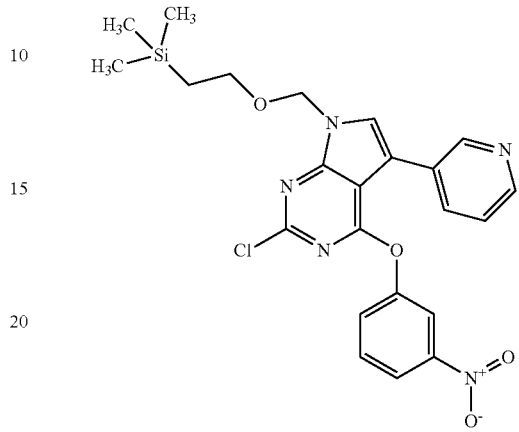

To a vial was added 2-chloro-5-iodo-4-(3-nitrophenoxy)-7-{[2-(trimethylsilyl)ethoxy]methyl}-7H-pyrrolo[2,3-d]pyrimidine (333.7 mg, 0.61 mmol), pyridin-3-ylboronic acid (79 mg, 0.64 mmol, 1.05 mol eq), 1,4-dioxane (4 mL), water (1 mL), Na$_2$CO$_3$ (78 mg, 0.73 mmol, 1.2 mol eq) and Pd(PPh$_3$)$_2$Cl$_2$ (21 mg, 0.05 mol eq). The reaction vial was capped, stirred at rt for 1 hr and was then heated to 60° C. (block temperature) for 2 days (note: the reaction progress was monitored by LCMS after couple hours and more pyridin-3-ylboronic acid was added as needed). The reaction was diluted with ethyl acetate (100 mL) and water (20 mL) and the organic layer was separated, washed with water (20 mL) and brine (20 mL), dried over Na$_2$SO$_4$ and evaporated to give crude product (TLC: Rf 0.3 in 50% ethyl acetate-50% heptane). The crude product was purified on silica gel to give the title compound as a light yellow solid (266 mg, 88% yield). $^1$H NMR (400 MHz, DMSO-d6) δ ppm 9.01 (d, J=2.01 Hz, 1H) 8.54 (dd, J=4.78, 1.51 Hz, 1H) 8.38 (t, J=2.14 Hz, 1H) 8.23 (dd, J=8.06, 2.01 Hz, 2H) 8.15 (s, 1H) 7.86-7.93 (m, 1H) 7.77-7.85 (m, 1H) 7.50 (dd, J=7.93, 4.66 Hz, 1H) 5.68 (s, 2H) 3.58-3.74 (m, 2H) 0.83-1.02 (m, 2H) 0.00 (s, 9H). m/z (APCI+) for C$_{23}$H$_{24}$ClN$_5$O$_4$Si 498.0 (M+H)$^+$.

Step 3: Preparation of N-(1-methyl-1H-pyrazol-4-yl)-4-(3-nitrophenoxy)-5-(pyridin-3-yl)-7-{[2-(trimethylsilyl)ethoxy]methyl}-7H-pyrrolo[2,3-d]pyrimidin-2-amine

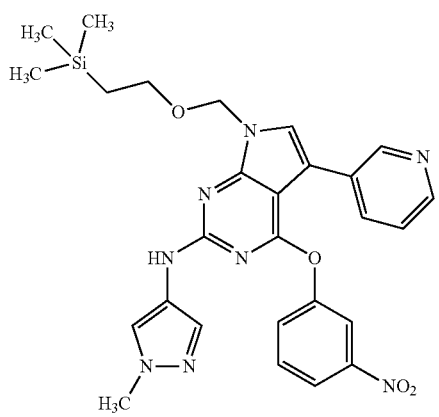

To a microwave reaction vial was added 2-chloro-4-(3-nitrophenoxy)-5-(pyridin-3-yl)-7-{[2-(trimethylsilyl)ethoxy]methyl}-7H-pyrrolo[2,3-d]pyrimidine (130 mg, 0.26 mmol), 1-methyl-1H-pyrazol-4-amine (28 mg, 0.29 mmol, 1.1 mol eq), 1,4-dioxane (5 mL), Cs$_2$CO$_3$ (ca. 170 mg), Xantphos (16 mg) and Pd$_2$(dba)$_3$ (24 mg). The reaction vial was flushed with nitrogen, capped, stirred and heated to 140° C. using microwave at high absorption level for 45 min. The reaction was diluted with EtOAc (120 mL) and water (20 mL). The organic layer was separated, washed with water (20 mL) and with brine (10 mL), dried over Na$_2$SO$_4$ and evaporated to give crude product (TLC: Rf 0.2 in 100 ethyl acetate). The crude product was purified on silica to give the title compound as a green gum (290 mg, 100% yield). $^1$H NMR (400 MHz, methanol-d4) δ ppm 8.99 (s, 1H) 8.48 (d, J=3.78 Hz, 1H) 8.18-8.32 (m, 3H) 7.71-7.81 (m, 2H) 7.48-7.55 (m, 2H) 5.70 (s, 2H) 3.77-3.87 (m, 2H) 3.70-3.77 (m, 3H) 0.94-1.06 (m, 2H) 0.00 (s, 9H). m/z (APCI+) for C$_{27}$H$_{30}$N$_8$O$_4$Si 559.1 (M+H)$^+$.

Step 4: Preparation of 4-(3-aminophenoxy)-N-(1-methyl-1H-pyrazol-4-yl)-5-(pyridin-3-yl)-7-{[2-(trimethylsilyl)ethoxy]methyl}-7H-pyrrolo[2,3-d]pyrimidin-2-amine

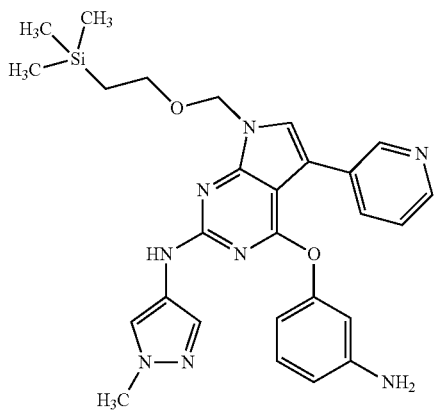 [SMILES: Cn1cc(Nc2nc(Oc3cccc([N+](=O)[O-])c3)c3c(-c4cccnc4)cn(COCC[Si](C)(C)C)c3n2)cn1]

To a solution of N-(1-methyl-1H-pyrazol-4-yl)-4-(3-nitrophenoxy)-5-(pyridin-3-yl)-7-{[2-(trimethylsilyl)ethoxy]methyl}-7H-pyrrolo[2,3-d]pyrimidin-2-amine (290 mg, ca. 0.52 mmol) in EtOAc (20 mL) was added water (5 mL), ammonium chloride (139 mg, 2.6 mmol, 5 mol eq) and zinc dust (170 mg, 2.6 mmol, 5 mol eq). The reaction mixture was stirred at rt for 16 hrs. The reaction mixture was filtered through Celite. The filtrate was diluted with EtOAc (100 mL) and saturated aqueous NaHCO$_3$ (15 mL). The insoluble material was removed by filtration through Celite. The organic layer of the filtrate was separated, washed with brine (10 mL), dried over Na$_2$SO$_4$ and evaporated to give a residue (195 mg) that was then dissolved in methanol and treated with an SCX resin (2 g), washed with methanol. The product was eluted with methanolic ammonia (3.5 N). The volatiles were removed to give the title compound as a light green gum (227 mg, 83% yield). $^1$H NMR (400 MHz, methanol-d4) δ ppm 8.94 (d, J=1.51 Hz, 1H) 8.39 (dd, J=5.04, 1.51 Hz, 1H) 8.20 (d, J=8.06 Hz, 1H) 7.43 (dd, J=7.93, 4.91 Hz, 1H) 7.38 (s, 1H) 7.18 (t, J=7.93 Hz, 1H) 6.67 (d, J=7.30 Hz, 1H) 6.58 (t, J=2.01 Hz, 1H) 6.51 (dd, J=8.06, 1.51 Hz, 1H) 5.57 (s, 2H) 3.70 (br. s., 2H) 3.60-3.68 (m, 3H) 0.92 (t, J=8.06 Hz, 2H) −0.06 (s, 9H). m/z (APCI+) for C$_{27}$H$_{32}$N$_8$O$_2$Si 529.1 (M+H)$^+$.

Step 5: Preparation of N-{3-[(2-[(1-methyl-1H-pyrazol-4-yl)amino]-5-(pyridin-3-yl)-7-{[2-(trimethylsilyl)ethoxy]methyl}-7H-pyrrolo[2,3-d]pyrimidin-4-yl)oxy]phenyl}prop-2-enamide

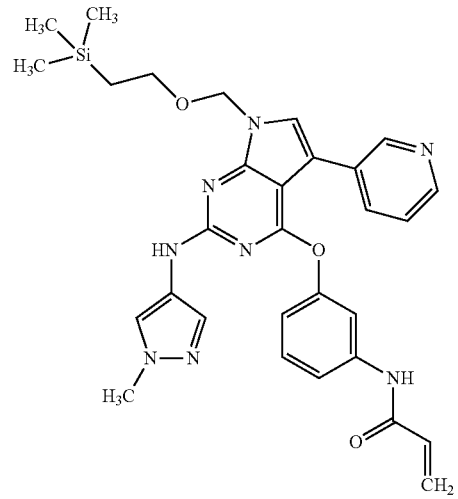 [SMILES: C=CC(=O)Nc1cccc(Oc2nc(Nc3cnn(C)c3)nc3c2c(-c2cccnc2)cn3COCC[Si](C)(C)C)c1]

To a solution of 4-(3-aminophenoxy)-N-(1-methyl-1H-pyrazol-4-yl)-5-(pyridin-3-yl)-7-{[2-(trimethylsilyl)ethoxy]methyl}-7H-pyrrolo[2,3-d]pyrimidin-2-amine (227 mg, 0.43 mmol) in DCM (10 mL) was added acrolyl chloride (35 μL, 0.43 mmol, 1 mol eq) and stirred at rt for 1 hr. Saturated aqueous NaHCO$_3$ (20 mL) was added and the volatiles were removed to give a light yellow solid. Water (30 mL) was added and the resulting precipitate was collected by filtration, washed with water and dried to give the crude title compound as a light yellow solid (TLC, Rf 0.3 in 100% ethyl acetate). The crude material was purified on silica to give the title compound (123 mg, 49% yield) as a colorless gum. $^1$H NMR (400 MHz, methanol-d4) δ ppm 8.93 (d, J=1.77 Hz, 1H) 8.38 (dd, J=5.05, 1.52 Hz, 1H) 8.19 (dt, J=8.08, 1.77 Hz, 1H) 7.65 (t, J=1.89 Hz, 1H) 7.61 (br. s., 0H) 7.42 (dd, J=8.08, 4.29 Hz, 2H) 7.39 (s, 1H) 7.17-7.37 (m, 1H) 7.00 (dd, J=7.96, 1.14 Hz, 1H) 6.30-6.48 (m, 2H) 5.72-5.81 (m, 1H) 5.56 (br. s., 2H) 3.65 (t, J=7.96 Hz, 5H) 0.92 (t, J=7.96 Hz, 2H) −0.07 (s, 9H). m/z (APCI+) for C$_{30}$H$_{34}$N$_8$O$_3$Si 583.1 (M+H)$^+$.

Step 6: Preparation of N-[3-({2-[(1-methyl-1H-pyrazol-4-yl)amino]-5-(pyridin-3-yl)-7H-pyrrolo[2,3-d]pyrimidin-4-yl}oxy)phenyl]prop-2-enamide

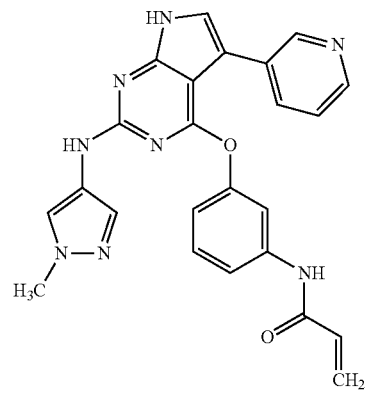 [SMILES: C=CC(=O)Nc1cccc(Oc2nc(Nc3cnn(C)c3)nc3[nH]cc(-c4cccnc4)c23)c1]

To a solution of N-{3-[(2-[(1-methyl-1H-pyrazol-4-yl)amino]-5-(pyridin-3-yl)-7-{[2-(trimethylsilyl)ethoxy]methyl}-7H-pyrrolo[2,3-d]pyrimidin-4-yl)oxy]phenyl}prop-2-enamide (123 mg, 0.21 mmol) in DCM (10 mL) was added TFA (0.6 mL). The reaction solution was stirred at rt for 3 hrs. The volatiles were removed to give a residue. To the residue was added ethanol (20 mL), water (2 mL), and K$_2$CO$_3$ (142 mg) and the reaction mixture was stirred at rt for 1 hr. The volatiles were removed and water (10 mL) was added. The resulting solid was collected by filtration, washed with water (10 mL) and dried to give the title product (92.8 mg, 100% yield) as a white solid. $^1$H NMR (400 MHz, DMSO-d6) δ ppm 11.80 (br. s., 1H) 10.32 (br. s., 1H) 8.99-9.14 (m, 1H) 8.95 (d, J=1.51 Hz, 1H) 8.41 (dd, J=4.78, 1.51 Hz, 1H) 8.12 (d, J=7.55 Hz, 1H) 7.64 (br. s., 2H) 7.47 (s, 2H) 7.39 (dd, J=7.93, 4.91 Hz, 1H) 7.21 (br. s., 1H) 7.04 (br. s., 1H) 6.34-6.48 (m, 1H) 6.19-6.31 (m, 1H) 5.70-5.82 (m, 1H) 3.58 (br. s., 3H). m/z (APCI+) for C$_{24}$H$_{20}$N$_8$O$_2$ 453.0 (M+H)$^+$.

Example 9

(Scheme F): Preparation of 1-{(3R,4R)-3-[5-chloro-2-(1-methyl-1H-pyrazol-4-ylamino)-7H-pyrrolo[2,3-d]pyrimidin-4-yloxymethyl]-4-methoxy-pyrrolidin-1-yl}propenone trifluoroacetate

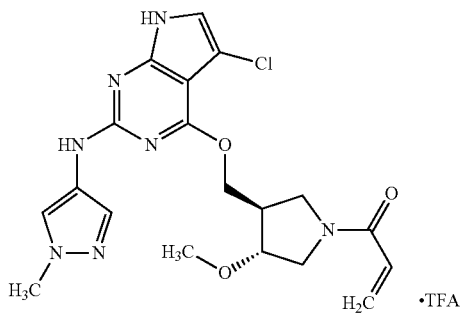 [SMILES: C=CC(=O)N1C[C@H](COc2nc(Nc3cnn(C)c3)nc3[nH]cc(Cl)c23)[C@@H](OC)C1]

Step 1: Preparation of (3S,4R)-1-benzyl-4-methoxy-pyrrolidine-3-carboxylic acid methyl ester

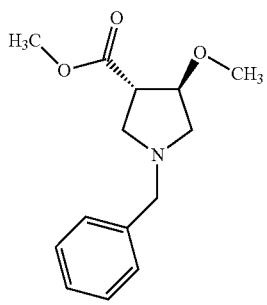

To a solution of (E)-3-methoxy-acrylic acid methyl ester (50 g, 430.6 mmol) in 2-Me-THF (600 mL) and TFA (6.7 mL) at 0° C. was added N-(methoxymethyl)-N-(trimethylsilylmethyl)-benzylamine (204 g, 2 eq) dropwise. After addition, reaction was allowed to warm to rt and stirred for 2 hrs. Reaction was transferred to a separatory funnel and washed with sat. NaHCO$_3$, sat. NaCl, then dried over Na$_2$SO$_4$ and the solvent removed to leave the crude racemic product as a yellow oil which was purified on SiO$_2$ (10%-35% EtOAc/heptane) to give the racemic trans product as a yellow oil (82.7 g). Enantiomer separation by chiral-SFC (Chiralpak AD-H 4.6×250 mm column 4% MeOH w/0.1% diethylamine, 140 bar, 3.0 mL/min) gave the desired single isomer product which was verified by comparison with a known standard (34 g, 31.7% yield). Specific rotation [α]$_D^{27}$=+23.8° (C=1.3, MeOH). $^1$H NMR (400 MHz, DMSO-d6) δ ppm 2.55-2.63 (m, 2H) 2.69 (dd, J=9.95, 6.42 Hz, 1H) 2.82-2.88 (m, 1H) 2.90-2.96 (m, 1H) 3.23 (s, 3H) 3.51-3.63 (m, 2H) 3.66 (s, 3H) 4.07-4.12 (m, 1H) 7.22-7.39 (m, 5H). m/z (APCI+) for (C$_{14}$H$_{19}$NO$_3$) 250.0 (M+H)$^+$.

Step 2: Preparation of (3S,4R)-4-methoxy-pyrrolidine-1,3-dicarboxylic acid 1-tert-butyl ester 3-methyl ester

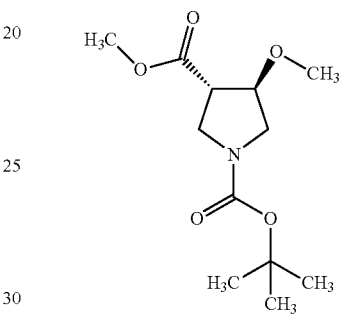

A solution of (3S,4R)-1-benzyl-4-methoxy-pyrrolidine-3-carboxylic acid methyl ester (35 g, 140.4 mmol) in ethanol (500 mL) was purged with nitrogen and then Pd(OH)$_2$ (2 g, 0.1 eq) was added and the mixture stirred overnight under an atmosphere of hydrogen gas at approximately 15 psi (via hydrogen balloon). The reaction was then filtered through Celite and di-tert-butyldicarbonate (30.9 g, 1 eq) was added to the resulting filtrate slowly with stirring. After one hr the reaction was concentrated and the crude material was purified through a short silica column eluting with 10 EtOAc/heptane for 2 volumes then 1:1 EtOAc/heptane until the product was completely eluted. Product fractions were combined and concentrated to give the title compound as a clear oil, (35.81 g, 98% yield). $^1$H NMR (400 MHz, DMSO-d6) δ ppm 1.39 (s, 9H) 3.17 (br. s., 1H) 3.23-3.28 (m, 4H) 3.35-3.53 (m, 3H) 3.65 (s, 3H) 4.06 (d, J=4.78 Hz, 1H). m/z (APCI+) for product minus Boc (C$_7$H$_{13}$NO$_3$) 160.1 (M+H)$^+$. Specific Rotation: [a]D=−12.5 degrees (C=0.87, MeOH).

Step 3: Preparation of (3R,4R)-3-hydroxymethyl-4-methoxy-pyrrolidine-1-carboxylic acid tert-butyl ester

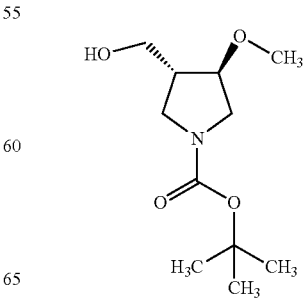

Lithium borohydride (12.7 g, 4 eq) was added portionwise to a solution of (3S,4R)-4-methoxy-pyrrolidine-1,3-dicarboxylic acid 1-tert-butyl ester 3-methyl ester (35.81 g, 138.1 mmol) in THF (600 mL), then the reaction was heated to 60° C. for 4 hrs. The reaction was quenched with water at 0° C. and extracted with EtOAc. The organic layer was washed with sat. NaCl and dried over $Na_2SO_4$. The solvent was removed and the residue was purified through a plug of $SiO_2$ (3:1 EtOAc/heptane) to yield the title compound as a clear oil (29.35 g, 92% yield). $^1$H NMR (400 MHz, chloroform-d) δ ppm 1.46 (s, 9H) 2.37-2.47 (m, 1H) 3.19 (dd, J=11.08, 5.29 Hz, 1H) 3.33 (d, J=4.03 Hz, 4H) 3.50-3.66 (m, 4H) 3.77-3.83 (m, 1H). m/z (APCI+) for product minus Boc ($C_6H_{13}NO_2$) 132.2 (M+H)$^+$. Specific Rotation: [a]D=+9.3 degrees (C=0.86, MeOH).

Step 4: Preparation of (3R,4R)-3-[5-chloro-2-(1-methyl-1H-pyrazol-4-ylamino)-7H-pyrrolo[2,3-d]pyrimidin-4-yloxymethyl]-4-methoxy-pyrrolidine-1-carboxylic acid tert-butyl ester

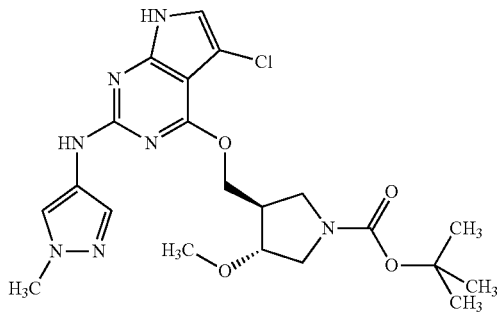 [SMILES: CO[C@H]1CN(C(=O)OC(C)(C)C)C[C@@H]1COc1nc(Nc2cnn(C)c2)nc2[nH]cc(Cl)c12]

Method A: (Using Microwave Heating)
To a solution 2,4,5-trichloro-7H-pyrrolo[2,3-d]pyrimidine (904 mg, 4.1 mmol) and (3R,4R)-3-hydroxymethyl-4-methoxy-pyrrolidine-1-carboxylic acid tert-butyl ester (940 mg, 4.1 mmol) in 1,4-dioxane (15 mL) in a microwave vial was added potassium tert-pentoxide (25% w/w in toluene, 1.6 mL, 3.5 mmol). The resulting solution was stirred at ambient temperature for 15 min. LCMS showed a quantitative formation of (3R,4R)-3-(2,5-dichloro-7H-pyrrolo[2,3-d]pyrimidin-4-yloxymethyl)-4-methoxy-pyrrolidine-1-carboxylic acid tert-butyl ester. To this resulting reaction solution was added 1-methyl-1H-pyrazol-4-ylamine (474 mg, 4.9 mmol) and t-BuXPhos palladacycle (110 mg, 0.04 mol eq). The reaction mixture was stirred and heated to 100° C. using microwave at normal absorption level for 45 min. The reaction mixture was filtered through Celite and the filtrate was evaporated to give a dark color residue. The crude material was purified via flash chromatography eluting with a gradient of 0%-100% EtOAc in heptanes to give the title compound (1.78 g, 76% yield). $^1$H NMR (400 MHz, DMSO-d6) δ ppm 11.50 (br. s., 1H) 9.06 (s, 1H) 7.85 (s, 1H) 7.52 (s, 1H) 7.05 (d, J=2.27 Hz, 1H) 4.30-4.53 (m, 2H) 3.86-3.96 (m, 1H) 3.80 (s, 3H) 3.55-3.68 (m, 1H) 3.43-3.53 (m, 1H) 3.24-3.31 (m, 3H) 2.71 (br. s., 1H) 1.39 (br. s., 9H). m/z (APCI+) for product minus Boc; $C_{16}H_{20}ClN_7O_2$ 378.1 (M+H)$^+$ with Cl isotope pattern.

Method B: Using Thermal Heating
To a solution 2,4,5-trichloro-7H-pyrrolo[2,3-d]pyrimidine (9.28 g, 41.7 mmol) and (3R,4R)-3-hydroxymethyl-4-methoxy-pyrrolidine-1-carboxylic acid tert-butyl ester (9.65 g, 41.7 mmol) in 1,4-dioxane (100 mL) in a round bottom flask was added potassium tert-pentoxide (25% w/w in toluene, 80 mL, 167 mmol). The resulting reaction solution was stirred at ambient temperature for 30 min. LCMS showed a quantitative formation of (3R,4R)-3-(2,5-dichloro-7H-pyrrolo[2,3-d]pyrimidin-4-yloxymethyl)-4-methoxy-pyrrolidine-1-carboxylic acid tert-butyl ester. To the resulting reaction solution was added 1-methyl-1H-pyrazol-4-ylamine (4.86 g, 50.1 mmol) and t-BuXPhos palladacycle (1.1 g, 1.67 mmol, 0.04 mol eq). The reaction mixture was stirred and heated to 90° C. in an oil bath for 1 hr. The reaction mixture was then filtered through Celite and the filtrate was evaporated to remove the volatiles to give a dark gum that was then dissolved in ethyl acetate (300 mL) and filtered through a silica gel plug. The filtrate was evaporated and the residue was purified via flash chromatography eluting with a gradient of 0%-100% EtOAc in heptanes to give the title compound (12.4 g, 62 yield). $^1$H NMR (400 MHz, DMSO-d6) δ ppm 11.51 (br. s., 1H) 9.07 (s, 1H) 7.86 (s, 1H) 7.52 (s, 1H) 7.06 (d, J=2.20 Hz, 1H) 4.31-4.54 (m, 2H) 3.92 (br. s., 1H) 3.80 (s, 3H) 3.55-3.68 (m, 1H) 3.44-3.55 (m, 1H) 3.30 (d, J=18.34 Hz, 3H) 2.72 (br. s., 1H) 1.39 (br. s., 9H). m/z (APCI+) for $O_{21}H_{28}ClN_7O_4$ 378.2 (M+H)$^+$ with Cl isotope pattern.

Step 5: Preparation of [5-chloro-4-((3R,4R)-4-methoxy-pyrrolidin-3-ylmethoxy)-7H-pyrrolo[2,3-d]pyrimidin-2-yl]-(1-methyl-1H-pyrazol-4-yl)-amine trifluoroacetate

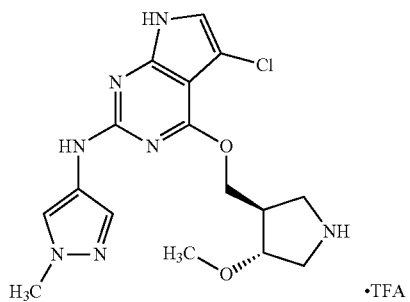 [SMILES: CO[C@H]1CNC[C@@H]1COc1nc(Nc2cnn(C)c2)nc2[nH]cc(Cl)c12]

To a solution of (3R,4R)-3-[5-chloro-2-(1-methyl-1H-pyrazol-4-ylamino)-7H-pyrrolo[2,3-d]pyrimidin-4-yloxymethyl]-4-methoxy-pyrrolidine-1-carboxylic acid tert-butyl ester (12.40 g, 26 mmol) in DCM (60 mL) at 0° C. was added TFA (10.1 mL, 208 mmol) and the resulting solution was stirred at ambient temperature for 2.5 hrs. The volatiles were removed and to the residue was added ethyl ether (150 mL). The resulting suspension was stirred for 2 hrs then filtered to afford a light pink solid. This was washed with ethyl ether (30 mL) and dried to give the title compound (15.69 g, quant) as a TFA salt. $^1$H NMR (400 MHz, DMSO-d6) δ ppm 11.56 (br. s., 1H) 9.09 (s, 3H) 7.85 (s, 1H) 7.54 (s, 1H) 7.09 (d, J=2.32 Hz, 1H) 4.48 (d, J=6.48 Hz, 2H) 4.11 (br. s., 1H) 3.81 (s, 3H) 3.46-3.60 (m, 1H) 3.35-3.45 (m, 2H) 3.32 (s, 3H) 3.15 (dq, J=12.01, 6.02 Hz, 1H) 2.88 (m, J=6.42, 6.42 Hz, 1H). m/z (APCI+) for parent molecule $C_{16}H_{20}ClN_7O_2$ 378.2 $(M+H)^+$ with Cl isotope pattern.

Step 6: Preparation of 1-{(3R,4R)-3-[5-chloro-2-(1-methyl-1H-pyrazol-4-ylamino)-7H-pyrrolo[2,3-d]pyrimidin-4-yloxymethyl]-4-methoxy-pyrrolidin-1-yl}propenone trifluoroacetate

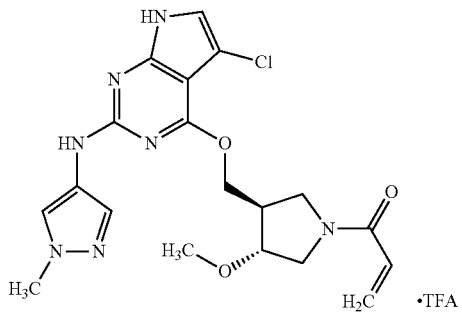 [SMILES: C=CC(=O)N1C[C@H](COc2nc(Nc3cnn(C)c3)nc3[nH]cc(Cl)c23)[C@@H](OC)C1]

A mixture of [5-chloro-4-((3R,4R)-4-methoxy-pyrrolidin-3-ylmethoxy)-7H-pyrrolo[2,3-d]pyrimidin-2-yl]-(1-methyl-1H-pyrazol-4-yl)-amine (15.0 g (2 TFA salt)), 24.7 mmol), ethyl acetate (200 mL) and saturated aqueous $NaHCO_3$ (100 mL) was stirred at 0° C. for 10 min. Acryloyl chloride (2.3 mL, 29 mmol, 1.1 mol eq) was added dropwise and the resulting mixture was stirred at ambient temperature for 30 min. Ethyl acetate (150 mL) was added and the organic layer was separated. The aqueous layer was extracted with ethyl acetate (150 mL) and the combined organic layers were dried over $Na_2SO_4$ and evaporated to give a solid that was purified by SFC (Zymor SPHER HAP 5μ 21.2×150 mm column eluting with 35% EtOH in $CO_2$ at 120 bar, flow 64 mL/min) to give the title compound as an off white solid (8.3 g, 78% yield). $^1$H NMR (400 MHz, DMSO-d6) δ ppm 11.51 (s, 1H) 9.07 (s, 1H) 7.86 (s, 1H) 7.52 (s, 1H) 7.05 (s, 1H) 6.59 (ddd, J=16.75, 10.27, 1.34 Hz, 1H) 6.14 (dd, J=16.75, 2.32 Hz, 1H) 5.68 (dt, J=10.27, 2.32 Hz, 1H) 4.44 (d, J=6.24 Hz, 2H) 3.82-4.09 (m, 2H) 3.80 (s, 3H) 3.57-3.76 (m, 2H) 3.47-3.54 (m, 1H) 3.31 (d, J=4.65 Hz, 3H) 2.67-2.92 (m, 1H). m/z (APCI+) for parent molecule $C19H_{22}ClN_7O_3$ 431.9 $(M+H)^+$ with Cl isotope pattern.

Example 10

(Scheme H): Preparation of 1-{(3R,4R)-3-[({5-chloro-2-[(1-methyl-1H-pyrazol-4-yl)amino]-7H-pyrrolo[2,3-d]pyrimidin-4-yl}oxy)methyl]-4-[(1S)-1-hydroxyethyl]pyrrolidin-1-yl}prop-2-en-1-one

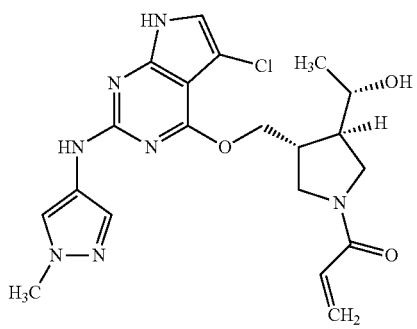 [SMILES: C=CC(=O)N1C[C@H](COc2nc(Nc3cnn(C)c3)nc3[nH]cc(Cl)c23)[C@@H]([C@H](C)O)C1]

Step 1: Preparation of (3,4-trans)-1-benzyl-4-[(S)-1-(tert-butyl-diphenyl-silanyloxy)-ethyl]-pyrrolidine-3-carboxylic acid ethyl ester

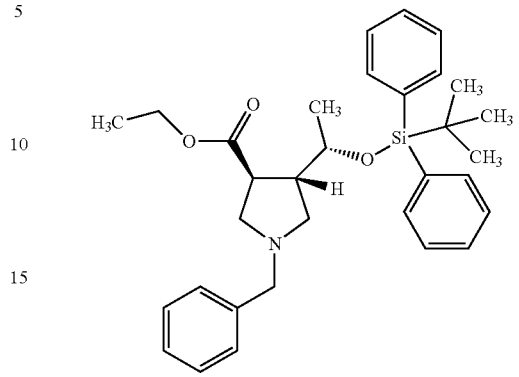

To a solution of (E)-(S)-4-(tert-butyl-diphenyl-silanyloxy)-pent-2-enoic acid ethyl ester (see, Org. Lett., 7 (11), 2266, 27.79 g, 73.1 mmol) in 2-methyl-tetrahydrofuran (400 mL) was added trifluoroacetic acid (1.14 mL, 0.2 eq) and the solution cooled to 0° C. To this solution was added N-(methoxymethyl)-N-(trimethylsilylmethyl)benzyl-amine (37.4 mL, 2 eq) dropwise. After addition was complete, the reaction was allowed to warm to rt and stirred for 2 hrs. The reaction was transferred to a separatory funnel and washed with sat. $NaHCO_3$, sat. NaCl, dried over $Na_2SO_4$ and the solvent removed to leave the product as a yellow oil which was purified on a plug of $SiO_2$ (1% EtOH/5% EtOAc/heptane) to give the title compound as a clear oil (35.9 g) which was taken on directly to the next reaction.

Step 2: Preparation of (3,4-trans)-4-[1-((S)-tert-butyl-diphenyl-silanyloxy)-ethyl]-pyrrolidine-1,3-dicarboxylic acid 1-tert-butyl ester 3-ethyl ester

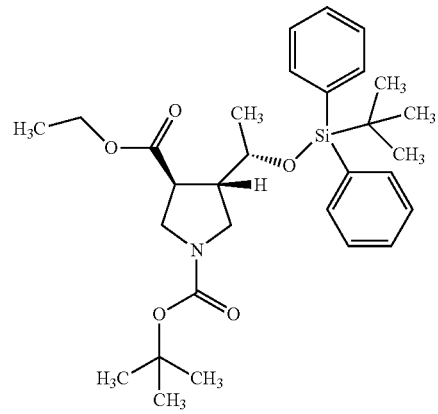 [SMILES: CCOC(=O)[C@@H]1CN(C(=O)OC(C)(C)C)C[C@H]1[C@H](C)O[Si](c1ccccc1)(c1ccccc1)C(C)(C)C]

To a solution of trans-1-benzyl-4-[(S)-1-(tert-butyl-diphenyl-silanyloxy)-ethyl]-pyrrolidine-3-carboxylic acid ethyl ester (35.9 g, 69.6 mmol) in EtOH (200 mL) purged with nitrogen was added $Pd(OH)_2$ and the mixture was then placed on the Parr shaker at 50° C. under 50 psi $H_2$ overnight. The reaction was then filtered through a pad of Celite and concentrated. The resulting oil was purified on $SiO_2$ (10% EtOAc/heptane) and the title compound was isolated as a clear oil (14.45 g, 39% yield). $^1$H NMR (400 MHz, chloroform-d) δ ppm 0.98-1.08 (m, 12H) 1.19-1.25 (m, 3H) 1.47 (d, J=6.80 Hz, 9H) 2.44-2.69 (m, 1H) 2.93-3.94 (m, 6H) 4.05-4.17 (m, 2H) 7.33-7.48 (m, 6H) 7.60-7.72 (m, 4H). m/z (APCI+) for product minus Boc ($C_{25}H_{35}NO_3Si$) 426.1 $(M+H)^+$.

Step 3: Preparation of (3,4-trans)-3-[(S)-1-(tert-butyl-diphenyl-silanyloxy)-ethyl]-4-hydroxymethyl-pyrrolidine-1-carboxylic acid tert-butyl ester

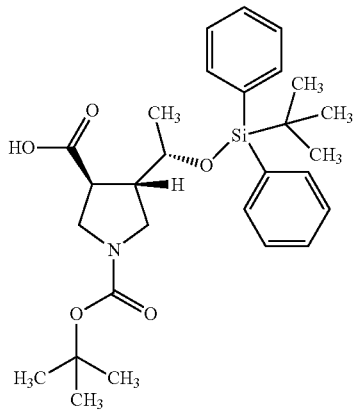 [SMILES: C[C@H](O[Si](c1ccccc1)(c1ccccc1)C(C)(C)C)[C@@H]1CN(C(=O)OC(C)(C)C)C[C@H]1C(=O)O]

To a solution of trans-4-[1-((S)-tert-butyl-diphenyl-silanyloxy)-ethyl]-pyrrolidine-1,3-dicarboxylic acid 1-tert-butyl ester 3-ethyl ester (14.45 g, 27.5 mmol) in THF (200 mL) was added LiBH$_4$ (3.15 g, 5 eq) portionwse. The reaction was heated to 60° C. for 2 hrs then cooled to 0° C. and quenched by dropwise addition of water. The reaction was extracted with EtOAc and the organics washed with sat. NaCl, dried over Na$_2$SO$_4$ and concentrated. The resulting oil was purified on SiO$_2$ (1:1 EtOAc/heptane) and the title compound isolated as a clear oil (11.6 g, 87% yield). $^1$H NMR (400 MHz, chloroform-d) δ ppm 1.02-1.10 (m, 12H) 1.46 (d, J=4.04 Hz, 9H) 2.20-2.32 (m, 1H) 2.34-2.47 (m, 1H) 2.96-3.30 (m, 2H) 3.38-3.60 (m, 4H) 3.88 (dq, J=6.19, 6.02 Hz, 1H) 3.95 (qd, J=6.27, 2.91 Hz, 1H) 7.36-7.49 (m, 6H) 7.66-7.72 (m, 4H). m/z (APCI+) for product minus Boc (C$_{23}$H$_{33}$NO$_2$Si) 384.1 (M+H)$^+$.

Step 4: Preparation of ((3,4-trans)-tert-butyl 3-((S)-1-((tert-butyldiphenylsilyl)oxy)ethyl)-4-(((5-chloro-2-((1-methyl-1H-pyrazol-4-yl)amino)-7H-pyrrolo[2,3-d]pyrimidin-4-yl)oxy)methyl)pyrrolidine-1-carboxylate)

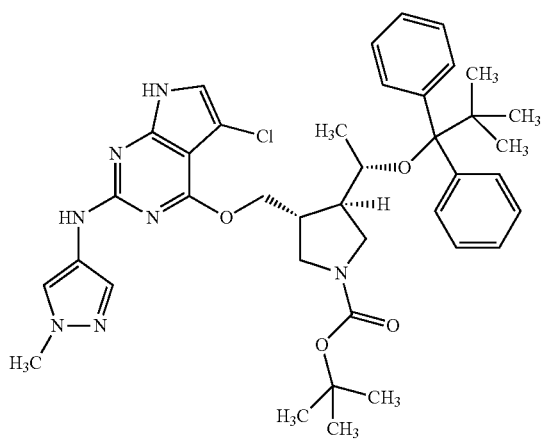 [SMILES: C[C@H](OC(c1ccccc1)(c1ccccc1)C(C)(C)C)[C@H]1CN(C(=O)OC(C)(C)C)C[C@@H]1COc1nc(Nc2cnn(C)c2)nc2[nH]cc(Cl)c12]

To a solution of trans-3-[(S)-1-(tert-butyl-diphenyl-silanyloxy)-ethyl]-4-hydroxymethyl-pyrrolidine-1-carboxylic acid tert-butyl ester (413 mg, 0.85 mmol) and 2,4,5-trichloro-7H-pyrrolo[2,3-d]pyrimidine (950 mg, 1 eq) in 1,4-dioxane was added potassium t-pentoxide (4 eq of a 1.7 M solution in toluene) and the reaction stirred for 30 min at ambient temperature. 1-Methyl-1H-pyrazol-4-ylamine (152 mg, 1.2 eq) and t-BuXPHOS palladacycle (48 mg, 0.015 eq) were added and the reaction heated in a microwave for 1 hr at 140° C. The reaction was diluted with EtOAc and washed with water, sat. NaCl and dried over Na$_2$SO$_4$. The volatiles removed in vacuo and the residue purified on SiO$_2$ (5% EtOH/EtOAc) afford the title compound as a yellow solid (575 mg, 55% yield). m/z (APCI+) for product minus Boc (C$_{33}$H$_{39}$ClN$_7$O$_2$Si) 731.1, 733.1 (M+H)$^+$.

Step 5: Preparation of (3,4-trans)-tert-butyl 3-(((5-chloro-2-((1-methyl-1H-pyrazol-4-yl)amino)-7H-pyrrolo[2,3-d]pyrimidin-4-yl)oxy)methyl)-4-((S)-1hydroxyethyl)pyrrolidine-1-carboxylate

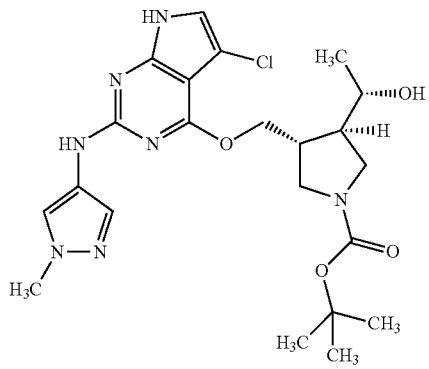 [SMILES: C[C@H](O)[C@H]1CN(C(=O)OC(C)(C)C)C[C@@H]1COc1nc(Nc2cnn(C)c2)nc2[nH]cc(Cl)c12]

((3,4-trans)-tert-Butyl 3-((S)-1-((tert-butyldiphenylsilyl)oxy)ethyl)-4-(((5-chloro-2-((1-methyl-1H-pyrazol-4-yl)amino)-7H-pyrrolo[2,3-d]pyrimidin-4yl)oxy)methyl)pyrrolidine-1-carboxylate) (575 mg, 0.784 mmol) was treated with TBAF (1 M in THF 2.36 mL, 3 eq) at 50° C. until TBDPS removal was complete, then concentrated, and the residue purified on SiO$_2$ (5% EtOH/EtOAc) to afford the title compound that was used as is in the next step.

Step 6: Preparation of 1-[(3,4-trans)-3-[5-chloro-2-(1-methyl-1H-pyrazol-4-ylamino)-7H-pyrrolo[2,3-d]pyrimidin-4-yloxymethyl]-4-((S)-1-hydroxy-ethyl)-pyrrolidin-1-yl]-propenone

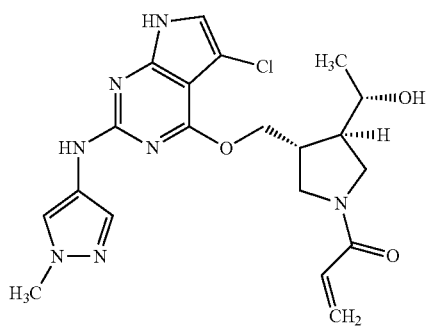 [SMILES: C=CC(=O)N1C[C@H](COc2nc(Nc3cnn(C)c3)nc3[nH]cc(Cl)c23)[C@@H]([C@H](C)O)C1]

Addition of 1:1 TFA/DCM to (3,4-trans)-tert-butyl 3-(((5-chloro-2-((1-methyl-1H-pyrazol-4-yl)amino)-7H-pyrrolo[2,3-d]pyrimidin-4-yl)oxy)methyl)-4-((S)-1-hydroxyethyl)pyrrolidine-1-carboxylate to remove the Boc group yielded crude (S)-1-((3,4-trans)-4-(((5-chloro-2-((1-methyl-1H-pyrazol-4-yl)amino)-7H-pyrrolo[2,3-d]pyrimidin-4-yl)oxy)methyl)pyrrolidin-3-yl)ethanol. The volatiles were removed in vacuo and the residue was then dissolved in DMF and Hunig's base (0.54 mL, 4 eq) added followed by addition of acryloyl chloride (64 µL, 1.0 eq). The reaction was filtered and purified by chiral-SFC (Chiralcel OD-H 4.6×100 mm 5p column 20% EtOH, 120 bar, 5.0 mL/min) to afford both single diastereomers as white solids. Peak 1: 48 mg, (13.8%) $^1$H NMR (600 MHz, DMSO-17 mm) δ ppm 1.09 (d, J=6.10 Hz, 3H) 2.05-2.23 (m, 1H) 2.57-2.75 (m, 1H) 3.17 (dd, J=12.46, 7.88 Hz, 1H) 3.30-3.39 (m, 1H) 3.70-3.90 (m, 7H) 4.30-4.39 (m, 1H) 4.94 (dd, J=8.14, 4.83 Hz, 1H) 5.66 (dd, J=10.30, 2.16 Hz, 1H) 6.11 (dd, J=16.66, 2.16 Hz, 1H) 6.48-6.62 (m, 1H) 7.01 (d, J=2.29 Hz, 1H) 7.50 (s, 1H) 7.87 (br. s., 1H) 9.05 (s, 1H) 11.46 (br. s., 1H). /z (APCI+) for ($C_{20}H_{24}ClN_7O_3$) 446.1 (M+H)$^+$. Peak 2: 42 mg, (12%) $^1$H NMR (600 MHz, DMSO-17 mm) δ ppm 1.10 (dd, J=6.36, 3.56 Hz, 3H) 2.07-2.24 (m, 1H) 2.54-2.73 (m, 1H) 3.28-3.45 (m, 2H) 3.69-4.07 (m, 7H) 4.34-4.41 (m, 1H) 4.83-4.92 (m, 1H) 5.62-5.70 (m, 1H) 6.11 (ddd, J=16.78, 2.29, 2.03 Hz, 1H) 6.49-6.63 (m, 1H) 7.01 (s, 1H) 7.51 (s, 1H) 7.86 (br. s., 1H) 9.04 (s, 1H) 11.47 (br. s., 1H). m/z (APCI+) for ($C_{20}H_{24}ClN_7O_3$) 446.1 (M+H)$^+$.

Example 11

(Scheme G): Preparation of N-[(3R)-1-{5-chloro-2-[(1-methyl-1H-pyrazol-4-yl)amino]-7H-pyrrolo[2,3-d]pyrimidin-4-yl}piperidin-3-yl]prop-2-enamide

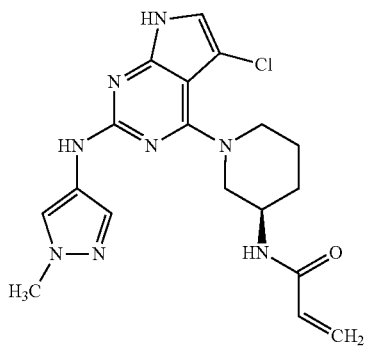 [SMILES: C=CC(=O)N[C@@H]1CCCN(c2nc(Nc3cnn(C)c3)nc3[nH]cc(Cl)c23)C1]

Step 1: Preparation of tert-butyl (1H-pyrazol-1-ylcarbonoimidoyl)carbamate

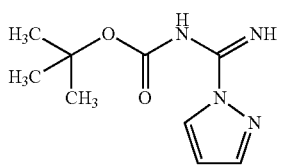

To a solution of (Boc)$_2$O (61 g, 0.28 mol) in THF (1 L) was added DMAP (17 g, 0.14 mol) and Et$_3$N (42 g, 0.42 mol). After stirring for 30 min, 1H-pyrazole-1-carboximidamide hydrochloride (20 g, 0.14 mol) was added and the mixture was stirred at 20° C. for 20 hrs. The reaction was then concentrated in vacuo and the residue was dissolved in EtOAc (500 mL). The solution was washed with aq. NH$_4$Cl (250 mL), dried over anhydrous Na$_2$SO$_4$, filtered and concentrated in vacuo. The residue was recrystallized from EtOAc (200 mL) to afford the title compound (22 g, 74.8% yield) as white solid that was used as-is in the next step.

Step 2: Preparation of di-tert-butyl [(Z)-1H-pyrazol-1-ylmethylylidene]biscarbamate

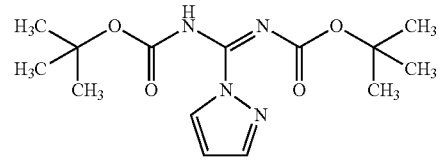 [SMILES: CC(C)(C)OC(=O)/N=C(/NC(=O)OC(C)(C)C)n1cccn1]

A THF (50 mL) solution of tert-butyl (1H-pyrazol-1-ylcarbonoimidoyl)carbamate (17 g, 0.08 mol) was added to a THF (50 mL) suspension of 60% NaH (6.4 g, 0.16 mol) over 1 hr while maintaining the temperature in the range of −5° C.~0° C. Then Boc$_2$O (34.6 g, 0.16 mol) in THF (60 mL) was added, and the mixture was stirred at 80° C. for 20 hrs. Acetic acid (10 mL) was added and stirred for 20 min. After removal of the volatiles, the residue was dissolved in EtOAc (200 mL) and the solution was washed with aq. NaHCO$_3$ (100 mL), dried over anhydrous Na$_2$SO$_4$, filtered and concentrated in vacuo to afford the title compound (17.5 g, 70% yield) as a yellow oil. The crude material was used in the next step.

Step 3: Preparation of di-tert-butyl {(E)-[(1-methyl-1H-pyrazol-4-yl)amino]methylylidene}biscarbamate

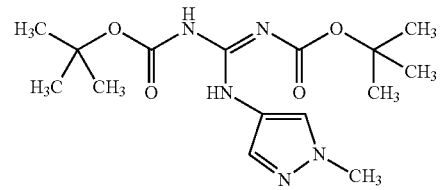

1-methyl-1H-pyrazol-4-amine (11.7 g, 0.12 mol) was added portion-wise to a solution of di-tert-butyl [(Z)-1H-pyrazol-1-ylmethylylidene]biscarbamate (17.5 g, 0.056 mol) in MeCN (100 mL). The mixture was stirred for 20 hrs then filtered to afford the title compound (17.5 g, 91% yield) as a crude solid which was used as is in the next step.

Step 4: Preparation of 1-(1-methyl-1H-pyrazol-4-yl)guanidine

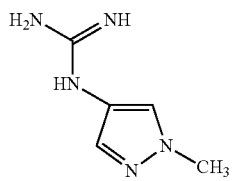

To a solution of di-tert-butyl {(E)-[(1-methyl-1H-pyrazol-4-yl)amino]methylylidene}biscarbamate (17.5 g, 50 mmol) in DCM (50 mL) was added TFA (50 mL) at 0° C. The reaction was allowed to warm to rt and stirred for 20 hrs. The reaction mixture was concentrated to dryness to afford the crude title compound (17.5 g, quant) as a yellow oil. $^1$H NMR (400 MHz, Methanol-d4) δ ppm 7.81-7.82 (d, 1H), 7.74 (s, 1H), 7.47 (s, 1H), 3.89 (s, 3H).

Step 5: Preparation of ethyl 2-cyano-4,4-diethoxybutanoate

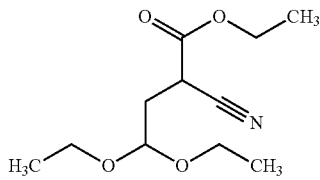 [SMILES: CCOC(=O)C(C#N)CC(OCC)OCC]

A mixture of ethyl 2-cyanoacetate (1000 g, 8.84 mol), 2-bromo-1,1-diethoxyethane (400 g, 2.03 mol), KI (33.4 g, 0.201 mol) and K$_2$CO$_3$ (280 g, 2.03 mol) was heated to reflux for 12 hrs. The reaction mixture was diluted with CH$_2$Cl$_2$ (1000 mL) and the resulting precipitate was filtered off and the filtrate was washed with brine and dried over anhydrous Na$_2$SO$_4$. The solvent was removed in vacuo and the residue distilled to give the title compound (136 g, 29.2% yield) as a light yellow oil that was used as is in the next step.

Step 6: Preparation of 2-((1-methyl-1H-pyrazol-4-yl)amino)-7H-pyrrolo[2,3-d]pyrimidin-4-ol

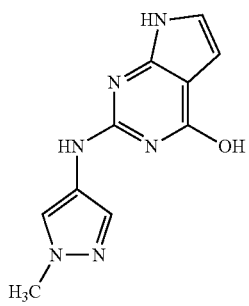 [SMILES: Cn1cc(Nc2nc(O)c3cc[nH]c3n2)cn1]

To a solution of crude 1-(1-methyl-1H-pyrazol-4-yl)guanidine (17.5 g, crude) and ethyl 2-cyano-4,4-diethoxybutanoate (13.08 g, 0.06 mol) in EtOH (50 mL) was added CH$_3$ONa/CH$_3$OH (150 mL, 0.06 mol) at 20° C., and the reaction mixture was stirred at 100° C. for 20 hrs. The pH was adjusted to 2 by HCl (6 M) and stirred for 30 min. Then pH was adjusted to 7-8 by aqueous NaOH (1 M). The reaction mixture was filtered and the filter cake was dried in vacuo to afford a first batch of pure product. The filtrate was concentrated in vacuo and the residue was purified by column chromatography eluted with CH$_2$Cl$_2$:MeOH=13:1 to afford the title compound (combined batches yielded 5 g, 43.5% yield over two steps). $^1$H NMR: (400 MHz, DMSO) δ ppm 11.21 (s, 1H), 10.28 (s, 1H), 8.44 (s, 1H), 7.88 (s, 1H), 7.50 (s, 1H), 6.67-6.68 (m, 1H), 6.22-6.24 (m, 1H), 3.79 (s, 3H).

Step 7: Preparation of 4-chloro-N-(1-methyl-1H-pyrazol-4-yl)-7H-pyrrolo[2,3-d]pyrimidin-2-amine

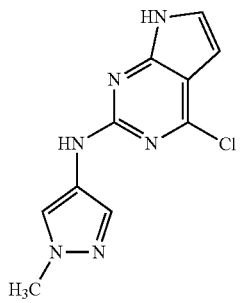 [SMILES: Cn1cc(Nc2nc(Cl)c3cc[nH]c3n2)cn1]

A solution of 2-((1-methyl-1H-pyrazol-4-yl)amino)-7H-pyrrolo[2,3-d]pyrimidin-4-ol (5 g, 0.02 mol) in POCl$_3$ (50 mL) was stirred at 120° C. for 4 hrs. After removal of POCl$_3$ by rotary evaporation, water (37 mL) was added. The pH was adjusted to 10 by aq. NaOH (2 mol/L, 30 mL) and then extracted with EtOAc/THF (2:1, three×200 mL). The combined organic layers were concentrated to dryness to afford the title compound (2.8 g, 56% yield) as a brown solid, which was used as is in the next step.

Step 8: Preparation of 4,5-dichloro-N-(1-methyl-1H-pyrazol-4-yl)-7H-pyrrolo[2,3-d]pyrimidin-2-amine

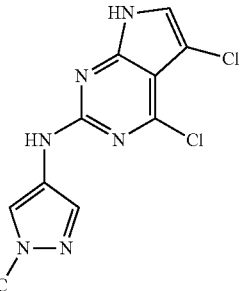

To a solution of 4-chloro-N-(1-methyl-1H-pyrazol-4-yl)-7H-pyrrolo[2,3-d]pyrimidin-2-amine (2 g, 8 mmol) in DMF (35 mL) was added N-chlorosuccinimide (1.28 g, 9.6 mmol). The reaction mixture was stirred at 50° C. overnight. Water (50 mL) was added and the solution was extracted with EtOAc (three×25 mL) and the combined organic layers were dried over Na$_2$SO$_4$, and concentrated to dryness. The residue was purified by preparative HPLC to afford the title compound (0.5 g, 22% yield) as a gray solid. $^1$H NMR (400 MHz, DMSO-d6) δ ppm 11.99 (brs, 1H), 9.62 (brs, 1H), 7.88 (s, 1H), 7.52 (s, 1H), 7.38 (s, 1H), 3.35 (s, 3H). m/z for C$_{10}$H$_8$Cl$_2$N$_6$: 283.0 (M+H)$^+$.

Step 9: Preparation of tert-butyl (1-{5-chloro-2-[(1-methyl-1H-pyrazol-4-yl)amino]-7H-pyrrolo[2,3-d]pyrimidin-4-yl}piperidin-3-yl)carbamate

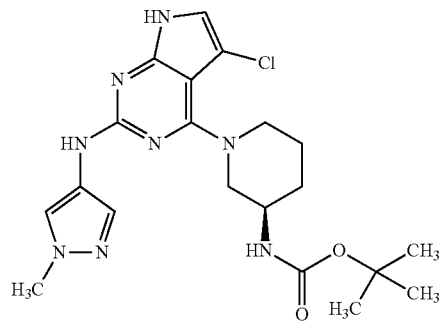 [SMILES: Cn1cc(Nc2nc(N3CCC[C@@H](NC(=O)OC(C)(C)C)C3)c3c(Cl)c[nH]c3n2)cn1]

A solution of 4,5-dichloro-N-(1-methyl-1H-pyrazol-4-yl)-7H-pyrrolo[2,3-d]pyrimidin-2-amine (85 mg, 0.30 mmol), (R)-tert-butyl piperidin-3-ylcarbamate (90 mg, 0.45 mmol) and DIEA (75 μL, 0.45 mmol) in DMSO (0.60 mL) was heated to 120° C. in a microwave for 10 min. The reaction solution was poured into water and filtered. The filtrate was extracted with EtOAc and the organic layer was dried over MgSO$_4$, filtered and concentrated in vacuo. The solids were combined and purified via flash chromatography eluting with a gradient of 1%-5% of (10% NH$_4$OH in MeOH) in DCM to give the title compound (59 mg, 44% yield). $^1$H NMR (400 MHz, DMSO-d6) δ ppm 11.38 (br. s., 1H), 8.74 (s, 1H), 7.82 (s, 1H), 7.49 (s, 1H), 7.04 (d, J=2.69 Hz, 1H), 6.89 (d, J=7.83 Hz, 1H), 3.96-4.11 (m, 2H), 3.78 (s, 3H), 3.51 (br. s., 1H), 2.85 (t, J=11.25 Hz, 1H), 2.75 (t, J=11.13 Hz, 1H), 1.85-1.94 (m, 1H), 1.75-1.84 (m, 1H), 1.70 (t, J=12.10 Hz, 1H), 1.38 (s, 9H), 1.31 (br. s., 1H). m/z (APCI+) for C$_{20}$H$_{27}$ClN$_8$O$_2$ 447.2 (M+H)$^+$.

Step 10: Preparation of N-[(3R)-1-{5-chloro-2-[(1-methyl-1H-pyrazol-4-yl)amino]-7H-pyrrolo[2,3-d]pyrimidin-4-yl}piperidin-3-yl]prop-2-enamide

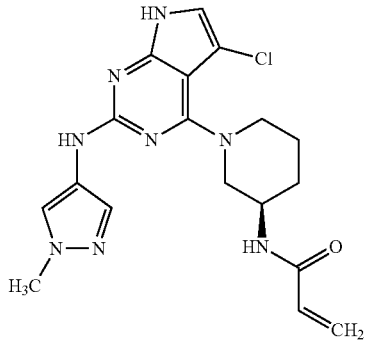 [SMILES: C=CC(=O)N[C@@H]1CCCN(c2nc(Nc3cnn(C)c3)nc3[nH]cc(Cl)c23)C1]

A solution of 4 M HCl in 1,4-dioxane (0.31 mL, 1.3 mmol) was added to a solution of tert-butyl (1-{5-chloro-2-[(1-methyl-1H-pyrazol-4-yl)amino]-7H-pyrrolo[2,3-d]pyrimidin-4-yl}piperidin-3-yl)carbamate (56 mg, 0.12 mmol) in methanol (1.3 mL). After 24 hrs, the mixture was concentrated to dryness by rotary evaporation. The resulting residue was suspended in EtOAc (2.5 mL) and saturated aqueous sodium bicarbonate solution (1.3 mL). Acryloyl chloride (13 µL, 0.16 mmol) was added and the mixture was stirred for 1 hr. The organic layer was separated, dried over MgSO₄ and evaporated to give the title compound (39 mg, 69% yield). ¹H NMR (400 MHz, DMSO-d6) δ ppm 11.40 (br. s., 1H), 8.76 (s, 1H), 8.14 (d, J=7.82 Hz, 1H), 7.83 (s, 1H), 7.47 (s, 1H), 7.05 (d, J=2.45 Hz, 1H), 6.19-6.31 (m, 1H), 6.07-6.16 (m, 1H), 5.60 (dd, J=10.03, 2.45 Hz, 1H), 4.13 (d, J=12.23 Hz, 1H), 4.03 (d, J=12.72 Hz, 1H), 3.85-3.98 (m, 1H), 3.77 (s, 3H), 2.96 (t, J=11.25 Hz, 1H), 2.80 (t, J=11.13 Hz, 1H), 1.89-2.00 (m, 1H), 1.79-1.88 (m, 1H), 1.67-1.79 (m, 1H), 1.40-1.57 (m, 1H). m/z (APCI+) for $C_{18}H_{21}ClN_8O$ 401.2 (M+H)⁺.

Example 12

(Scheme I): Preparation of N-[trans-3-({2-[(1-methyl-1H-pyrazol-4-yl)amino]-5-(pyridin-2-yl)-7H-pyrrolo[2,3-d]pyrimidin-4-yl}oxy)cyclobutyl]prop-2-enamide

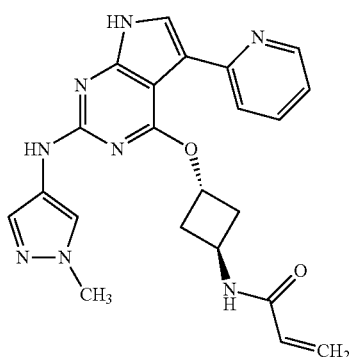

Step 1: Preparation of 2,4-dichloro-5-(pyridin-2-yl)-7-{[2-(trimethylsilyl)ethoxy]methyl}-7H-pyrrolo[2,3-d]pyrimidine

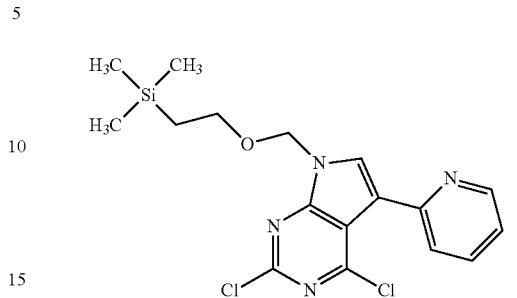

To a solution of 2,4-dichloro-5-iodo-7-{[2-(trimethylsilyl)ethoxy]methyl}-7H-pyrrolo[2,3-d]pyrimidine (1.0 g, 2.25 mmol), as prepared in Example 5, step 1, in THF (11 mL) was added tetrakis(triphenylphosphine)palladium(0) (131 mg, 0.113 mmol) and pyridin-2-ylzinc(II) bromide (9 mL, 4.5 mmol, 0.5 M solution in THF) which was then heated to 65° C. and stirred for 3 hrs. EtOAc (10 mL) was added and the resulting mixture was washed with water (20 mL). The aqueous layer was extracted with EtOAc (three×10 mL), and the combined organic layers were then washed with 1 M aqueous Na₂SO₃ (20 mL), sat. aqueous NaHCO₃ (20 mL), brine (20 mL), dried over Na₂SO₄, filtered and concentrated in vacuo. The residue was then purified via flash chromatography (20%-50% EtOAc/heptane) to give the title compound as a clear oil (378 mg, 43% yield). ¹H NMR (400 MHz, DMSO-d6) δ ppm 8.59-8.71 (m, 1H) 8.21 (s, 1H) 7.89 (td, J=7.77, 1.89 Hz, 1H) 7.70 (d, J=7.83 Hz, 1H) 7.39 (ddd, J=7.52, 4.86, 1.01 Hz, 1H) 5.67 (s, 2H) 3.50-3.67 (m, 2H) 0.79-0.95 (m, 2H) −0.17-0.00 (m, 9H). m/z (APCI+) for $C_{17}H_{20}N_4OCl_2Si$ 395.00/397.00 (M+H)⁺.

Step 2: Preparation of tert-butyl(trans-3-{[2-chloro-5-(pyridin-2-yl)-7-{[2-(trimethylsilyl)ethoxy]methyl}-7H-pyrrolo[2,3-d]pyrimidin-4-yl]oxy}cyclobutyl)carbamate

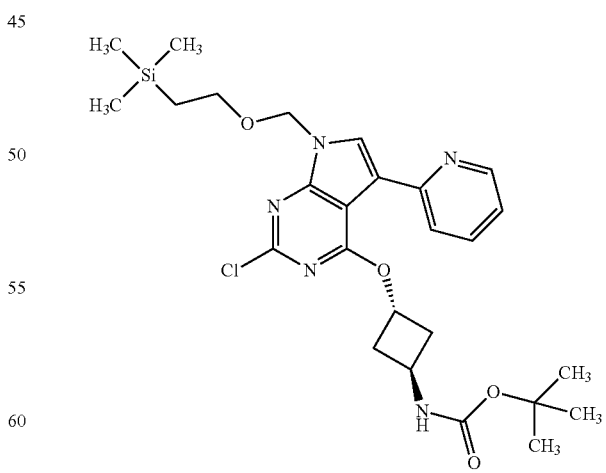

To a solution of 2,4-dichloro-5-(pyridin-2-yl)-7-{[2-(trimethylsilyl)ethoxy]methyl}-7H-pyrrolo[2,3-d]pyrimidine (318 mg, 0.804 mmol) in tetrahydrofuran (8 mL) was added tert-butyl(trans-3-hydroxycyclobutyl)carbamate and potassium hexamethyldisilizane (642 mg, 3.2 mmol) and the mixture stirred at ambient temperature for 1 hr. The reaction mixture was diluted with EtOAc (10 mL) and washed with water (20 mL). The aqueous layer was extracted with EtOAc (three×10 mL) and the combined organics were dried over MgSO$_4$, filtered and stripped to give the title compound (485 mg, 110 yield). The crude material was used for the next step. m/z (APCI+) for C$_{17}$H$_{33}$N$_5$O$_4$ClSi 546.2 (M+H)$^+$.

Step 3: Preparation of tert-butyl {trans-3-[(2-[(1-methyl-1H-pyrazol-4-yl)amino]-5-(pyridin-2-yl)-7-{[2-(trimethylsilyl)ethoxy]methyl}-7H-pyrrolo[2,3-d]pyrimidin-4-yl)oxy]cyclobutyl}carbamate

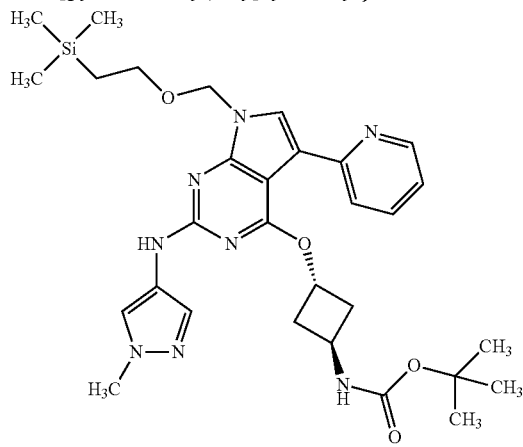

To a solution tert-butyl(trans-3-{[2-chloro-5-(pyridin-2-yl)-7-{[2-(trimethylsilyl)ethoxy]methyl}-7H-pyrrolo[2,3-d]pyrimidin-4-yl]oxy}cyclobutyl)carbamate (439 mg, 0.804 mmol) in 1,4-dioxane (8 mL) in a microwave vial was added 1-methyl-1H-pyrazol-4-amine (78.1 mg, 0.804 mmol) followed by cesium carbonate (524 mg, 1.61 mmol), tris(dibenzylideneacetone)dipalladium(0) (73.3 mg, 0.08 mmol) and 9,9-dimethyl-4,5-bis(diphenylphosphino)xanthene (46.3 mg, 0.08 mmol) and the resulting mixture heated in the microwave to 140° C. for 45 minutes. The reaction was cooled to rt, filtered through a celite plug and stripped to a dark oil that was purified via flash chromatography (20%-100% EtOAc I heptane, then 10% methanol in EtOAc) to afford the title compound as a tan solid (365 mg, 75% yield). $^1$H NMR (400 MHz, DMSO-d6) δ ppm 9.03-9.14 (m, 1H) 8.44-8.55 (m, 1H) 8.00-8.09 (m, 1H) 7.81-7.92 (m, 1H) 7.74-7.80 (m, 1H) 7.57-7.64 (m, 1H) 7.42-7.48 (m, 1H) 7.21-7.32 (m, 1H) 7.11-7.20 (m, 1H) 5.45-5.53 (m, 2H) 5.35-5.42 (m, 1H) 4.02-4.15 (m, 1H) 3.74 (s, 3H) 3.45-3.56 (m, 2H) 2.28-2.39 (m, 4H) 1.31 (s, 9H) 0.74-0.81 (m, 2H) −0.20 (s, 9H). m/z (APCI+) for C$_{30}$H$_{42}$N$_8$O$_4$Si 607.2 (M+H)$^+$.

Step 4: Preparation of {4-[(trans-3-aminocyclobutyl)oxy]-2-[(1-methyl-1H-pyrazol-4-yl)amino]-5-(pyridin-2-yl)-7H-pyrrolo[2,3-d]pyrimidin-7-yl}methanol

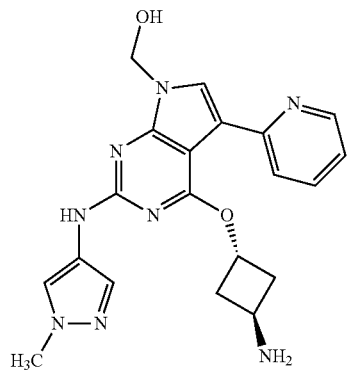 [SMILES: Cn1cc(Nc2nc(O[C@H]3C[C@H](N)C3)c3c(-c4ccccn4)cn(CO)c3n2)cn1]

To a solution tert-butyl {trans-3-[(2-[(1-methyl-1H-pyrazol-4-yl)amino]-5-(pyridin-2-yl)-7-{[2-(trimethylsilyl)ethoxy]methyl}-7H-pyrrolo[2,3-d]pyrimidin-4-yl)oxy]cyclobutyl}carbamate (359 mg, 0.592 mmol) in DCM (3 mL) was added trifluoroacetic acid (2 mL) and stirred at ambient temperature for 2 hrs. The reaction was concentrated down to a dark oil to give the title compound that was used as is for next step. m/z (ESI+) for C$_{20}$H$_{22}$N$_8$O$_2$ 407.0 (M+H)$^+$.

Step 5: Preparation of N-[trans-3-({2-[(1-methyl-1H-pyrazol-4-yl)amino]-5-(pyridin-2-yl)-7H-pyrrolo[2,3-d]pyrimidin-4-yl}oxy)cyclobutyl]prop-2-enamide

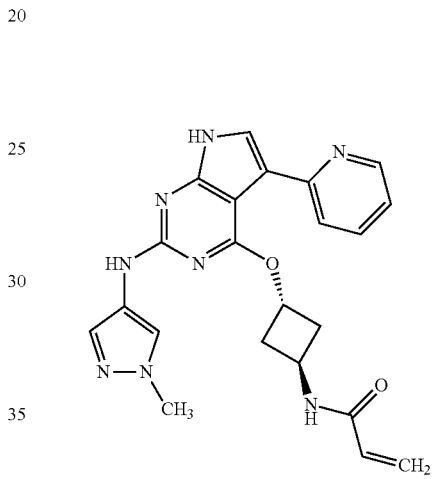

To a solution of {4-[(trans-3-aminocyclobutyl)oxy]-2-[(1-methyl-1H-pyrazol-4-yl)amino]-5-(pyridin-2-yl)-7H-pyrrolo[2,3-d]pyrimidin-7-yl}methanol in ethyl acetate (5 mL) was added saturated aqueous sodium bicarbonate (5 mL) and stirred at ambient temperature for 15 min and then added acroyl chloride (53.6 mg, 0.592 mmol) and stirred at ambient temperature for 2 hours. The volatiles were removed to give N-(trans-3-{[7-(hydroxymethyl)-2-[(1-methyl-1H-pyrazol-4-yl)amino]-5-(pyridin-2-yl)-7H-pyrrolo[2,3-d]pyrimidin-4-yl]oxy}cyclobutyl)prop-2-enamide. Ethanol (10 mL) was then added to the residue, followed by potassium carbonate until the pH of the reaction mixture was about 12. The reaction mixture was then stirred at ambient temperature for 2 hrs. The solid was then removed and the volatiles were concentrated down in vacuo and purified by preparative SFC method using a Zymor, Inc. Pyr/Diol, 150×21.2 mm, 5 µm column using the ethanol/CO$_2$ with flow rate 50.0 mL/min using gradient 20%-40% ethanol ramp at 4%/min, hold 40% ethanol for 0.5 min which was then lyophilized to afford the title compound (18.8 mg, 7.4% yield) as a white solid. $^1$H NMR (700 MHz, DMSO) δ ppm 11.41-11.96 (m, 1H) 8.88-9.01 (m, 1H) 8.57-8.63 (m, 1H) 8.52-8.55 (m, 1H) 8.10-8.15 (m, 1H) 7.87-7.93 (m, 1H) 7.80-7.85 (m, 1H) 7.47-7.55 (m, 2H) 7.18-7.24 (m, 1H) 6.21-6.32 (m, 1H) 6.09-6.15 (m, 1H) 5.61-5.67 (m, 1H) 5.52-5.60 (m, 1H) 4.42-4.52 (m, 1H) 3.78-3.86 (m, 3H) 2.52-2.56 (m, 4H). m/z (ESI+) for $C_{22}H_{22}N_8O_2$ 431.1 $(M+H)^+$.

Example 13

(Scheme J): Preparation of N-methyl-N-[trans-3-({2-[(1-methyl-1H-pyrazol-4-yl)amino]-5-(pyridin-3-yl)-7H-pyrrolo[2,3-d]pyrimidin-4-yl}oxy)cyclobutyl]prop-2-enamide

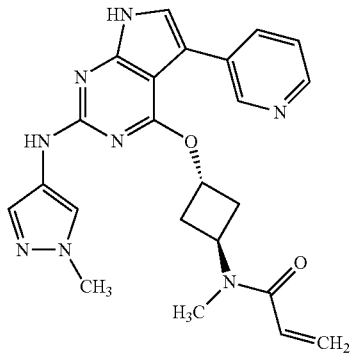 [SMILES: C=CC(=O)N(C)[C@H]1C[C@H](Oc2nc(Nc3cnn(C)c3)nc3[nH]cc(-c4cccnc4)c23)C1]

Step 1: Preparation of tert-butyl {trans-3-[(2-chloro-5-iodo-7-{[2-(trimethylsilyl)ethoxy]methyl}-7H-pyrrolo[2,3-d]pyrimidin-4-yl)oxy]cyclobutyl}methylcarbamate

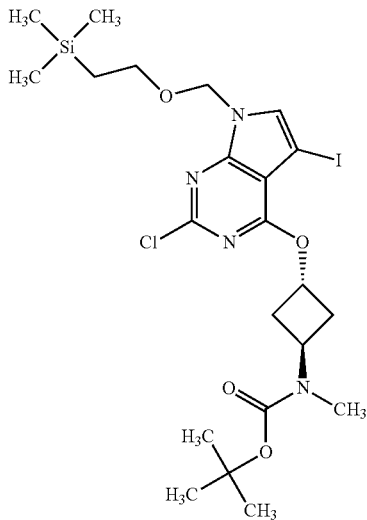

To a solution of 2,4-dichloro-5-iodo-7-{[2-(trimethylsilyl)ethoxy]methyl}-7H-pyrrolo[2,3-d]pyrimidine (416 mg, 0.94 mmol), as prepared in Example 5, step 1, in THF (10 mL) was added tert-butyl(trans-3-hydroxycyclobutyl)methylcarbamate (175 mg, 0.94 mmol) and potassium hexamethyldisilazane (560 mg, 2.8 mmol, 3.0 mol eq) and the reaction was stirred at ambient temperature for 20 hrs. The reaction was then quenched with brine (3 mL) and stirred for 10 min, and diluted with ethyl acetate (60 mL) and water (10 mL). The organic layer was separated, washed with brine (10 mL), dried over $Na_2SO_4$, filtered and evaporated to give an oil which was purified via flash chromatography (eluting with a gradient of 0 iodobenzene diacetate 100% EtOAc in heptanes) to give the title compound (452 mg, 80% yield) as a colorless oil. $^1$H NMR (400 MHz, DMSO-d6) δ ppm 7.80 (s, 1H) 5.48 (s, 2H) 5.38 (t, J=6.54 Hz, 1H) 4.86 (br. s., 1H) 3.44-3.59 (m, 2H) 2.81 (s, 3H) 2.61-2.74 (m, 2H) 2.27-2.43 (m, 2H) 1.40 (s, 9H) 0.71-0.97 (m, 2H) –0.08 (s, 9H). m/z (APCI+) for $C_{22}H_{34}ClN_4O_4Si$ 509.0 $(M+H)^+$.

Step 2: Preparation of tert-butyl(trans-3-{[2-chloro-5-(pyridin-3-yl)-7-{[2-(trimethylsilyl)ethoxy]methyl}-7H-pyrrolo[2,3-d]pyrimidin-4-yl]oxy}cyclobutyl)methylcarbamate

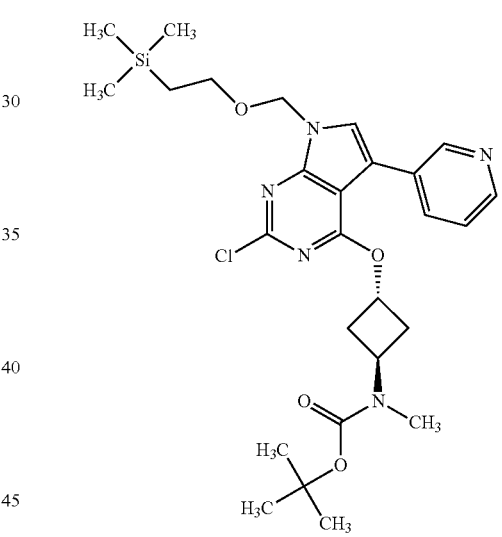

A mixture of tert-butyl {trans-3-[(2-chloro-5-iodo-7-{[2-(trimethylsilyl)ethoxy]methyl}-7H-pyrrolo[2,3-d]pyrimidin-4yl)oxy]cyclobutyl}methylcarbamate (450 mg, 0.7 mmol), pyridin-3-ylboronic acid (95 mg, 0.8 mmol), 1,4-dioxane (10 mL), water (3 mL), sodium carbonate (94 mg, 0.9 mmol), $PdCl_2(dppf)$ (54 mg, 0.07 mmol) was stirred and heated at 70° C. for 1 hr. The reaction was diluted with ethyl acetate (60 mL) and water (15 mL). The organic layer was separated, washed with brine (20 mL), dried over $Na_2SO_4$ and evaporated to give a residue, which was purified via flash chromatography (eluting with a gradient of 0%-100% EtOAc in heptanes) to give the title compound (304 mg, 73% yield). $^1$H NMR (400 MHz, DMSO-d6) δ ppm 8.90 (d, J=1.83 Hz, 1H) 8.53 (dd, J=4.71, 1.41 Hz, 1H) 8.12 (dt, J=8.01, 1.86 Hz, 1H) 7.98 (s, 1H) 7.48 (dd, J=7.82, 4.89 Hz, 1H) 5.58 (s, 2H) 5.40 (t, J=6.60 Hz, 1H) 4.67 (br. s., 1H) 3.52-3.65 (m, 2H) 2.78 (s, 3H) 2.59-2.71 (m, 2H) 2.21-2.37 (m, 2H) 1.38 (s, 9H)

0.82-0.93 (m, 2H) −0.06 (s, 9H). m/z (APCI+) for $C_{27}H_{38}ClN_5O_4Si$ 560.2 (M+H)$^+$.

Step 3: Preparation of tert-butyl methyl{trans-3-[(2-[(1-methyl-1H-pyrazol-4-yl)amino]-5-(pyridin-3-yl)-7-{[2-(trimethylsilyl)ethoxy]methyl}-7H-pyrrolo[2,3-d]pyrimidin-4-yl)oxy]cyclobutyl}carbamate

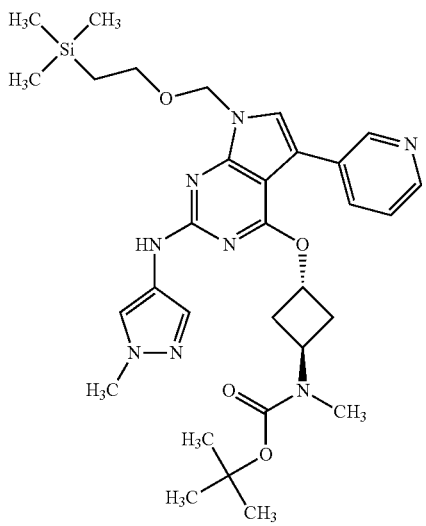 [SMILES: Cn1cc(Nc2nc(O[C@H]3C[C@H](N(C)C(=O)OC(C)(C)C)C3)c3c(-c4cccnc4)cn(COCC[Si](C)(C)C)c3n2)cn1]

To a microwave reaction vial was added tert-butyl(trans-3-{[2-chloro-5-(pyridin-3-yl)-7-{[2-(trimethylsilyl)ethoxy]methyl}-7H-pyrrolo[2,3-d]pyrimidin-4-yl]oxy}cyclobutyl)methylcarbamate (300 mg, 0.54 mmol), 1-methyl-1H-pyrazol-4-amine (57 mg, 0.59 mmol), 1,4-dioxane (5 mL), $Cs_2CO_3$ (349 mg, 1.1 mmol), Xantphos (32 mg, 0.1 mol eq) and $Pd_2(dba)_3$ (50 mg, 0.1 mol eq). The reaction vial was flushed with nitrogen, capped, stirred and heated to 140° C. using microwave for 45 min. The reaction was then cooled and diluted with ethyl acetate (40 mL) and water (8 mL). The organic layer was separated, dried over $Na_2SO_4$ and evaporated to give a residue, which was purified via flash chromatography (eluting with a gradient of 0%-100% EtOAc in heptanes) to give the title compound (255 mg, 77% yield). $^1$H NMR (400 MHz, DMSO-d6) δ ppm 9.17 (s, 1H) 8.89 (d, J=1.71 Hz, 1H) 8.47 (dd, J=4.77, 1.59 Hz, 1H) 8.10 (dt, J=7.98, 1.88 Hz, 1H) 7.93 (br. s., 1H) 7.49-7.59 (m, 2H) 7.44 (dd, J=7.76, 4.83 Hz, 1H) 5.54 (br. s., 2H) 5.42 (br. s., 1H) 4.66 (br. s., 1H) 3.82 (s, 3H) 3.53-3.68 (m, 2H) 2.82 (s, 3H) 2.56-2.72 (m, 2H) 2.22-2.41 (m, 2H) 1.38 (s, 9H) 0.78-0.94 (m, 2H) −0.10 (s, 9H). m/z (APCI+) for $O_{31}H_{44}N_8O_4Si$ 621.3 (M+H)$^+$.

Step 4: Preparation of 4-{[trans-3-(methylamino)cyclobutyl]oxy}-N-(1-methyl-1H-pyrazol-4-yl)-5-(pyridin-3-yl)-7H-pyrrolo[2,3-d]pyrimidin-2-amine

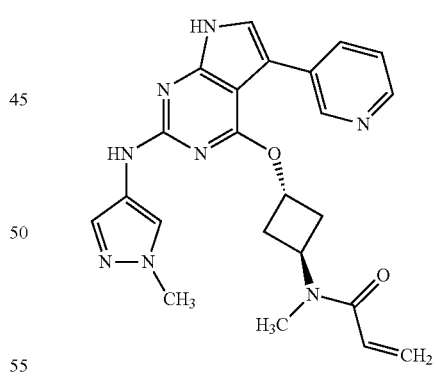

To a solution of tert-butyl methyl{trans-3-[(2-[(1-methyl-1H-pyrazol-4-yl)amino]-5-(pyridin-3-yl)-7-{[2-(trimethylsilyl)ethoxy]methyl}-7H-pyrrolo[2,3-d]pyrimidin-4-yl)oxy]cyclobutyl}carbamate (250 mg, 0.4 mmol) in DCM (10 mL) was added TFA (0.33 mL). The reaction solution was stirred at ambient temperature for 20 hrs. The volatiles were removed in vacuo to give a residue, which was dissolved in methanol (8 mL). Water (4 mL) and solid $K_2CO_3$ (223 mg) were added, and the mixture was stirred at ambient temperature for 2 hrs. The volatiles were then removed in vacuo to give the title compound that was used as crude in the next step.

Step 5: Preparation of N-methyl-N-[trans-3-({2-[(1-methyl-1H-pyrazol-4-yl)amino]-5-(pyridin-3-yl)-7H-pyrrolo[2,3-d]pyrimidin-4-yl}oxy)cyclobutyl]prop-2-enamide Crude 4-{[trans-3-(methylamino)cyclobutyl]oxy}-N-(1-methyl-1H-pyrazol-4-yl)-5-(pyridin-3-yl)-7H-pyrrolo[2,3-d]pyrimidin-2-amine (0.4 mmol) was partitioned between water (8 mL) and ethyl acetate (15 mL). Acryloyl chloride (36 μL, 0.44 mmol) was added and the mixture stirred at ambient temperature for 1 hr. The organic layer was separated, dried over $Na_2SO_4$ and evaporated to give a residue, which was purified by SFC (Zymor Spher Diol Monol, 150×21.2 mm, 5 μm column at 35° C. eluting with a 20%-50% EtOH gradient at 5%/min in $CO_2$ at 140 bar with a flow rate of 60 mL/min) to give the title compound (7.4 mg, 4% yield). $^1$H NMR (700 MHz, DMSO-17 mm) δ ppm 11.64 (br. s., 1H) 8.87-9.00 (m, 2H) 8.43 (d, J=3.96 Hz, 1H) 8.12 (d, J=7.26 Hz, 1H) 7.87 (br. s., 1H) 7.52 (s, 1H) 7.42 (br. s., 1H) 7.33 (s, 1H) 6.59-6.80 (m, 1H) 5.95-6.15 (m, 1H) 5.65 (br. s., 2H) 5.47 (br. s., 1H) 3.74-3.88 (m, 3H) 3.07 (br. s., 1H) 2.91-3.00 (m, 1H) 2.72 (br. s., 2H) 2.29-2.46 (m, 2H). m/z (APCI+) for $C_{23}H_{24}N_8O_2$ 445.2 (M+H)$^+$.

Experimental Procedures for Key Intermediates

Preparation 1. Preparation of 1-(tetrahydrofuran-3-yl)-1H-pyrazol-4-amine

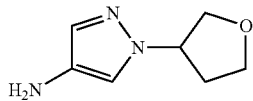

To a solution of 4-nitropyrazole (1 g, 8.8 mmol), 3-hydroxy-tetrahydrofuran (779 mg, 8.8 mmol) and triphenylphosphine (2.81 g, 10.56 mmol) in THF (30 mL) at 0° C. was added diisopropylazodicarboxylate (2.27 g, 1 mmol) dropwise and the reaction was allowed to warm to rt overnight. The reaction was concentrated and purified on SiO$_2$ (30% EtOAc/heptane) to give 4-nitro-1-(tetrahydrofuran-3-yl)-1H-pyrazole as a clear oil. The oil was then dissolved in EtOH (30 mL) and hydrogenated via H-cube with 10% Pd/C at 30 psi H$_2$ for 3 hrs. The solvent was removed and the residue was purified on SiO$_2$ (1%-10% EtOH/EtOAc) to give the title compound (1.0 g, 42% yield) as an orange oil. $^1$H NMR (400 MHz, DMSO-d6) δ ppm 2.10-2.21 (m, 1H), 2.22-2.35 (m, 1H), 3.72-3.85 (m, 4H), 3.85-3.96 (m, 2H), 4.76-4.85 (m, 1H), 6.93 (s, 1H), 7.05 (s, 1H). m/z (APCI+) for $C_7H_{11}N_3O$ 154.1 (M+H)$^+$.

Preparation 2. Preparation of 2-methyl-1-(4-nitro-1H-pyrazol-1-yl)propan-2-ol

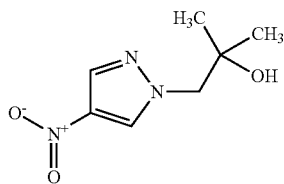

A 250 mL round bottom flask was charged with 1-chloro-2-methylpropan-2-ol (2.0 g, 18 mmol). DCM (60 mL) was added, followed by Et$_3$SiCl (3.4 mL, 20 mmol) and then NMM (3 mL, 27 mmol) and the reaction was stirred at rt for 36 hrs. Water (50 mL) and DCM (50 mL) were added and the aqueous layer extracted with DCM (two×30 mL). The combined organic extracts were washed with water and dried over MgSO$_4$. After filtering, the solvents were removed in vacuo, keeping the bath temperature at 22° C. The intermediate was placed under a 10 mm Hg vacuum for 15 min to provide (ca. 18 mmol, 100% yield) of ((1-chloro-2-methylpropan-2-yl)oxy)triethylsilane as a pale yellow oil. This material was used as is in the next step.

4-nitro-1H-pyrazole (2.1 g, 18.4 mmol) was dissolved in DMF (30 mL, 0.61 M). This solution was chilled to 0° C. under N$_2$ and NaH (810 mg, 20 mmol) was added in portions. The ice bath was removed and the solution allowed to stir for 30 min at rt. ((1-chloro-2-methylpropan-2-yl)oxy)triethylsilane (ca. 18 mmol) was added dropwise as a solution in DMF (10 mL) over 15 min and the reaction was monitored by TLC. At rt overnight, no reaction was observed by TLC or by LCMS. The reaction was heated at 110° C. for 1 hr and then 126° C. for another 1 hr. LCMS showed a higher Rf product forming believed to be product based on a fragment observed at M+H=186. The reaction was cooled to rt and was poured over ice (20 g) and brine (20 mL). The aqueous was extracted with EtOAc (four times). The combined organic extract was washed with brine (one time). After drying over MgSO$_4$, the material was concentrated to afford an amber oil. The crude NMR of the mixture indicated that the major product was 2-methyl-1-(4-nitro-1H-pyrazol-1-yl)propan-2-ol, and not the silylether. The product was purified by flash chromatography, eluting with a gradient of 12%-60% EtOAc in heptanes, to afford of the title compound (2.0 g, 60% yield over 2 steps) as a colorless oil. $^1$H NMR (400 MHz, chloroform-d) δ ppm 1.24 (s, 6H), 4.13 (s, 2H), 8.10 (s, 1H), 8.26 (s, 1H); m/z (APCI+) for $C_7H_{11}N_3O_3$ 186 (M+H)$^+$.

Preparation 3. Preparation of 1-(4-amino-1H-pyrazol-1-yl)-2-methylpropan-2-ol

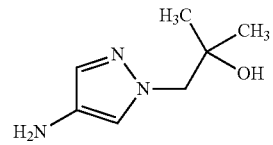

2-methyl-1-(4-nitro-1H-pyrazol-1-yl)propan-2-ol (2.0 g, 10.8 mmol) was dissolved in MeOH (50 mL) and 10% Pd/C (240 mg) was added. A hydrogen balloon was fitted over the reaction and the reaction was allowed to stir at rt for 16 hrs. The reaction was checked using the polar APCI method and LCMS showed 70% complete with 30% starting material remaining. Another 200 mg of 10% Pd/C was added and the balloon was re-charged with fresh hydrogen. After 4 hrs, the reaction was complete. The reaction was filtered through Celite, washing with MeOH (three×50 mL) and the combined filtrate was concentrated to dryness. Purification was accomplished via flash chromatography eluting with gradient of 3%-20% MeOH in DCM. The pure fractions were pooled and concentrated to afford the title compound (1.4 g, 84% yield) as a purple solid. $^1$H NMR (400 MHz, chloroform-d) δ ppm 1.14 (s, 6H), 3.92 (s, 2H), 7.04 (s, 1H), 7.19 (s, 1H); m/z (APCI+) for $C_7H_{13}N_3O$ 156.0 (M+H)$^+$.

Preparation 4. Preparation of tert-butyl(trans)-3-(hydroxymethyl)-4-(2,2,2-trifluoroethyl)pyrrolidine-1-carboxylate

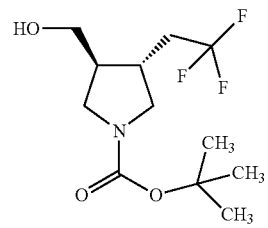 [SMILES: CC(C)(C)OC(=O)N1C[C@@H](CO)[C@H](CC(F)(F)F)C1]

Step 1: Preparation of ethyl (2E)-5,5,5-trifluoropent-2-enoate

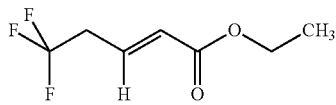

To a stirred suspension of NaH (60% in oil, 2.15 g, 53.5 mmol) in dry THF (50 mL) was added dropwise ethyl(diethoxyphosphoryl)acetate (11 g, 49 mmol) at 0° C. under N₂ atmosphere. The resulting mixture was stirred at 0° C. for 10 min and then cooled to −70° C. A solution of 3,3,3-trifluoropropanal (5.0 g, 44.5 mmol) in dry THF (50 mL) was added to the mixture at −70° C. After the addition, the stirred mixture was allowed to warm to −20° C. over 2 hrs. The reaction mixture was quenched by addition of 5% aqueous NH₄Cl (100 mL) at 0° C. and extracted with EtOAc (100 mL). The organic layer was washed with brine (300 mL), dried over Na₂SO₄ and concentrated in vacuo. The residue was purified by column chromatography (silica gel, petroleum ether:EtOAc=100:1) to give the title compound (3.0 g, 37%) as a colorless oil.

Step 2: Preparation of ethyl trans-1-benzyl-4-(2,2,2-trifluoroethyl)pyrrolidine-3-carboxylate

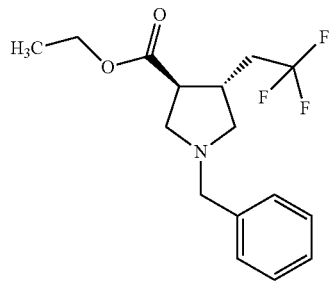 [SMILES: CCOC(=O)[C@@H]1CN(Cc2ccccc2)C[C@H]1CC(F)(F)F]

To a stirred solution of ethyl (2E)-5,5,5-trifluoropent-2-enoate (3.0 g, 16.5 mmol) and TFA (0.38 g, 3.3 mmol) in DCM (40 mL) was added dropwise {benzyl[(trimethylsilyl)methyl]amino}methanol (7.8 g, 33 mmol) at 0° C. over a period of 30 min. After the addition, the mixture was refluxed overnight. TLC (petroleum ether:EtOAc 10:1) indicated ethyl (2E)-5,5,5-trifluoropent-2-enoate was consumed. The reaction mixture was washed with sat. NaHCO₃ (40 mL), brine (40 mL), dried over Na₂SO₄ and concentrated in vacuo. The residue was purified by column chromatography (silica gel, petroleum ether:EtOAc=100:1 to 10:1) to give the title compound (5.1 g, 98% yield) as a yellow oil.

Step 3: Preparation of ethyl trans-1-(2-tert-butoxy-2-oxoethyl)-4-(2,2,2-trifluoroethyl)pyrrolidine-3-carboxylate

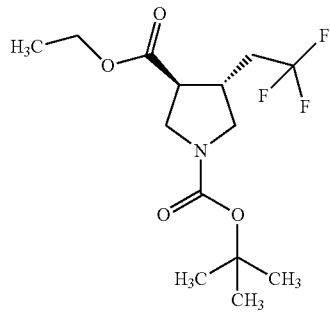 [SMILES: CCOC(=O)[C@@H]1CN(C(=O)OC(C)(C)C)C[C@H]1CC(F)(F)F]

A mixture of ethyl trans-1-benzyl-4-(2,2,2-trifluoroethyl)pyrrolidine-3-carboxylate (5.1 g, 16.5 mmol), Pd(OH)₂ (1.5 g) and Boc₂O (5.4 g, 24.8 mmol) in EtOH (100 mL) was stirred at 50° C. under H₂ atmosphere (50 psi) overnight. TLC (petroleum ether:EtOAc 5:1) indicated the reaction was complete. The mixture was filtered and the cake was washed with EtOH (100 mL). The filtrate was combined and concentrated in vacuo. The residue was purified by column chromatography (silica gel, petroleum ether:EtOAc=50:1 to 10:1) to give the title compound (3.9 g, 73% yield) as a colorless oil.

Step 4: Preparation of tert-butyl(trans)-3-(hydroxymethyl)-4-(2,2,2-trifluoroethyl)pyrrolidine-1-carboxylate

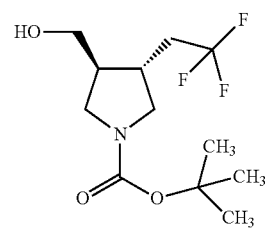 [SMILES: CC(C)(C)OC(=O)N1C[C@@H](CO)[C@H](CC(F)(F)F)C1]

A mixture of ethyl trans-1-(2-tert-butoxy-2-oxoethyl)-4-(2,2,2-trifluoroethyl)pyrrolidine-3-carboxylate (3.9 g, 12 mmol) and LiBH₄ (1.26 g, 60 mmol) in dry THF (75 mL) was refluxed overnight. TLC (petroleum ether:EtOAc 5:1) indicated the reaction was complete. The reaction mixture was quenched by addition of water (75 mL) and extracted with EtOAc (75 mL). The organic layer was washed with brine (75 mL), dried over Na₂SO₄ and concentrated in vacuo. The residue was purified by column chromatography (silica gel, petroleum ether:EtOAc=20:1 to 3:1) to give the title compound (1.7 g, 50% yield) as a yellow oil. ¹H NMR (400 MHz, DMSO-D6): δ ppm 4.75-4.73 (m, 1H), 3.55-3.44 (m, 2H), 3.42-3.33 (m, 2H), 3.05-2.97 (m, 2H), 2.66-2.59 (m, 1H), 2.32-2.20 (m, 1H), 2.17-2.11 (m, 1H), 2.01-1.98 (m, 1H), 1.38 (s, 9H). m/z (APCI+) for C₁₂H₂₀F₃NO₃ 227.9 (M−$^t$Bu+H)⁺.

Preparation 5. Preparation of tert-butyl(trans)-3-cyclopropyl-4-(hydroxymethyl)pyrrolidine-1-carboxylate

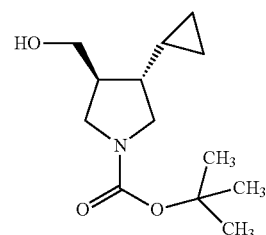

Step 1: Preparation of ethyl (2E)-3-cyclopropylacrylate

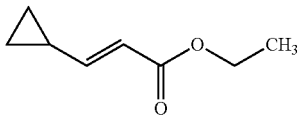

To a stirred suspension of NaH (60% in oil, 2.1 g, 51.5 mmol) in dry THF (50 mL) was added dropwise ethyl(diethoxyphosphoryl)acetate (10.6 g, 47.1 mmol) at 0° C. under $N_2$ atmosphere. The resulting mixture was stirred at 0° C. for 0.5 hr and added dropwise a solution of cyclopropanecarbaldehyde (3.0 g, 42.9 mmol) in dry THF (50 mL). After the addition, the mixture was stirred at rt for 16 hrs. Then the reaction mixture was quenched by addition of 5% $NH_4Cl$ (100 mL) at 0° C. and extracted with EtOAc (100 mL). The organic layer was washed with brine (100 mL), dried over $Na_2SO_4$ and concentrated in vacuo. The residue was purified by column chromatography (silica gel, petroleum ether: EtOAc=30:1) to give the title compound (5.3 g, 88.3% yield) as a colorless oil.

Step 2: Preparation of ethyl trans-1-benzyl-4-cyclopropylpyrrolidine-3-carboxylate

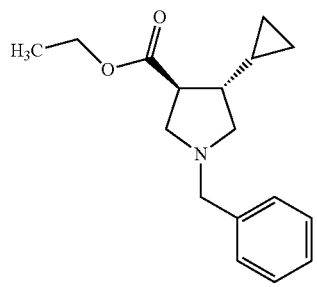 [SMILES: CCOC(=O)[C@@H]1CN(Cc2ccccc2)C[C@H]1C1CC1]

To a stirred solution of ethyl (2E)-3-cyclopropylacrylate (5.3 g, 37.9 mmol) and TFA (0.43 g, 3.79 mmol) in DCM (100 mL) was added dropwise {benzyl[(trimethylsilyl)methyl]amino}methanol (13.5 g, 56.8 mmol) at 0° C. After the addition, the mixture was refluxed overnight. TLC (petroleum ether: EtOAc 10:1) indicated most of ethyl (2E)-3-cyclopropylacrylate was consumed. The reaction mixture was quenched with sat. $NaHCO_3$ (100 mL), brine (100 mL), dried over $Na_2SO_4$ and concentrated in vacuo. The residue was purified by column chromatography (silica gel, petroleum ether: EtOAc=50:1 to 30:1) to give the title compound (5.8 g, 54% yield) as a yellow oil.

Step 3: Preparation of 1-tert-butyl 3-ethyl(trans)-4-cyclopropylpyrrolidine-1,3-dicarboxylate

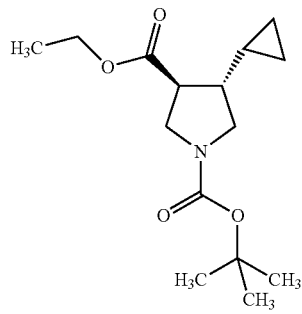 [SMILES: CCOC(=O)[C@@H]1CN(C(=O)OC(C)(C)C)C[C@H]1C1CC1]

A mixture of ethyl trans-1-benzyl-4-cyclopropylpyrrolidine-3-carboxylate (4.5 g, 15.9 mmol), $Pd(OH)_2$ (1.2 g) and $Boc_2O$ (5.2 g, 23.9 mmol) in EtOH (100 mL) was stirred at 50° C. under $H_2$ atmosphere (50 psi) overnight. TLC (petroleum ether:EtOAc 5:1) indicated the reaction was complete. The mixture was filtered and the cake was washed with EtOH (100 mL). The filtrate was combined and concentrated in vacuo. The residue was purified by column chromatography (silica gel, petroleum ether: EtOAc=100:1 to 50:1) to give the title compound (3.7 g, 82% yield) as a colorless oil.

Step 4: Preparation of tert-butyl(trans)-3-cyclopropyl-4-(hydroxymethyl)pyrrolidine-1-carboxylate

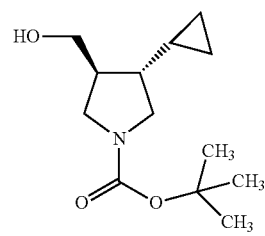

A mixture of 1-tert-butyl 3-ethyl(trans)-4-cyclopropylpyrrolidine-1,3-dicarboxylate (9.2 g, 13 mmol) and $LiBH_4$ (1.37 g, 65 mmol) in dry THF (75 mL) was refluxed overnight. TLC (petroleum ether:EtOAc 5:1) indicated the reaction was complete. The reaction mixture was quenched by addition of water (75 mL) and extracted with EtOAc (75 mL). The organic layer was washed with brine (75 mL), dried over $Na_2SO_4$ and concentrated in vacuo. The residue was purified by column chromatography (silica gel, petroleum ether:EtOAc=20:1 to 3:1) to give the title compound (2.4 g, 76%) as a yellow oil. $^1H$ NMR (400 MHz, $CDCl_3$): δ ppm 3.80-3.78 (d, 1H), 3.64-3.49 (m, 3H), 3.19-3.07 (m, 2H), 2.21 (s, 1H), 1.94-1.81 (d, 1H), 1.44-1.42 (d, 9H), 1.14-1.23 (m, 1H), 0.67-0.62 (m, 1H), 0.50-0.48 (d, 2H), 0.14-0.08 (m, 2H). m/z (APCI+) for $C_{13}H_{23}NO_3$ 186.0 (M−$^tBu$+H)+.

Preparation 6. Preparation of (3-hydroxy-3-methyl-cyclobutyl)-carbamic acid tert-butyl ester

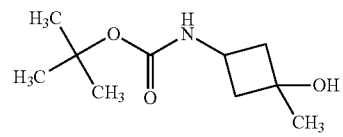

Step 1: Preparation of (1-oxa-spiro[2.3]hex-5-yl)-carbamic acid tert-butyl ester

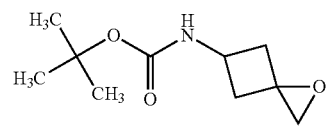

A solution of (3-methylene-cyclobutyl)-carbamic acid tert-butyl ester (4.27 g, 23.3 mmol) in dichloromethane (95 mL) was cooled to 0° C. in an ice/water bath. 3-Chloroperbenzoic acid (77% technical grade, 5.84 g, 26 mmol) was added in small portions. After stirring at 0° C. for 1.5 hours, the mixture was transferred to a separatory funnel and washed sequentially with 10% aqueous Na₂SO₃ (50 mL), saturated aqueous NaHCO₃ (30 mL), and saturated aqueous NaCl (30 mL). The organic layer was dried over magnesium sulfate, filtered, concentrated, and purified by silica gel chromatography (eluting with 30-100% ethyl acetate in heptane), affording the title compound (2.84 g, 61%) as a white solid. NMR showed a 1:1 mixture of N,O-cis/trans isomers. $^1$H NMR (400 MHz, chloroform-d) δ ppm 1.46 (d, J=1.26 Hz, 9H) 2.35-2.45 (m, 2H) 2.67-2.83 (m, 4H) 3.97-4.36 (m, 1H) 4.77 (br. s., 1H)

Step 2: Preparation of (3-hydroxy-3-methyl-cyclobutyl)-carbamic acid tert-butyl ester

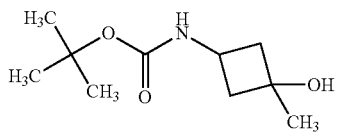

(1-Oxa-spiro[2.3]hex-5-yl)-carbamic acid tert-butyl ester (~1:1 cis/trans mixture, 3.93 g, 19.7 mmol) was dissolved in anhydrous THF (100 mL) and cooled to 0° C. in an ice/water bath. To this was added a 1.0 M solution of lithium triethylborohydride in THF (25 mL) via dropping addition funnel, over 10 min, then the mixture stirred at 0° C. for 3.5 hours. While still cooled to 0° C., 30 mL deionized water was added dropwise over 5 minutes to quench the reaction. After warming to rt, solid potassium carbonate was added to saturate the aqueous phase, allowing the layers to be separated. The aqueous layer was further extracted with ethyl acetate (2×30 mL). The combined organic layers (THF and EtOAc) were dried over magnesium sulfate, filtered, concentrated, and purified by silica gel chromatography (eluting with 40-80% ethyl acetate in heptanes), affording the title compound (3.16 g, 80%) as a white solid. NMR shows a 55:45 ratio of N,O-cis/trans isomers. $^1$H NMR (400 MHz, chloroform-d) δ ppm [1.37 (s) and 1.41 (s), 3H together] 1.44 (s, 9H) 1.66 (br. s., 1H) 1.89-2.03 (m, 2H) 2.42-2.54 (m, 2H)

Preparation 7. Preparation of 1-(4-amino-1H-pyrazol-1-yl)-3-(dimethylamino)propan-2-ol

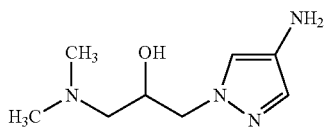

Step 1: Preparation of 1-(dimethylamino)-3-(4-nitro-1H-pyrazol-1-yl)propan-2-ol

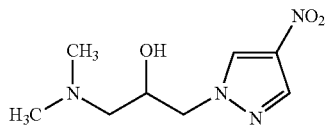

To a solution of 3-(dimethylamino)propane-1,2-diol (934 mg, 7.84 mmol) in CH₂Cl₂ (8 mL) were added Bu₂SnO (42 mg, 0.16 mmol), tosyl chloride (1.49 g, 7.84 mmol), and Et₃N (1.10 mL, 7.92 mmol). The reaction mixture was stirred at rt for 2 hrs. The mixture was quenched with water (30 mL) and extracted with EtOAc (two×30 mL). The combined organic layers were dried over MgSO₄ and concentrated to afford 3-dimethylamino-2-hydroxypropyl 4-methylbenzenesulfonate; [m/z (APCI+) 274.10 (M+H)⁺]. The residue was dissolved in THF (10 mL), then DBU (2.56 mL, 16.6 mmol) and 4-nitro-1H-pyrazole (602 mg, 5.32 mmol) were added and the resulting mixture was stirred at rt for 30 min. The mixture was then quenched with water (30 mL) and extracted with EtOAc (two×30 mL). The combined organic layer were dried over MgSO₄ and concentrated to give the title compound as a pale yellow oil (526 mg, 46° A yield) which was used without purification. m/z (APCI+) for $C_8H_{14}N_4O_3$ 215.10 (M+H)⁺.

Step 2: Preparation of 1-(4-amino-1H-pyrazol-1-yl)-3-(dimethylamino)propan-2-ol

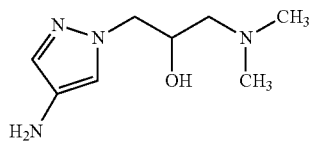

Pd(OH)₂ (25 mg) was added to a solution of 1-(dimethylamino)-3-(4-nitro-1H-pyrazol-1-yl)propan-2-ol (526 mg, 2.46 mmol) in EtOH (3 mL) and the mixture was stirred at rt under H₂ balloon for 5 hrs. The mixture was filtered through Celite. The filtrate was concentrated to give the crude title compound as an orange oil (452 mg, 100%) which was used crude in subsequent steps. m/z (APCI+) for $C_8H_{16}N_4O$ 185.10 (M+H)⁺.

Preparation 8. Preparation of tert-butyl-3-(hydroxymethyl)-4-(methoxymethyl)pyrrolidine-1-carboxylate

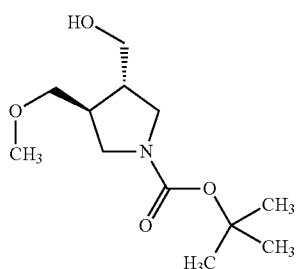

Step 1: Preparation of ethyl (2E)-4-{[tert-butyl(dimethyl)silyl]oxy}but-2-enoate

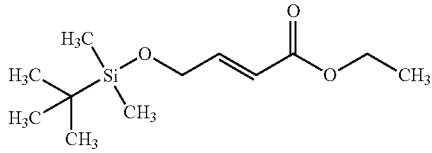 [SMILES: CCOC(=O)/C=C/CO[Si](C)(C)C(C)(C)C]

DIEA (2.75 mL, 16.6 mmol) and LiCl (5.54 g, 129 mmol) were added to a solution of tert-butyldimethylsilyloxy acetaldehyde (3.22 g, 18.5 mmol) and diethylmethylphosphonoacetate (4.66 g, 22.2 mmol) in CH$_3$CN (40 mL) and the mixture was stirred at rt for 24 hrs. The mixture was quenched with water (50 mL) and extracted with EtOAc (50 mL). The organic layer was dried over MgSO$_4$ and concentrated. The residue was purified via flash chromatography eluting with 25% EtOAc/heptane to give the title compound as a colorless oil (3.27 g, 72% yield). $^1$H NMR (400 MHz, chloroform-d) δ ppm 6.91 (dt, J=15.42, 3.49 Hz, 1H) 6.01 (dt, J=15.61, 2.27 Hz, 1H) 4.25 (dd, J=3.27, 2.27 Hz, 2H) 4.12 (q, J=7.22 Hz, 2H) 1.21 (t, J=7.18 Hz, 3H) 0.84 (s, 9H) 0.00 (s, 6H).

Step 2: Preparation of trans-ethyl-1-benzyl-4-({[tert-butyl(dimethyl)silyl]oxy}methyl)pyrrolidine-3-carboxylate

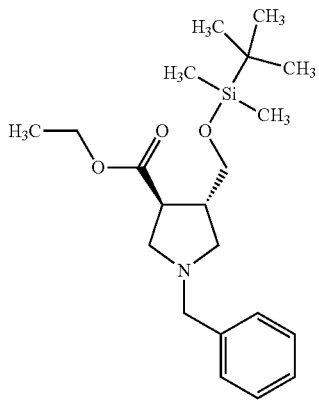 [SMILES: CCOC(=O)[C@@H]1CN(Cc2ccccc2)C[C@H]1CO[Si](C)(C)C(C)(C)C]

To a solution of ethyl (2E)-4-{[tert-butyl(dimethyl)silyl]oxy}but-2-enoate (3.27 g, 13.4 mmol) and N-benzyl-1-methoxy-N-((trimethylsilyl)methyl)methanamine (4.14 g, 17.5 mmol) in CH$_2$Cl$_2$ (30 mL) was added TFA (0.280 mL, 3.64 mmol) at 0° C. The reaction was stirred at rt overnight. The mixture was quenched with water (50 mL) and extracted with EtOAc (two×50 mL). The combined organic layers were dried over MgSO$_4$ and concentrated. The residue was purified via flash chromatography eluting with 20% EtOAc/heptane to give the title compound as a pale yellow oil (2.61 g, 53 yield). $^1$H NMR (400 MHz, chloroform-d) δ ppm 7.08-7.41 (m, 5H), 4.10 (q, J=7.13 Hz, 2H), 3.42-3.73 (m, 4H), 2.37-2.90 (m, 6H), 1.22 (t, J=7.05 Hz, 3H), 0.84 (s, 9H), 0.00 (d, J=1.26 Hz, 6H).

Step 3: Preparation of trans-1-tert-butyl 3-ethyl-4-({[tert-butyl(dimethyl)silyl]oxy}methyl)pyrrolidine-1,3-dicarboxylate

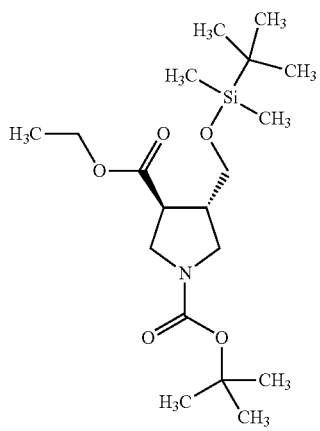 [SMILES: CCOC(=O)[C@@H]1CN(C(=O)OC(C)(C)C)C[C@H]1CO[Si](C)(C)C(C)(C)C]

To a solution of trans-ethyl-1-benzyl-4-({[tert-butyl(dimethyl)silyl]oxy}methyl)pyrrolidine-3-carboxylate (trans mixture) (3.25 g, 8.61 mmol) in EtOH (40 mL) was added Pd(OH)$_2$ (300 mg) and Boc$_2$O (1.90 g, 8.61 mmol). The mixture was stirred under H$_2$ (50 psi, 50° C.) overnight. The mixture was filtered through Celite and the filtrate was concentrated. The residue was purified via flash chromatography eluting with 5%-10% EtOAc/heptane to give the title compound as a colorless oil (3.08 g, 92% yield). $^1$H NMR (400 MHz, chloroform-d) δ ppm 4.13-4.25 (m, 2H) 3.65 (m, 5H) 3.14-3.29 (m, 1H) 2.84-3.00 (m, 1H) 2.47-2.70 (m, 1H) 1.46 (s, 9H) 1.27 (td, J=7.11, 2.64 Hz, 3H) 0.85-0.92 (m, 9H) 0.05 (s, 6H).

Step 4: Preparation of trans-tert-butyl-3-({[tert-butyl(dimethyl)silyl]oxy}methyl)-4-(hydroxymethyl)pyrrolidine-1-carboxylate

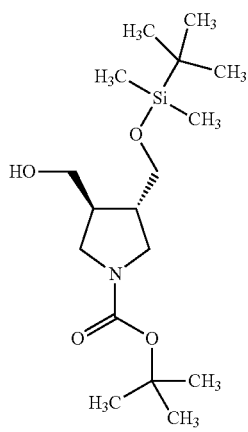 [SMILES: CC(C)(C)OC(=O)N1C[C@@H](CO)[C@H](CO[Si](C)(C)C(C)(C)C)C1]

LiBH$_4$ (911 mg, 39.7 mmol) was added to a solution of trans-1-tert-butyl 3-ethyl-4-({[tert-butyl(dimethyl)silyl]

oxy}methyl)pyrrolidine-1,3-dicarboxylate (3.08 g, 7.95 mmol) in THF (25 mL). The mixture was heated to reflux for 3 hrs. The reaction mixture was cooled to rt, then quenched with water (15 mL) and stirred at rt for 1 hr. The mixture was diluted with water (60 mL) and extracted with ethyl acetate (two×80 mL). The combined organic layers were washed with brine, dried over $Na_2SO_4$ and concentrated in vacuo to give a colorless oil. The crude product was purified via flash chromatography eluting with 30% EtOAc/heptane to give the title compound as a colorless oil (2.34 g, 86% yield). $^1$H NMR (400 MHz, chloroform-d) δ ppm 3.73 (m, 1H), 3.61 (m, 2H), 3.52 (m, 2H), 3.45 (m, 1H), 2.90-3.09 (m, 2H), 2.04-2.32 (m, 2H), 1.46 (s, 9H), 0.92 (s, 9H), 0.10 (d, J=1.01 Hz, 6H).

Step 5: Preparation of trans-tert-butyl-3-({[tert-butyl (dimethyl)silyl]oxy}methyl)-4-(methoxymethyl) pyrrolidine-1-carboxylate

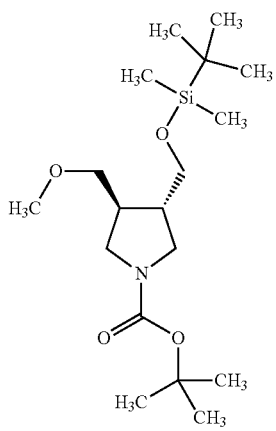 [SMILES: COC[C@@H]1CN(C(=O)OC(C)(C)C)C[C@H]1CO[Si](C)(C)C(C)(C)C]

Tetrabutylammonium iodide (0.110 g, 0.28 mmol), 50% aqueous NaOH (20 mL) and dimethyl sulfate (0.325 mL, 3.41 mmol) were added to a solution of trans-tert-butyl-3-({[tert-butyl(dimethyl)silyl]oxy}methyl)-4-(hydroxymethyl)pyrrolidine-1-carboxylate (0.982 g, 2.84 mmol) in $CH_2Cl_2$ (20 mL). The reaction was stirred at rt overnight. TLC showed some starting material remaining so additional dimethyl sulfate (0.150 mL) was added to the reaction mixture and stirred at rt for 3 hrs. Aqueous $NH_3OH$ (30 mL) was added to the reaction mixture and stirred at rt for 1 hr. The mixture was diluted with water (20 mL) and extracted with $CH_2Cl_2$ (two× 30 mL). The organic layer was dried over $MgSO_4$ and concentrated. The residue was purified via flash chromatography eluting with 10% EtOAc/heptane to give the title compound as a colorless oil (451 mg, 44% yield). $^1$H NMR (400 MHz, chloroform-d) δ ppm 3.60-3.70 (m, 1H), 3.55 (br. s., 2H), 3.37-3.48 (m, 1H), 3.34 (m, 4H), 3.05-3.23 (m, 2H), 2.22-2.40 (m, 1H), 2.07-2.21 (m, 1H), 1.43-1.49 (m, 9H), 0.89 (s, 9H), 0.05 (s, 6H).

Step 6: Preparation of trans-tert-butyl-3-(hydroxymethyl)-4-(methoxymethyl)pyrrolidine-1-carboxylate

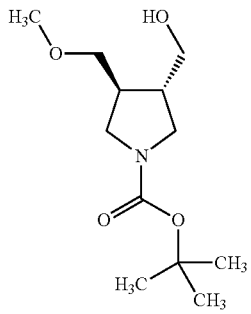 [SMILES: COC[C@@H]1CN(C(=O)OC(C)(C)C)C[C@H]1CO]

TBAF (1.0 M in THF, 2.45 mL, 2.45 mmol) was added to a solution of trans-tert-butyl-3-({[tert-butyl(dimethyl)silyl]oxy}methyl)-4-(methoxymethyl)pyrrolidine-1-carboxylate (290 mg, 0.81 mmol) in THF (5 mL). The mixture was stirred at rt for 1 hr. The mixture was quenched with water and extracted with EtOAc. The organic layer was dried over $MgSO_4$ and concentrated. The crude product was used without purification in subsequent steps.

Alternative Preparation of 4,5-dichloro-N-(1-methyl-1H-pyrazol-4-yl)-7H-pyrrolo[2,3-d]pyrimidin-2-amine

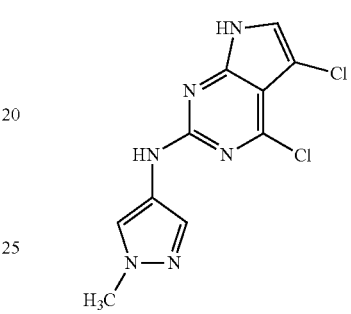

Step 1: Preparation of 5-chloro-N-(1-methyl-1H-pyrazol-4-yl)-4-(1-phenylethoxy)-7H-pyrrolo[2,3-d]pyrimidin-2-amine

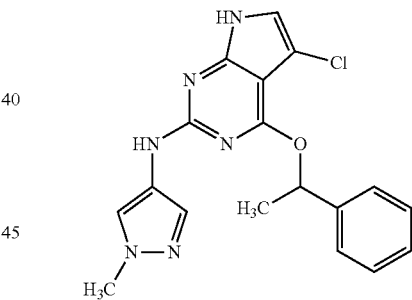

To a solution of 2,4,5-trichloro-7H-pyrrolo[2,3-d]pyrimidine (3.00 g, 13.4 mmol) in 1,4-dioxane (45 mL) was added potassium t-pentoxide (31.2 mL, 1.7 M in toluene) followed by 1-phenylethanol (1.62 mL, 13.4 mmol). The reaction solution was stirred at ambient temperature for 0.5 hr. To the same reaction vessel, 1-methyl-1H-pyrazol-4-amine (1.96 g, 20.2 mmol) and BrettPhos Palladacycle (214 mg, 0.020 mmol) were added and nitrogen gas was bubbled through the reaction mixture for 5 min. The reaction mixture was then sealed and heated to 80° C. for 2 hrs. A black precipitate was filtered off and washed with EtOAc. The combined filtrates were combined and diluted with water (75 mL), extracted EtOAc (2×75 mL), washed with brine, dried over sodium sulfate, filtered and concentrated under in vacuo. The crude residue was purified by flash chromatography (eluting with a gradient of 30%-100% EtOAc in heptanes) to give the title compound (1.76 g, 34%) as a green foam. m/z (APCI+) for $C_{18}H_{17}ClN_6O$ 369.1/370.2 $(M+H)^+$.

Step 2: Preparation of 4,5-dichloro-N-(1-methyl-1H-pyrazol-4-yl)-7H-pyrrolo[2,3-d]pyrimidin-2-amine

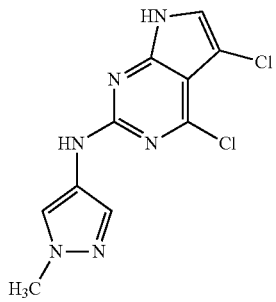 [SMILES: Cn1cc(Nc2nc(Cl)c3c(Cl)c[nH]c3n2)cn1]

5-chloro-N-(1-methyl-1H-pyrazol-4-yl)-4-(1-phenylethoxy)-7H-pyrrolo[2,3-d]pyrimidin-2-amine (1.65 g, 4.47 mmol) was suspended in POCl$_3$ (9 mL) and the reaction was heated to 70° C. for 40 min, then further heated to 100° C. for 0.5 hr. The reaction mixture was cooled, concentrated in vacuo and diluted with water (50 mL). NH$_4$OH was added to adjusted the pH 8 and the mixture was extracted with EtOAc (three×75 mL), and concentrated under reduced pressure. A precipitate was formed upon concentrating that was filtered off, and the filtrate was concentrated and the resulting residue was purified by flash chromatography eluting with a gradient of 30% 100% EtOAc in heptanes to afford the title compound (282 mg, 22% yield). $^1$H NMR (400 MHz, DMSO-d6) δ ppm 11.96 (br. s., 1H) 9.58 (br. s., 1H) 7.87 (s, 1H) 7.52 (s, 1H) 7.37 (s, 1H) 3.81 (s, 3H). m/z (APCI+) for C$_{10}$H$_8$Cl$_2$N$_6$ 283.15 (M+H)$^+$.

Preparation 9. Preparation of 3-[2-(dimethylamino)ethoxy]-1-methyl-1H-pyrazol-5-amine

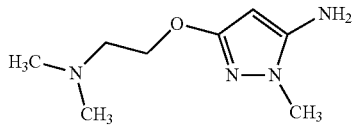

Step 1: Preparation of ethyl 3-hydroxy-1-methyl-1H-pyrazole-5-carboxylate

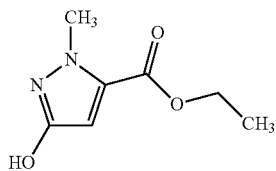

To a solution of diethyl but-2-ynedioate (100 g, 0.588 mol) in a mixture of EtOH (600 mL) and water (600 mL) was added a solution of 1,1-dimethylhydrazine hydrochloride (68 g, 0.705 mol) and NaOH (28.2 g, 0.705 mol) in water (150 mL) dropwise at 0° C. over a period of 20 min. The mixture was stirred at 0° C. for 30 min and 20° C. for 60 min. To the reaction mixture was added EtOAc (800 mL) and stirred. The mixture was separated and the aqueous layer was concentrated. The residue was dissolved in 1N HCl (1 L) and stirred at rt for 90 min. CH$_2$Cl$_2$ (500 mL) was added and the mixture stirred, separated and the aqueous layer was concentrated.

The residue was purified by chromatography (petroleum ether/EtOAc 10:1-3:1) to give the title compound (17 g, 17% yield) as a white solid.

Step 2: Preparation of ethyl 3-(2-(dimethylamino)ethoxy)-1-methyl-1H-pyrazole-5-carboxylate

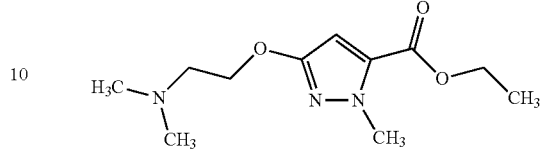

To a stirred solution of ethyl 3-hydroxy-1-methyl-1H-pyrazole-5-carboxylate (10 g, 58.8 mmol), 2-(dimethylamino)ethanol (5.76 g, 64.7 mmol) and PPh$_3$ (21.6 g, 82.3 mmol) in anhydrous THF (200 mL) was added dropwise DIAD (16.6 g, 82.3 mmol) at 0° C. After the addition, the reaction mixture was stirred at rt overnight. The reaction mixture was concentrated in vacuo and the residue was purified by column chromatography on silica gel (CH$_2$Cl$_2$/MeOH 30:1) to give the title compound (5.6 g, 40% yield) as a brown oil.

Step 3: Preparation of 3-(2-(dimethylamino)ethoxy)-1-methyl-1H-pyrazole-5-carboxylic acid

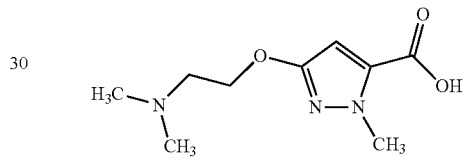

KOH (2.09 g, 37.4 mmol) was dissolved into EtOH (30 mL) and to this solution was added ethyl 3-(2-(dimethylamino)ethoxy)-1-methyl-1H-pyrazole-5-carboxylate (4.5 g, 18.7 mmol) and the mixture stirred at rt overnight. To the reaction mixture was added concentrated HCl (3.1 mL) with stirring and the resulting suspension was filtered and the cake was washed with EtOH (two×20 mL). The filtrate was concentrated to give the title compound (3.3 g, 83% yield) as a brown gum.

Step 4: Preparation of benzyl (3-(2-(dimethylamino)ethoxy)-1-methyl-1H-pyrazol-5-yl)carbamate

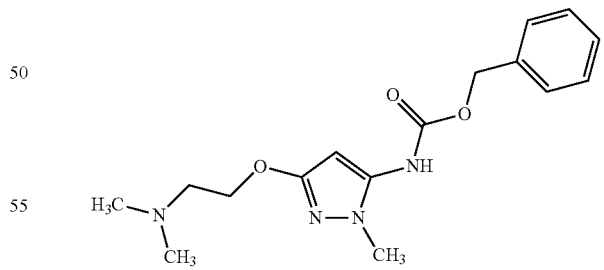

To a stirred solution of 3-(2-(dimethylamino)ethoxy)-1-methyl-1H-pyrazole-5-carboxylic acid (3.3 g, 15.5 mmol) and triethylamine (2.35 g, 23.2 mmol) in dry toluene (50 mL) was added DPPA (4.69 g, 17 mmol) under N$_2$ and the mixture was refluxed for 1 hr. After the addition of benzyl alcohol (3.35 g, 31 mmol), the mixture was refluxed overnight. The mixture was concentrated in vacuo to give crude product, which was purified by column chromatography (silica gel, CH$_2$Cl$_2$/MeOH 30:1) to give the title compound (1.42 g, 29% yield) as a colorless oil.

Step 5: Preparation of 3-[2-(dimethylamino)ethoxy]-1-methyl-1H-pyrazol-5-amine

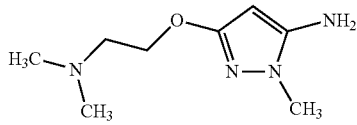

A mixture of benzyl (3-(2-(dimethylamino)ethoxy)-1-methyl-1H-pyrazol-5-yl)carbamate (1.42 g, 4.46 mmol) and 10% Pd/C (0.2 g) in MeOH (40 mL) was hydrogenated with fully inflated $H_2$ balloon at rt overnight. The mixture was filtered and the filtrate was concentrated in vacuo to give the title compound (0.65 g, 79% yield) as a pale solid. $^1$H NMR (400 MHz, CDCl$_3$) δ ppm 5.04 (s, 1H), 4.19-4.16 (t, 2H), 3.51 (s, 3H), 3.45 (bs, 2H), 2.67-2.64 (t, 2H), 2.32 (s, 6H). m/z for $C_8H_{16}N_4O$ 185.14 (M+H)$^+$.

Preparation 10. Preparation of tert-butyl(trans-3-aminocyclobutyl)methylcarbamate

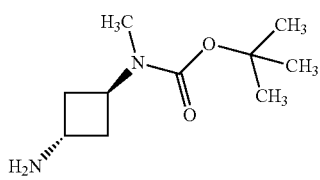

Step 1: Preparation of 3-methylidenecyclobutanecarboxylic acid

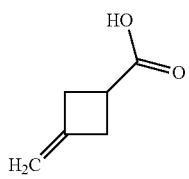

To a solution of 3-methylidenecyclobutanecarbonitrile (110 g, 1.18 mol) in ethanol (500 mL) and water (500 mL) was added potassium hydroxide (264 g, 4.7 mol) and the resulting mixture was refluxed overnight. The ethanol was removed under reduced pressure, and then the solution was cooled to below 10° C. and acidified with concentrated HCl to pH 1. The mixture was extracted with EtOAc (two×500 mL) and the combined organic extracts were dried over anhydrous sodium sulfate and concentrated under vacuum to afford compound the title compound (132 g, 100% yield) as yellow oil.

Step 2: Preparation of tert-butyl (3-methylidenecyclobutyl)carbamate

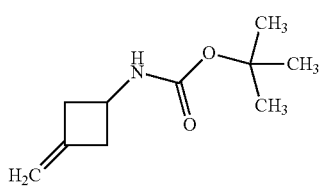

To a solution of 3-methylidenecyclobutanecarboxylic acid (132 g, 1.17 mol) and Et$_3$N (178 g, 1.76 mol) in tert-butyl alcohol (1 L) was added dropwise DPPA (574 g, 1.41 mol) and the resulting mixture was refluxed overnight. The mixture was then quenched with water (100 mL). After removal of the tert-butyl alcohol, the residue was treated with sat. NH$_4$Cl (500 mL), and the resulting solid precipitate was collected, washed with sat. NH$_4$Cl and sat. NaHCO$_3$ to give the title compound (165 g, 77% yield) as a white solid.

Step 3: Preparation of tert-butyl (3-oxocyclobutyl)carbamate

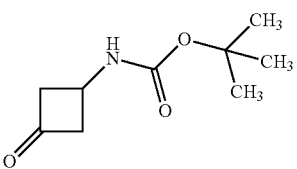

To a solution of tert-butyl (3-methylidenecyclobutyl)carbamate (165 g, 0.91 mol) in CH$_2$Cl$_2$ (1000 mL) and MeOH (1000 mL) was bubbled O$_3$ at −78° C. until the solution turned blue. TLC (petroleum ether:EtOAc=10:1) showed that the starting material was consumed completely. Nitrogen gas was then bubbled through the reaction to remove excess O$_3$, and then the mixture was quenched with Me$_2$S (200 mL) and stirred for an hour. The solution was concentrated to give a residue, which was washed with sat. NaHCO$_3$ and water to yield the title compound (118 g, 70% yield) as a white solid.

Step 4: Preparation of tert-butyl(cis-3-hydroxycyclobutyl)carbamate

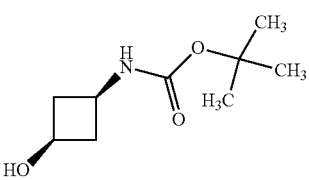

To a solution of tert-butyl (3-oxocyclobutyl)carbamate (100 g, 54 mmol) in THF (2000 mL) at −72° C. was added dropwise a solution of lithium trisec-butylhidridoborate (648 mL, 1 M) in THF over 1.5 hrs. The resulting solution was allowed to warm up to rt and stirred for another 1 hr. TLC (petroleum ether: EtOAc=2:1) showed that the starting material was consumed completely. The reaction was quenched with NH$_4$Cl aqueous. Water (1000 mL) and EtOAc (2000 mL) were added to the mixture. The organic layer was separated, dried over MgSO$_4$ and concentrated to give crude material, which was purified by column chromatography with petroleum ether: EtOAc from 10:1 to 1:2 to afford the title compound (62 g, 61% yield) as a white solid.

Step 5: Preparation of tert-butyl {cis-3-[1-methyl-1-(trimethylsilyl)ethoxy]cyclobutyl}carbamate

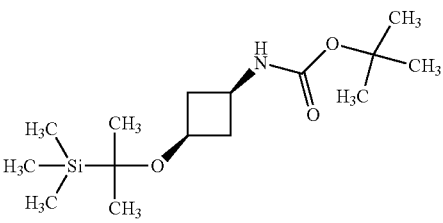 [SMILES: CC(C)(C)OC(=O)N[C@H]1C[C@@H](OC(C)(C)[Si](C)(C)C)C1]

To a solution of tert-butyl(cis-3-hydroxycyclobutyl)carbamate (62 g, 0.33 mol) in pyridine (1 L) was added TBSCl (159 g, 1.056 mol). After addition, the mixture was stirred at ambient temperature overnight. TLC (petroleum ether: EtOAc=2:1) showed the starting material was consumed completely. The reaction was then concentrated and diluted with EtOAc (1 L), and the organic layer was separated and washed with water (three×300 mL) and brine (200 mL), dried over MgSO$_4$, filtered and concentrated to dryness to give crude title compound (108 g), which was used for the next step directly without further purification.

Step 6: Preparation of tert-butyl methyl{cis-3-[1-methyl-1-(trimethylsilyl)ethoxy]cyclobutyl}carbamate

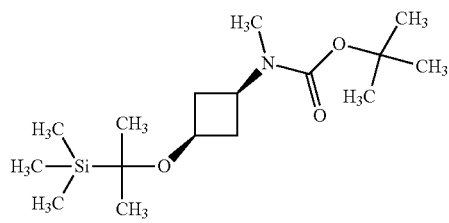 [SMILES: CN(C(=O)OC(C)(C)C)[C@H]1C[C@@H](OC(C)(C)[Si](C)(C)C)C1]

To a solution of crude tert-butyl {cis-3-[1-methyl-1-(trimethylsilyl)ethoxy]cyclobutyl}carbamate (108 g) in THF (1 L) was added NaH (60% in oil, 39.6 g, 0.99 mol) in portions and the resulting mixture was stirred at rt for 30 min. The mixture was then cooled to 0° C. and iodomethane (140.58 g, 0.99 mol) was added dropwise. After addition, the mixture was stirred from 0° C. to rt overnight. The mixture was quenched with sat. NH$_4$Cl, and water was added (200 mL), and extracted with EtOAc. The organic layer was washed with brine, dried over Na$_2$SO$_4$, then evaporated to give crude product which was purified via silica gel chromatography to give the title compound (68.9 g, 87% yield) as an oil.

Step 7: Preparation of tert-butyl(cis-3-hydroxycyclobutyl)methylcarbamate

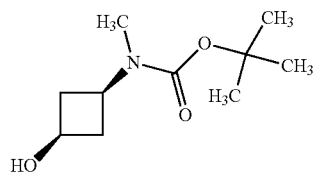

To a solution of tert-butyl methyl{cis-3-[1-methyl-1-(trimethylsilyl)ethoxy]cyclobutyl}carbamate (68.9 g, 0.217 mol) in pyridine (800 mL) was added TBAF (62 g, 0.24 mol) in portions. After addition, the mixture was stirred at rt for 2 hrs. The mixture was evaporated to dryness, and the residue was dissolved in 1000 mL of ethyl acetate and washed with conc. NH$_4$Cl (three×200 mL). The organic layer was dried over Na$_2$SO$_4$, filtered and concentrated to give the crude product, which was purified by column chromatography with EtOAc/petroleum ether from 1/20 to 1/5 to afford the title compound (26.3 g, 60% yield) as a white solid.

Step 8: Preparation of cis-3-[(tert-butoxycarbonyl)(methyl)amino]cyclobutyl methanesulfonate

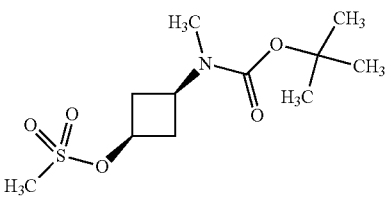 [SMILES: CN(C(=O)OC(C)(C)C)[C@H]1C[C@@H](OS(C)(=O)=O)C1]

Triethylamine (4.14 mL, 29.79 mmol) was added into the solution of tert-butyl(cis-3-hydroxycyclobutyl)methylcarbamate (2.0 g, 9.93 mmol) in CH$_2$Cl$_2$ (30 mL) and the resulting mixture was cooled to −30° C. upon vigorous stirring. Mesyl chloride (1.36 g, 11.91 mmol) was added dropwise over a ten minute period. The mixture was then allowed to warm to rt and stirred for an hour until TLC analysis (MeOH/CH$_2$Cl$_2$=1/15) showed the reaction was complete. The reaction mixture was then washed with water (two×10 mL), aq. NH$_4$Cl (10 mL), brine (10 mL), dried over anhydrous Na$_2$SO$_4$ and concentrated to give the title compound (2.5 g, 91% yield) as yellow solid, which was used for next step directly.

Step 9: Preparation of tert-butyl(trans-3-azidocyclobutyl)methylcarbamate

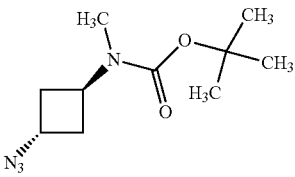 [SMILES: CN(C(=O)OC(C)(C)C)[C@H]1C[C@H](N=[N+]=[N-])C1]

Cis-3-[(tert-butoxycarbonyl)(methyl)amino]cyclobutyl methanesulfonate (2.5 g, 8.94 mmol) was dissolved in DMF (25 mL) and NaN$_3$ (2.84 g, 43.69 mmol) was added. The resulting mixture was then heated to 70° C. and stirred overnight. After cooling, water (150 mL) was added and the mixture was extracted with EtOAc (three×50 mL). The combined organic phases were washed with water (three×20 mL) and brine (20 mL), dried over anhydrous Na$_2$SO$_4$, then concentrated in vacuo to give the title compound (1.8 g, 89% yield) as a yellow liquid, which was used without further purification.

Step 10: Preparation of tert-butyl(trans-3-aminocyclobutyl)methylcarbamate

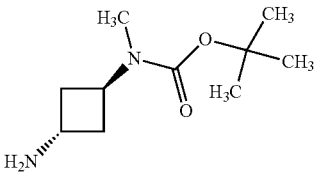

To the mixture of tert-butyl(trans-3-azidocyclobutyl)methylcarbamate (1.8 g, 7.95 mmol) and Pd/C (200 mg) in MeOH (5 mL) under hydrogen atmosphere (hydrogen balloon) was added NH₃(g)/MeOH (saturated, 50 mL) via syringe. The resulting mixture was stirred at rt for three hours until TLC analysis (EtOAc:petroleum ether=1:2) showed the reaction was complete. Pd/C was filtered off and the resulting solution was concentrated and dried in vacuum to afford crude title compound (1.6 g), which was used for the next steps without further purification.

Preparation 11. Preparation of (4-amino-3-methyl-1H-pyrazol-1-yl)acetonitrile

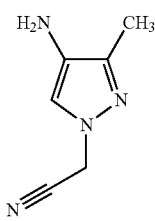

Step 1: Preparation of (3-methyl-4-nitro-1H-pyrazol-1-yl)acetonitrile

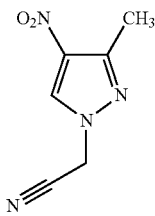

A mixture of 3-methyl-4-nitro-1H-pyrazole (7 g, 0.055 mol), bromoacetonitrile (13.2 g, 0.11 mol) and K₂CO₃ (23 g, 0.165 mol) in DMF (120 mL) was stirred at 80° C. for 2 hrs. TLC (petroleum ether:EtOAc=2:1) showed the reaction was complete. The mixture was filtered, concentrated and the residue purified by flash chromatography (petroleum ether:EtOAc=4:1) to give the title compound (3.5 g, 38% yield) as light yellow oil.

Step 2: Preparation of (4-amino-3-methyl-1H-pyrazol-1-yl)acetonitrile

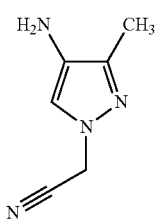

A mixture of (3-methyl-4-nitro-1H-pyrazol-1-yl)acetonitrile (2.6 g, 15.7 mmol), NH₄Cl (3.4 g, 62.7 mmol) and Fe powder (3.5 g, 62.7 mmol) in MeOH (60 mL) and water (12 mL) was stirred at 80° C. for 2 days. The mixture was filtered, concentrated and the residue was purified by flash chromatography (MeOH: CH₂Cl₂ 20:1) to give the title compound (440 mg, 15% yield) as brown oil.

Preparation 12: Preparation of tert-butyl (3,4-trans)-3-fluoro-4-(hydroxymethyl)pyrrolidine-1-carboxylate

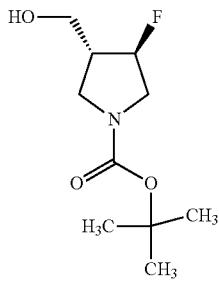

Step 1: Preparation of (1Z)-3-ethoxy-3-oxoprop-1-en-1-yl benzoate

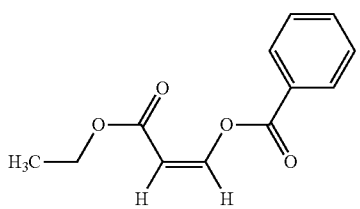 [SMILES: CCOC(=O)/C=C\OC(=O)c1ccccc1]

To a suspension of benzoic acid (24.4 g, 200 mmol), silver hexafluorophosphate(V) (253 mg, 1 mmol), chlorotriphenylphosphine gold(I) (495 mg, 1 mmol) in toluene (125 mL) was added ethyl prop-2-ynoate (5.1 mL, 50 mmol). The reaction mixture was stirred and heated at 60° C. for 16 hrs. The volatiles were removed to give a residue, which was dissolved in ethyl acetate (200 mL) with some trace insoluble material being removed by filtration. The filtrate was washed with saturated aqueous NaHCO₃ (with gas evolved—CAUTION) until there was no further gas evolution, and evaporated to give a light brown oil. This oil was purified via flash chromatography (eluting with a gradient of 0%-100% EtOAc in heptanes) to give the title compound (10.96 g, 99% yield) as a colorless oil, which solidified to afford needle-liked crystals. $^1$H NMR (400 MHz, chloroform-d) δ ppm 8.24-8.32 (m, 2H) 7.85 (d, J=7.09 Hz, 1H) 7.63-7.72 (m, 1H) 7.48-7.58 (m, 2H) 5.44 (d, J=7.21 Hz, 1H) 4.29 (q, J=7.21 Hz, 2H) 1.38 (t, J=7.15 Hz, 3H). $^{13}$C NMR (101 MHz, chloroform-d) δ ppm 164.15 (s, 1C) 162.55 (s, 1C) 144.54 (s, 1C) 134.31 (s, 1C) 130.66 (s, 2C) 128.74 (s, 2C) 127.90 (s, 1C) 103.38 (s, 1C) 60.30 (s, 1C) 14.28 (s, 1C).

Step 2: Preparation of ethyl (3,4-cis)-4-(benzoyloxy)-1-benzylpyrrolidine-3-carboxylate

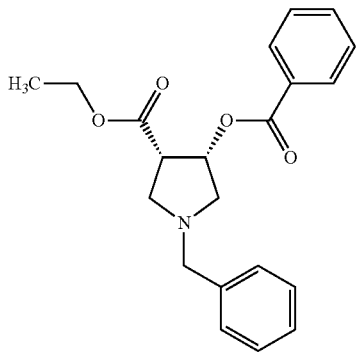 [SMILES: CCOC(=O)[C@H]1CN(Cc2ccccc2)C[C@H]1OC(=O)c1ccccc1]

A solution of (1Z)-3-ethoxy-3-oxoprop-1-en-1-yl benzoate (6.6 g, 30 mmol) in 2-MeTHF (80 mL) was cooled to 0° C. in a water/ice bath and TFA (605 µL, 6 mmol) was added. A solution of N-benzyl-1-methoxy-N-[(trimethylsilyl)methyl]methanamine (11.5 mL, 45 mmol) in 2-MeTHF (20 mL) was added dropwise and the resulting solution was stirred at ambient temperature for 20 hrs. The reaction was diluted with ethyl acetate (100 mL) and saturated aqueous NaHCO$_3$ (30 mL). The organic layer was separated, dried over Na$_2$SO$_4$ and evaporated to give a light yellow oil, which was purified via flash chromatography (eluting with a gradient of 0%-100% EtOAc in heptanes) to give the title compound (10.48 g, 99% yield) as a colorless oil. $^1$H NMR (400 MHz, chloroform-d) δ ppm 7.95-8.03 (m, 2H) 7.53-7.61 (m, 1H) 7.41-7.48 (m, 2H) 7.28-7.38 (m, 5H) 7.21-7.27 (m, 1H) 5.72 (ddd, J=7.58, 5.87, 3.91 Hz, 1H) 3.97-4.17 (m, 2H) 3.73 (d, J=3.30 Hz, 2H) 3.32-3.47 (m, 2H) 3.01-3.17 (m, 2H) 2.62 (dd, J=10.88, 3.91 Hz, 1H) 1.09 (t, J=7.15 Hz, 3H). m/z (APCI+) for C$_{21}$H$_{23}$NO$_4$ 354.2 (M+H)$^+$.

Step 3: Preparation of 1-tert-butyl 3-ethyl (3,4-cis)-4-(benzoyloxy)pyrrolidine-1,3-dicarboxylate

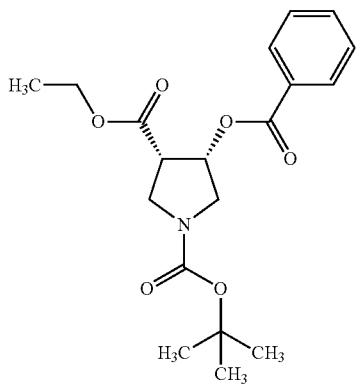 [SMILES: CCOC(=O)[C@H]1CN(C(=O)OC(C)(C)C)C[C@H]1OC(=O)c1ccccc1]

A solution of ethyl (3,4-cis)-4-(benzoyloxy)-1-benzylpyrrolidine-3-carboxylate (7.78 g, 22 mmol) in ethyl acetate (200 mL) was degassed with nitrogen and di-tert-butyl dicarbonate (5.3 g, 24 mmol), Pd(OH)$_2$ (20 wt % on carbon, 1 g) was then added. The resulting reaction mixture was stirred under hydrogen atmosphere (balloon) for 20 hrs. The catalyst was removed by filtration, and the filtrate was evaporated to give a colorless oil. This oil was purified via flash chromatography (eluting with a gradient of 0%-100% EtOAc in heptanes) to give the title compound as a colorless oil, which solidified to a white solid (6.85 g, 86% yield). The cis-configuration of the title compound was confirmed by small molecule X-ray crystallography. $^1$H NMR (400 MHz, chloroform-d) δ ppm 7.98 (d, J=7.34 Hz, 2H) 7.53-7.62 (m, 1H) 7.38-7.50 (m, 2H) 5.76 (br. s., 1H) 4.00-4.23 (m, 2H) 3.57- 3.99 (m, 4H) 3.35 (br. s., 1H) 1.47 (d, J=10.15 Hz, 9H) 1.13 (t, J=7.09 Hz, 3H). m/z (APCI+) for C$_{19}$H$_{25}$NO$_6$ 264.2 (M+H)$^+$.

Step 4: Preparation of tert-butyl (3,4-cis)-3-hydroxy-4-(hydroxymethyl)pyrrolidine-1-carboxylate

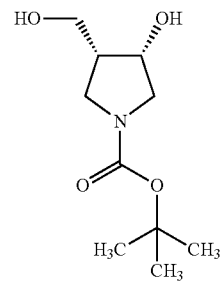

A solution of 1-tert-butyl 3-ethyl (3,4-cis)-4-(benzoyloxy)pyrrolidine-1,3-dicarboxylate (3.5 g, 9.6 mmol) in THF (60 mL) was cooled in an ice/water bath under nitrogen atmosphere and borane dimethylsulfide (3.7 mL, 39 mmol) was added. The resulting reaction solution was stirred and heated at 50° C. (oil bath temperature) for 20 hrs. The reaction was then cooled in a water/ice bath and was carefully quenched with methanol (couple drops at first, 20 mL total) under nitrogen atmosphere. The volatiles were removed to give a colorless residue, which was purified via flash chromatography (eluting with a gradient of 0%-100% EtOAc in heptanes) to give the title compound as a colorless oil (1.88 g, 90% yield) which solidified on standing to a white solid. $^1$H NMR (400 MHz, chloroform-d) δ ppm 4.48 (d, J=2.57 Hz, 1H) 3.90 (br. s., 2H) 3.40-3.56 (m, 3H) 3.30-3.40 (m, 1H) 3.14-3.27 (m, 1H) 2.73-2.99 (m, 1H) 2.34 (br. s., 1H) 1.46 (s, 9H). m/z (APCI+) for C$_{10}$H$_{19}$NO$_4$ 118.2 (M+H)$^+$.

Step 5: Preparation of tert-butyl (3,4-cis)-3-[(acetyloxy)methyl]-4-hydroxypyrrolidine-1-carboxylate

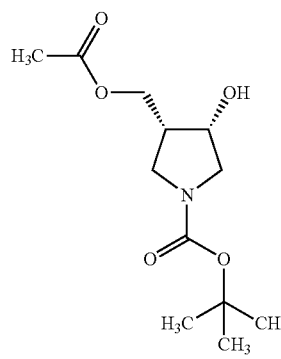

A solution of tert-butyl (3,4-cis)-3-hydroxy-4-(hydroxymethyl)pyrrolidine-1-carboxylate (1.4 g, 6.4 mmol) in THF (30 mL) was cooled in an ice/water bath and 2,6-dimethylpyridine (1.50 mL, 13 mmol) was added. Acetyl chloride (0.47 mL, 6.4 mmol) was added slowly over few minutes. The reaction mixture turned cloudy and was stirred in the cold bath and allowed to warm to ambient temperature for 1 hr. More 2,6-dimethylpyridine (1.5 mL, 13 mmol) and then acetyl chloride (0.47 mL, 6.4 mmol) were added while cooling in ice/water bath. Stirring at ambient temperature continued for another 2 hrs. The reaction was cooled in a water bath and was quenched with water (2 mL) and brine (5 mL) and diluted with ethyl acetate (30 mL). The organic layer was separated, dried over Na$_2$SO$_4$ and evaporated to give a colorless oil, which was purified via flash chromatography (eluting with a gradient of 0%-100% EtOAc in heptanes) to give the title compound (1.64 g, 98% yield) as a colorless oil. $^1$H NMR (400 MHz, chloroform-d) δ ppm 4.48 (q, J=11.33 Hz, 1H) 4.24 (d, J=11.37 Hz, 1H) 4.04 (d, J=11.13 Hz, 1H) 3.41-3.65 (m, 3H) 3.15 (t, J=10.76 Hz, 1H) 2.53 (s, 1H) 2.41 (br. s., 1H) 2.11 (s, 4H) 1.46 (s, 9H). m/z (APCI+) for C$_{12}$H$_{21}$NO$_5$ 160.1 (M+H)$^+$.

Step 6: Preparation of tert-butyl (3,4-trans)-3-[(acetyloxy)methyl]-4-fluoropyrrolidine-1-carboxylate

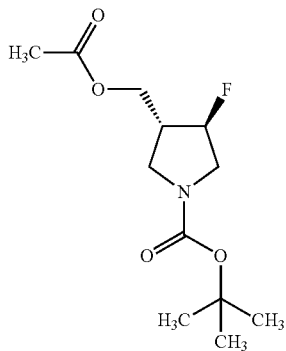 [SMILES: CC(=O)OC[C@H]1CN(C(=O)OC(C)(C)C)C[C@@H]1F]

To a solution of tert-butyl (3,4-cis)-3-[(acetyloxy)methyl]-4-hydroxypyrrolidine-1-carboxylate (1.20 g, 4.6 mmol) in CH$_2$Cl$_2$ (30 mL) under a nitrogen atmosphere at 0° C. was added Deoxo-Fluor® (1.29 mL, 6.9 mmol). The mixture was stirred at 0° C. for 1 hr. More Deoxo-Fluor® (0.7 mL) was added and stirring continued for another 15 min. The reaction was carefully quenched with saturated aqueous NaHCO$_3$ (5 mL). The organic layer was separated, dried over Na$_2$SO$_4$ and evaporated to give a residue, which was purified via flash chromatography (eluting with a gradient of 0%-100% EtOAc in heptanes) to give a colorless oil (718 mg). NMR and LCMS showed a mixture of the title compound and tert-butyl 3-[(acetyloxy)methyl]-2,5-dihydro-1H-pyrrole-1-carboxylate product at about 6:4 ratio. This material was used crude in the next step.

Step 7: Preparation of tert-butyl (3,4-trans)-3-fluoro-4-(hydroxymethyl)pyrrolidine-1-carboxylate

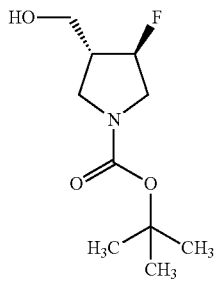

To a crude solution of tert-butyl (3,4-trans)-3-[(acetyloxy)methyl]-4-fluoropyrrolidine-1-carboxylate (crude 4.5 mol ca.) in THF (10 mL) was added water (5 mL) and solid LiOH (269 mg, 11.2 mmol). The reaction mixture was stirred at ambient temperature for 2 hrs, then the reaction was diluted with ethyl ether (20 mL). The organic layer was separated, dried over Na$_2$SO$_4$ and evaporated to give a colorless oil. LCMS and NMR indicated a mixture of the title compound and tert-butyl 3-(hydroxymethyl)-2,5-dihydro-1H-pyrrole-1-carboxylate at about 6:4 ratio. This was used as is in subsequent steps.

Preparation 13: Preparation of benzyl(trans-3-hydroxy-1-methylcyclobutyl)carbamate and benzyl(cis-3-hydroxy-1-methylcyclobutyl)carbamate

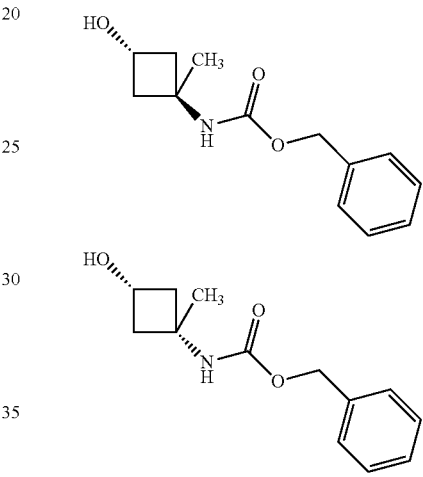

Step 1: Preparation of 1-methyl-3-methylidenecyclobutanecarbonitrile

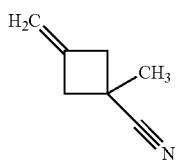

To a solution of 3-methylenecyclobutanecarbonitrile (4.96 g, 53.3 mmol) in THF (30 mL) was added lithium diisopropylamide (2.0 M solution in hexane/THF, 30 mL, 60 mmol) slowly at −78° C. The mixture was stirred at −78° C. for 45 min, and then iodomethane (4.05 mL, 63.9 mmol) was added. The resulting solution was stirred at −78° C. for 40 min, and then allowed to warm to rt. The reaction was quenched NH$_4$Cl (sat. 50 mL) and the organic layer separated. The aqueous layer was extracted with EtOAc (50 mL) and the combined organics were washed with water (50 mL), brine (50 mL), dried over MgSO$_4$ and concentrated to give the title compound as a brown oil which was used without purification.

Step 2: Preparation of 1-methyl-3-methylidenecyclobutanecarboxylic acid

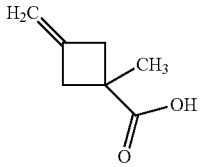

To a solution of KOH (12.0 g, 213 mmol) in water (10 mL) and EtOH (10 mL) was added 1-methyl-3-methylidenecyclobutanecarbonitrile (53.3 mmol, crude) and the resulting solution was heated to reflux for 2.5 hrs. The mixture was cooled to rt and the solvent was removed under vacuum. The residue was diluted with water (30 mL) and washed with EtOAc (30 mL). The aqueous layer was acidified with concentrated HCl to pH~1 in ice bath, and then extracted with EtOAc (two×30 mL). The combined organics were dried over MgSO$_4$ and concentrated to give the title compound acid as pale brown liquid. $^1$H NMR (400 MHz, chloroform-d) δ ppm 4.90 (quin, J=2.41 Hz, 2H), 3.16-3.34 (m, 2H), 2.54 (qd, J=2.10, 16.57 Hz, 2H), 1.49 (s, 3H).

Step 3: Preparation of benzyl (1-methyl-3-methylidenecyclobutyl)carbamate

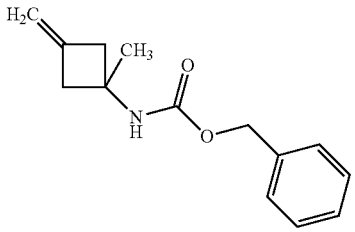 [SMILES: C=C1CC(C)(NC(=O)OCc2ccccc2)C1]

To a stirred solution of 1-methyl-3-methylidenecyclobutanecarboxylic acid (2.60 g, 20.6 mmol) in toluene (30 mL) was added Et$_3$N (4.30 mL, 30.9 mmol), followed by diphenylphosphoic azide (6.10 mL, 28.3 mmol). The mixture was stirred at rt for 45 min, then benzyl alcohol (7.60 mL, 73.4 mmol) was added, and the mixture was heated at 80° C. overnight. The mixture was then cooled to rt, diluted with EtOAc (30 mL), washed with sat. NH$_4$Cl (three×40 mL), brine (40 mL), dried over Na$_2$SO$_4$ and concentrated to give the crude title compound as a pale yellow oil. m/z (APCI+) for C$_{14}$H$_{17}$NO$_2$ 232.20 (M+H)$^+$.

Step 4: Preparation of benzyl (1-methyl-3-oxocyclobutyl)carbamate

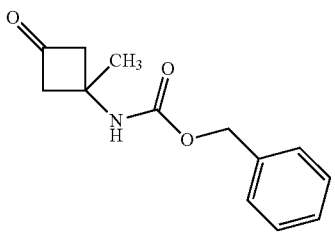 [SMILES: CC1(NC(=O)OCc2ccccc2)CC(=O)C1]

Crude benzyl (1-methyl-3-methylidenecyclobutyl)carbamate (20.6 mmol) was dissolved in THF (10 mL), then water (0.100 mL), 2,6-dimethylpyridine (0.400 mL, 3.4 mmol), OsO$_4$ (2.5% wt in 2-methyl-2-propanol, 0.340 mL, 0.027 mmol), and PhI(OAc)$_2$ (1.0 g, 3.07 mmol) were added and the reaction mixture was stirred at rt for 3 hrs. The reaction was quenched with sat. sodium thiosulfate (20 mL) and extracted with EtOAc (two×30 mL). The combined organics were washed with sat. aqueous copper sulfate (three×50 mL), dried over MgSO$_4$ and concentrated. The residue was purified via flash chromatography (eluting with 10%-20% EtOAc/heptanes) to give the title compound (558 mg, 12% yield) as a colorless oil. $^1$H NMR (400 MHz, chloroform-d) δ ppm 7.31-7.47 (m, 5H) 5.12 (s, 3H) 3.36-3.64 (m, 2H) 2.96-3.12 (m, 2H) 1.63 (s, 3H)); m/z (APCI+) for C$_{13}$H$_{15}$NO$_3$ 234.20 (M+H)$^+$.

Step 5: Preparation of benzyl(trans-3-hydroxy-1-methylcyclobutyl)carbamate and benzyl(cis-3-hydroxy-1-methylcyclobutyl)carbamate

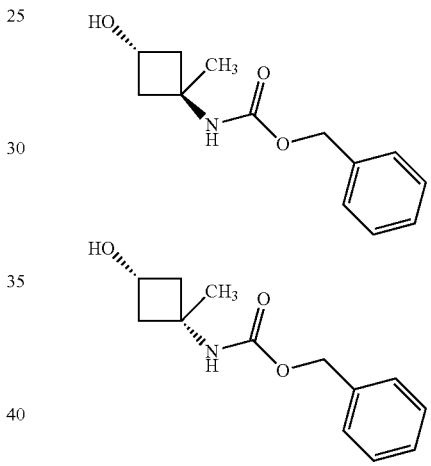

NaBH$_4$ (46 mg, 1.22 mmol) was added to a solution of benzyl (1-methyl-3-oxocyclobutyl)carbamate (571 mg, 2.45 mmol) in EtOH (5 mL) at 0° C. The mixture was stirred at rt for 2 hrs and then quenched with water (0.5 mL). The solvent was evaporated under reduced pressure and the residue was diluted with water (60 mL) and extracted with EtOAc (two× 60 mL). The combined organics were dried over MgSO$_4$ and concentrated. The residue was purified via flash chromatography (eluting with 20%-30% EtOAc/heptanes) to give a cis/trans mixture of the title compounds as a colorless oil (543 mg, 94% yield) which was separated via chiral SFC (Chiralpak AD-H 4.6×250 mm column, 20% MeOH, 140 bar, 3.0 mL/min) to give benzyl(trans-3-hydroxy-1-methylcyclobutyl)carbamate as colorless oil (202 mg, 35% yield), $^1$H NMR (400 MHz, chloroform-d) δ ppm 7.29-7.43 (m, 5H), 5.08 (br. s., 2H), 4.75-4.87 (m, 1H), 4.45 (t, J=6.55 Hz, 1H), 2.56-2.79 (m, 2H), 1.88-2.09 (m, 2H), 1.50 (s, 3H); m/z (APCI+) for C$_{13}$H$_{17}$NO$_3$ 236.00 (M+H)$^+$, and benzyl(cis-3-hydroxy-1-methylcyclobutyl)carbamate (confirmed by small molecule x-ray) as a white solid (271 mg, 47%), $^1$H NMR (400 MHz, chloroform-d) δ ppm 7.30-7.47 (m, 5H), 5.10 (s, 2H), 4.93 (br. s., 1H), 4.12 (quin, J=6.74 Hz, 1H), 2.48-2.60 (m, 2H), 2.44 (br. s., 1H), 1.37-1.37 (m, 2H), 1.28-1.41 (m, 3H).

Preparation 14: Preparation of (3R,4S)-tert-butyl 3-amino-4-(difluoromethyl)pyrrolidine-1-carboxylate

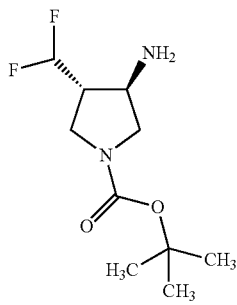 [SMILES: CC(C)(C)OC(=O)N1C[C@H](C(F)F)[C@@H](N)C1]

Step 1: Preparation of 1-ethoxy-2,2-difluoroethanol

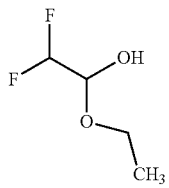

To a solution of ethyl 2,2-difluoroacetate (200 g, 1.59 mol) in tert-butyl methyl ether (1200 mL) was added LiAlH$_4$ (33 g, 0.78 mol) portionwise at 78° C. under a nitrogen atmosphere. Once the addition was complete, the reaction mixture was continually stirred for 6 hrs at 78° C. EtOH (75 mL, 98%) was added dropwise to quench the reaction at 78° C., and the resulting mixture was allowed to warm to rt. The mixture was poured into ice/water, and concentrated H$_2$SO$_4$ (100 mL) was added carefully with stirring. The mixture was extracted with tert-butyl methyl ether (two×1 L) and the combined organic layers were washed with water, dried over Na$_2$SO$_4$, and concentrated to afford crude material that was submitted to distillation under reduced pressure. The fraction was collected at 45-55° C./−0.1 MPa to afford the title compound (75 g, 37% yield) as a colorless liquid.

Step 2: Preparation of 1,1-difluoro-3-nitropropan-2-ol

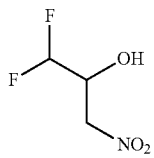

A mixture of 1-ethoxy-2,2-difluoroethanol (60 g, 0.47 mol), CH$_3$NO$_2$ (32.9 g, 0.56 mol) and Na$_2$CO$_3$ (3 g) was stirred at 60° C. for 3 hrs, then at rt overnight. The mixture was diluted with water (40 mL), extracted with tert-butyl methyl ether (200 mL) and the organic layer was dried over Na$_2$SO$_4$ and concentrated under low temperature to give the title compound, which was used for next step directly.

Step 3: Preparation of (E)-3,3-difluoro-1-nitroprop-1-ene

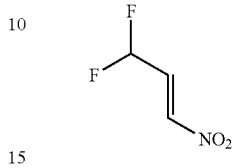

A mixture of 1,1-difluoro-3-nitropropan-2-ol (20 g, 0.14 mol) and P$_2$O$_5$ (25 g) was refluxed for 2 hrs and then the mixture was distilled at atmospheric pressure to give the title compound (5 g, 29% yield) as green oil.

Step 4: Preparation of trans-1-benzyl-3-(difluoromethyl)-4-nitropyrrolidine

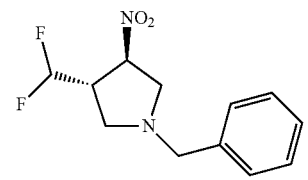 [SMILES: O=[N+]([O-])[C@H]1CN(Cc2ccccc2)C[C@@H]1C(F)F]

To a solution of N-benzyl-1-methoxy-N-((trimethylsilyl)methyl)methanamine (56.6 g, 0.24 mol) in dry CH$_2$Cl$_2$ (160 ml) was added (E)-3,3-difluoro-1-nitroprop-1-ene (25 g, 0.2 mmol) and a few drops of TFA at 0° C. The resulting mixture was stirred at rt overnight. The mixture was concentrated and purified by flash column chromatography (petroleum ether: EtOAc=100:1 to 25:1) to give the title compound (25 g, 49% yield) as a yellow oil.

Step 5: Preparation of trans-tert-butyl 3-amino-4-(difluoromethyl)pyrrolidine-1-carboxylate

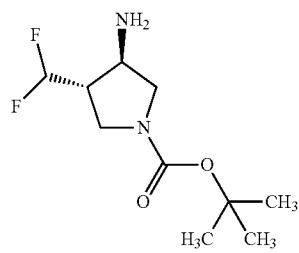

A mixture of trans-1-benzyl-3-(difluoromethyl)-4-nitropyrrolidine (25 g, 0.097 mol) and Pd (OH)$_2$/C (4 g) in MeOH (200 mL) was placed under a hydrogen atmosphere (50 psi) at rt overnight. The mixture was filtered to yield trans-4-(difluoromethyl)pyrrolidin-3-amine in solution. Boc$_2$O was added at 0° C. and the resulting mixture was stirred at 0° C. for 4 hrs, then concentrated and purified by column chromatography (100% EtOAc) to give the title compound (14 g, 61% yield) as a yellow oil.

Step 6: Preparation of (3R,4S)-tert-butyl 3-(((benzyloxy)carbonyl)amino)-4-(difluoromethyl)pyrrolidine-1-carboxylate and (3S,4R)-tert-butyl 3-(((benzyloxy)carbonyl)amino)-4-(difluoromethyl) pyrrolidine-1-carboxylate

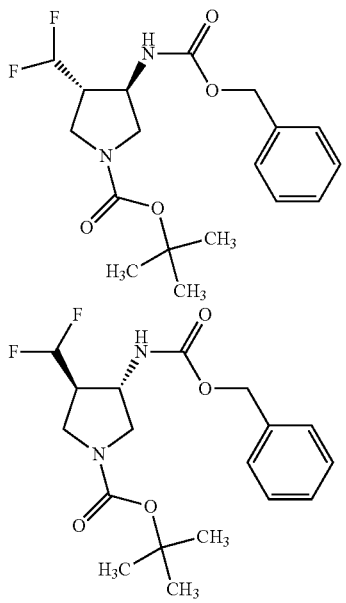

To a solution of trans-tert-butyl 3-amino-4-(difluoromethyl)pyrrolidine-1-carboxylate (14 g, 0.059 mol) in CH$_2$Cl$_2$ (200 mL) was added benzyl chloroformate (10.9 g, 0.07 mol) dropwise at 0° C. The resulting mixture was stirred at 0° C. for 3 hrs then concentrated and purified by flash column chromatography (petroleum ether: EtOAc=100:1 to 25:1) to give a racemic mixture (20 g, 92% yield), which was separated by chiral SFC to give the title compounds.

Step 7: Preparation of (3R,4S)-tert-butyl 3-amino-4-(difluoromethyl)pyrrolidine-1-carboxylate and (3S,4R)-tert-butyl 3-amino-4-(difluoromethyl)pyrrolidine-1-carboxylate

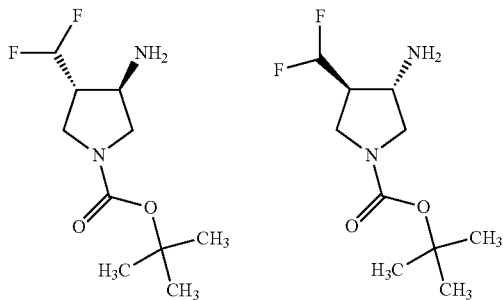 [SMILES: CC(C)(C)OC(=O)N1C[C@H](C(F)F)[C@@H](N)C1 ; CC(C)(C)OC(=O)N1C[C@@H](N)[C@H](C(F)F)C1]

In separate flasks were placed (3R,4S)-tert-butyl-3-(((benzyloxy)carbonyl)amino)-4-(difluoromethyl)pyrrolidine-1-carboxylate and (3S,4R)-tert-butyl-3-(((benzyloxy)carbonyl)amino)-4-(difluoromethyl)pyrrolidine-1-carboxylate (6 g, 0.016 mol). To each was added Pd/C (1 g) in MeOH (50 mL) and the mixtures stirred under H$_2$ (50 PSI) at rt for 4 hrs. The reactions were filtered and the filtrate was concentrated to give the title compounds (3.2 g, 84.2% yield) as oils. $^1$H NMR (400 MHz, DMSO) δ ppm 6.0-6.1 (t, 1H), 3.46-3.49 (s, 3H), 3.23-3.25 (s, 1H), 2.90-2.93 (s, 1H), 2.51-2.52 (s, 1H), 1.79 (s, 2H), 1.40 (s, 9H). m/z for C$_{10}$H$_{18}$F$_2$N$_2$O$_2$ 137 [M−100]$^+$+ 181 [M−56]$^+$.

Preparation 15: Preparation of (3R,4S)-tert-butyl 3-amino-4-(trifluoromethyl)pyrrolidine-1-carboxylate and (3S,4R)-tert-butyl 3-amino-4-(trifluoromethyl)pyrrolidine-1-carboxylate

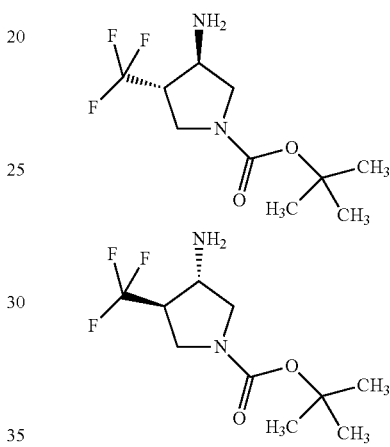

Step 1: Preparation of trans-ethyl 1-benzyl-4-(trifluoromethyl)pyrrolidine-3-carboxylate

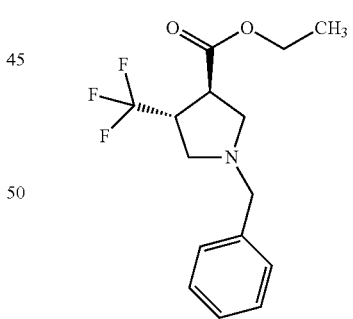

To a solution of (E)-ethyl 4,4,4-trifluorobut-2-enoate (100 g, 0.6 mol) in DCM (1.8 L) was added dropwise TFA (20.52 g, 0.18 mol) at 0° C. and then N-benzyl-1-methoxy-N-((trimethylsilyl)methyl)methanamine (170.64 g, 0.72 mol) was added and the resulting mixture was stirred at rt overnight. The reaction mixture was washed with sat. aqueous NaHCO$_3$ (two×500 mL), dried over Na$_2$SO$_4$ and concentrated in vacuo and the residue was purified by silica column chromatography eluted with petroleum ether/EtOAc=100:1 to give the title compound (142 g, 79% yield) as a yellow oil.

Step 2: Preparation of trans-1-tert-butyl 3-ethyl 4-(trifluoromethyl)pyrrolidine-1,3-dicarboxylate

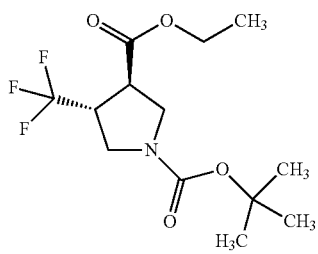 [SMILES: CCOC(=O)[C@H]1CN(C(=O)OC(C)(C)C)C[C@@H]1C(F)(F)F]

A mixture a of trans-ethyl 1-benzyl-4-(trifluoromethyl)pyrrolidine-3-carboxylate (53 g, 0.176 mol), Boc$_2$O (42.3 g, 0.194 mol) and Pd/C (11 g, 10%) in EtOH (1000 mL) was stirred under 50 psi hydrogen at 25° C. for 8 hrs and left standing overnight. The reaction mixture was filtered through a pad of Celite and the filtrate was concentrated in vacuo to give the title compound (61 g, >100%) as colorless oil. Used as is for next steps.

Step 3: Preparation of trans-1-(tert-butoxycarbonyl)-4-(trifluoromethyl)pyrrolidine-3-carboxylic acid

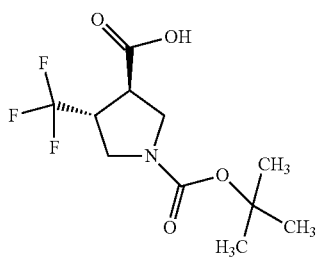 [SMILES: CC(C)(C)OC(=O)N1C[C@H](C(=O)O)[C@@H](C(F)(F)F)C1]

A mixture of trans-1-tert-butyl 3-ethyl 4-(trifluoromethyl)pyrrolidine-1,3-dicarboxylate (61.2 g, 0.19 mol), LiOH (39.9 g, 0.95 mol) in a mixed solvent of water (300 mL), THF (300 mL) and MeOH (150 mL) was stirred at rt overnight. The reaction mixture was concentrated in vacuum, then acidified with 1N HCl to pH=1, and extracted with EtOAc (three×300 mL). The combined organics were dried over Na$_2$SO$_4$ and concentrated to give the title compound (47 g, 87% yield) as a yellow solid.

Step 4: Preparation of (3R,4S)-tert-butyl 3-(((benzyloxy)carbonyl)amino)-4-(trifluoromethyl)pyrrolidine-1-carboxylate and (3S,4R)-tert-butyl 3-(((benzyloxy)carbonyl)amino)-4-(trifluoromethyl)pyrrolidine-1-carboxylate

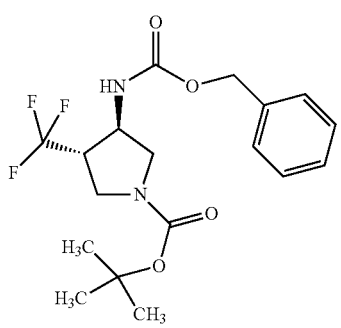

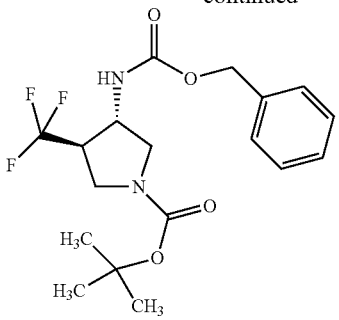

A mixture of trans-1-(tert-butoxycarbonyl)-4-(trifluoromethyl)pyrrolidine-3-carboxylic acid (50 g, 0.177 mol), DPPA (53.4 g, 0.195 mol) and Et$_3$N (21.4 g, 0.212 mol) in xylene (750 mL) was stirred at 130° C. under N$_2$ for 1 hr. Benzyl alcohol (21.06 g, 0.195 mol) was then added dropwise and the resulting solution was stirred at 130° C. for 3 hrs. The reaction mixture was poured into 1 N NaOH (500 mL) and extracted with ethyl acetate (three×500 mL). The combined organics were washed with water (300 mL), 10% citric solution (300 mL), brine (300 mL), dried over Na$_2$SO$_4$ and concentrated in vacuum. The residue was purified by silica column chromatography eluted with PE:EA=20:1 to give crude material, which was further purified by preparative HPLC then by chiral SFC to give the title compounds (14.3 g, 34% yield) as brown oils.

Step 5: Preparation of (3R,4S)-tert-butyl 3-amino-4-(trifluoromethyl)pyrrolidine-1-carboxylate and (3S,4R)-tert-butyl 3-amino-4-(trifluoromethyl)pyrrolidine-1-carboxylate

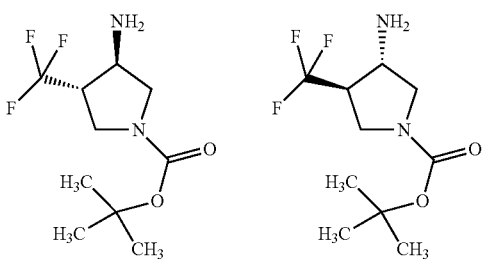 [SMILES: CC(C)(C)OC(=O)N1C[C@H](N)[C@@H](C(F)(F)F)C1 ; CC(C)(C)OC(=O)N1C[C@@H](N)[C@H](C(F)(F)F)C1]

In separate flasks were placed (3R,4S)-tert-butyl 3-(((benzyloxy)carbonyl)amino)-4-(trifluoromethyl)pyrrolidine-1-carboxylate and (3S,4R)-tert-butyl 3-(((benzyloxy)carbonyl)amino)-4-(trifluoromethyl)pyrrolidine-1-carboxylate (29.7 g, 0.08 mol) and Pd/C (9 g, 10%) in ethyl acetate (500 mL). The reactions were stirred at 25° C. under 30 psi of H$_2$ overnight. The reaction mixtures were filtered through a pad of Celite and the filtrates concentrated in vacuum to give the title compounds (16 g, 79% yield) as pale yellow solids. $^1$H NMR (400 MHz, CDCl$_3$) δ ppm 3.73~3.80 (m, 3H), 3.47 (br, 1H), 3.09 (br, 1H), 2.64~2.65 (br, 1H), 1.47 (s, 9H); m/z for C$_{10}$H$_{17}$F$_3$N$_2$O$_2$: 254 [M−56]$^+$.

Preparation 16: Preparation of tert-butyl(cis)-3a-methoxyhexahydropyrrolo[3,4-c]pyrrole-2(1H)-carboxylate

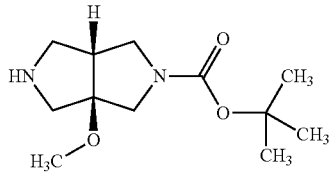

Step 1: Preparation of (cis)-5-benzyl-3a-methoxytetrahydropyrrolo[3,4-c]pyrrole-1,3(2H,3aH)-dione

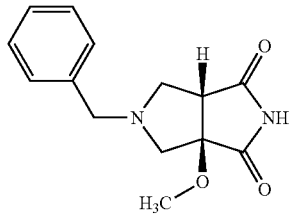 [SMILES: CO[C@@]12CN(Cc3ccccc3)C[C@@H]1C(=O)NC2=O]

To a 0° C. solution of 3-methoxy-1H-pyrrole-2,5-dione ({see M. Couturier, J. L. Tucker, B. M. Andresen, P. Dube, J. T. Negri, Org. Lett., 2001, 3, 465-467}, 950 mg, 7.47 mmol) and TFA (0.070 mL, 0.897 mmol) in DCM (70 mL) was added slowly a solution of N-benzyl-1-methoxy-N-[(trimethylsilyl)methyl]methanamine (3.06 mL, 12.0 mmol) in DCM (30 mL) at a rate such to maintain the internal reaction temperature <2° C. The resulting bright yellow solution was slowly warmed to ambient temperature and stirred for 18 hrs. The reaction mixture was then cooled to 0° C. and a solution of N-benzyl-1-methoxy-N-[(trimethylsilyl)methyl]methanamine (0.956 mL, 3.74 mmol) in DCM (1 mL) was added dropwise and was warmed to rt and stirred for 3 hrs. The reaction mixture was diluted with saturated sodium bicarbonate (25 mL), the layers were separated and the organic solution was dried (magnesium sulfate), filtered and concentrated under reduced pressure, giving a thick, yellow oil. The crude residue was purified by column chromatography eluting with 5%-50% EtOAc/heptane and again with 0%-25% EtOAc/Heptane to afford the titled compound (1.19 g, 61% yield, 70% purity) as a clear oil that was carried forward to the next step without further purification.

Step 2: Preparation of (cis)-2-benzyl-3a-methoxyoctahydropyrrolo[3,4-c]pyrrole

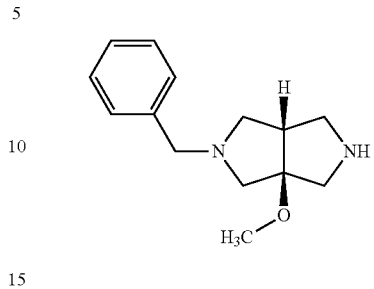

To a stirred solution of (cis)-5-benzyl-3a-methoxytetrahydropyrrolo[3,4-c]pyrrole-1,3(2H,3aH)-dione (400 mg, 1.54 mmol) in diethyl ether (7 mL), under nitrogen, was added LAH (7.92 mL, 1.0 M in diethyl ether) to form a white suspension that was stirred at ambient temperature for 21 hrs. The reaction was then cooled to 0° C. and quenched by the addition of water (0.3 mL), 15% NaOH (0.3 mL) and water (0.9 mL), as described by Fieser, L. F.; Fieser, M. Reagents for Organic Synthesis Vol. 1, Wiley, New York 1967, pp 581-595. The mixture was filtered and washed with EtOAc (100 mL). The filtrate was concentrated with toluene to give the crude title compound as a clear oil that was carried forward to the next step without further purification assuming quantitative yield. m/z (APCI+) for $C_{14}H_{20}N_2O$ 233.20 $(M+H)^+$.

Step 3: Preparation of tert-butyl(cis)-5-benzyl-3a-methoxyhexahydropyrrolo[3,4-c]pyrrole-2(1H)-carboxylate

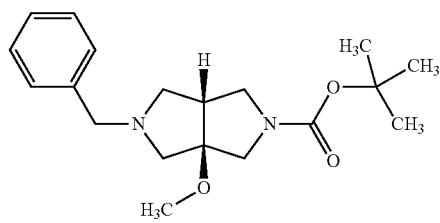 [SMILES: CO[C@@]12CN(Cc3ccccc3)C[C@@H]1CN(C(=O)OC(C)(C)C)C2]

To a solution of (cis)-2-benzyl-3a-methoxyoctahydropyrrolo[3,4-c]pyrrole (357 mg, 3.53 mmol) in acetonitrile (9 mL) was added in portions di-tert-butyl dicarbonate (0.770 mmol) and the resulting mixture was stirred for 18 hrs at rt. Starting material was still observed thus 200 mg of di-tert-butyl dicarbonate was added. After 4 hrs, di-tert-butyl dicarbonate (300 mg), DMAP (43.1 mg, 0.353 mmol), and triethylamine(0.492 mL, 3.53 mmol) were added and stirred for 20 hrs. The volatiles were removed under reduced pressure and the crude material was purified by column chromatography with silica gel, eluting with 2%-30% EtOAc/Heptane (visualized by TLC with KMnO4 stain) to afford the title compound (187 mg, 16% yield for 2 steps including LAH reduction). $^1$H NMR (400 MHz, DMSO-d6) δ ppm 7.17-7.39 (m, 5H) 3.50-3.69 (m, 4H) 3.33 (s, 1H) 3.15 (s, 3H) 3.08 (dd, J=11.37, 4.29 Hz, 1H) 2.53-2.72 (m, 4H) 2.36 (dd, J=8.97, 3.66 Hz, 1H) 1.40 (s, 9H); m/z (APCI+) for $C_{19}H_{28}N_2O_3$ 333.20 (M+H)$^+$.

Step 4: Preparation of tert-butyl(cis)-3a-methoxy-hexahydropyrrolo[3,4-c]pyrrole-2(1H)-carboxylate

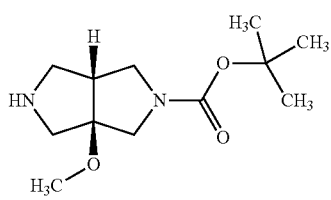 [SMILES: CO[C@@]12CNC[C@@H]1CN(C(=O)OC(C)(C)C)C2]

To a solution of tert-butyl(cis)-5-benzyl-3a-methoxy-hexahydropyrrolo[3,4-c]pyrrole-2(1H)-carboxylate (185 mg, 0.556 mmol) in EtOH (5.5 mL) purged with nitrogen was added Pd(OH)$_2$/C (78 mg) and stirred under H$_2$ (balloon) for 18 hrs. The reaction mixture was filtered and concentrated under reduced pressure to afford the title compound (128 mg, 95% yield). $^1$H NMR (400 MHz, chloroform-d) δ ppm 3.83-4.02 (m, 1H) 3.38-3.80 (m, 5H) 3.34 (s, 3H) 3.14-3.33 (m, 2H) 2.78-3.05 (m, 2H) 1.47 (s, J=2.57 Hz, 9H); m/z (APCI+) for $C_{12}H_{22}N_2O_3$ 243.20 (M+H)$^+$.

Preparation 17: Preparation of tert-butyl(cis)-3a-[(tert-butoxycarbonyl)oxy]hexahydropyrrolo[3,4-c]pyrrole-2(1H)-carboxylate

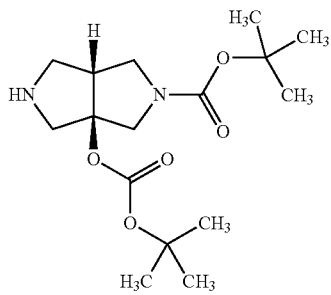 [SMILES: CC(C)(C)OC(=O)O[C@@]12CNC[C@@H]1CN(C(=O)OC(C)(C)C)C2]

Step 1: Preparation of (cis)-5-benzyl-3a-hydroxytetrahydropyrrolo[3,4-c]pyrrole-1,3(2H,3aH)-dione

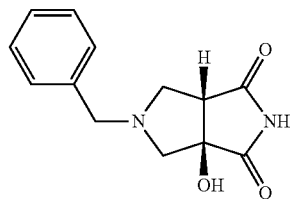 [SMILES: O=C1NC(=O)[C@]2(O)CN(Cc3ccccc3)C[C@H]12]

To a cooled −78° C. solution of (cis)-5-benzyl-3a-methoxytetrahydropyrrolo[3,4-c]pyrrole-1,3(2H,3aH)-dione (403 mg, 1.55 mmol) in DCM (5.15 mL was added BBr$_3$ (0.293 mL, 3.10 mmol). After 1 hr, the reaction mixture was warmed to 0° C. and stirred for an additional 1 hr and eventually warmed to rt and stirred for 24 hrs. The reaction mixture was cooled to 0° C., quenched with MeOH until the evolution of gas subsided. The mixture was concentrated and the residue was redissolved in MeOH (4 mL). Pd/C (40 mg) and was added and stirred under nitrogen to remove the borane (org letters, 2001, p 465-467) for 72 hrs. The mixture was filtered and concentrated to afford the crude title compound that was carried forward to the next step without further purification. m/z (APCI+) for $C_{13}H_{14}N_2O_3$ 247.10 (M+H)$^+$.

Step 2: Preparation of (cis)-2-benzylhexahydropyrrolo[3,4-c]pyrrol-3a(1H)-ol

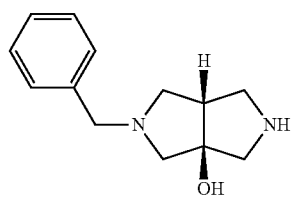 [SMILES: O[C@]12CNC[C@H]1CN(Cc1ccccc1)C2]

To a stirred solution of (cis)-5-benzyl-3a-hydroxytetrahydropyrrolo[3,4-c]pyrrole-1,3(2H,3aH)-dione (450 mg, 1.83 mmol) in THF (9 mL) under nitrogen, was added LAH (9.42 mL, 1.0 M in diethyl ether) to form a white suspension. The resulting mixture was stirred at ambient temperature for 21 hrs. The reaction mixture was cooled to 0° C. and quenched by the addition of water (0.3 mL), 15% NaOH (0.3 mL) and water (0.9 mL), as described by Fieser, L. F.; Fieser, M. Reagents for Organic Synthesis Vol. 1, Wiley, New York 1967, pp 581-595. The mixture was filtered and the precipitate washed with EtOAc (60 mL). The filtrates were combined and concentrated with toluene to give the crude title compound as a clear oil that was carried forward to the next step without further purification. m/z (APCI+) for $C_{13}H_{18}N_2O$ 219.2 (M+H)+.

Step 3: Preparation of tert-butyl(cis)-5-benzyl-3a-[(tert-butoxycarbonyl)oxy]hexahydropyrrolo[3,4-c]pyrrole-2(1H)-carboxylate

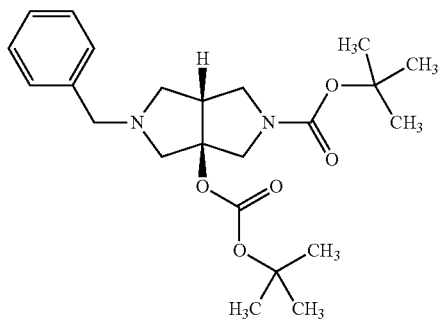 [SMILES: CC(C)(C)OC(=O)O[C@@]12CN(Cc3ccccc3)C[C@@H]1CN(C(=O)OC(C)(C)C)C2]

To a solution of (cis)-2-benzylhexahydropyrrolo[3,4-c]pyrrol-3a(1H)-ol (188 mg, 0.861 mmol) in acetonitrile (2.15 mL) was added portionwise di-tert-butyl dicarbonate (207 mg, 0.947 mmol) and the mixture stirred at rt for 18 hrs. Di-tert-butyl dicarbonate (100 mg), DMAP (10.5 mg, 0.0860 mmol) and triethylamine (0.120 mL, 0.861 mmol) were added and the mixture stirred at rt for 5 hrs. The reaction mixture was diluted with water (50 mL), extracted with EtOAc (three×60 mL), dried over $MgSO_4$, filtered and concentrated to afford the crude title compound that was carried forward without further purification. m/z (APCI+) for $C_{23}H_{34}N_2O_5$ 419.20 (M+H)+.

Step 4: Preparation of tert-butyl(cis)-3a-[(tert-butoxycarbonyl)oxy]hexahydropyrrolo[3,4-c]pyrrole-2(1H)-carboxylate To a solution of tert-butyl(cis)-5-benzyl-3a-[(tert-butoxycarbonyl)oxy]hexahydropyrrolo[3,4-c]pyrrole-2(1H)-carboxylate (274 mg, 0.861 mmol) in EtOH (8.61 mL) purged with nitrogen was added $Pd(OH)_2/C$ (27 mg) and the resulting mixture stirred under a $H_2$ balloon for 18 hrs. The reaction mixture was filtered and then concentrated under reduced pressure to obtain the crude title compound that was carried forward to the next step without further purification. m/z (APCI+) for $C_{16}H_{28}N_2O_5$ 429.20 (M+H)+.

The following examples were made with non-critical changes or substitutions to the exemplified procedures that would be understood to one skilled in the art.

TABLE 1

| Example No. (Scheme) | Structure and Compound Name | LRMS m/z | 1H NMR |
|---|---|---|---|
| 1 (Scheme A) | N-[3-({5-fluoro-2-[(1-methyl-1H-pyrazol-3-yl)amino]-7H-pyrrolo[2,3-d]pyrimidin-4-yl}oxy)phenyl]prop-2-enamide | 394.1 | 1H NMR (400 MHz, DMSO-d6) δ ppm 11.25 (br. s., 1H) 10.27 (s, 1H) 9.25 (s, 1H) 7.64 (s, 1H) 7.53-7.60 (m, 1H) 7.41 (t, J = 8.06 Hz, 1H) 7.28 (d, J = 1.26 Hz, 1H) 7.02 (dd, J = 7.93, 1.89 Hz, 1H) 6.99 (s, 1H) 6.38-6.48 (m, 1H) 6.05 (br. s., 1H) 5.77 (dd, J = 10.07, 1.51 Hz, 1H) 3.65 (s, 4H) |

TABLE 1-continued

| Example No. (Scheme) | Structure and Compound Name | LRMS m/z | $^1$H NMR |
|---|---|---|---|
| 2 (Scheme B) | N-(3-{[2-({1-[2-(dimethylamino)ethyl]-1H-pyrazol-4-yl}amino)-7H-pyrrolo[2,3-d]pyrimidin-4-yl]oxy}phenyl)prop-2-enamide | 433.2 | $^1$H NMR (600 MHz, DMSO-d6) δ ppm 11.06-11.23 (m, 1H) 9.96-10.08 (m, 1H) 8.56-8.64 (m, 1H) 7.56-7.66 (m, 2H) 7.39-7.47 (m, 2H) 7.30-7.36 (m, 1H) 6.94-7.02 (m, 2H) 6.37-6.47 (m, 1H) 6.18-6.30 (m, 2H) 5.68-5.80 (m, 1H) 3.89-4.04 (m, 2H) 2.57-2.64 (m, 2H) 2.18 (s, 6H) |
| 3* (Scheme B) | 1-{(3S,4S)-3-methyl-4-[({2-[(1-methyl-1H-pyrazol-4-yl)amino]-7H-pyrrolo[2,3-d]pyrimidin-4-yl}oxy)methyl]pyrrolidin-1-yl}prop-2-en-1-one | 404.0 | $^1$H NMR(400 MHz, DMSO-d6): δ ppm 11.32 (brs, 1H), 8.91 (s, 1H), 7.89 (s, 1H), 7.53 (s, 1H), 6.93-6.92 (s, 1H), 6.61-6.55 (m, 1H), 6.28-6.11 (m, 2H), 5.69-5.65 (m, 1H), 4.56-4.44 (m, 2H), 3.91-3.77 (m, 2H), 3.87 (s, 3H), 3.28-3.18 (m, 2H), 2.40-2.10 (m, 2H), 1.12-1.11 (d, 3H). |
| 4* (Scheme B) | 1-{(3R,4R)-3-methyl-4-[({2-[(1-methyl-1H-pyrazol-4-yl)amino]-7H-pyrrolo[2,3-d]pyrimidin-4-yl}oxy)methyl]pyrrolidin-1-yl}prop-2-en-1-one | 404.0 | $^1$H NMR (400 MHz, DMSO-d6): δ ppm 11.32 (brs, 1H), 8.91 (s, 1H), 7.89 (s, 1H), 7.53 (s, 1H), 6.93-6.92 (s, 1H), 6.61-6.55 (m, 1H), 6.28-6.11 (m, 2H), 5.69-5.65 (m, 1H), 4.56-4.44 (m, 2H), 3.91-3.77 (m, 2H), 3.87 (s, 3H), 3.28-3.18 (m, 2H), 2.40-2.10 (m, 2H), 1.12-1.11 (d, 3H). |

TABLE 1-continued

| Example No. (Scheme) | Structure and Compound Name | LRMS m/z | ¹H NMR |
|---|---|---|---|
| 5 (Scheme B) | 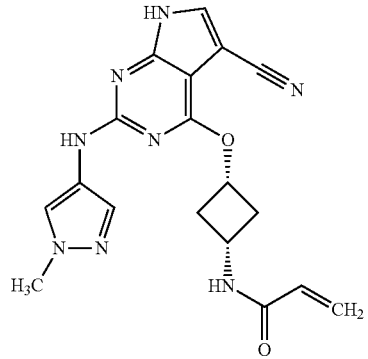 N-[cis-3-({5-cyano-2-[(1-methyl-1H-pyrazol-4-yl)amino]-7H-pyrrolo[2,3-d]pyrimidin-4-yl}oxy)cyclobutyl]prop-2-enamide | 379.1 | ¹H NMR (400 MHz, DMSO-d6) δ ppm 12.29 (br. s., 1H) 9.16 (s, 1H) 8.50 (d, J = 7.81 Hz, 1H) 7.90 (s, 1H) 7.86 (s, 1H) 7.54 (s, 1H) 6.01-6.27 (m, 2H) 5.53-5.70 (m, 1H) 5.13 (quin, J = 6.92 Hz, 1H) 4.13 (sxt, J = 7.76 Hz, 1H) 3.82 (s, 3H) 2.82-2.99 (m, 2H) 2.04-2.21 (m, 2H) |
| 6 (Scheme B) | 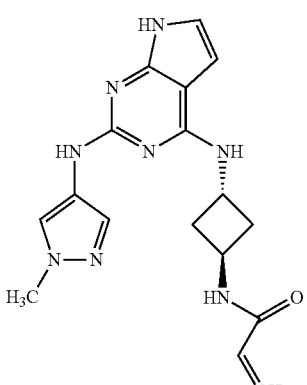 N-[trans-3-({2-[(1-methyl-1H-pyrazol-4-yl)amino]-7H-pyrrolo[2,3-d]pyrimidin-4-yl}amino)cyclobutyl]prop-2-enamide | 353.1 | ¹H NMR (400 MHz, DMSO-d6) δ ppm 10.8 (br. s., 1H), 8.52 (d, J = 6.80 Hz, 1H), 8.32 (s, 1H), 7.86 (s, 1H), 7.45 (s, 1H), 6.87 (s, 1H), 6.72 (br. s., 1H), 6.64 (s, 1H), 6.18-6.29 (m, 1H), 6.12 (d, J = 1.76 Hz, 1H), 5.60 (dd, J = 10.07, 2.01 Hz, 1H), 4.68 (d, J = 6.29 Hz, 1H), 4.40 (d, J = 6.55 Hz, 1H), 2.37 (br. s., 3H), 2.18 (s, 2H) |
| 7 (Scheme C) | 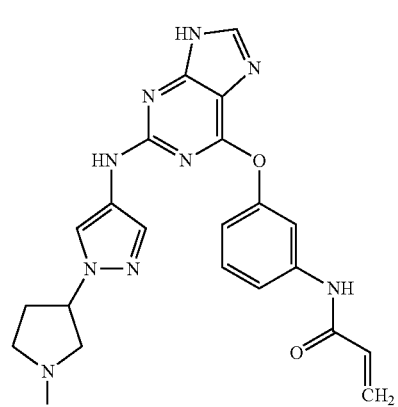 N{3-[(2-{[1-(1-methylpyrrolidin-3-yl)-1H-pyrazol-4-yl]amino}-9H-purin-6-yl)oxy]phenyl}prop-2-enamide | 446.05 | ¹H NMR (400 MHz, DMSO-d6) δ ppm 12.80 (br. s., 1H) 10.37 (br. s., 1H) 9.20 (br. s., 1H) 8.01-8.11 (m, 1H) 7.61-7.78 (m, 1H) 7.48 (br. s., 1H) 7.37 (d, J = 6.32 Hz, 1H) 7.03 (d, J = 7.33 Hz, 2H) 6.36-6.59 (m, 1H) 6.20-6.34 (m, 1H) 5.77 (dd, J = 10.23, 1.89 Hz, 1H) 4.57 (br. s., 1H) 3.99-4.27 (m, 1H) 3.65-3.94 (m, 3H) 3.00 (br. s., 2H) 2.79 (m, J = 15.66 Hz, 1H) 2.00 (br. s., 1H) 1.23 (s, 1H) |

TABLE 1-continued

| Example No. (Scheme) | Structure and Compound Name | LRMS m/z | ¹H NMR |
|---|---|---|---|
| 8 (Scheme D) | 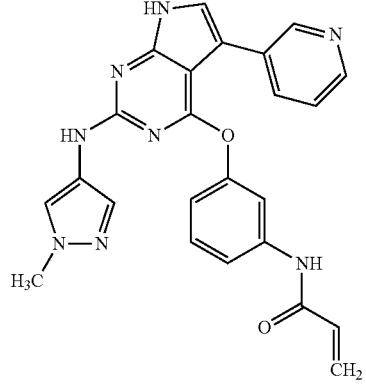<br>N-[3-({2-[(1-methyl-1H-pyrazol-4-yl)amino]-5-(pyridin-3-yl)-7H-pyrrolo[2,3-d]pyrimidin-4-yl}oxy)phenyl]prop-2-enamide | 453.0 | ¹H NMR (400 MHz, DMSO-d6) δ ppm 11.80 (br. s., 1H) 10.32 (br. s., 1H) 8.99-9.14 (m, 1H) 8.95 (d, J = 1.51 Hz, 1H) 8.41 (dd, J = 4.78, 1.51 Hz, 1H) 8.12 (d, J = 7.55 Hz, 1H) 7.64 (br. s., 2H) 7.47 (s, 2H) 7.39 (dd, J = 7.93, 4.91 Hz, 1H) 7.21 (br. s., 1H) 7.04 (br. s., 1H) 6.34-6.48 (m, 1H) 6.19-6.31 (m, 1H) 5.70-5.82 (m, 1H) 3.58 (br. s., 3H). |
| 9 (Scheme F) | 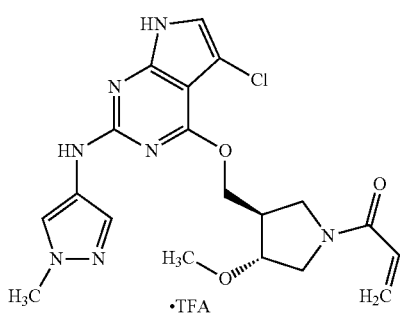<br>1-{(3R,4R)-3-[({5-chloro-2-[(1-methyl-1H-pyrazol-4-yl)amino]-7H-pyrrolo[2,3-d]pyrimidin-4-yl}oxy)methyl]-4-methoxypyrrolidin-1-yl}prop-2-en-1-one trifluoroacetate | 431.9 | ¹H NMR (400 MHz, DMSO-d6) δ ppm 11.51 (s, 1H) 9.07 (s, 1H) 7.86 (s, 1H) 7.52 (s, 1H) 7.05 (s, 1H) 6.59 (ddd, J = 16.75, 10.27, 1.34 Hz, 1H) 6.14 (dd, J = 16.75, 2.32 Hz, 1H) 5.68 (dt, J = 10.27, 2.32 Hz, 1H) 4.44 (d, J = 6.24 Hz, 2H) 3.82-4.09 (m, 2H) 3.80 (s, 3H) 3.57-3.76 (m, 2H) 3.47-3.54 (m, 1H) 3.31 (d, J = 4.65 Hz, 3H) 2.67-2.92 (m, 1H). |
| 10 (Scheme H) | 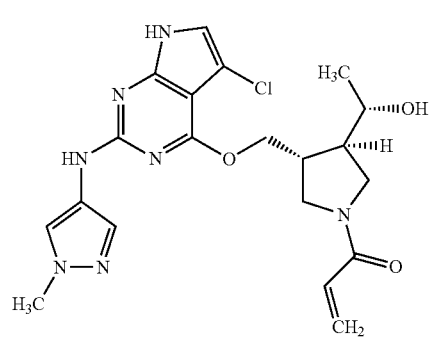<br>1-{(3R,4R)-3-[({5-chloro-2-[(1-methyl-1H-pyrazol-4-yl)amino]-7H-pyrrolo[2,3-d]pyrimidin-4-yl}oxy)methyl]-4-[(1S)-1-hydroxyethyl]pyrrolidin-1-yl}prop-2-en-1-one | 446.1 | ¹H NMR (600 MHz, DMSO-17 mm) δ ppm 1.10 (dd, J = 6.36, 3.56 Hz, 3H) 2.07-2.24 (m, 1H) 2.54-2.73 (m, 1H) 3.28-3.45 (m, 2H) 3.69-4.07 (m, 7H) 4.34-4.41 (m, 1H) 4.83-4.92 (m, 1H) 5.62-5.70 (m, 1H) 6.11 (ddd, J = 16.78, 2.29, 2.03 Hz, 1H) 6.49-6.63 (m, 1H) 7.01 (s, 1H) 7.51 (s, 1H) 7.86 (br. s., 1H) 9.04 (s, 1H) 11.47 (br. s., 1H). |

TABLE 1-continued

| Example No. (Scheme) | Structure and Compound Name | LRMS m/z | 1H NMR |
|---|---|---|---|
| 11 (Scheme G) | 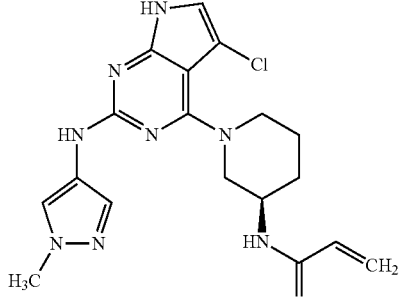 N-[(3R)-1-{5-chloro-2-[(1-methyl-1H-pyrazol-4-yl)amino]-7H-pyrrolo[2,3-d]pyrimidin-4-yl}piperidin-3-yl]prop-2-enamide | 401.2 | 1H NMR (400 MHz, DMSO-d6) δ ppm 11.40 (br. s., 1H), 8.76 (s, 1H), 8.14 (d, J = 7.82 Hz, 1H), 7.83 (s, 1H), 7.47 (s, 1H), 7.05 (d, J = 2.45 Hz, 1H), 6.19-6.31 (m, 1H), 6.07-6.16 (m, 1H), 5.60 (dd, J = 10.03, 2.45 Hz, 1H), 4.13 (d, J = 12.23 Hz, 1H), 4.03 (d, J = 12.72 Hz, 1H), 3.85-3.98 (m, 1H), 3.77 (s, 3H), 2.96 (t, J = 11.25 Hz, 1H), 2.80 (t, J = 11.13 Hz, 1H), 1.89-2.00 (m, 1H), 1.79-1.88 (m, 1H), 1.67-1.79 (m, 1H), 1.40-1.57 (m, 1H) |
| 12 (Scheme I) | 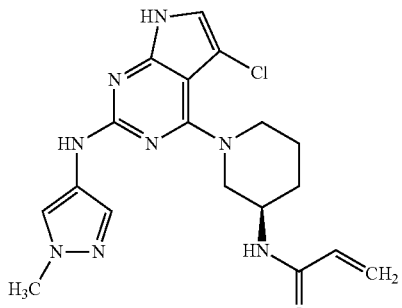 N-[(3R)-1-{5-chloro-2-[(1-methyl-1H-pyrazol-4-yl)amino]-7H-pyrrolo[2,3-d]pyrimidin-4-yl}piperidin-3-yl]prop-2-enamide | 431.1 | 1H NMR (700 MHz, DMSO) δ ppm 11.41-11.96 (m, 1H) 8.88-9.01 (m, 1H) 8.57-8.63 (m, 1H) 8.52-8.55 (m, 1H) 8.10-8.15 (m, 1H) 7.87-7.93 (m, 1H) 7.80-7.85 (m, 1H) 7.47-7.55 (m, 2H) 7.18-7.24 (m, 1H) 6.21-6.32 (m, 1H) 6.09-6.15 (m, 1H) 5.61-5.67 (m, 1H) 5.52-5.60 (m, 1H) 4.42-4.52 (m, 1H) 3.78-3.86 (m, 3H) 2.52-2.56 (m, 4H) |
| 13 (Scheme J) | 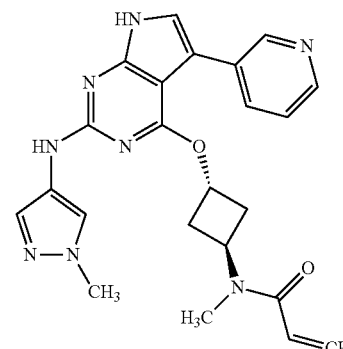 N-methyl-N-[trans-3-({2-[(1-methyl-1H-pyrazol-4-yl)amino]-5-(pyridin-3-yl)-7H-pyrrolo[2,3-d]pyrimidin-4-yl}oxy)cyclobutyl]prop-2-enamide | 445.2 | 1H NMR (700 MHz, DMSO) δ ppm 11.64 (br. s., 1H) 8.87-9.00 (m, 2H) 8.43 (d, J = 3.96 Hz, 1H) 8.12 (d, J = 7.26 Hz, 1H) 7.87 (br. s., 1H) 7.52 (s, 1H) 7.42 (br. s., 1H) 7.33 (s, 1H) 6.59-6.80 (m, 1H) 5.95-6.15 (m, 1H) 5.65 (br. s., 2H) 5.47 (br. s., 1H) 3.74-3.88 (m, 3H) 3.07 (br. s., 1H) 2.91-3.00 (m, 1H) 2.72 (br. s., 2H) 2.29-2.46 (m, 2H) |

TABLE 1-continued

| Example No. (Scheme) | Structure and Compound Name | LRMS m/z | $^1$H NMR |
|---|---|---|---|
| 14 (Scheme B) | 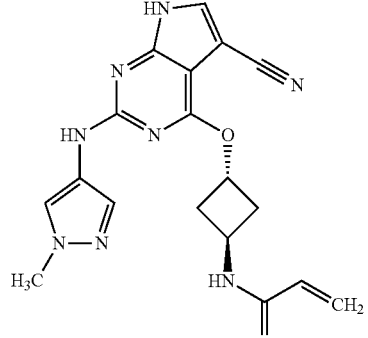<br>N-[trans-3-({5-cyano-2-[(1-methyl-1H-pyrazol-4-yl)amino]-7H-pyrrolo[2,3-d]pyrimidin-4-yl}oxy)cyclobutyl]prop-2-enamide | 379.1 | $^1$H NMR (400 MHz, DMSO-d6) δ ppm 12.29 (br. s., 1H) 9.16 (s, 1H) 8.50 (d, J = 7.81 Hz, 1H) 7.90 (s, 1H) 7.86 (s, 1H) 7.54 (s, 1H) 6.01-6.27 (m, 2H) 5.53-5.70 (m, 1H) 5.13 (quin, J = 6.92 Hz, 1H) 4.13 (sxt, J = 7.76 Hz, 1H) 3.82 (s, 3H) 2.82-2.99 (m, 2H) 2.04-2.21 (m, 2H) |
| 15* (Scheme B) | 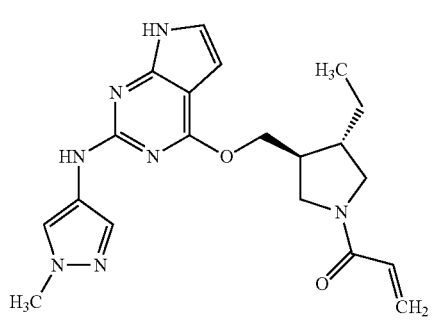<br>1-{trans-3-ethyl-4-[({2-[(1-methyl-1H-pyrazol-4-yl)amino]-7H-pyrrolo[2,3-d]pyrimidin-4-yl}oxy)methyl]pyrrolidin-1-yl}prop-2-en-1-one | 396.1 | $^1$H NMR (400 MHz, DMSO-d6) δ ppm 11.27 (br. s., 1H) 8.86 (s, 1H) 7.87 (s, 1H) 7.52 (s, 1H) 6.87-6.98 (m, 1H) 6.51-6.70 (m, 1H) 6.21-6.31 (m, 1H) 6.13 (dd, J = 16.7, 2.5 Hz, 1H) 5.66 (ddd, J = 10.4, 4.4, 2.4 Hz, 1H) 4.50-4.63 (m, 1H) 4.35-4.50 (m, 1H) 3.66-3.98 (m, 5H) 3.01-3.29 (m, 1H) 2.27-2.47 (m, 1H) 1.91-2.16 (m, 1H) 1.58-1.78 (m, 1H) 1.27-1.46 (m, 1H) 0.74-1.00 (m, 4H) |
| 16 (Scheme A) | 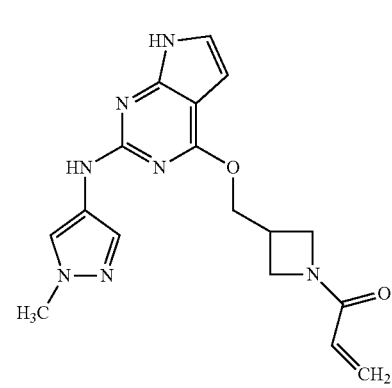<br>·TFA<br>1-{3-[({2-[(1-methyl-1H-pyrazol-4-yl)amino]-7H-pyrrolo[2,3-d]pyrimidin-4-yl}oxy)methyl]azetidin-1-yl}prop-2-en-1-one trifluoroacetate | 354.1 | $^1$H NMR (400 MHz, DMSO-d6) δ ppm 11.24 (br. s., 1H) 8.89 (br. s., 1H) 7.83 (s, 1H) 7.47 (s, 1H) 6.87 (d, J = 2.27 Hz, 1H) 6.29 (d, J = 6.55 Hz, 1H) 6.24-6.33 (m, 1H) 6.18 (dd, J = 3.27, 2.01 Hz, 1H) 6.06 (dd, J = 17.00, 2.14 Hz, 1H) 5.62 (dd, J = 10.32, 2.27 Hz, 1H) 4.58 (d, J = 6.55 Hz, 3H) 4.32 (t, J = 8.44 Hz, 1H) 4.04 (dd, J = 9.06, 6.04 Hz, 2H) 3.98-4.10 (m, 2H) 3.08 (d, J = 6.04 Hz, 1H) |

TABLE 1-continued

| Example No. (Scheme) | Structure and Compound Name | LRMS m/z | $^1$H NMR |
|---|---|---|---|
| 17 (Scheme B) | 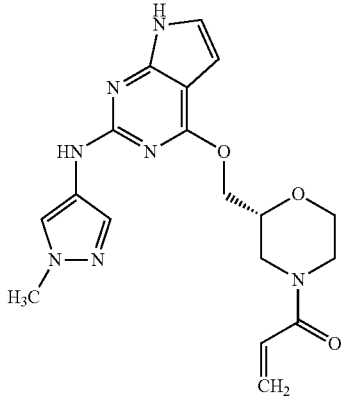<br>•TFA<br>1-{(2R)-2-[({2-[(1-methyl-1H-pyrazol-4-yl)amino]-7H-pyrrolo[2,3-d]pyrimidin-4-yl}oxy)methyl]morpholin-4-yl}prop-2-en-1-one trifluoroacetate | 384.1 | $^1$H NMR (400 MHz, DMSO-d6) δ ppm 11.30 (br. s., 1H) 8.93 (br. s., 1H) 7.88 (s, 1H) 7.52 (br. s., 1H) 6.90-6.96 (m, 1H) 6.81 (dd, J = 16.62, 10.32 Hz, 1H) 6.28 (br. s., 1H) 6.14 (dd, J = 16.74, 2.14 Hz, 1H) 5.71 (dd, J = 10.32, 2.27 Hz, 2H) 4.40-4.60 (m, 4H) 4.01-4.22 (m, 1H) 3.87-4.00 (m, 2H) 3.49 (m, 2H) 3.20 (m, 2H) |
| 18 (Scheme B) | 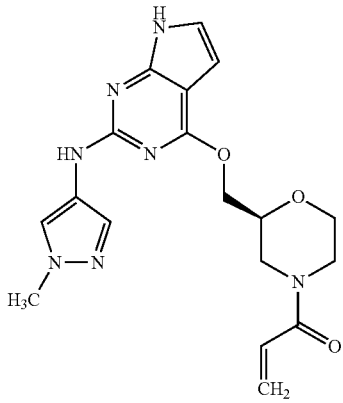<br>1-{(2S)-2-[({2-[(1-methyl-1H-pyrazol-4-yl)amino]-7H-pyrrolo[2,3-d]pyrimidin-4-yl}oxy)methyl]morpholin-4-yl}prop-2-en-1-one | 384.2 | $^1$H NMR (700 MHz, DMSO-d6) δ ppm 11.29 (br. s., 1H), 8.92 (d, J = 6.82 Hz, 1H), 7.89 (br. s., 1H), 7.52 (d, J = 10.12 Hz, 1H), 6.90-7.02 (m, 1H), 6.81 (dd, J = 10.56, 16.51 Hz, 1H), 6.28 (d, J = 10.56 Hz, 1H), 6.15 (dd, J = 1.98, 16.73 Hz, 1H), 5.72 (dd, J = 1.98, 10.56 Hz, 1H), 4.38-4.56 (m, 2H), 3.88-4.02 (m, 2H), 3.81 (s, 4H), 3.50 (m, 3H) 3.13-3.29 (m, 1H) |

TABLE 1-continued

| Example No. (Scheme) | Structure and Compound Name | LRMS m/z | ¹H NMR |
|---|---|---|---|
| 19 (Scheme B) | 1-[(3S,4S)-3-[({2-[(1-methyl-1H-pyrazol-4-yl)amino]-7H-pyrrolo[2,3-d]pyrimidin-4-yl}oxy)methyl]-4-(trifluoromethyl)pyrrolidin-1-yl]prop-2-en-1-one | 458.0 [M + Na]⁺ | ¹H NMR (400 MHz, DMSO-d6): δ ppm 11.29 (brs, 1H), 8.90 (s, 1H), 7.85 (s, 1H), 7.49 (s, 1H), 6.92-6.91 (s, 1H), 6.64-6.57 (m, 1H), 6.24-6.13 (m, 2H), 5.72-5.67 (m, 1H), 4.57-4.44 (m, 2H), 4.05-3.56 (m, 4H), 3.82 (s, 3H), 3.04-2.94 (m, 2H) |
| 20 (Scheme B) | 4-{[(3R)-1-acryloylpyrrolidin-3-yl]oxy}-2-[(1-methyl-1H-pyrazol-4-yl)amino]-7H-pyrrolo[2,3-d]pyrimidine-5-carbonitrile | 379.4 | ¹H NMR (600 MHz, DMSO-d6) δ ppm 9.28 (d, J = 5.67Hz, 1 H)7.89 (d, J = 1.89 Hz, 1H) 7.78-7.87 (m, 1H) 7.53 (s, 1 H)7.08 (br. s., 1H) 6.48-6.68 (m, 1H) 5.98-6.23 (m, 1H) 5.54-5.83 (m, 2H) 3.84-4.06 (m, 1H) 3.81 (s, 3H) 3.65-3.78 (m, 2H) 3.49-3.56 (m, 1H)2.13-2.40 (m, 2H) |
| 21 (Scheme A) | N-[3-({5-chloro-2-[(1-methyl-1H-pyrazol-3-yl)amino]-7H-pyrrolo[2,3-d]pyrimidin-4-yl}oxy)phenyl]prop-2-enamide | 410.1 | ¹H NMR (400 MHz, DMSO-d6) δ ppm 11.71 (br. s., 1H) 10.26 (s, 1H) 9.26 (s, 1H) 7.64 (s, 1H) 7.57 (d, J = 8.06 Hz, 1H) 7.41 (t, J = 8.06 Hz, 1H) 7.26-7.32 (m, 1H) 7.22 (s, 1H) 6.97-7.07 (m, 1H) 6.37-6.50 (m, 1H) 6.19-6.32 (m, 1H) 6.04 (br. s., 1H) 5.70-5.83 (m, 1H) 3.66 (s, 3H) |

TABLE 1-continued

| Example No. (Scheme) | Structure and Compound Name | LRMS m/z | ¹H NMR |
|---|---|---|---|
| 22 (Scheme A) | N-[3-({2-[(1-ethyl-1H-pyrazol-3-yl)amino]-7H-pyrrolo[2,3-d]pyrimidin-4-yl}oxy)phenyl]prop-2-enamide | 389.9 | ¹H NMR (400 MHz, DMSO-d6): δ ppm 11.492 (s, 1H), 10.306 (s, 1H), 9.171 (s, 1H), 7.620 (s, 1H), 7.57-7.55 (d, 1H). 7.41-7.38 (t, 1H), 7.329 (s, 1H), 7.04-7.03 (m, 1H), 6.99-6.97 (d, 1H), 6.45-6.38 (m, 1H), 6.26-6.21 (m, 1H), 6.18 (s, 1H), 6.11 (s, 1H), 5.77-5.74 (d, 1H) 3.95-3.90 (m, 2H), 1.30-1.26 (t, 3H) |
| 23 (Scheme B) | 1-[(3R,4R)-3-[({2-[(1-methyl-1H-pyrazol-4-yl)amino]-7H-pyrrolo[2,3-d]pyrimidin-4-yl}oxy)methyl]-4-(trifluoromethyl)pyrrolidin-1-yl]prop-2-en-1-one | 458.0 [M + Na]⁺ | ¹H NMR (400 MHz, DMSO-d6): δ ppm 11.29 (brs, 1H), 8.90 (s, 1H), 7.85 (s, 1H), 7.49 (s, 1H), 6.92-6.91 (s, 1H), 6.64-6.57 (m, 1H), 6.24-6.13 (m, 2H), 5.72-5.67 (m, 1H), 4.57-4.44 (m, 2H), 4.05-3.56 (m, 4H), 3.82 (s, 3H), 3.04-2.94 (m, 2H) |
| 24 (Scheme B) | N-[3-({2-[(1,5-dimethyl-1H-pyrazol-4-yl)amino]-7H-pyrrolo[2,3-d]pyrimidin-4-yl}oxy)phenyl]prop-2-enamide | 390.3 | ¹H NMR (600 MHz, DMSO-d6) δ ppm 11.38 (br. s., 1H) 10.32 (br. s., 1H) 8.07 (br. s., 1H) 7.58-7.70 (m, 1H) 7.52 (d, J = 8.31 Hz, 1H) 7.38 (t, J = 8.12 Hz, 1H) 7.30 (br. s., 1H) 6.90-7.01 (m, 2H) 6.42 (dd, J = 17.00, 10.20 Hz, 1H) 6.26 (dd, J = 17.00, 1.89 Hz, 1H) 6.12 (d, J = 3.02 Hz, 1H) 5.68-5.85 (m, 1H) 3.58-3.77 (m, 3H) 2.07 (s, 3H) |

| Example No. (Scheme) | Structure and Compound Name | LRMS m/z | $^1$H NMR |
|---|---|---|---|
| 25 (Scheme B) | 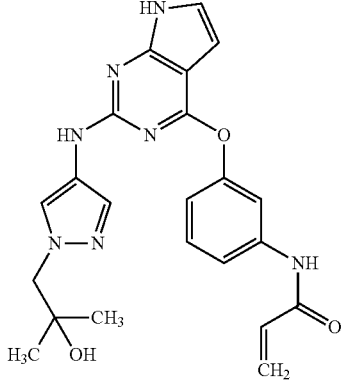 N-{3-[(2-{[1-(2-hydroxy-2-methylpropyl)-1H-pyrazol-4-yl]amino}-7H-pyrrolo[2,3-d]pyrimidin-4-yl)oxy]phenyl}prop-2-enamide | 434.2 | $^1$H NMR (600 MHz, DMSO-d6) δ ppm 11.42 (br. s., 1H) 10.37 (br. s., 1H) 8.94 (br. s., 1H) 7.63 (br. s., 1H) 7.58 (br. s., 1H) 7.40-7.48 (m, 1H) 7.36 (d, J = 16.39 Hz, 1H) 6.98 (dd, J = 8.19, 2.05 Hz, 1H) 7.02 (br. s., 1H) 6.41 (dd, J = 17.41, 10.24 Hz, 1H) 6.17-6.33 (m, 2H) 5.68-5.84 (m, 1H) 4.64 (br. s., 1H) 3.76 (br. s., 2H) 0.98 (br. s., 6H) |
| 26 (Scheme A) | 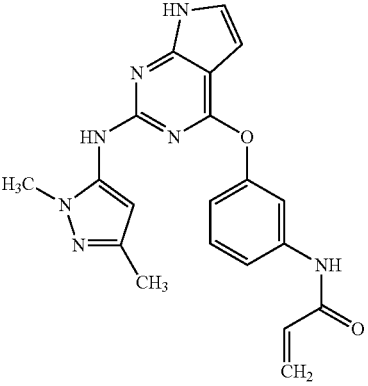 N-[3-({2-[(1,3-dimethyl-1H-pyrazol-5-yl)amino]-7H-pyrrolo[2,3-d]pyrimidin-4-yl}oxy)phenyl]prop-2-enamide | 390.2 | $^1$H NMR (400 MHz, DMSO-d6): δ ppm 11.60 (s, 1H) 10.30 (s, 1H) 8.85 (s, 1H) 7.65 (t, J = 2.01 Hz, 1H) 7.56 (d, J = 9.32 Hz, 1H) 7.41 (t, J = 8.06 Hz, 1H) 7.08 (dd, J = 3.53, 2.27 Hz, 1H) 6.98 (dd, J = 7.68, 1.89 Hz, 1H) 6.38-6.48 (m, 1H) 6.19-6.31 (m, 2H) 5.74-5.81 (m, 2H) 3.53 (s, 3H) 2.00 (s, 3H) |
| 27 (Scheme A) | 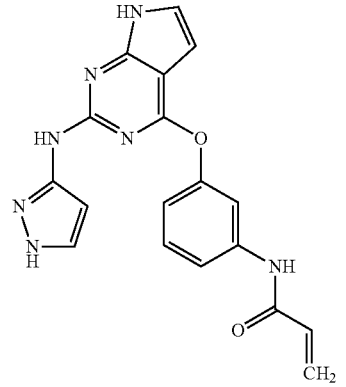 N-(3-{[2-(1H-pyrazol-3-ylamino)-7H-pyrrolo[2,3-d]pyrimidin-4-yl]oxy}phenyl)prop-2-enamide | 383.8 [M + Na]$^+$ | $^1$H NMR(400 MHz, DMSO-d6): δ ppm 10.28 (s, 1H), 10.25 (s, 1H), 8.25 (s, 1H), 7.63 (s, 1H), 7.56-7.52 (m, 1H), 7.43-7.37 (m, 1H), 7.32-7.28 (s, 1H), 7.09-7.03 (m, 1H), 7.02-6.97 (m, 1H), 6.46-6.38 (m, 1H), 6.27-6.2 (m, 2H), 5.79-5.72 (m, 1H) |

TABLE 1-continued

| Example No. (Scheme) | Structure and Compound Name | LRMS m/z | $^1$H NMR |
|---|---|---|---|
| 28 (Scheme B) | 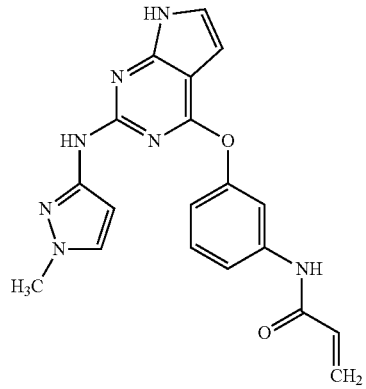 N-[3-({2-[(1-methyl-1H-pyrazol-3-yl)amino]-7H-pyrrolo[2,3-d]pyrimidin-4-yl}oxy)phenyl]prop-2-enamide | 376.2 | $^1$H NMR(400 MHz, DMSO-d6)) δ ppm 11.48 (br. s., 1H) 10.27 (s, 1H) 9.13 (br. s., 1H) 7.61-7.67 (m, 1H) 7.57 (d, J = 8.06 Hz, 1H) 7.41 (t, J = 8.18 Hz, 1H) 7.30 (d, J = 2.01 Hz, 1H) 7.05 (d, J = 3.53 Hz, 1H) 6.99 (dd, J = 8.06, 1.76 Hz, 1H) 6.36-6.48 (m, 1H) 6.22-6.31 (m, 1H) 6.10-6.21 (m, 2H) 5.65-5.85 (m, 1H) 3.66 (s, 3H) |
| 29 (Scheme B) | 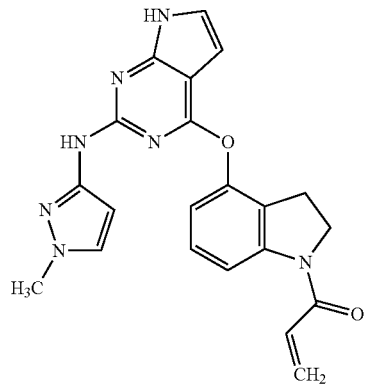 1-[4-({2-[(1-methyl-1H-pyrazol-3-yl)amino]-7H-pyrrolo[2,3-d]pyrimidin-4-yl}oxy)-2,3-dihydro-1H-indol-1-yl]prop-2-en-1-one | 402.3 | $^1$H NMR (600 MHz, DMSO-d6) δ ppm 11.49 (br. s., 1H) 9.16 (br. s., 1H) 8.10 (d, J = 6.80 Hz, 1H) 7.25-7.38 (m, 2H) 7.05 (br. s., 1H) 6.96 (d, J = 7.93 Hz, 1H) 6.61-6.77 (m, 1H) 6.32 (d, J = 16.62 Hz, 1H) 6.23 (br. s., 1H) 6.06 (br. s., 1H) 5.83 (d, J = 11.71 Hz, 1H) 4.18 (br. s., 2H) 3.64 (s, 3H) 2.96 (t, J = 7.93 Hz, 2H) |
| 30 (Scheme B) | 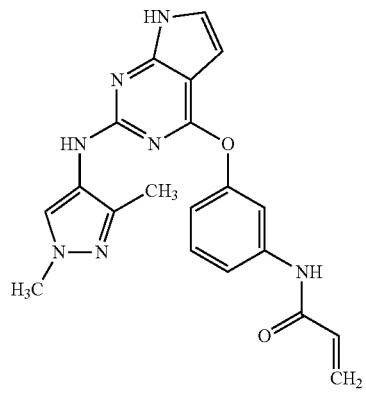 N-[3-({2-[(1,3-dimethyl-1H-pyrazol-4-yl)amino]-7H-pyrrolo[2,3-d]pyrimidin-4-yl}oxy)phenyl]prop-2-enamide | 390.1 | $^1$H NMR (600 MHz, DMSO-d6) δ ppm 11.41 (br. s., 1H) 10.38 (s, 1H) 8.27 (br. s., 1H) 7.65 (s, 1H) 7.61 (d, J = 7.55 Hz, 1H) 7.45 (t, J = 7.93 Hz, 1H) 6.94-7.05 (m, 2H) 6.43 (dd, J = 17.00, 10.20 Hz, 1H) 6.26 (dd, J = 17.00, 1.89 Hz, 2H) 5.67-5.82 (m, 1H) 3.53 (br. s., 3H) 2.06 (s, 3H) |

TABLE 1-continued

| Example No. (Scheme) | Structure and Compound Name | LRMS m/z | ¹H NMR |
|---|---|---|---|
| 31 (Scheme B) | N-{3-[(2-{[1-(propan-2-yl)-1H-pyrazol-4-yl]amino}-7H-pyrrolo[2,3-d]pyrimidin-4-yl)oxy]phenyl}prop-2-enamide | 404.3 | ¹H NMR(600 MHz, DMSO-d6) δ ppm 11.36-11.47 (m, 1H) 10.27-10.48 (m, 1H) 8.90-9.01 (m, 1H) 7.56-7.70 (m,2) H7.41-7.49 (m, 1H) 7.12-7.34 (m, 1H) 7.02-7.07 (m, 1H) 6.95-7.01 (m, 1H) 6.37-6.47 (m, 1H) 6.30-6.36 (m, 1H) 6.20-6.28 (m, 1H) 5.73-5.81 (m, 1H) 4.01-4.35 (m, 1H) 0.97-1.50 (m, 6H) |
| 32 (Scheme B) | N-{3-[(2-{[1-methyl-3-(trifluoromethyl)-1H-pyrazol-4-yl]amino}-7H-pyrrolo[2,3-d]pyrimidin-4-yl)oxy]phenyl}prop-2-enamide | 444.1 | ¹H NMR (600 MHz, DMSO-d6) δ ppm 11.35-11.61 (m, 1H) 10.28-10.46 (m, 1H) 8.06-8.24 (m, 1H) 7.53-7.68 (m, 3H) 7.40-7.49 (m, 1H) 7.04-7.08 (m, 1H) 6.96-7.03 (m, 1H) 6.37-6.47 (m, 1H) 6.21-6.31 (m, 2H) 5.66-5.85 (m, 1H) 3.68-3.79 (m, 3H) |
| 33 (Scheme B) | N-{3-[(2-{[1-(1-methylpiperidin-4-yl)-1H-pyrazol-4-yl]amino}-7H-pyrrolo[2,3-d]pyrimidin-4-yl)oxy]phenyl}prop-2-enamide | 459.1 | ¹H NMR (400 MHz, MeOD) δ ppm 7.61-7.69 (m, 1H) 7.50 (t, J = 2.0 Hz, 1H) 7.35-7.45 (m, 2H) 7.26 (s, 1H) 6.94 (dd, J = 8.5, 1.9 Hz, 1H) 6.89 (d, J = 3.5 Hz, 1H) 6.26-6.38 (m, 3H) 5.71 (dd, J = 9.5, 2.4 Hz, 1H) 3.68-3.88 (m, 1H) 2.90 (d, J = 12.1 Hz, 2H) 2.28 (s, 3H) 2.09-2.21 (m, 2H) 1.76-1.95 (m, 4H) |

TABLE 1-continued

| Example No. (Scheme) | Structure and Compound Name | LRMS m/z | ¹H NMR |
|---|---|---|---|
| 34 (Scheme B) | 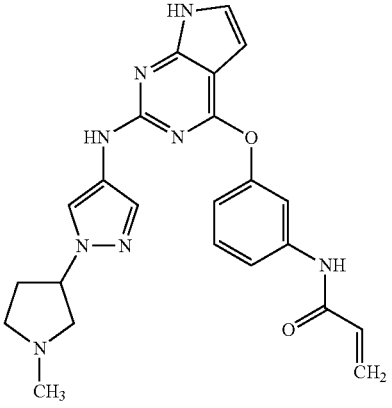<br>N-{3-[(2-{[1-(1-methylpyrrolidin-3-yl)-1H-pyrazol-4-yl]amino}-7H-pyrrolo[2,3-d]pyrimidin-4-yl)oxy]phenyl}prop-2-enamide | 445.1 | ¹H NMR (400 MHz, DMSO-d6) δ ppm 11.17 (br. s., 1H) 10.05 (br. s., 1H) 8.60 (s, 1H) 7.58-7.69 (m, 2H) 7.54 (s, 1H) 7.33-7.46 (m, 2H) 6.95-7.00 (m, 2H) 6.35-6.49 (m, 1H) 6.21-6.30 (m, 2H) 5.67-5.81 (m, 1H) 4.55-4.66 (m, 1H) 2.83 (dd, J = 9.57, 7.30 Hz, 1H) 2.59-2.74 (m, 2H) 2.15-2.35 (m, 5H) 1.96-2.11 (m, 1H) |
| 35 (Scheme B) | 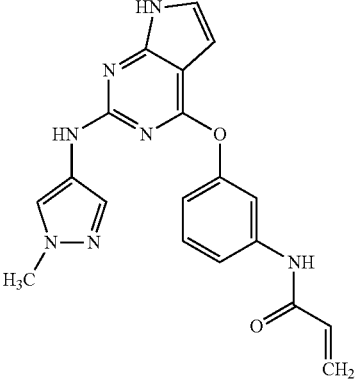<br>N-[3-({2-[(1-methyl-1H-pyrazol-4-yl)amino]-7H-pyrrolo[2,3-d]pyrimidin-4-yl}oxy)phenyl]prop-2-enamide | 376.2 | ¹H NMR (400 MHz, DMSO-d6) δ ppm 11.41 (br. s., 1H) 10.33 (s, 1H) 8.93 (s, 1H) 7.57-7.70 (m, 2H) 7.46 (t, J = 8.06 Hz, 1H) 7.24 (br. s., 1H) 7.04 (br. s., 1H) 6.96-7.01 (m, 1H) 6.37-6.48 (m, 1H) 6.31 (br. s., 1H) 6.21-6.28 (m, 1H) 5.72-5.80 (m, 1H) 3.60 (br. s., 3H) |
| 36 (Scheme A) | 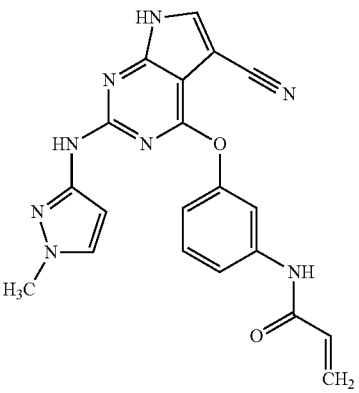<br>N-[3-({5-cyano-2-[(1-methyl-1H-pyrazol-3-yl)amino]-7H-pyrrolo[2,3-d]pyrimidin-4-yl}oxy)phenyl]prop-2-enamide | 401.1 | ¹H NMR (400 MHz, DMSO-d6) δ ppm 12.45 (br. s., 1H) 10.21 (s, 1H) 9.59 (s, 0H) 8.01 (s, 1H) 7.61 (br. s., 1H) 7.50 (br. s., 1H) 7.36 (t, J = 8.06 Hz, 1H) 7.23 (br. s., 1H) 7.00 (d, J = 7.30 Hz, 1H) 6.31-6.44 (m, 1H) 6.14-6.26 (m, 1H) 5.97 (br. s., 1H) 5.71 (d, J = 10.07 Hz, 1H) 3.59 (s, 3H) |

TABLE 1-continued

| Example No. (Scheme) | Structure and Compound Name | LRMS m/z | ¹H NMR |
|---|---|---|---|
| 37 (Scheme B) | 4-[(1-acryloyl-2,3-dihydro-1H-indol-4-yl)oxy]-2-[(1-methyl-1H-pyrazol-4-yl)amino]-7H-pyrrolo[2,3-d]pyrimidine-5-carbonitrile | 427.2 | ¹H NMR (700 MHz, DMSO-d6) δ ppm 9.20-9.51 (m, 1H) 8.11-8.27 (m, 1H) 8.01-8.10 (m, 1H) 7.31-7.62 (m, 2H) 7.01-7.11 (m, 1H) 6.50-6.91 (m, 2H) 6.22-6.43 (m, 1H) 5.80-5.94 (m, 1H) 4.15-4.30 (m, 2H) 3.30-3.39 (m, 3H) 2.90-3.05 (m, 2H) |
| 38 (Scheme B) | 1-[4-({2-[(1-methyl-1H-pyrazol-4-yl)amino]-7H-pyrrolo[2,3-d]pyrimidin-4-yl}oxy)-2,3-dihydro-1H-indol-1-yl]prop-2-en-1-one | 402.2 | ¹H NMR (400 MHz, DMSO-d6) d ppm 11.38-11.54 (m, 1H) 8.89-9.08 (m, 1H) 8.08-8.32 (m, 1H) 7.29-7.50 (m, 2H) 7.16-7.28 (m, 1H) 7.03-7.10 (m, 1H) 6.93-7.02 (m, 1H) 6.66-6.80 (m, 1H) 6.28-6.39 (m, 2H) 5.77-5.88 (m, 1H) 4.16-4.32 (m, 2H) 3.48-3.81 (m, 3H) 2.88-3.13 (m, 2H) |
| 39 (Scheme B) | N-{3-[(2-{[1-(tetrahydrofuran-3-yl)-1H-pyrazol-4-yl]amino}-7H-pyrrolo[2,3-d]pyrimidin-4-yl)oxy]phenyl}prop-2-enamide | 432.1 | ¹H NMR (600 MHz, DMSO-d6) δ ppm 11.43 (br. s., 1H) 10.35 (br. s., 1H) 8.99 (br. s., 1H) 7.56-7.71 (m, 2H) 7.46 (br. s., 1H) 7.30 (br. s., 1H) 7.04-7.08 (m, 1H) 6.99 (dd, J = 8.12, 1.70 Hz, 1H) 6.42 (dd, J = 17.00, 10.20 Hz, 1H) 6.32 (br. s., 1H) 6.25 (dd, J = 17.00, 1.89 Hz, 1H) 5.68-5.85 (m, 1H) 4.65 (br. s., 1H) 3.89 (br. s., 2H) 3.74-3.80 (m, 1H) 3.69 (br. s., 1H) 2.19-2.32 (m, 1H) 2.08 (d, J = 13.22 Hz, 1H) |

| Example No. (Scheme) | Structure and Compound Name | LRMS m/z | ¹H NMR |
|---|---|---|---|
| 40 (Scheme B) | 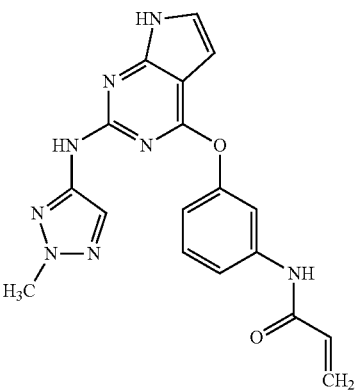<br>N-[3-({2-[(2-methyl-2H-1,2,3-triazol-4-yl)amino]-7H-pyrrolo[2,3-d]pyrimidin-4-yl}oxy)phenyl]prop-2-enamide | 377.3 | ¹HNMR (600 MHz, DMSO-d6) δ ppm 11.61 (br. s., 1H) 10.41 (br. s., 1H) 9.81 (br. s., 1H) 7.66 (br. s., 2H) 7.51 (t, J = 8.31 Hz, 1H) 7.12 (br. s., 1H) 7.03 (dd, J = 8.69, 1.51 Hz, 1H) 6.43 (dd, J = 16.62, 10.20 Hz, 1H) 6.35 (br. s., 1H) 6.26 (dd, J = 17.00, 1.89 Hz, 1H) 5.67-5.86 (m, 1H) 3.78 (br. s., 3H) |
| 41*** (Scheme B) | 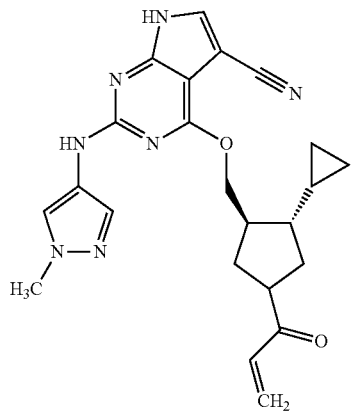<br>4-{[trans-1-acryloyl-4-cyclopropylpyrrolidin-3-yl]methoxy}-2-[(1-methyl-1H-pyrazol-4-yl)amino]-7H-pyrrolo[2,3-d]pyrimidine-5-carbonitrile | 433.3 | ¹H NMR (600 MHz, DMSO-d6) δ ppm 9.27 (d, J = 6.36 Hz, 1H), 7.90 (s, 1H), 7.86 (br. s., 1H), 7.54 (s, 1H), 6.45-6.69 (m, 1H), 6.13 (m, 1H), 5.66 (m, 1H), 4.56-4.86 (m, 1H), 4.33-4.48 (m, 1H), 3.96 (m, 1H), 3.82-3.90 (m, 1H), 3.80 (s, 3H), 3.70 (dd, J = 7.63, 11.95 Hz, 1H), 3.18 (dd, J = 9.16, 11.95 Hz, 1H), 2.52-2.74 (m, 1H), 1.43-1.75 (m, 1H), 0.69-0.91 (m, 1H), 0.47-0.58 (m, 1H), 0.35-0.45 (m, 1H), 0.08-0.29 (m, 2H) |

TABLE 1-continued

| Example No. (Scheme) | Structure and Compound Name | LRMS m/z | $^1$H NMR |
|---|---|---|---|
| 42*** (Scheme B) | 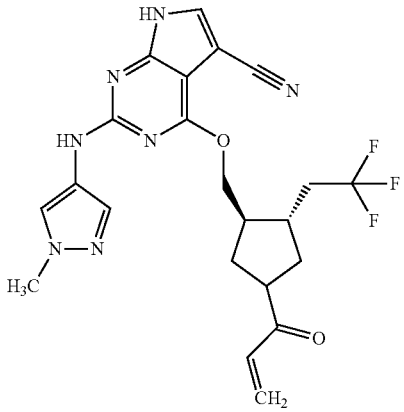<br>4-{[trans-1-acryloyl-4-(2,2,2-trifluoroethyl)pyrrolidin-3-yl]methoxy}-2-[(1-methyl-1H-pyrazol-4-yl)amino]-7H-pyrrolo[2,3-d]pyrimidine-5-carbonitrile | 475.0 | $^1$H NMR (600 MHz, DMSO-D6) δ ppm 9.00 (d, J = 11.27 Hz, 1H) 7.90 (s, 1H) 7.80 (d, J = 5.12 Hz, 1H) 7.50 (s, 1H) 6.45-6.69 (m, 1H) 6.04-6.27 (m, 1H) 5.58-5.80 (m, 1H) 4.45-4.73 (m, 2H) 3.93 (m, 1H) 3.74-3.87 (m, 4H) 3.11-3.28 (m, 1H) 2.73-3.01 (m, 1H) 2.56-2.66 (m, 1H) 2.30-2.47 (m, 3H) |
| 43 (Scheme B) | 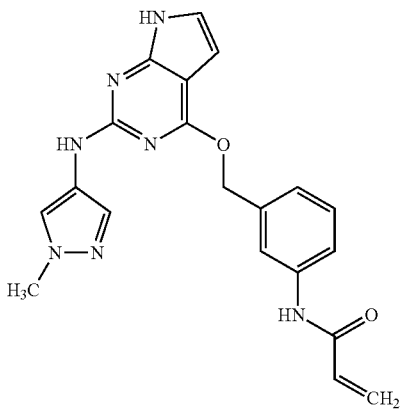<br>•HCl<br>N-{3-[({2-[(1-methyl-1H-pyrazol-4-yl)amino]-7H-pyrrolo[2,3-d]pyrimidin-4-yl}oxy)methyl]phenyl}prop-2-enamide hydrochloride | 390.10 | $^1$H NMR (400 MHz, DMSO-D6) δ ppm 11.31 (br. s., 1H) 10.20 (s, 1H) 8.92 (br. s., 1H) 7.85 (br. s., 1H) 7.78 (s, 1H) 7.67 (d, J = 8.31 Hz, 1H) 7.50 (s, 1H) 7.36 (t, J = 7.93 Hz, 1H) 7.20 (d, J = 7.30 Hz, 1H) 6.95 (dd, J = 3.53, 2.27 Hz, 1H) 6.38-6.50 (m, 1H) 6.18-6.33 (m, 2H) 5.72-5.79 (m, 1H) 5.54 (s, 2H) 3.79 (s, 3H) |

TABLE 1-continued

| Example No. (Scheme) | Structure and Compound Name | LRMS m/z | ¹H NMR |
|---|---|---|---|
| 44 (Scheme B) | 4-{[1-(ethenylsulfonyl)-2,3-dihydro-1H-indol-4-yl]oxy}-N-(1-methyl-1H-pyrazol-4-yl)-7H-pyrrolo[2,3-d]pyrimidin-2-amine | 438.1 | N/A |
| 45 (Scheme A) | N-{3-[(2-{[3-(methoxymethyl)-1-methyl-1H-pyrazol-5-yl]amino}-7H-pyrrolo[2,3-d]pyrimidin-4-yl)oxy]phenyl}prop-2-enamide | 420.1 | ¹H NMR (400 MHz, DMSO-D6) δ ppm 11.63 (s, 1H), 10.30 (s, 1H), 8.93 (s, 1H), 7.55-7.52 (m, 1H), 7.48-7.45 (m, 2H), 7.09-6.95 (m, 2H), 6.45-6.41 (m, 1H), 6.25-6.20 (m, 2H), 6.00 (s, 1H), 5.78-5.75 (m, 1H), 4.14 (s, 2H), 3.57 (s, 3H), 3.19 (s, 3H) |
| 46 (Scheme A) | N-[3-({2-[(3-cyclopropyl-1-methyl-1H-pyrazol-5-yl)amino]-7H-pyrrolo[2,3-d]pyrimidin-4-yl}oxy)phenyl]prop-2-enamide | 438.1 | ¹H NMR (400 MHz, DMSO-D6) δ ppm 11.60 (s, 1H), 10.31 (s, 1H), 8.85 (s, 1H), 7.64 (s, 1H), 7.54-7.56 (d, 1H), 7.38-7.42 (m, 1H), 7.07-7.08 (m, 1H), 6.96-6.98 (m, 1H), 6.39-6.46 (m, 1H), 6.22-6.27 (m, 1H), 5.68-5.78 (m, 1H), 5.68 (s, 1H), 3.53 (s, 3H), 1.65 (m, 1H), 0.70-0.74 (m, 2H), 0.46-0.47 (m, 2H) |

| Example No. (Scheme) | Structure and Compound Name | LRMS m/z | $^1$H NMR |
|---|---|---|---|
| 47 (Scheme A) | N-[3-({2-[(3-ethyl-1-methyl-1H-pyrazol-5-yl)amino]-7H-pyrrolo[2,3-d]pyrimidin-4-yl}oxy)phenyl]prop-2-enamide | 404.1 | $^1$H NMR (400 MHz, DMSO-D6) δ ppm 11.60 (s, 1H), 10.31 (s, 1H), 8.87 (s, 1H), 7.64 (s, 1H), 7.55-7.53 (d, 1H), 7.41-7.37 (t, 1H), 7.08-7.07 (m, 1H), 6.98-6.96 (m, 1H), 6.45-6.38 (m, 1H), 6.27-6.22 (m, 2H), 5.78-5.75 (m, 2H), 3.53 (s, 3H), 2.37-2.32 (q, 2H), 1.07-1.03 (t, 3H) |
| 48 (Scheme A) | N-[3-({2-[(1-methyl-1H-pyrazol-3-yl)amino]-7H-pyrrolo[2,3-d]pyrimidin-4-yl}oxy)phenyl]prop-2-enamide | 398.0 | $^1$H NMR (400 MHz, DMSO-D6) δ ppm 11.44 (s, 1H), 10.25 (s, 1H), 9.11 (s, 1H), 7.72-7.58 (m, 2H), 7.41-7.30 (m, 1H), 7.28-7.22 (m, 1H), 7.05-6.88 (m, 2H), 6.43-6.31 (m, 1H), 6.25-6.05 (m, 3H), 5.80-5.68 (m, 1H), 3.60 (s, 3H) |
| 49 (Scheme A) | N-[3-fluoro-5-({2-[(1-methyl-1H-pyrazol-3-yl)amino]-7H-pyrrolo[2,3-d]pyrimidin-4-yl}oxy)phenyl]prop-2-enamide | 394.0 | $^1$H NMR (400 MHz, DMSO-D6) δ ppm 11.53 (s, 1H), 10.45 (s, 1H), 9.23 (s, 1H), 7.60-7.57 (d, 1H), 7.34-7.30 (d, 2H), 7.08 (s, 1H), 7.00-6.98 (d, 1H), 6.38-6.17 (m, 4H), 5.82-5.80 (d, 1H), 3.66 (s, 3H) |

TABLE 1-continued

| Example No. (Scheme) | Structure and Compound Name | LRMS m/z | ¹H NMR |
|---|---|---|---|
| 50 (Scheme C) | 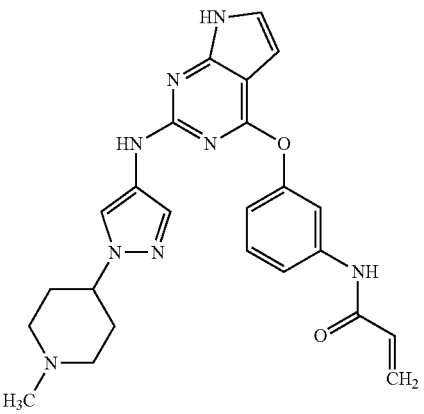<br>N-{3-[(2-{[1-(1-methylpiperidin-4-yl)-1H-pyrazol-4-yl]amino}-9H-purin-6-yl)oxy]phenyl}prop-2-enamide | 460.1 | ¹H NMR (400 MHz, DMSO-D6) δ ppm 12.79 (br. s., 1H) 10.42 (br. s., 1H) 9.23 (br. s., 1H) 8.07 (br. s., 1H) 7.58 (br. s., 1H) 7.50 (br. s., 1H) 7.36 (d, J = 12.63 Hz, 1H) 7.04 (d, J = 7.58 Hz, 2H) 6.38-6.57 (m, 1H) 6.27 (dd, J = 17.05, 1.64 Hz, 1H) 5.79 (dd, J = 10.11, 1.77 Hz, 1H) 3.79 (br. s., 2H) 3.62 (m, J = 11.87 Hz, 2H) 2.93 (br. s., 1H) 2.65-2.82 (m, 2H) 1.81-2.14 (m, 3H) 1.18-1.31 (m, 1H) 0.75-0.92 (m, 1H) |
| 51 (Scheme B) | 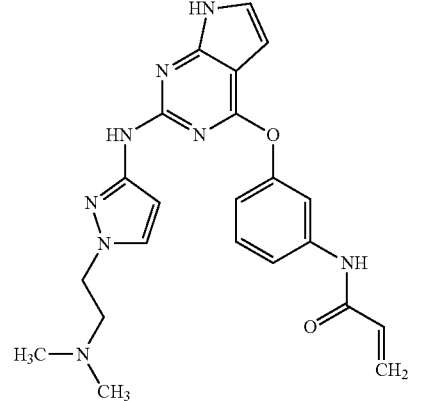<br>N-(3-{[2-({1-[2-(dimethylamino)ethl]-1H-pyrazol-3-yl}amino)-7H-pyrrolo[2,3-d]pyrimidin-4-yl]oxy}phenyl)prop-2-enamide | 434.1 | ¹H NMR (700 MHz, DMSO-D6) δ ppm 9.11 (br. s., 1H) 7.62 (s, 1H) 7.57 (d, J = 8.14 Hz, 1H) 7.41 (t, J = 8.14 Hz, 1H) 7.33 (s, 1H) 7.03 (d, J = 3.52 Hz, 1H) 6.98 (dd, J = 8.03, 1.65 Hz, 1H) 6.42 (dd, J = 17.06, 10.23 Hz, 1H) 6.25 (dd, J = 16.95, 1.76 Hz, 1H) 6.18 (d, J = 3.30 Hz, 1H) 6.11 (br. s., 1H) 5.76 (dd, J = 10.12, 1.76 Hz, 1H) 3.98 (t, J = 6.60 Hz, 2H) 2.53-2.57 (m, 2H) 2.12 (s, 6H) |
| 52 (Scheme C) | 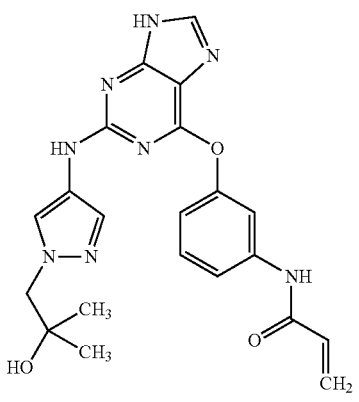<br>N-{3-[(2-{[1-(2-hydroxy-2-methylpropyl)-1H-pyrazol-4-yl]amino}-9H-purin-6-yl)oxy]phenyl}prop-2-enamide | 435.0 | ¹H NMR (400 MHz, DMSO-D6) δ ppm 12.56 (s, 1H) 10.03 (s, 1H) 8.81 (s, 1H) 7.99 (s, 1H) 7.57-7.67 (m, 2H) 7.50 (s, 1H) 7.40-7.47 (m, 1H) 7.38 (s, 1H) 7.00 (ddd, J = 8.12, 2.20, 1.01 Hz, 1H) 6.38-6.49 (m, 1H) 6.21-6.32 (m, 1H) 5.74 (dd, J = 10.07, 2.01 Hz, 1H) 4.28 (s, 1H) 3.81 (s, 2H) 1.03 (s, 6H) |

TABLE 1-continued

| Example No. (Scheme) | Structure and Compound Name | LRMS m/z | $^1$H NMR |
|---|---|---|---|
| 53 (Scheme C) | N-(3-{[2-({1-[2-(dimethylamino)ethyl]-1H-pyrazol-4-yl}amino)-9H-purin-6-yl]oxy}phenyl)prop-2-enamide | 434.2 | $^1$H NMR (400 MHz, DMSO-D6) δ ppm 12.57 (s, 1H) 10.13 (s, 1H) 8.88 (br. s., 1H) 8.01 (br. s., 1H) 7.58-7.67 (m, 2H) 7.27-7.57 (m, 3H) 6.94-7.08 (m, 1H) 6.37-6.52 (m, 1H) 6.23-6.30 (m, 1H) 5.74 (dd, J = 10.20, 1.89 Hz, 1H) 4.12 (t, J = 6.80 Hz, 2H) 2.45 (s, 6H) 2.34-2.43 (m, 2H) |
| 54 (Scheme A) | N-[3-({2-[(1-methyl-1H-pyrazol-4-yl)amino]-9H-purin-6-yl}oxy)phenyl]prop-2-enamide | 377.0 | $^1$H NMR (400 MHz, DMSO-D6) δ ppm 12.57 (br. s., 1H) 10.06 (s, 1H) 8.79 (s, 1H) 7.99 (s, 1H) 7.64 (d, J = 1.51 Hz, 1H) 7.61-7.64 (m, 1H) 7.42-7.48 (m, 1H) 7.34 (s, 1H) 7.29 (s, 1H) 6.97-7.04 (m, 1H) 6.43 (dd, J = 17.08, 10.07 Hz, 1H) 6.26 (dd, J = 16.84, 2.01 Hz, 1H) 5.74 (dd, J = 10.20, 1.89 Hz, 1H) 3.63 (s, 3H) |
| 55** (Scheme B) | N-[(cis)3-({2-[(1-methyl-1H-pyrazol-4-yl)amino]-9H-purin-6-yl}oxy)cyclobutyl]prop-2-enamide | 355.2 | N/A |

TABLE 1-continued

| Example No. (Scheme) | Structure and Compound Name | LRMS m/z | $^1$H NMR |
|---|---|---|---|
| 56** (Scheme B) | 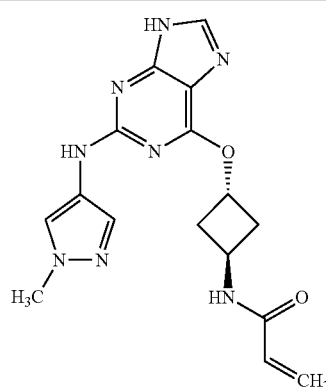 N-[(trans)3-({2-[(1-methyl-1H-pyrazol-4-yl)amino]-9H-purin-6-yl}oxy)cyclobutyl]prop-2-enamide | 355.2 | N/A |
| 57 (Scheme A) | 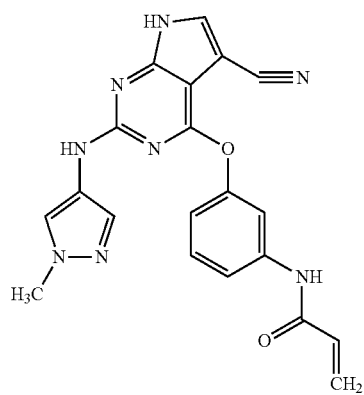 N-[3-({5-cyano-2-[(1-methyl-1H-pyrazol-4-yl)amino]-7H-pyrrolo[2,3-d]pyrimidin-4-yl}oxy)phenyl]prop-2-enamide | 401.0 | $^1$H NMR (DMSO-d$_6$, 400 MHz): d (ppm) 10.07 (s, 1H), 8.97 (s, 1H), 7.93 (s, 1H), 7.65-7.70 (m, 1H), 7.59-7.64 (m, 1H), 7.46 (t, J = 8.2 Hz, 1H), 7.35 (br. s., 1H), 7.30 (s, 1H), 6.94-7.09 (m, 1H), 6.36-6.50 (m, 1H), 6.19-6.31 (m, 1H), 5.61-5.78 (m, 1H), 3.64 (s, 3H) |
| 58 (Scheme B) | 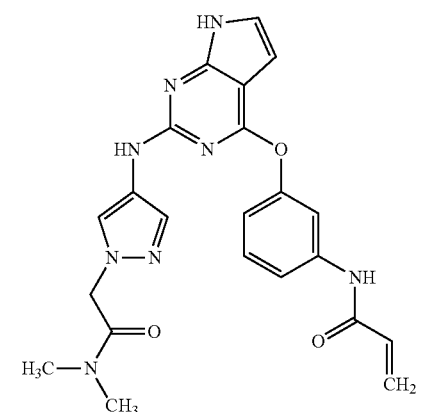 N-(3-{[2-({1-[2-(dimethylamino)-2-oxoethyl]-1H-pyrazol-4-yl}amino)-7H-pyrrolo[2,3-d]pyrimidin-4-yl]oxy}phenyl)prop-2-enamide | 447.0 | $^1$H NMR (400 MHz, DMSO-D6) δ ppm 11.42 (br. s., 1H) 10.30 (s, 1H) 8.97 (s, 1H) 7.65 (m, J = 12.63 Hz, 1H) 7.55 (br. s., 1H) 7.17-7.48 (m, 3H) 6.92-7.10 (m, 2H) 6.42 (m, J = 10.11 Hz, 1H) 6.17-6.32 (m, 2H) 5.76 (d, J = 9.85 Hz, 1H) 4.82 (s, 2H) 3.00 (s, 3H) 2.83 (s, 3H) |

| Example No. (Scheme) | Structure and Compound Name | LRMS m/z | ¹H NMR |
|---|---|---|---|
| 59 (Scheme A) | N-[2-fluoro-3-({2-[(1-methyl-1H-pyrazol-3-yl)amino]-7H-pyrrolo[2,3-d]pyrimidin-4-yl}oxy)phenyl]prop-2-enamide | 394.0 | ¹H NMR (400 MHz, DMSO-D6) δ ppm 11.57 (s, 1H), 10.11 (s, 1H), 9.24 (s, 1H), 8.02 (m, 1H), 7.28-7.22 (m, 3H), 7.11 (s, 1H), 6.64-6.60 (q, 1H), 6.38-6.29 (m, 2H), 5.91 (s, 1H), 5.82-5.79 (d, 1H), 3.65 (s, 3H) |
| 60 (Scheme D) | N-[3-({5-(1-methyl-1H-pyrazol-4-yl)-2-[(1-methyl-1H-pyrazol-4-yl)amino]-7H-pyrrolo[2,3-d]pyrimidin-4-yl}oxy)phenyl]prop-2-enamide | 456.0 | ¹H NMR (400 MHz, DMSO-D6) δ ppm 11.45 (br. s., 1H) 10.34 (br. s., 1H) 8.97 (br. s., 1H) 7.95 (s, 1H) 7.80 (s, 1H) 7.68 (br. s., 2H) 7.50 (br. s., 1H) 7.25 (br. s., 2H) 7.06 (d, J = 7.81 Hz, 1H) 6.35-6.56 (m, 1H) 6.21-6.33 (m, 1H) 5.78 (d, J = 10.32 Hz, 1H) 3.84 (s, 3H) 3.60 (br. s., 3H) |
| 61 (Scheme B) | N-[3-({5-cyano-2-[(1-methyl-1H-pyrazol-4-yl)amino]-7H-pyrrolo[2,3-d]pyrimidin-4-yl}oxy)cyclobutyl]-N-methylprop-2-enamide | 393.1 | ¹H NMR(600 MHz, DMSO-D6) δ ppm 9.17 (m), 7.76-8.00 (m), 7.44-7.61 (m), 6.75 (m), 6.09 (m), 5.69 (m), 5.47 (m), 4.96-5.24 (m), 4.63 (m), 4.41 (m), 3.81 (m), 3.80 (m), 2.64-2.87 (m), 2.54 (s), 2.37 (m), 2.26 (m) |

TABLE 1-continued

| Example No. (Scheme) | Structure and Compound Name | LRMS m/z | ¹H NMR |
|---|---|---|---|
| 62 (Scheme F) | N-[trans-3-({5-chloro-2-[(1,3-dimethyl-1H-pyrazol-4-yl)amino]-7H-pyrrolo[2,3-d]pyrimidin-4-yl}oxy)cyclobutyl]-N-methylprop-2-enamide | 415.2/ 417.2 | ¹H NMR (400 MHz, DMSO-d6) δ ppm 11.46 (br. s., 1H) 8.21 (br. s., 1H) 7.77 (s, 1H) 7.02 (s, 1H) 6.71 (br. s., 1H) 6.07 (br. s., 1H) 5.68 (d, 1H) 5.43 (br. s., 1H) 4.79-5.21 (m, 1H) 3.73 (s, 3H) 3.06 (br. s., 3H) 2.70 (br. s., 2H) 2.31-2.47 (m, 2H) 2.08 (s, 3H) |
| 63 (Scheme F) | N-[trans-3-({5-chloro-2-[(1-methyl-1H-pyrazol-4-yl)amino]-7H-pyrrolo[2,3-d]pyrimidin-4-yl}oxy)cyclobutyl]prop-2-enamide | 388.1/ 391.1 | ¹H NMR (Acetone) δ ppm 8.19 (1H, s), 7.94 (1H, s), 7.71 (1H, d, J = 6.1 Hz), 7.54 (1H, s), 6.99 (1H, s), 6.06-6.41 (2H, m), 5.59 (1H, dd, J = 2.8 and 9.6 Hz), 5.40-5.56 (1H, m), 4.45-4.71 (1H, m), 3.83 (3H, s), 2.51-2.69 (4H, m) |
| 64 (Scheme F) | 1-{(3R)-3-[({5-chloro-2-[(1-methyl-1H-pyrazol-4-yl)amino]-7H-pyrrolo[2,3-d]pyrimidin-4-yl}oxy)methyl]pyrrolidin-1-yl}prop-2-en-1-one | 402.0/ 403.0 | ¹H NMR (400 MHz, DMSO-d6) δ ppm 11.48 (br.s., 1H), 9.03 (s, 1H), 7.85 (s, 1H), 7.52 (s, 1H), 7.04 (s, 1H), 6.58 (ddd, J = 3.02, 10.32, 16.87 Hz, 1H), 6.13 (ddd, J = 0.76, 2.39, 16.74 Hz, 1H), 5.58-5.82 (m, 1H), 4.45 (dq, J = 6.80, 10.58 Hz, 2H), 3.71-3.88 (m, 4H), 3.55-3.70 (m, 2H), 3.34-3.53 (m, 1H), 2.63-2.90 (m, 1H), 2.01-2.24 (m, 1H), 1.71-1.97 (m, 1H) |

TABLE 1-continued

| Example No. (Scheme) | Structure and Compound Name | LRMS m/z | $^1$H NMR |
|---|---|---|---|
| 65 (Scheme F) | 1-[(3R)-3-({5-chloro-2-[(1-methyl-1H-pyrazol-4-yl)amino]-7H-pyrrolo[2,3-d]pyrimidin-4-yl}oxy)pyrrolidin-1-yl]prop-2-en-1-one | 388.0/ 389.0 | $^1$H NMR (400 MHz, DMSO-d6) δ ppm 9.06 (d, J = 2.52 Hz, 1H) 7.85 (s, 1H) 7.53 (s, 1H) 7.04 (d, J = 1.26 Hz, 1H) 6.47-6.77 (m, 1H) 6.15 (ddd, J = 16.81, 5.60, 2.52 Hz, 1H) 5.58-5.85 (m, 2H) 4.00 (m, 0.5H) 3.77-3.88 (m, 4.5H) 3.64-3.77 (m, 2H) 3.45-3.59 (m, 1H) 2.13-2.44 (m, 2H) |
| 66 (Scheme F) | 1-[(1R,5S,6s)-6-({5-chloro-2-[(1-methyl-1H-pyrazol-4-yl)amino]-7H-pyrrolo[2,3-d]pyrimidin-4-yl}oxy)-3-azabicyclo[3.1.0]hex-3-yl]prop-2-en-1-one | 400.2/ 401.1 | $^1$H NMR (400 MHz, DMSO-d6) δ ppm 9.05 (s, 1H), 7.90 (s, 1H), 7.51 (s, 1H), 7.05 (s, 1H), 6.37-6.73 (m, 1H), 6.18 (d, J = 2.27 Hz, 1H), 5.70 (d, J = 12.84 Hz, 1H), 4.03-4.16 (m, 1H), 3.86-4.00 (m, 2H), 3.80 (m, 4H), 3.45-3.61 (m, 1H), 2.07-2.19 (m, 1H), 1.92-2.05 (m, 1H) |
| 67 (Scheme F) | 1-{(3R,4R)-3-[({5-chloro-2-[(2-ethyl-2H-1,2,3-triazol-4-yl)amino]-7H-pyrrolo[2,3-d]pyrimidin-4-yl}oxy)methyl]-4-methoxypyrrolidin-1-yl}prop-2-en-1-one | 447/ 448.9 | $^1$H NMR (DMSO-d6, 400 MHz) δ ppm 11.57 (br. s., 1H), 9.76 (s, 1H), 7.94 (s, 1H), 7.05 (d, J = 1.8 Hz, 1H), 6.49 (ddd, J = 16.8, 10.2, 2.0 Hz, 1H), 6.04 (dd, J = 16.8, 2.4 Hz, 1H), 5.58 (dd, J = 10.5, 2.1 Hz, 1H), 4.32-4.48 (m, 2H), 4.23 (q, J = 7.3 Hz, 2H), 3.91-3.99 (m, 1H), 3.82-3.91 (m, 1H), 3.59-3.79 (m, 1H), 3.47-3.59 (m, 1H), 3.35-3.47 (m, 1H), 3.21 (d, J = 4.3 Hz, 3H), 2.62-2.85 (m, 1H), 1.34 (t, J = 7.3 Hz, 3H) |

TABLE 1-continued

| Example No. (Scheme) | Structure and Compound Name | LRMS m/z | ¹H NMR |
|---|---|---|---|
| 68 (Scheme F) | 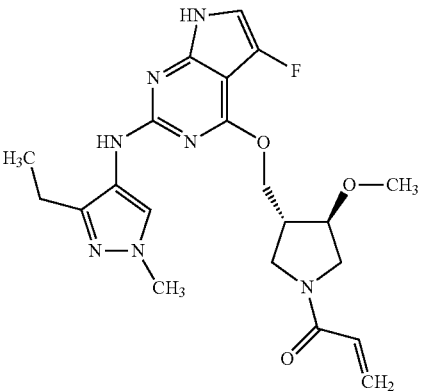<br>1-{(3R,4R)-3-[({2-[(3-ethyl-1-methyl-1Hpyrazol-4-yl)amino]-5-fluoro-7H-pyrrolo[2,3-d]pyrimidin-4-yl}oxy)methyl]-4-methoxypyrrolidin-1-yl}prop-2-en-1-one | 444.1 | ¹H NMR (400 MHz, DMSO-d6) δ ppm 11.02 (br. s., 1H) 8.21 (s, 1H) 7.76 (d, J = 4.03 Hz, 1H) 6.78 (t, J = 2.27 Hz, 1H) 6.59 (dd, J = 16.62, 10.32 Hz, 1H) 6.14 (d, J = 16.87 Hz, 1H) 5.68 (dt, J = 10.26, 2.68 Hz, 1H) 4.34-4.53 (m, 2H) 3.94-4.00 (m, 1H) 3.86-3.93 (m, 1H) 3.79 (dd, J = 10.70, 7.68 Hz, 1H) 3.74 (s, 3H) 3.42-3.65 (m, 3H) 3.29 (d, J = 4.53 Hz, 3H) 2.68-2.91 (m, 2H) 1.11 (t, J = 7.55 Hz, 3H) |
| 69 (Scheme B) | 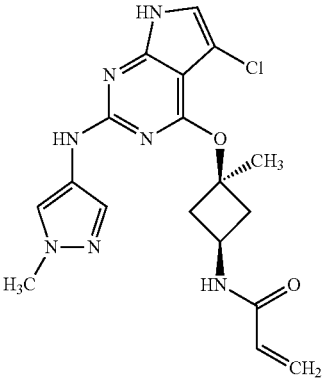<br>N-[cis-3-({5-chloro-2-[(1-methyl-1H-pyrazol-4-yl)amino]-7H-pyrrolo[2,3-d]pyrimidin-4-yl}oxy)-3-methylcyclobutyl]prop-2-enamide | 402.1/ 404.1 | ¹H NMR (400 MHz, DMSO-d6) δ ppm 1.69-1.90 (m, 3H) 2.27 (dd, J = 13.60, 6.39 Hz, 2H) 2.86 (dd, J = 13.05, 8.83 Hz, 2H) 3.79 (s, 3H) 4.24-4.37 (m, 1H) 5.59 (dd, J = 10.09, 2.02 Hz, 1H) 6.08 (m, J = 16.81, 1.96 Hz, 1H) 6.22 (dd, J = 16.93, 10.09 Hz, 1H) 7.01 (d, J = 2.08 Hz, 1H) 7.51 (s, 1H) 7.82 (br. s., 1H) 8.44 (d, J = 6.54 Hz, 1H) 8.85 (s, 1H) 11.43 (br. s., 1H) |
| 70 (Scheme F) | 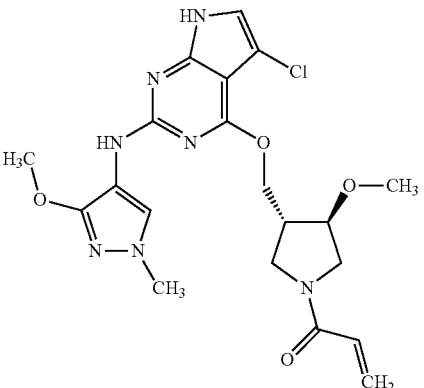<br>1-{(3R,4R)-3-[({5-chloro-2-[(3-methoxy-1-methyl-1H-pyrazol-4-yl)amino]-7H-pyrrolo[2,3-d]pyrimidin-4-yl}oxy)methyl]-4-methoxypyrrolidin-1-yl}prop-2-en-1-one | 462.1 | ¹H NMR (400 MHz, DMSO-d6) δ ppm 11.43 (br. s., 1H) 7.80 (s, 1H) 7.56 (d, J = 2.27 Hz, 1H) 6.91 (s, 1H) 6.49 (dd, J = 16.80, 10.23 Hz, 1H) 6.04 (dd, J = 16.67, 2.27 Hz, 1H) 5.58 (dt, J = 10.29, 1.80 Hz, 1H) 4.21-4.39 (m, 2H) 3.89-3.99 (m, 1H) 3.79-3.87 (m, 1H) 3.64-3.74 (m, 3H) 3.62 (d, J = 5.05 Hz, 1H) 3.55-3.60 (m, 3H) 3.45-3.54 (m, 1H) 3.29-3.44 (m, 1H) 3.20 (d, J = 4.55 Hz, 3H) 2.59-2.77 (m, 1H) |

TABLE 1-continued

| Example No. (Scheme) | Structure and Compound Name | LRMS m/z | ¹H NMR |
|---|---|---|---|
| 71 (Scheme B) | 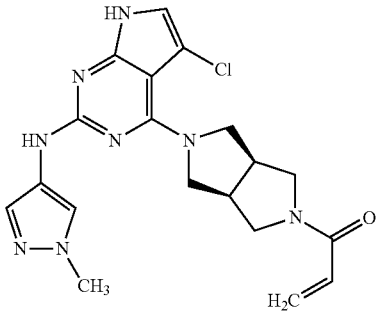<br>1-[(3aR,6aS)-5-{5-chloro-2-[(1-methyl-1H-pyrazol-4-yl)amino]-7H-pyrrolo[2,3-d] pyrimidin-4-yl}hexahydropyrrolo[3,4-c]pyrrol-2(1H)-yl]prop-2-en-1-one | 413.1/ 414.1 | ¹H NMR (400 MHz, DMSO-d6) δ ppm 8.54 (s, 1H), 7.79 (s, 1H), 7.48 (s, 1H), 7.00 (s, 1H), 6.49-6.69 (m, 1H), 5.99-6.25 (m, 1H), 5.55-5.73 (m, 1H), 4.03 (d, J = 3.02 Hz, 2H), 3.83-3.91 (m, 1H), 3.78 (s, 3H), 3.68 (m, 3H), 3.48-3.55 (m, 1H), 3.34-3.40 (m, 1H), 3.07-3.15 (m, 1H), 2.96-3.03 (m, 1H) |
| 72 (Scheme F) | 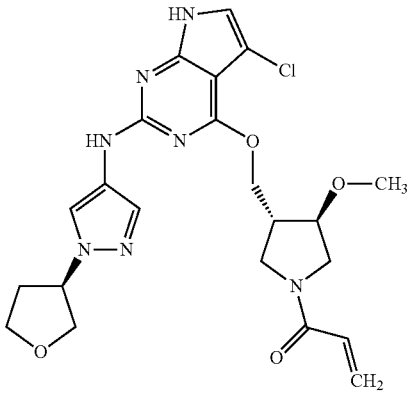<br>1-[(3R,4R)-3-({[5-chloro-2-({1-[(3R)-tetrahydrofuran-3-yl]-1H-pyrazol-4-yl}amino)-7H-pyrrolo[2,3-d]pyrimidin-4-yl]oxy}methyl)-4-methoxypyrrolidin-1-yl]prop-2-en-1-one | 489.9/ 487.9 | ¹H NMR (600 MHz, DMSO-17 mm) δ ppm 11.39-11.58 (m, 1H) 9.10 (d, J = 1.02 Hz, 1H) 7.84-8.09 (m, 1H) 7.44-7.59 (m, 1H) 7.03 (d, J = 2.29 Hz, 1H) 6.48-6.66 (m, 1H) 6.05-6.18 (m, 1H) 5.59-5.75 (m, 1H) 4.88-5.00 (m, 1H) 4.37-4.47 (m, 2H) 3.65-4.07 (m, 9H) 3.28 (d, J = 6.10 Hz, 3H) 2.68-2.89 (m, 1H) 2.30-2.41 (m, 1H) 2.11-2.24 (m, 1H) |
| 73 (SchemeH) | 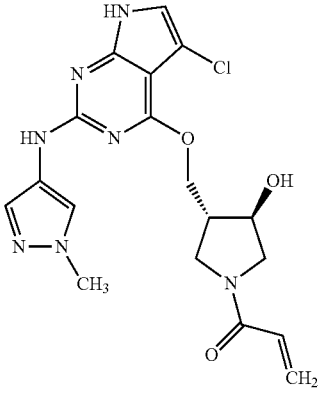<br>1-{(3R,4R)-3-[({5-chloro-2-[(1-methyl-1H-pyrazol-4-yl)amino]-7H-pyrrolo[2,3-d]pyrimidin-4-yl}oxy)methyl]-4-hydroxypyrrolidin-1-yl}prop-2-en-1-one | 418.1 | ¹H NMR (600 MHz, DMSO-17 mm) δ ppm 9.07 (s, 1H) 7.86 (br. s., 1H) 7.50 (s, 1H) 7.04 (d, J = 1.11 Hz, 1H) 6.56 (td, J = 17.21, 10.37 Hz, 1H) 6.12 (dd, J = 16.72, 2.35 Hz, 1H) 5.66 (dt, J = 10.30, 2.73 Hz, 1H) 4.50 (br. s., 1H) 4.39 (br. s., 1H) 4.28 (d, J = 4.70 Hz, 1H) 3.85-3.97 (m, 1H) 3.79 (s, 3H) 3.64-3.71 (m, 1H) 3.59 (dd, J = 10.64, 5.39 Hz, 1H) 3.21-3.29 (m, 2H) 2.55-2.69 (m, 1H) |

TABLE 1-continued

| Example No. (Scheme) | Structure and Compound Name | LRMS m/z | ¹H NMR |
|---|---|---|---|
| 74 (Scheme F) | 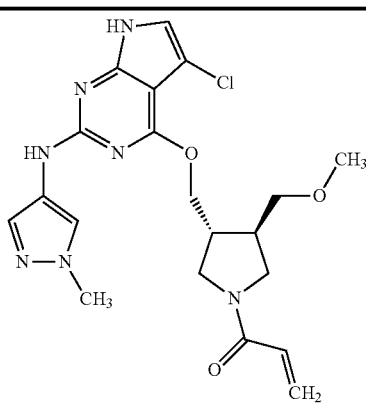<br>1-[(3R,4R)-3-[({5-chloro-2-[(1-methyl-1H-pyrazol-4-yl)amino]-7H-pyrrolo[2,3-d]pyrimidin-4-yl}oxy)methyl]-4-(methoxymethyl)pyrrolidin-1-yl]prop-2-en-1-one | 444.3/ 446.2 | ¹H NMR (400 MHz, DMSO-d6) δ ppm 11.50 (br. s., 1H) 9.06 (s, 1H) 7.85 (s, 1H) 7.52 (s, 1H) 7.05 (d, J = 1.76 Hz, 1H) 6.42-6.74 (m, 1H) 6.12 (dt, J = 16.81, 1.79 Hz, 1H) 5.49-5.76 (m, 1H) 4.51-4.60 (m, 1H) 4.47 (d, J = 5.29 Hz, 1H) 3.88 (d, J = 7.55 Hz, 1H) 3.80 (m, 4H) 3.48-3.60 (m, 1H) 3.35-3.43 (m, 1H) 3.28-3.34 (m, 4H) 3.17 (d, J = 5.04 Hz, 1H) 2.56-2.65 (m, 1H) 2.35-2.46 (m, 1H) |
| 75 (Scheme F) | 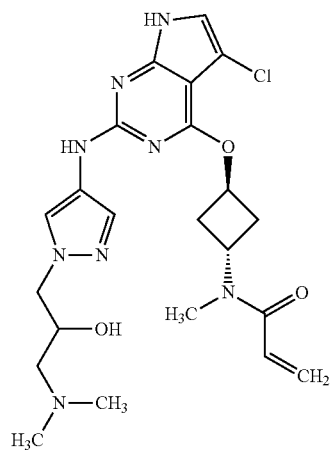<br>N-(trans-3-{[5-chloro-2-({1-[3-(dimethylamino)-2-hydroxypropyl]-1H-pyrazol-4-yl}amino)-7H-pyrrolo[2,3-d]pyrimidin-4-yl]oxy}cyclobutyl)-N-methylprop-2-enamide | 489.1 | Broad peaks only |

TABLE 1-continued

| Example No. (Scheme) | Structure and Compound Name | LRMS m/z | $^1$H NMR |
|---|---|---|---|
| 76 (Scheme B) | 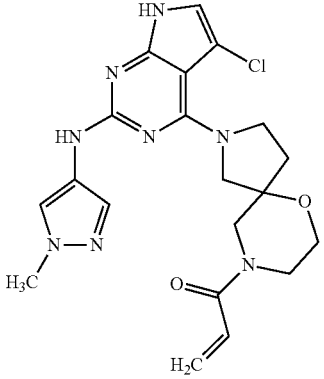<br>1-(2-{5-chloro-2-[(1-methyl-1H-pyrazol-4-yl)amino]-7H-pyrrolo[2,3-d]pyrimidin-4-yl}-6-oxa-2,9-diazaspiro[4.5]dec-9-yl)prop-2-en-1-one | 443.3/ 445.3 | $^1$H NMR (400 MHz, DMSO-d6) δ ppm 10.89-11.19 (m, 1H), 8.00-8.25 (m, 1H), 7.68 (s, 1H), 7.40 (s, 1H), 6.83 (d, J = 2.52 Hz, 1H), 6.55-6.69 (m, 1H), 6.04 (dd, J = 2.27, 16.87 Hz, 1H), 5.45-5.69 (m, 1H), 3.42-3.99 (m, 13H), 1.94 (s, 2H) |
| 77 (Scheme F) | 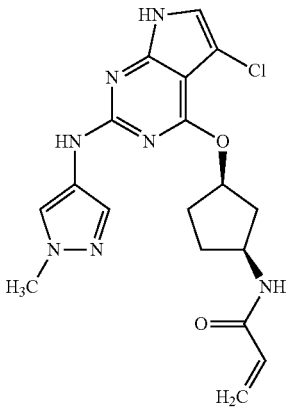<br>N-[(1S,3R)-3-({5-chloro-2-[(1-methyl-1H-pyrazol-4-yl)amino]-7H-pyrrolo[2,3-d]pyrimidin-4-yl}oxy)cyclopentyl]prop-2-enamide | 402.2 | $^1$H NMR (400 MHz, DMSO-d$_6$) δ ppm 11.43 (br. s., 1H) 8.99 (s, 1H) 8.12 (d, J = 7.07 Hz, 1H) 7.84 (s, 1H) 7.51 (s, 1H) 7.01 (d, J = 2.53 Hz, 1H) 6.13-6.28 (m, 1H) 5.99-6.11 (m, 1H) 5.52-5.63 (m, 1H) 5.48 (br. s., 1H) 4.11-4.24 (m, 1H) 3.80 (s, 3H) 2.57 (dt, J = 14.02, 7.14 Hz, 1H) 1.86-2.13 (m, 3H) 1.59-1.75 (m, 2H) |
| 78 (Scheme B) | 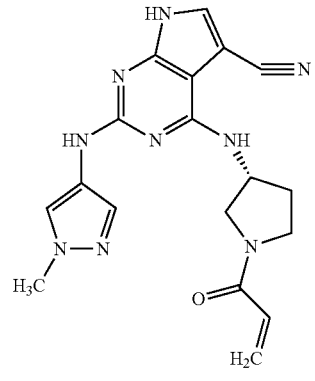<br>4-{[(3R)-1-acryloylpyrrolidin-3-yl]amino}-2-[(1-methyl-1H-pyrazol-4-yl)amino]-7H-pyrrolo[2,3-d]pyrimidine-5-carbonitrile | 378.20 | $^1$H NMR (400 MHz, DMSO-d6) δ ppm 8.86 (s, 1H), 8.35 (s, 1H), 7.82 (s, 1H), 7.78 (d, 1H), 7.42 (s, 1H), 6.56 (m, 1H), 6.17 (m, 2H), 5.67 (m, 1H), 4.67 (m, 1H), 4.05 (m, 0.5H), 3.87 (m, 0.5H), 3.77 (s, 3H), 3.50-3.70 (m, 2H), 2.00-2.40 (m, 2H). |

TABLE 1-continued

| Example No. (Scheme) | Structure and Compound Name | LRMS m/z | ¹H NMR |
|---|---|---|---|
| 79 (Scheme B) | 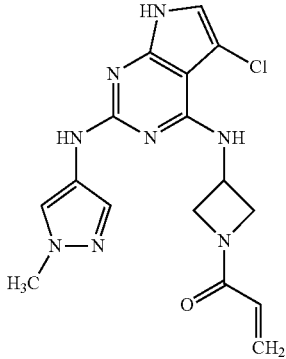<br>1-[3-({5-chloro-2-[(1-methyl-1H-pyrazol-4-yl)amino]-7H-pyrrolo[2,3-d]pyrimidin-4-yl}amino)azetidin-1-yl]prop-2-en-1-one | 395.2 (M + Na)⁺ | ¹H NMR (400 MHz, DMSO-d6) δ ppm 11.22 (brs, 1H), 8.61 (s, 1H), 7.81 (s, 1H), 7.47 (s, 1H), 6.91-6.90 (d, 1H), 6.81-6.80 (d, 1H), 6.37-6.30 (p, 1H), 6.13-6.09 (dd, 1H), 5.68-5.65 (dd, 1H), 4.95-4.82 (m, 1H), 4.58-4.52 (t, 1H), 4.26-4.22 (m, 2H), 3.99-3.90 (m, 1H), 3.78 (s, 3H) |
| 80 (Scheme B) | 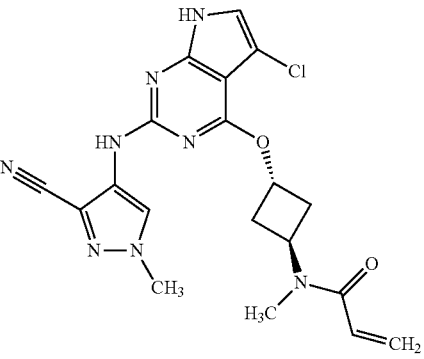<br>N-[trans-3-({5-chloro-2-[(3-cyano-1-methyl-1H-pyrazol-4-yl)amino]-7H-pyrrolo[2,3-d]pyrimidin-4-yl}oxy)cyclobutyl]-N-methylprop-2-enamide | 427.0/ 429.1 | ¹H NMR (600 MHz, DMSO) δ ppm 11.55-11.75 (m, 1H) 9.01-9.20 (m, 1H) 8.01-8.18 (m, 1H) 7.03-7.17 (m, 1H) 6.58-6.81 (m, 1H) 5.97-6.18 (m, 1H) 5.58-5.75 (m, 1H) 5.36-5.50 (m, 1H) 4.77-5.20 (m, 1H) 3.86-4.01 (m, 3H) 2.92-3.14 (m, 3H) 2.60-2.79 (m, 2H) 2.33-2.49 (m, 2H) |
| 81 (Scheme I) | 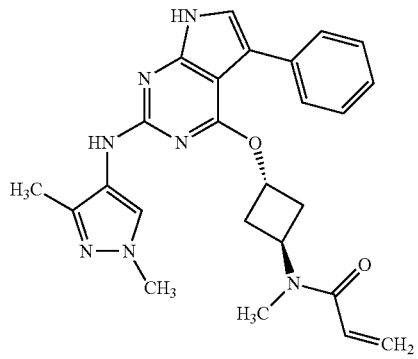<br>N-[trans-3-({2-[(1,3-dimethyl-1H-pyrazol-4-yl)amino]-5-(pyridin-2-yl)-7H-pyrrolo[2,3-d]pyrimidin-4-yl}oxy)cyclobutyl]-N-methylprop-2-enamide | 459.1 | ¹H NMR (400 MHz, DMSO-d6) δ ppm 11.38-11.69 (m, 1H) 8.44 (d, J = 4.04 Hz, 1H) 7.96-8.14 (m, 2H) 7.72 (s, 2H) 7.40 (s, 1H) 7.11 (ddd, J = 7.39, 4.86, 0.88 Hz, 1H) 6.48-6.78 (m, 1H) 5.84-6.10 (m, 1H) 5.49-5.66 (m, 1H) 5.33-5.51 (m, 1H) 4.65-5.25 (m, 1H) 3.66 (s, 3H) 2.98 (br. s., 3H) 2.58-2.71 (m, 2H) 2.17-2.40 (m, 2H) 2.03 (s, 3H) |

| Example No. (Scheme) | Structure and Compound Name | LRMS m/z | ¹H NMR |
|---|---|---|---|
| 82 (Scheme B) | 1-[(3S,4R)-3-({5-chloro-2-[(1-methyl-1H-pyrazol-4-yl)amino]-7H-pyrrolo[2,3-d]pyrimidin-4-yl}amino)-4-(1H-1,2,3-triazol-1-yl)pyrrolidin-1-yl]prop-2-en-1-one | 454.4 | ¹H NMR (400 MHz, DMSO-d6) δ ppm 11.29 (s, 1H), 8.82-8.81 (d, 1H), 8.11-8.08 (d, 1H), 7.86 (s, 1H), 7.79 (s, 1H), 7.50 (s, 1H), 6.89-6.88 (d, 1H), 6.70-6.66 (m, 1H), 6.25,-6.21 (d, 1H), 5.78-5.63 (m, 2H), 5.52-4.98 (m, 1H), 5.33-5.11 (m, 1H), 4.32-4.15 (m, 1H), 4.05-4.06 (d, 1H), 3.79-3.51 (m, 4H) |
| 83* (Scheme B) | 1-[(trans)-3-({5-chloro-2-[(1-methyl-1H-pyrazol-4-yl)amino]-7H-pyrrolo[2,3-d]pyrimidin-4-yl}amino)-4-fluoropyrrolidin-1-yl]prop-2-en-1-one | 405.9/ 406.9 | ¹H NMR (400 MHz, METHANOL-d₄) δ ppm 7.83-7.92 (m, 1H), 7.42-7.50 (m, 1H), 6.69 (s, 1H), 6.49-6.65 (m, 1H), 6.21-6.33 (m, 1H), 5.69-5.80 (m, 1H), 5.26-5.55 (m, 1H), 4.79-4.96 (m, 1H), 3.99-4.14 (m, 1H), 3.79-3.97 (m, 3H), 3.77 (s, 3H) |
| 84 (Scheme G-OBoc protected fused heterocycle used for scheme with global deprotection at penultimate step) | 1-[(3aS,6aS)-5-{5-chloro-2-[(1-methyl-1H-pyrazol-4-yl)amino]-7H-pyrrolo[2,3-d]pyrimidin-4-yl}-3a-hydroxyhexahydropyrrolo[3,4-c]pyrrol-2(1H)-yl]prop-2-en-1-one | 429.1 | ¹H NMR (400 MHz, DMSO-d₆) δ ppm 11.32 (br. s., 1H) 8.56 (s, 1H) 7.78 (s, 1H) 7.48 (s, 1H) 7.00 (d, J = 2.53 Hz, 1H) 6.56 (dt, J = 16.74, 10.71 Hz, 1H) 6.13 (dt, J = 16.74, 1.99 Hz, 1H) 5.71-5.84 (m, 1H) 5.57-5.69 (m, 1H) 4.06-4.18 (m, 1H) 3.84-4.03 (m, 3H) 3.79-3.83 (m, 1H) 3.77 (s, 3H) 3.71-3.76 (m, 1H) 3.59-3.70 (m, 2H) 3.48-3.55 (m, 1H) |

| Example No. (Scheme) | Structure and Compound Name | LRMS m/z | ¹H NMR |
|---|---|---|---|
| 85 (Scheme B) | 1-[(3R,4S)-3-({5-chloro-2-[(1-methyl-1H-pyrazol-4-yl)amino]-7H-pyrrolo[2,3-d]pyrimidin-4-yl}amino)-4-(difluoromethyl)pyrrolidin-1-yl]prop-2-en-1-one | 437.0 | ¹H NMR (400 MHz, CDCl3) δ ppm 8.73-8.60 (br, 1H), 7.73 (s, 1H), 7.50 (s, 1H), 6.60 (s, 1H), 6.50-6.40 (m, 3H), 5.80-5.70 (m, 2H), 4.90-4.70 (m, 1H), 4.25-3.95 (m, 2H), 3.87 (s, 3H), 3.87-3.50 (m, 2H), 3.00-2.57 (m, 1H) |
| 86 (Scheme I) | N-methyl-N-[trans-3-({5-(1-methyl-1H-pyrazol-3-yl)-2-[(1-methyl-1H-pyrazol-4-yl)amino]-7H-pyrrolo[2,3-d]pyrimidin-4-yl}oxy)cyclobutyl]prop-2-enamide | 448.1 | ¹H NMR (700 MHz, DMSO) δ ppm 11.38 (br. s., 1H) 8.87 (s, 1H) 7.87 (br. s., 1H) 7.68 (d, J = 1.98 Hz, 1H) 7.52 (s, 1H) 7.19 (s, 1H) 6.77 (s, 1H) 6.67 (br. s., 1H) 5.93-6.19 (m, 1H) 5.68 (br. s., 1H) 5.51 (br. s., 1H) 4.36 (br. s., 1H) 3.86 (s, 3H) 3.82 (s, 3H) 2.76 (br. s., 2H) 2.55 (s, 3H) 2.35-2.46 (m, 2H) |
| 87 (Scheme B) | 1-[(3R,4S)-3-({5-chloro-2-[(1-methyl-1H-pyrazol-4-yl)amino]-7H-pyrrolo[2,3-d]pyrimidin-4-yl}amino)-4-(trifluoromethyl)pyrrolidin-1-yl]prop-2-en-1-one | 454.1 | ¹H NMR (400 MHz, CDCl₃) δ ppm 8.84 (s, 1H), 7.73 (s, 1H), 7.50 (s, 1H), 6.56-6.54 (d, 1H), 6.47-6.41 (m, 3H), 5.84-5.74 (m, 2H), 4.96-4.88 (m, 1H), 4.27-4.23 (t, 1H), 4.13-4.07 (m, 1H), 4.00-3.77 (m, 4H), 3.71-3.64 (m, 1H), 3.22-3.18 (m, 1H) |

TABLE 1-continued

| Example No. (Scheme) | Structure and Compound Name | LRMS m/z | $^1$H NMR |
|---|---|---|---|
| 88* (Scheme G) | 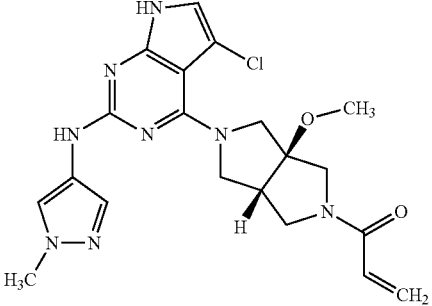<br>1-[5-{5-chloro-2-[(1-methyl-1H-pyrazol-4-yl)amino]-7H-pyrrolo[2,3-d]pyrimidin-4-yl}-3a-methoxyhexahydropyrrolo[3,4-c]pyrrol-2(1H)-yl]prop-2-en-1-one | 443.9 | $^1$H NMR (700 MHz, DMSO-17 mm) δ ppm 8.57 (s, 1H) 7.80 (br. s., 1H) 7.75 (d, J = 7.74 Hz, 1H) 7.46 (s, 1H) 7.34-7.42 (m, 1H) 6.99 (s, 1H) 6.56 (dt, J = 16.78, 10.97 Hz, 1H) 6.14 (d, J = 16.35 Hz, 1H) 5.65-5.76 (m, 1H) 3.98-4.11 (m, 2H) 3.87-3.95 (m, 1H) 3.29 (d, J = 6.45 Hz, 3H) 2.82-2.93 (m, 2H) 1.45 (d, J = 6.88 Hz, 2H) 1.20 (s, 3H) 1.13 (t, J = 7.10 Hz, 1H) |
| 89 (Scheme I) | 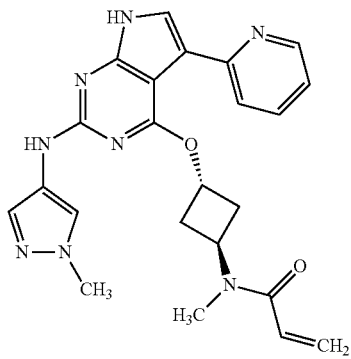<br>N-methyl-N-[trans-3-({2-[(1-methyl-1H-pyrazol-4-yl)amino]-5-(pyridin-2-yl)-7H-pyrrolo[2,3-d]pyrimidin-4-yl}oxy)cyclobutyl]prop-2-enamide | 445.1 | $^1$H NMR (700 MHz, DMSO) δ ppm 11.68 (br. s., 1H) 8.96 (s, 1H) 8.55 (d, J = 3.96 Hz, 1H) 8.15 (d, J = 7.70 Hz, 1H) 7.75-7.94 (m, 2H) 7.54 (d, J = 8.36 Hz, 2H) 7.21 (dd, J = 6.93, 5.17 Hz, 1H) 6.57-6.92 (m, 1H) 5.92-6.22 (m, 1H) 5.61-5.82 (m, 1H) 5.54 (br. s., 1H) 5.25 (br. s., 1H) 3.83 (s, 3H) 2.97-3.15 (m, 3H) 2.76 (br. s., 2H) 2.34-2.49 (m, 2H) |
| 90 (Scheme F) | 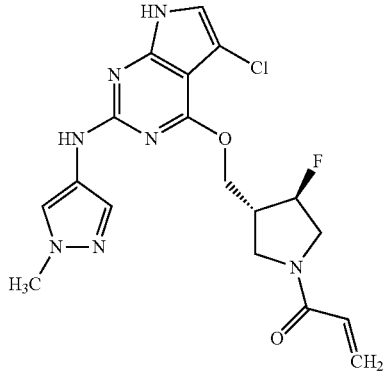<br>1-{(3R,4R)-3-[({5-chloro-2-[(1-methyl-1H-pyrazol-4-yl)amino]-7H-pyrrolo[2,3-d]pyrimidin-4-yl}oxy)methyl]-4-fluoropyrrolidin-1-yl}prop-2-en-1-one | 419.9 | $^1$H NMR (400 MHz, DMSO-d6) δ ppm 11.50 (br. s., 1H) 9.08 (s, 1H) 7.85 (s, 1H) 7.51 (s, 1H) 6.98-7.08 (m, 1H) 6.59 (ddd, J = 18.13, 16.84, 10.27 Hz, 1H) 6.15 (dd, J = 16.81, 2.38 Hz, 1H) 5.64-5.73 (m, 1H) 5.20-5.54 (m, 1H) 4.37-4.57 (m, 2H) 3.82-4.17 (m, 2H) 3.79 (s, 3H) 3.56-3.77 (m, 2H) 2.83-3.17 (m, 1H) |

TABLE 1-continued

| Example No. (Scheme) | Structure and Compound Name | LRMS m/z | ¹H NMR |
|---|---|---|---|
| 91 (Scheme F) | 1-{(3S,4S)-3-[({5-chloro-2-[(1-methyl-1H-pyrazol-4-yl)amino]-7H-pyrrolo[2,3-d]pyrimidin-4-yl}oxy)methyl]-4-fluoropyrrolidin-1-yl}prop-2-en-1-one | 419.9 | ¹H NMR (400 MHz, DMSO-d6) δ ppm 11.50 (br. s., 1H) 9.08 (s, 1H) 7.85 (s, 1H) 7.51 (s, 1H) 6.95-7.13 (m, 1H) 6.59 (ddd, J = 18.16, 16.81, 10.27 Hz, 1H) 6.15 (dd, J = 16.75, 2.32 Hz, 1H) 5.69 (dt, J = 10.24, 3.01 Hz, 1H) 5.22-5.55 (m, 1H) 4.35-4.59 (m, 2H) 3.83-4.19 (m, 2H) 3.79 (s, 3H) 3.57-3.77 (m, 2H) 2.82-3.17 (m, 1H). |
| 92 (Scheme F- N1-Boc pyrazole used for Buchwald step) | N-methyl-N-[trans-3-({2-[(1-methyl-1H-pyrazol-4-yl)amino]-5-(pyridin-2-yl)-7H-pyrrolo[2,3-d]pyrimidin-4-yl}oxy)cyclobutyl]prop-2-enamide | 387.1/ 389.1 | ¹H NMR (400 MHz, DMSO-d6) δ ppm 8.97 (s, 1H) 7.74 (br. s., 2H) 7.05 (s, 1H) 6.73 (br. s., 1H) 6.09 (br. s., 1H) 5.66 (br. s., 1H) 5.43 (br. s., 1H) 4.35 (br. s., 2H) 3.04 (br. s., 3H) 2.75 (br. s., 2H) 2.65-2.70 (m, 1H) 2.31-2.37 (m, 1H) |
| 93 (Scheme B) | {4-[(4-{[(3R,4R)-1-acryloyl-4-methoxypyrrolidin-3-yl]methoxy}-5-chloro-7H-pyrrolo[2,3-d]pyrimidin-2-yl)amino]-1H-pyrazol-1-yl]acetonitrile | 457.1 | ¹H NMR (400 MHz, DMSO) δ ppm 11.58 (brs, 1H), 9.27 (s, 1H), 8.03 (s, 1H), 7.71-7.70 (d, 1H), 7.10 (s, 1H), 6.63-6.56 (m, 1H), 6.17-6.12 (m, 1H), 5.70-5.67 (m, 1H), 5.47 (s, 2H), 4.47-4.45 (d, 2H), 4.05-3.94 (m, 2H), 3.85-3.48 (m, 3H), 3.32-3.30 (d, 3H), 2.88-2.76 (m, 1H) |

TABLE 1-continued

| Example No. (Scheme) | Structure and Compound Name | LRMS m/z | ¹H NMR |
|---|---|---|---|
| 94 (Scheme G) | 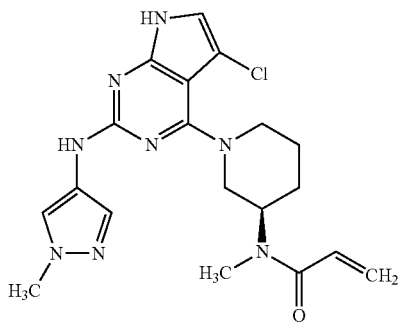<br>N-[(3R)-1-{5-chloro-2-[(1-methyl-1H-pyrazol-4-yl)amino]-7H-pyrrolo[2,3-d]pyrimidin-4-yl}piperidin-3-yl]-N-methylprop-2-enamide | 414.2/ 416.2 | ¹H NMR (700 MHz, DMSO) δ ppm 11.39 (br. s., 1H) 8.74 (br. s., 1H) 7.82 (br. s., 1H) 7.47 (br. s., 1H) 7.04 (d, J = 6.38 Hz, 1H) 6.76 (dd, J = 16.29, 10.56 Hz, 1H) 6.08 (dd, J = 53.48, 16.51 Hz, 1H) 5.64 (dd, J = 68.11, 10.45 Hz, 1H) 4.14 (d, J = 12.54 Hz, 1H) 3.94-4.09 (m, 1H) 3.76 (s, 3H) 2.97-3.14 (m, 3H) 2.86 (s, 3H) 1.70-1.87 (m, 4H) |
| 95 (Scheme J) | 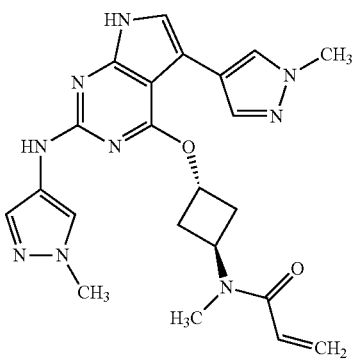<br>N-methyl-N-[trans-3-({5-(1-methyl-1H-pyrazol-4-yl)-2-[(1-methyl-1H-pyrazol-4-yl)amino]-7H-pyrrolo[2,3-d]pyrimidin-4-yl}oxy)cyclobutyl]prop-2-enamide | 448.2/ 449.2 | ¹H NMR (400 MHz, DMSO-d6): broad peaks only |
| 96 (Scheme B) | 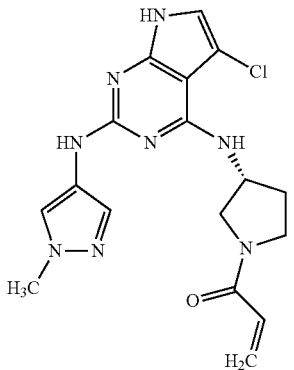<br>1-[(3R)-3-({5-chloro-2-[(1-methyl-1H-pyrazol-4-yl)amino]-7H-pyrrolo[2,3-d]pyrimidin-4-yl}amino)pyrrolidin-1-yl]prop-2-en-1-one | 387.1/ 389.1 | ¹H NMR (400 MHz, DMSO-d6) δ ppm = 11.23 (br. s., 1H), 8.69 (s, 1H), 7.82 (s, 1H), 7.48 (s, 1H), 6.94-6.87 (m, 1H), 6.69-6.50 (m, 1H), 6.20-6.00 (m, 2H), 5.73-5.61 (m, 1H), 4.82-4.60 (m, 1H), 4.07-3.82 (m, 1H), 3.81-3.72 (m, 3H), 3.71-3.51 (m, 2H), 3.50-3.36 (m, 1H), 2.39-1.98 (m, 2H) |

| Example No. (Scheme) | Structure and Compound Name | LRMS m/z | ¹H NMR |
|---|---|---|---|
| 97 (Scheme B) | 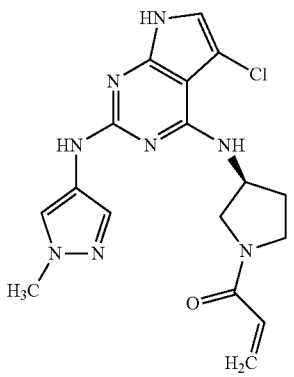<br>1-[(3S)-3-({5-chloro-2-[(1-methyl-1H-pyrazol-4-yl)amino]-7H-pyrrolo[2,3-d]pyrimidin-4-yl}amino)pyrrolidin-1-yl]prop-2-en-1-one | 387.1 | ¹H NMR (400 MHz, DMSO-d6) δ ppm 8.68 (s, 1H), 8.14 (s 1H), 7.81 (s 1H), 7.47 (s 1H), 6.90 (s 1H), 6.53-6.62 (m, 1H), 6.03-6.16 (m, 2H), 5.64-5.70 (m, 1H), 3.76 (s, 1H), 3.51-3.52 (m, 4H), 3.34 (m, 2H), 2.50 (s, 1H), 2.32 (m, 1H) |
| 98 (Scheme B) | 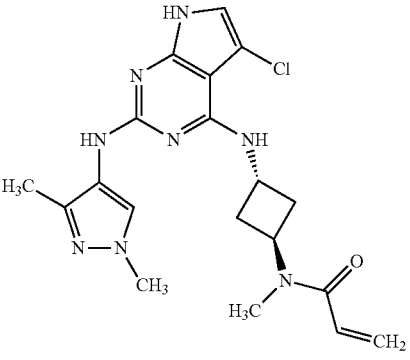<br>N-[trans-3-({5-chloro-2-[(1,3-dimethyl-1H-pyrazol-4-yl)amino]-7H-pyrrolo[2,3-d]pyrimidin-4-yl}amino)cyclobutyl]-N-methylprop-2-enamide | 415.1 | ¹H NMR (400 MHz, DMSO-d6) δ ppm 11.16 (br. s., 1H) 7.77 (s, 2H) 6.88 (s, 1H) 6.74 (dd, J = 16.63, 10.52 Hz, 1H) 6.30 (d, J = 6.11 Hz, 1H) 6.07 (d, J = 15.89 Hz, 1H) 5.66 (d, J = 10.03 Hz, 1H) 4.81-5.19 (m, 1H) 4.59 (br. s., 1H) 3.71 (s, 3H) 2.93-3.15 (m, 3H) 2.62 (br. s., 2H) 2.39 (br. s., 2H) 2.08 (s, 3H) |
| 99 (Scheme B) | 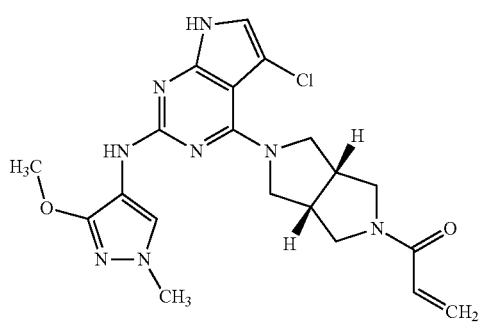<br>1-[(3aR,6aS)-5-{5-chloro-2-[(3-methoxy-1-methyl-1H-pyrazol-4-yl)amino]-7H-pyrrolo[2,3-d]pyrimidin-4-yl}hexahydropyrrolo[3,4-c]pyrrol-2(1H)-yl]prop-2-en-1-one | 443.1 | ¹H NMR (400 MHz, DMSO-d₆) δ ppm 11.36 (br. s., 1H) 7.62 (s, 1H) 7.22 (s, 1H) 6.95 (d, J = 2.57 Hz, 1H) 6.57 (dd, J = 16.81, 10.33 Hz, 1H) 6.12 (dd, J = 16.81, 2.38 Hz, 1H) 5.65 (dd, J = 10.33, 2.38 Hz, 1H) 3.92-4.07 (m, 2 H) 3.84 (dd, J = 10.70, 7.64 Hz, 1H) 3.76 (s, 3H) 3.63-3.66 (m, 3H) 3.57-3.71 (m, 3H) 3.49 (dd, J = 10.70, 4.95 Hz, 1H) 3.34 (d, J = 4.65 Hz, 1H) 3.02-3.13 (m, 1H) 2.90-3.01 (m, 1H) |

TABLE 1-continued

| Example No. (Scheme) | Structure and Compound Name | LRMS m/z | ¹H NMR |
|---|---|---|---|
| 100* (Scheme F) | 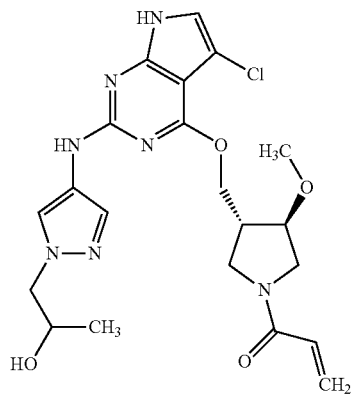<br>1-[(3R,4R)-3-{[(5-chloro-2-{[1-(2-hydroxypropyl)-1H-pyrazol-4-yl]amino}-7H-pyrrolo[2,3-d]pyrimidin-4-yl)oxy]methyl}-4-methoxypyrrolidin-1-yl]prop-2-en-1-one | 475.9 | ¹H NMR (600 MHz, DMSO-17 mm) δ ppm 11.48 (br. s., 1H) 9.07 (br. s., 1H) 7.90 (br. s., 1H) 7.52 (br. s., 1H) 7.01 (br. s., 1H) 6.56 (dd, J = 16.86, 10.23 Hz, 1H) 6.12 (d, J = 16.86 Hz, 1H) 5.67 (d, J = 10.50 Hz, 1H) 4.85-5.18 (m, 1H) 4.42 (br. s., 2H) 4.01 (br. s., 1H) 3.89-3.97 (m, 5H) 3.41-3.52 (m, 1H) 3.28 (d, J = 6.91 Hz, 3H) 2.83 (br. s., 1H) 2.73 (br. s., 1H) 1.01 (d, J = 5.25 Hz, 3H) |
| 101 (Scheme F-TBS protected hydroxyl used in Buchwald step with global deprotection at penultimate stage) | 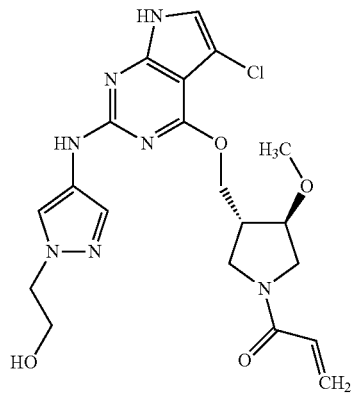<br>1-[(3R,4R)-3-{[(5-chloro-2-{[1-(2-hydroxyethyl)-1H-pyrazol-4-yl]amino}-7H-pyrrolo[2,3-d]pyrimidin-4-yl)oxy]methyl}-4-methoxypyrrolidin-1-yl]prop-2-en-1-one | 462.1 | ¹H NMR (400 MHz, DMSO-d₆) δ ppm 11.50 (br. s., 1H) 9.06 (s, 1H) 7.91 (s, 1H) 7.53 (d, J = 2.27 Hz, 1H) 7.04 (d, J = 2.27 Hz, 1H) 6.51-6.65 (m, 1H) 6.13 (dd, J = 16.80, 2.40 Hz, 1H) 5.67 (dt, J = 10.23, 2.46 Hz, 1H) 4.88 (t, J = 5.05 Hz, 1H) 4.43 (d, J = 6.32 Hz, 2H) 4.05-4.12 (m, 2H) 4.00-4.05 (m, 1H) 3.90-3.99 (m, 1H) 3.81 (dd, J = 10.61, 7.58 Hz, 0.5H) 3.67-3.76 (m, 2.5H) 3.56-3.66 (m, 1H) 3.44-3.53 (m, 1H) 3.30 (d, J = 4.55 Hz, 3H) 2.84 (m, 0.5H) 2.75 (m, 0.5H) |

| Example No. (Scheme) | Structure and Compound Name | LRMS m/z | ¹H NMR |
|---|---|---|---|
| 102 (Scheme F) | 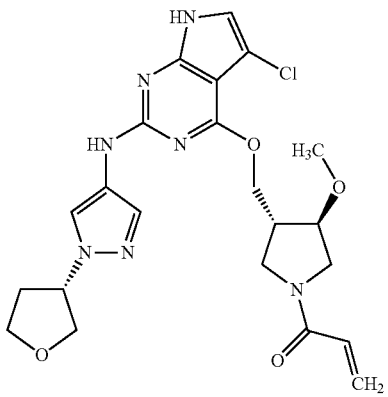<br>1-[(3R,4R)-3-({[5-chloro-2-({1-[(3S)-tetrahydrofuran-3-yl]-1H-pyrazol-4-yl}amino)-7H-pyrrolo[2,3-d]pyrimidin-4-yl]oxy}methyl)-4-methoxypyrrolidin-1-yl]prop-2-en-1-one | 489.9/ 488.9/ 487.9 | ¹H NMR (600 MHz, DMSO) δ ppm 11.45-11.56 (m, 1H) 9.04-9.15 (m, 1H) 7.90-8.01 (m, 1H) 7.46-7.58 (m, 1H) 7.00-7.09 (m, 1H) 6.48-6.63 (m, 1H) 6.03-6.17 (m, 1H) 5.62-5.74 (m, 1H) 4.90-5.00 (m, 1H) 4.37-4.45 (m, 2H) 3.76-4.06 (m, 9H) 3.25-3.31 (m, 3H) 2.67-2.90 (m, 1H) 2.30-2.41 (m, 1H) 2.11-2.23 (m, 1H) |
| 103 (Scheme F) | 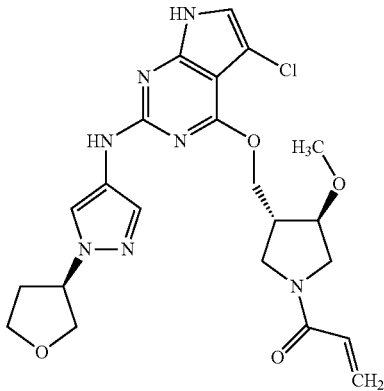<br>1-[(3R,4R)-3-({[5-chloro-2-({1-[(3R)-tetrahydrofuran-3-yl]-1H-pyrazol-4-yl}amino)-7H-pyrrolo[2,3-d]pyrimidin-4-yl]oxy}methyl)-4-methoxypyrrolidin-1-yl]prop-2-en-1-one | 489.9/ 488.9/ 487.9 | ¹H NMR (600 MHz, DMSO) δ ppm 11.39-11.58 (m, 1H) 9.10 (d, J = 1.02 Hz, 1H) 7.84-8.09 (m, 1H) 7.44-7.59 (m, 1H) 7.03 (d, J = 2.29 Hz, 1H) 6.48-6.66 (m, 1H) 6.05-6.18 (m, 1H) 5.59-5.75 (m, 1H) 4.88-5.00 (m, 1H) 4.37-4.47 (m, 2H) 3.65-4.07 (m, 9H) 3.28 (d, J = 6.10 Hz, 3H) 2.68-2.89 (m, 1H) 2.30-2.41 (m, 1H) 2.11-2.24 (m, 1H) |

TABLE 1-continued

| Example No. (Scheme) | Structure and Compound Name | LRMS m/z | $^1$H NMR |
|---|---|---|---|
| 104 (Scheme A) | 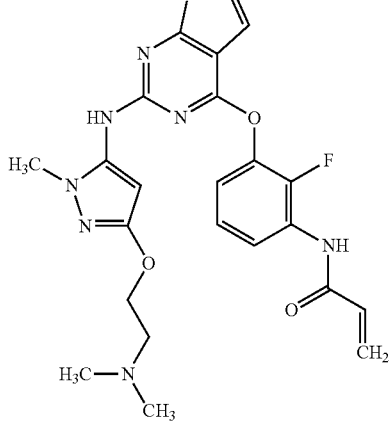<br>N-(3-{[2-({3-[2-(dimethylamino)ethoxy]-1-methyl-1H-pyrazol-5-yl}amino)-7H-pyrrolo[2,3-d]pyrimidin-4-yl]oxy}-2-fluorophenyl)prop-2-enamide | 481.0 | $^1$H NMR (400 MHz, Methanol-d4) δ ppm 8.01 (m, 1H), 7.23-7.21 (m, 1H), 7.15-7.14 (m, 1H), 7.06-7.05 (m, 1H), 6.54-6.38 (m, 3H), 5.82-5.80 (dd, 1H), 5.59 (s, 1H), 4.08-4.06 (t, 2H), 3.50 (s, 3H), 2.74-2.72 (t, 2H), 2.34 (s, 6H) |
| 105 (Scheme F) | 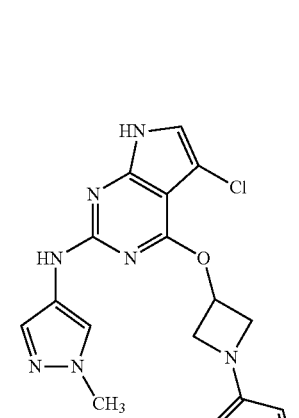<br>1-[3-({5-chloro-2-[(1-methyl-1H-pyrazol-4-yl)amino]-7H-pyrrolo[2,3-d]pyrimidin-4-yl}oxy)azetidin-1-yl]prop-2-en-1-one | 374.0 | $^1$H NMR (400 MHz, DMSO-d6) δ ppm 11.57 (br. s., 1H), 9.04 (s, 1H), 7.85 (br. s., 1H), 7.52 (s, 1H), 7.09 (d, J = 2.53 Hz, 1H), 6.37 (dd, J = 17.18, 10.36 Hz, 1H), 6.14 (dd, J = 16.93, 2.02 Hz, 1H), 5.70 (dd, J = 10.36, 2.27 Hz, 1H), 5.53 (br. s., 1H), 4.69 (dd, J = 9.47, 7.20 Hz, 1H), 4.44 (dd, J = 11.37, 6.82 Hz, 1H), 4.30 (dd, J = 9.98, 3.66 Hz, 1H), 3.97 (dd, J = 11.49, 3.66 Hz, 1H), 3.82 (s, 3H) |

TABLE 1-continued

| Example No. (Scheme) | Structure and Compound Name | LRMS m/z | ¹H NMR |
|---|---|---|---|
| 106 (Scheme A) | N-(2-fluoro-3-{[2-({1-[(3S)-1-methylpyrrolidin-3-yl]-1H-pyrazol-4-yl}amino)-7H-pyrrolo[2,3-d]pyrimidin-4-yl]oxy}phenyl)prop-2-enamide | 463.2 | ¹H NMR (400 MHz, CDCl3): δ ppm 8.62 (m, 1H), 8.31 (m, 1H), 7.60-7.41 (m, 2H). 7.25 (s, 1H), 7.19-7.14 (m, 1H), 7.03-6.99 (t, 1H), 6.85-6.54 (m, 1H), 6.50 (s, 1H), 6.43-6.39 (m, 2H), 6.25-6.18 (m, 1H), 5.78-5.75 (d, 1H), 4.61 (m, 1H), 2.82-2.71 (m, 3H), 2.50-2.44 (m, 1H), 2.33-2.20 (s + m, 3 + 1H), 2.12-2.03 (m, 1H) |
| 107 (Scheme A) | N-(3-fluoro-5-{[2-({1-[(3R)-1-methylpyrrolidin-3-yl]-1H-pyrazol-4-yl}amino)-7H-pyrrolo[2,3-d]pyrimidin-4-yl]oxy}phenyl)prop-2-enamide | 463.2 | ¹H NMR (400 MHz, DMSO-d6): δ ppm 11.49 (s, 1H), 10.53 (s, 1H), 9.03 (s, 1H), 7.65-7.62 (d, 1H), 7.54-7.25 (m, 2H), 7.09-7.08 (d, 1H), 7.01-6.98 (d, 1H), 6.44-6.27 (m, 3H), 5.83-5.80 (m, 1H), 4.62-4.53 (m, 2H), 2.79-2.76 (m, 1H), 2.79-2.76 (m, 1H), 2.51 (m, 1H), 2.25-2.03 (m, 4H), 1.76 (s, 1H) |
| 108 (Scheme F) | N-[trans-3-({5-chloro-2-[(1-methyl-1H-pyrazol-4-yl)amino]-7H-pyrrolo[2,3-d]pyrimidin-4-yl}oxy)cyclobutyl]-N-methylprop-2-enamide | 402.1/ 404.0 | ¹H NMR (400 MHz, DMSO-d6) δ ppm 11.48 (br. s., 1H) 8.99 (s, 1H) 7.81-7.89 (m, 1H) 7.50 (s, 1H) 7.05 (d, J = 2.45 Hz, 1H) 6.73 (br. s., 1H) 6.07 (br. s., 1H) 5.67 (d, J = 8.56 Hz, 1H) 5.44 (br. s., 1H) 3.80(s, 3H) 2.94-3.19 (m, 3H) 2.66-2.85 (m, 2H) 2.35-2.47 (m, 3H) |

TABLE 1-continued

| Example No. (Scheme) | Structure and Compound Name | LRMS m/z | ¹H NMR |
|---|---|---|---|
| 109 (Scheme J) | N-[cis-3-({2-[(1-methyl-1H-pyrazol-4-yl)amino]-5-(pyridin-3-yl)-7H-pyrrolo[2,3-d]pyrimidin-4-yl}oxy)cyclobutyl]prop-2-enamide | 431.1 | ¹H NMR (400 MHz, DMSO-d6) δ ppm 11.57 (s, 1H) 8.88 (s, 1H) 8.83 (d, J = 2.01 Hz, 1H) 8.31-8.41 (m, 2H) 8.00 (dt, J = 8.06, 1.89 Hz, 1H) 7.81 (s, 1H) 7.47 (s, 1H) 7.32 (dd, J = 7.81, 4.78 Hz, 1H) 7.27(s, 1H) 5.94-6.16 (m, 2H) 5.44-5.60 (m, 1H) 5.04 (t, J = 7.30 Hz, 1H) 4.02 (sxt, J = 8.01 Hz, 1H) 3.75 (s, 3H) 2.81 (m, J = 9.41, 6.94, 6.94, 2.90 Hz, 2H) 1.89-2.06 (m, 2H) |
| 110 (Scheme F) | 1-[(3R,4R)-3-[({5-chloro-2-[(1-methyl-1H-pyrazol-4-yl)amino]-7H-pyrrolo[2,3-d]pyrimidin-4-yl}oxy)methyl]-4-(trifluoromethyl)pyrrolidin-1-yl]prop-2-en-1-one | 469.1/ 471.1 | ¹H NMR (400 MHz, DMSO-d6) δ ppm 11.44 (br. s., 1H) 9.07 (s, 1H) 7.85 (s, 1H) 7.51 (s, 1H) 7.05 (s, 1H) 6.48-6.73 (m, 1H) 6.08-6.21 (m, 1H) 5.61-5.76 (m, 1H) 4.39-4.64 (m, 2H) 3.73-4.14 (m, 6H) 3.59-3.72 (m, 1H) 3.50 (dd, J = 12.63, 5.56 Hz, 1H) 2.89-3.12 (m, 1H) |
| 111 (Scheme F) | 1-{(3R,4R)-3-[({5-chloro-2-[(1-methyl-1H-pyrazol-3-yl)amino]-7H-pyrrolo[2,3-d]pyrimidin-4-yl}oxy)methyl]-4-methoxypyrrolidin-1-yl}prop-2-en-1-one | 431.9/ 434.9 | ¹H NMR (METHANOL-d4, 400 MHz) δ ppm 7.47 (br. s., 1H), 6.90 (s, 1H), 6.70-6.79 (m, 1H), 6.63 (ddd, J = 16.7, 10.5, 3.3 Hz, 1H), 6.29 (dd, J = 16.8, 6.7 Hz, 1H), 5.69-5.83 (m, 1H), 4.13-4.34 (m, 1H), 4.01-4.13 (m, 1H), 3.84-3.98 (m, 1H), 3.81 (s, 3H), 3.58-3.78 (m, 4H), 3.43 (d, J = 2.5 Hz, 3H), 2.74-3.04 (m, 1H) |

TABLE 1-continued

| Example No. (Scheme) | Structure and Compound Name | LRMS m/z | ¹H NMR |
|---|---|---|---|
| 112* (Scheme B) | 1-(2-{5-chloro-2-[(1-methyl-1H-pyrazol-4-yl)amino]-7H-pyrrolo[2,3-d]pyrimidin-4-yl}-6-oxa-2,9-diazaspiro[4.5]dec-9-yl)pro-2-en-1-one | 443.1 | ¹H NMR (400 MHz, DMSO-d6) δ ppm 11.22 (br. s., 1H), 8.47 (s, 1H), 7.71 (s, 1H), 7.38 (s, 1H), 6.90 (s, 1H), 6.53-6.82 (m, 1H), 6.07 (d, J = 16.93 Hz, 1H), 5.42-5.83 (m, 1H), 3.38-3.96 (m, 13H), 1.86-2.13 (m, 2H) |
| 113 (Scheme F-CBZ PG used instead of Boc) | N-[trans-3-({5-chloro-2-[(1-methyl-1H-pyrazol-4-yl)amino]-7H-pyrrolo[2,3-d]pyrimidin-4-yl}oxy)-1-methylcyclobutyl]prop-2-enamide | 402.2 | ¹H NMR (400 MHz, CHLOROFORM-d) δ ppm 9.21 (br. s., 1H), 7.76 (s, 1H), 7.50 (s, 1H), 6.69 (s, 1H), 6.61 (s, 1H), 6.31 (dd, J = 1.26, 16.87 Hz, 1H), 6.11 (dd, J = 10.32, 16.87 Hz, 1H), 5.78 (s, 1H), 5.65 (dd, J = 1.13, 10.20 Hz, 1H), 5.43-5.58 (m, 1H), 3.85 (s, 3H), 2.99-3.15 (m, 2H), 2.35 (dd, J = 5.29, 13.85 Hz, 2H), 1.62 (s, 3H) |
| 114 (Scheme F*CBZ PG used instead of Boc) | N-[cis-3-({5-chloro-2-[(1-methyl-1H-pyrazol-4-yl)amino]-7H-pyrrolo[2,3-d]pyrimidin-4-yl}oxy)-1-methylcyclobutyl]prop-2-enamide | 402.2 | ¹H NMR (400 MHz, CHLOROFORM-d) δ ppm 8.73-8.95 (m, 1H), 7.75 (s, 1H), 7.52 (s, 1H), 6.69 (br. s., 1H), 6.63 (br. s., 1H), 6.28 (dd, J = 1.26, 16.87 Hz, 1H), 6.01-6.12 (m, 1H), 5.89 (br. s., 1H), 5.63 (dd, J = 1.38, 10.20 Hz, 1H), 5.26 (t, J = 6.92 Hz, 1H), 3.88 (s, 3H), 2.73-2.94 (m, 2H), 2.45-2.59 (m, 2H), 1.61 (s, 3H) |

| Example No. (Scheme) | Structure and Compound Name | LRMS m/z | ¹H NMR |
|---|---|---|---|
| 115 (Scheme B) | 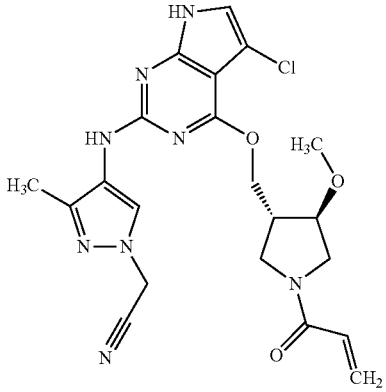<br>{4-[(4-{[(3R,4R)-1-acryloyl-4-methoxypyrrolidin-3-yl]methoxy}-5-chloro-7H-pyrrolo[2,3-d]pyrimidin-2-yl)amino]-3-methyl-1H-pyrazol-1-yl}acetonitrile | 471.0 | ¹H NMR (400 MHz, DMSO)δ ppm 11.53 (s, 1H), 8.48 (s, 1H), 7.98 (s, 1H), 7.05 (d, 1H), 6.58-6.54 (m, 1H), 6.15-6.10 (d, 1H), 5.67-5.64 (d, 1H), 5.35 (s, 2H), 4.42-4.41 (d, 2H), 4.01-3.48 (m, 5H), 3.29-3.28 (d, 3H), 2.83-2.78 (m, 1H) 14 (s, 3H) |
| 116 (Scheme B) | 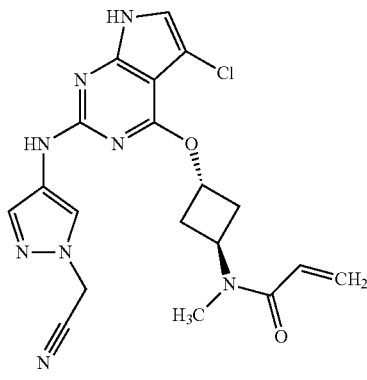<br>N-{trans-3-[(5-chloro-2-{[1-(cyanomethyl)-1H-pyrazol-4-yl]amino}-7H-pyrrolo[2,3-d]pyrimidin-4-yl)oxy]cyclobutyl}-N-methylprop-2-enamide | 449.2 (M + Na) | ¹H NMR (400 MHz, CDCl3) δ ppm 8.26 (s, 1H), 8.13 (s, 1H), 7.56 (s, 1H), 6.81 (s, 1H), 6.61-6.54 (m, 2H), 6.31 (s, 1H), 5.71-5.69 (m, 1H), 5.30-5.09 (m, 3H), 3.11-3.08 (d, 3H), 2.83-2.75 (m, 2H), 2.67-2.62 (m, 2H) |

| Example No. (Scheme) | Structure and Compound Name | LRMS m/z | $^1$H NMR |
|---|---|---|---|
| 117 (Scheme I) | 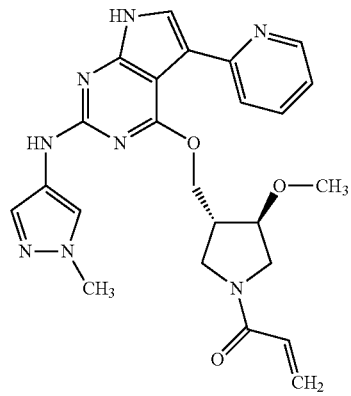  1-{(3R,4R)-3-methoxy-4-[({2-[(1-methyl-1H-pyrazol-4-yl)amino]-5-(pyridin-2-yl)-7H-pyrrolo[2,3-d]pyrimidin-4-yl}oxy)methyl]pyrrolidin-1-yl}prop-2-en-1-one | 475.2 | $^1$H NMR (400 MHz, DMSO-d6) δ ppm 11.68 (br. s., 1H) 8.99 (s, 1H) 8.44-8.62 (m, 1H) 7.94-8.06 (m, 1H) 7.89 (s, 1H) 7.67-7.79 (m, 1H) 7.53 (s, 1H) 7.49 (d, J = 3.91 Hz, 1H) 7.16 (dd, J = 7.34, 4.89 Hz, 1H) 6.55 (ddd, J = 19.23, 16.72, 10.27 Hz, 1H) 6.14 (dt, J = 16.84, 2.89 Hz, 1H) 5.68 (dd, J = 10.27, 2.32 Hz, 1H) 4.53 (td, J = 10.58, 7.09 Hz, 1H) 4.34-4.46 (m, 1H) 3.83-4.00 (m, 2H) 3.80 (s, 3H) 3.54-3.71 (m, 2H) 3.39-3.50 (m, 1H) 3.24 (d, J = 4.16 Hz, 3H) 2.69-2.89 (m, 1H) |

*Compounds are single enantiomers; However, absolute stereochemistry is unknown.
**Compounds are single isomers; However, the geometry is unknown.
***Compounds are racemates containing two trans enantiomers pEGFR Y1068 ELISA Assay In order to profile the effect of EGFR T790M inhibitors in cells with different EGFR mutation status, inhibition of phosphorylation of EGFR at Tyr1068 was determined in cells with wildtype EGFR or various EGFR mutations—either EGFR single mutant (L858R, E746-A750 deletion) or EGFR double mutant (L858R+T790M, deletion+T790M). Phosphorylation of EGFR at Y1068 was measured by PathScan® Phospho-EGF Receptor (Try1068) Sandwich ELISA kit (#7240, Cell Signaling Technology®, Danvers, Mass.). The PathScan® Phospho-EGF Receptor (Tyr1068) Sandwich ELISA Kit is a solid phase sandwich enzyme-linked immunosorbent assay (ELISA) that detects endogenous levels of phospho-EGF Receptor (Tyr1068) protein. The following cell lines were evaluated in this assay: A549 (EGFR wildtype, endogenous), NCI-H1975 (EGFR L858R+T790M, endogenous), NCI-H3255 (EGFR L858R, endogenous), NIH3T3/EGFR_wildtype, NIH3T3/EGFR_L858R, NIH3T3/EGFR_E746-A750 deletion, NIH3T3/EGFR_L858R+T790M, and NIH3T3/EGFR_E746-A750_deletion+T790M. NIH/3T3 parental, A549, and NCI-H1975 cells were purchased from the American Type Culture Collection (Manassas, Va.). All cells were cultured according to ATCC recommendations. A549 cells were grown in RPMI media (Invitrogen, Carlsbad) supplemented with 10% FBS (Sigma, St Louis, Mo.), and with 1% Penn/Strep (Invitrogen). NCI-H1975 cells were grown in RPMI (Invitrogen) supplemented with 10% FBS (Sigma), and with 1% Penn/Strep (Invitrogen). NCI-H3255 cells were grown in RPMI (Invitrogen) supplemented with 10% FBS (Sigma), and with 1% Penn/Strep (Invitrogen). NIH/3T3 cells were grown in DMEM (Invitrogen) supplemented with 10% newborn calf serum (Invitrogen), and NIH3T3/EGFR mutant cells were grown in complete media with 5 μg/mL puromycin (Invitrogen). Plasmids (pLPCX) with various EGFR constructs were made by GenScript (Piscataway, N.J.), and stable pools of NIH/3T3 cells expressing these constructs were made at Pfizer La Jolla. Cells were plated in complete culture media (50 μL/well) on the bottom of clear tissue culture treated microtiter plates (#3595, Corning Inc, Corning, N.Y.) and allowed to adhere overnight at 37° C., 5% $CO_2$. Cells were seeded at the following concentrations: (A549: 40,000/well, NCI-H1975: 40,000/well, NCI-H3255: 25,000/well, NIH3T3: 20,000/well). The following day, compound dilution plates were prepared in 96 well clear V-bottom 0.5 mL polypropylene block plates (#3956, Corning, Inc). All cell lines were not evaluated for each compound. Each compound evaluated was prepared as a DMSO stock solution (10 mM). Compounds were tested in duplicate on each plate, with an 11-point serial dilution curve (1:3 dilution). Compound treatment (50 μL) was added from the compound dilution plate to the cell plate. The highest compound concentration was 1 or 10 μM (final), with a 0.3% final DMSO (#D-5879, Sigma) concentration. Plates were then incubated for 2 hrs at 37° C., 5% $CO_2$. For NIH3T3/wildtype assay, cells were serum starved for 24 hrs prior to compound treatment; cells were treated in serum-free media as described and then stimulated for 10 min with EGF (100 ng/mL, Calbiochem/EMD Chemicals, Gibbstown, N.J.). For A549/wildtype assay, cells were plated in full-serum (10%) media for 24 hrs prior to compound treatment; cells were treated in full serum media as described and then stimulated for 10 min with EGF (40 ng/mL/starvation media, Invitrogen). Immediately prior to the end of the incubation, ice-cold lysis buffer was prepared (1× Cell Lysis Buffer (#9803, Cell Signaling Technology), 1 mM sodium orthovanadate ($Na_3VO_4$, #96508, Sigma), 1 mM phenylmethanesulfonyl fluoride (PMSF, 52332, CalBiochem/EMD Chemicals), complete Mini EDTA-free Protease Inhibitor Cocktail Tablet (1 tablet/10 mL, #11836170001, Roche, Indianapolis, Ind.), and PhosSTOP Phosphatase Inhibitor Cocktail Tablet (1 tablet/10 mL, #04906837001, Roche) in pure water. At the end of 2 hrs, media was flicked off and cells were washed once with ice-cold 1 mM Na$_3$VO$_4$ in PBS (100 μL/well, Invitrogen). The wash was then flicked off and ice-cold lysis buffer was added to the cells (50 μL/well). The plate was shaken for 20-30 min at 4° C. to completely lyse the cells. Sample diluent (50 μL/well) was added to the ELISA plate, and the lysate (50 μL) was diluted into the sample diluent in each well of the ELISA plate. Plates were sealed and incubated overnight at 4° C. with shaking. The next day, wells were washed four times with 1× Wash Buffer; plates were taped on lint-free paper after the final wash prior to adding Add Detection Antibody (green, 100 μL/well) to each well and incubating for 1 hr at 37° C. After incubation, wells were washed as described. HRP-Linked secondary antibody (red, 100 μL/well) was added to each well and incubated for 30 min at 37° C. After incubation, the wells were washed as described. TMB Substrate (100 μL/well) was added to each well and the plate incubated for 10 minutes at 37° C. or 30 minutes at room temperature maximum. Stop Solution (100 μL/well) was added to each well at the end of the incubation and plates were shaken gently for a few seconds. Absorbance was read at 450 nm within 30 min after addition of Stop Solution on a Perki-nElmer EnVision Excite Multilabel Reader Method for Absorbance or on a Molecular Devices SpectraMax$^{384}$ Reader for absorbance. Data were analyzed using a four-parameter fit in Microsoft Excel.

The results of the pEGFR Y1068 ELISA assay for the compounds tested are listed in Table 2. The pEGFR ELISA IC$_{50}$ data shown in Table 2 for T790M_L858R and L858R is for 3T3 cell lines, unless otherwise indicated.

TABLE 2

| Example Number | pEGFRY1068 ELISA3T3T790M_L858R IC$_{50}$ (nM) | pEGFRY1068 ELISA3T3 L858R IC$_{50}$ (nM) | pEGFRY1068 ELISAA549 IC$_{50}$ (nM) | ELISA7E 3T3 Del IC$_{50}$ (nM) | EGFR_ELISA9E PC9 Del IC$_{50}$ (nM) |
|---|---|---|---|---|---|
| 1 | 33 | 585 | >10,000 | N/D | N/D |
| 2 | 11 | 141 | 2,920 | 29 | N/D |
| 3 | 57 | 733 | 9060 | N/D | N/D |
| 4 | 77 | 547 | >10,000 | N/D | N/D |
| 5 | 221 | 1,810 | >10,000 | 1323 | 982 |
| 6 | >10,000 | >10,000 | >10,000 | N/D | N/D |
| 7 | 396 | 1,120 | >10,000 | 1130 | N/D |
| 8 | 17 | 25 | 1,370 | 8 | 3 |
| 9 | 7 | 103 | >4,287 | 175 | 222 |
| 10 | 80 | 1805 | >10,000 | 1020 | N/D |
| 11 | 525 (H1975) | 8861 | >10,000 | N/D | N/D |
| 12 | 689 (H1975) | 782 (H3255) | >10000 | N/D | 2777 |
| 13 | 89 (H1975) | 48 (H3255) | N/D | N/D | 91 |
| 14 | 1,800 | >10,000 | >10,000 | N/D | N/D |
| 15 | 182 | 834 | >10,000 | N/D | N/D |
| 16 | 308 | 2,510 | >10,000 | N/D | N/D |
| 17 | 104 | 2,030 | >10,000 | N/D | N/D |
| 18 | 79 | 1,500 | >10,000 | N/D | N/D |
| 19 | 81 | 875 | >10,000 | 536 | N/D |
| 20 | 1,820 | >10,000 | >10,000 | 8405 | N/D |
| 21 | 13 | 202 | 7,850 | 33 | N/D |
| 22 | 11 | 81 | >10,000 | 27 | N/D |
| 23 | 42 | 87 | 8,100 | 467 | 433 |
| 24 | 20 | 275 | 6,740 | N/D | N/D |
| 25 | 69 | 1,030 | >10,000 | N/D | N/D |
| 26 | 21 | 177 | 6,760 | 135 | N/D |
| 27 | 146 (H1975) | N/D | >10,000 | 56 | N/D |
| 28 | 12 | 124 | 8,680 | 65 | N/D |
| 29 | N/D | N/D | N/D | 116 | N/D |
| 30 | 9 | 91 | 2,390 | 25 | N/D |
| 31 | 11 | 105 | 947 | N/D | N/D |
| 32 | 9 | 47 | 1,340 | 98 | N/D |
| 33 | 20 | 120 | 2,210 | 27 | N/D |
| 34 | 14 | 170 | 4,030 | N/D | N/D |
| 35 | 5 | 46 | 1,560 | 20 | N/D |
| 36 | 20 | 418 | >10,000 | 45 | N/D |
| 37 | 41 | 67 | >10,000 | N/D | N/D |
| 38 | 8 | 90 | 5,900 | N/D | N/D |
| 39 | 15 | 190 | 2,800 | 100 | N/D |
| 40 | 20 | 99 | >6,380 | 44 | N/D |
| 41 | 162 | 1,010 | 2,340 | N/D | N/D |
| 42 | 446 | 1,930 | >10,000 | N/D | N/D |
| 43 | 5,340 | >10,000 | >10,000 | N/D | N/D |
| 44 | 25 | 552 | 3,560 | 90 | N/D |
| 45 | 84 | 700 | >10,000 | N/D | N/D |
| 46 | 80 | 495 | >10,000 | N/D | N/D |
| 47 | 50 | 752 | >10,000 | 317 | N/D |
| 48 | 11 | 124 | 6,520 | 65 | N/D |
| 49 | 7 | 97 | 2,020 | 22 | N/D |
| 50 | N/D | N/D | N/D | 633 | N/D |
| 51 | 35 | 431 | >10,000 | 137 | N/D |
| 53 | 355 | 1,140 | >10,000 | 663 | N/D |
| 54 | 168 | 672 | >10,000 | 192 | N/D |
| 55 | N/D | N/D | N/D | >10,000 | N/D |
| 56 | N/D | N/D | N/D | >10,000 | N/D |
| 57 | 67 | 105 | >10,000 | 25 | 44 |

TABLE 2-continued

| Example Number | pEGFRY1068 ELISA3T3T790M_L858R IC$_{50}$ (nM) | pEGFRY1068 ELISA3T3 L858R IC$_{50}$ (nM) | pEGFRY1068 ELISAA549 IC$_{50}$ (nM) | ELISA7E 3T3 Del IC$_{50}$ (nM) | EGFR_ELISA9E PC9 Del IC$_{50}$ (nM) |
|---|---|---|---|---|---|
| 58 | 681 | >10,000 | >10,000 | N/D | N/D |
| 59 | 7 | 78 | >7,890 | 36 | N/D |
| 60 | 16 | 23 | 1,860 | 12 | N/D |
| 61 | 189 | 1,700 | >10,000 | 581 | N/D |
| 62 | 10 | 218 | >10,000 | 237 | 558 |
| 63 | 67 | 2008 | >10,000 | 1224 | N/D |
| 64 | 16 | 310 | >3,330 | 152 | N/D |
| 65 | 44 | 510 | >10,000 | 1169 | N/D |
| 66 | 9 | 120 | >10,000 | 309 | N/D |
| 67 | 8 | 49 | >10,000 | 172 | 141 |
| 68 | 42 | 208 | >10,000 | 1064 | N/D |
| 69 | 19 | 287 | >9,370 | 117 | 465 |
| 70 | 12 | 113 | >10,000 | 269 | 592 |
| 71 | 20 | 143 | >5,459 | 356 | N/D |
| 72 | 15 | 332 | >10,000 | 512 | N/D |
| 73 | 124 | 6617 | >10,000 | 8193 | N/D |
| 74 | 8 (H1975) | 231 | >9,116 | N/D | N/D |
| 75 | 69 | 3552 | >10,000 | N/D | N/D |
| 76 | 26 | 855 | >10,000 | N/D | N/D |
| 77 | 301 (H1975) | 5188 | >10,000 | N/D | N/D |
| 78 | TBD | TBD | >10,000 | N/D | 3221 |
| 79 | 136 (H1975) | 776 (H3255) | >10000 | N/D | >6755 |
| 80 | 25 (H1975) | 273 (H3255) | >10000 | N/D | 891 |
| 81 | 41 (H1975) | 60 (H3255) | 6125 | N/D | 240 |
| 82 | 638 (H1975) | 973 (H3255) | >10000 | N/D | >10000 |
| 83 | 5 (H1975) | 31 (H3255) | 450 | N/D | 87 |
| 84 | 175 (H1975) | 1101 (H3255) | N/D | N/D | 5238 |
| 85 | 191 | 61 (H3255) | N/D | N/D | 154 |
| 86 | 266 (H1975) | 477 (H3255) | >10000 | N/D | 2336 |
| 87 | 14 (H1975) | 43 (H3255) | 948 | N/D | 48 |
| 88 | 34 (H1975) | 41 (H3255) | N/D | N/D | 630 |
| 89 | 6 (H1975) | 33 (H3255) | 1650 | N/D | 42 |
| 90 | 9 (H1975) | 19 (H3255) | 4241 | N/D | 100 |
| 92 | 86 (H1975) | 311 (H3255) | N/D | N/D | 1319 |
| 93 | 31 (H1975) | 26 (H3255) | N/D | N/D | 383 |
| 94 | 385 (H1975) | 608 (H3255) | N/D | N/D | 4430 |
| 95 | 1566 (H1975) | 2443 (H3255) | >10000 | N/D | 8568 |
| 96 | 15 (H1975) | 101 (H3255) | 2185 | N/D | 342 |
| 98 | 27 | 139 (H3255) | 4286 | N/D | 472 |
| 99 | 377 | 482 | 3439 | N/D | 812 |
| 100 | 153 (H1975) | 101 (H3255) | >10000 | N/D | 4249 |
| 101 | 48 (H1975) | 1012 | >10000 | N/D | 6539 |
| 102 | 21 | 297 | 4963 | 709 | N/D |
| 103 | 15 | 332 | >10000 | 512 | N/D |
| 104 | 25 | 123 | >10000 | 110 | N/D |
| 105 | 37 | 490 | >10000 | N/D | N/D |
| 106 | 8 | 15 | >10000 | 9 | N/D |
| 107 | 3 | 26 | 2165 | 12 | N/D |
| 108 | 7 | 164 | >10000 | 81 | 352 |
| 109 | 153 | 271 | 5541 | 32 | 29 |
| 110 | 3 | 151 | 3467 | 156 | N/D |
| 111 | 14 | 352 | >10000 | 886 | N/D |
| 112 | 63 (H1975) | 241 (H3255) | >10000 | N/D | N/D |
| 113 | 457 (H1975) | >8577 (H3255) | >10000 | N/D | >10000 |
| 114 | 39 (H1975) | 667 (H3255) | >10000 | N/D | 1196 |
| 115 | 73 (H1975) | 85 (H3255) | >10000 | N/D | 953 |
| 116 | 24 (H1975) | 107 (H3255) | N/D | N/D | 328 |
| 117 | N/D | N/D | >10000 | N/D | 838 |

Cell Proliferation Assay

In order to profile the effect of EGFR T790M inhibitors in various tumorigenic cell lines, the cell lines tested in the cell proliferation assay exhibit different EGFR mutation status—either EGFR single mutant (L858R, E746-A750 deletion) or EGFR double mutant (L858R+T790M, deletion+T790M). Cell proliferation was measured using the CellTiter-Glo® Luminescent Cell Viability Assay. The assay involves the addition of a single reagent (CellTiter-Glo® Reagent) directly to cells cultured in serum-supplemented medium. The assay uses this one-step addition to induce cell lysis and generate a luminescent signal proportional to the amount of ATP present which is directly proportional to the number of metabolically active cells present in culture. The following cell lines were evaluated in this assay: NIH3T3/EGFR_L858R, NIH3T3/EGFR_E746-A750_deletion, NIH3T3/EGFR L858R+T790M, NIH3T3/EGFR_E746-A750_deletion+T790M, PC-9, PC9-DRH, NCI-H1975, and NCI-H3255. NIH/3T3 parental cells, NCI-H1975, and NCI-H3255 were purchased from the American Type Culture Collection (Manassas, Va.), and PC-9 cells were obtained from Japan. All cells were cultured according to recommendations. NIH/3T3 cells were grown in DMEM (Invitrogen, Carlsbad, Calif.) supplemented with 10% newborn calf serum (Invitrogen), and NIH3T3/EGFR mutant cells were grown in complete media with 5 μg/mL puromycin (Invitrogen). PC-9, NCI-H1975, and NCI-H3255 were grown in RPMI (Invitrogen, Carlsbad, Calif.) supplemented with 10% FBS (Sigma, St Louis, Mo.), and PC9-DRH cells were grown in complete media with 2 uM PF-00299804. Plasmids (pLPCX) with various EGFR constructs were made by GenScript (Piscataway, N.J.), and stable pools of NIH/3T3 cells expressing these constructs were made at Pfizer La Jolla. PC9-DRH cells were generated at Pfizer La Jolla by exposing cells to increasing concentrations of PF-00299804. Cells were plated in complete culture media (3000-5000 cells/well, 50 μl/well) on the bottom of white clear-bottom tissue culture treated microtiter plates (#3610, Corning Inc, Corning, N.Y.) and allowed to adhere overnight at 37° C., 5% $CO_2$. The following day, compound dilution plates were prepared in 96 well clear V-bottom 0.5 mL polypropylene block plates (#3956, Corning, Inc). All cell lines were not evaluated for each compound. Each compound evaluated was prepared as a DMSO stock solution (10 mM). Compounds were tested in duplicate on each plate, with an 11-point serial dilution curve (1:3 dilution). Compound treatment (50 μl) was added from the compound dilution plate to the cell plate. The highest compound concentration was 1 or 10 μM (final), with a 0.3% final DMSO (#D-5879, Sigma, St Louis, Mo.) concentration. Plates were then incubated at 37° C., 5% $CO_2$. After three to five days of compound treatment, CellTiter-Glo® Reagent (#G7573, Promega, Madison, Wis.) was prepared in one of two ways. If thawing a frozen aliquot of CellTiter-Glo® Reagent, the aliquot was thawed and equilibrated to room temperature prior to use while keeping it protected from light. Alternatively, new bottles of CellTiter-Glo® Buffer and CellTiter-Glo® Substrate were thawed and equilibrated to room temperature prior to use. CellTiter-Glo® Buffer (100 mL) was transferred into the amber bottle containing CellTiter-Glo® Substrate to reconstitute the lyophilized enzyme/substrate mixture, forming the CellTiter-Glo® Reagent. The reconstituted reagent was mixed by gently inverting the contents to obtain a homogeneous solution, and went into solution easily in less than one minute. Any unused reconstituted CellTiter-Glo® Reagent was immediately aliquoted and frozen at −20° C., protected from light. Cell plates were equilibrated at room temperature for approximately 30 minutes. An equivolume amount of CellTiter-Glo® Reagent (100 μL) was added to each well. Plates were mixed for two minutes on an orbital shaker to induce cell lysis, and then allowed to incubate at room temperature for 10 minutes to stabilize the luminescent signal. Luminescence was recorded using the PerkinElmer EnVision Excite Multilabel Reader used for endpoint reading for Luminescence detection (Waltham, Mass.). Data were analyzed using a four-parameter fit in Microsoft Excel.

The results of the cell proliferation assay for the compounds tested are listed in Table 3. The data reported in Table 3 is for 3T3 cell lines, unless otherwise indicated. As shown below in Table 3, activity is binned into 4 categories:

A<10 nM; B=10-100 nM; C=100 nM–1 uM; D>1 uM

TABLE 3

| Example Number | 3T3 L858R $IC_{50}$ | 3T3 del $IC_{50}$ | 3T3 L858R_T790M $IC_{50}$ | 3T3 del_T790M $IC_{50}$ |
|---|---|---|---|---|
| 2 | C | A | A | A |
| 5 | D | C | C | C |
| 9 | C | B | C | A |
| 10 | D | C | D | B |
| 11 | D | D | C | C |

TABLE 3-continued

| Example Number | 3T3 L858R $IC_{50}$ | 3T3 del $IC_{50}$ | 3T3 L858R_T790M $IC_{50}$ | 3T3 del_T790M $IC_{50}$ |
|---|---|---|---|---|
| 13 | C (H3255) | C (PC9) | C | C (PC9-DRH) |
| 21 | D | B | B | A |
| 22 | C | A | B | A |
| 31 | D | B | B | B |
| 32 | D | B | B | A |
| 34 | C | A | B | A |
| 35 | C | A | A | A |
| 36 | D | B | C | B |
| 40 | D | B | B | A |
| 41 | C | A | C | A |
| 42 | A | B | C | B |
| 57 | D | A | B | B |
| 62 | B | B | B | A |
| 63 | D | D | D | C |
| 64 | B | A | B | A |
| 65 | C | C | C | B |
| 68 | C | C | C | B |
| 70 | C | C | C | B |
| 71 | C | B | C | B |
| 72 | C | C | C | B |
| 74 | C | B | C | B |
| 75 | D | C | C | B |
| 76 | D | C | C | C |
| 77 | D | D | C | C |
| 83 | B (H3255) | C (PC9) | B | B (PC9-DRH) |
| 85 | B (H3255) | D (PC9) | B | C (PC9-DRH) |
| 87 | B (H3255) | D (PC9) | C | C (PC9-DRH) |
| 89 | C (H3255) | C (PC9) | B | B |
| 90 | B (H3255) | N/D | B | N/D |
| 96 | C (H3255) | C (PC9) | B | B (PC9-DRH) |
| 98 | B (H3255) | C (PC9) | B | B (PC9-DRH) |
| 99 | D (H3255) | D (PC9) | C | C (PC9-DRH) |
| 101 | C (H3255) | D (PC9) | D (H1975) | C (PC9RK) |
| 102 | C (H3255) | C (PC9) | C (H1975) | C (PC9RK) |
| 103 | C | C | C | B |
| 105 | C | C | C | C |
| 107 | B | A | B | A |
| 108 | C | B | B | A |
| 109 | C (H3255) | B (PC9) | C (H1975) | C (PC9RK) |
| 110 | C (H3255) | C (PC9) | D (H1975) | N/D |
| 111 | C (H3255) | C (PC9) | D (H1975) | N/D |
| 114 | B (H3255) | C (PC9) | C (H1975) | C (PC9RK) |
| 116 | N/D | N/D | B | N/D |

What is claimed is:
1. A compound of formula (I):

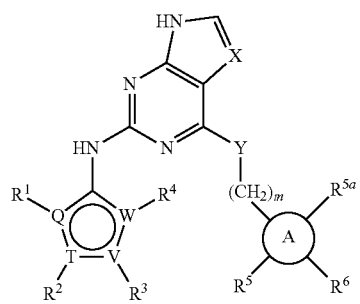

wherein
X is N or $CR^7$;
Y is absent, O, S or $NR^8$;
Q, T, V and W are each independently C or N, provided that at least two of Q, T, V and W are N and at least one of Q, T, V and W is C, and provided that when Q and T are N, at least one of $R^1$ and $R^2$ is absent, and further provided that when T and V are N, at least one of $R^2$ and $R^3$ is absent;

$R^1$ and $R^4$ are each independently absent, hydrogen, cyano, difluoromethyl, trifluoromethyl, $C_1$-$C_6$ alkyl, $C_2$-$C_6$ alkenyl, $C_2$-$C_6$ alkynyl, $C_1$-$C_6$ alkoxy, —$N(R^9)(R^{10})$, $C_3$-$C_5$ cycloalkyl or 4-6 membered heterocycloalkyl, wherein the $C_1$-$C_6$ alkyl may be optionally substituted by halogen, hydroxy, $C_1$-$C_6$ alkoxy or $N(R^{11})(R^{12})$;

$R^2$ and $R^3$ are each independently absent, hydrogen, $C_1$-$C_6$ alkyl, $C_2$-$C_6$ alkynyl, $C_1$-$C_6$ alkoxy, $C_3$-$C_7$ cycloalkyl or 3-7 membered heterocycloalkyl, wherein the $C_1$-$C_6$ alkyl and $C_1$-$C_6$ alkoxy in $R^2$ and $R^3$ are each independently optionally substituted by one or more $R^{13}$ groups, and further wherein the $C_3$-$C_7$ cycloalkyl and the 3-7 membered heterocycloalkyl in $R^2$ and $R^3$ are each independently optionally substituted by one or more $R^{14}$ groups; or $R^1$ and $R^2$ or $R^2$ and $R^3$ may combine to form a $C_5$-$C_7$ cycloalkyl ring or a 5-7 membered heterocycloalkyl ring, wherein the $C_5$-$C_7$ cycloalkyl ring and the 5-7 membered heterocycloalkyl ring are each independently optionally substituted by one or more $R^{13}$ groups;

ring A is absent, $C_3$-$C_{10}$ cycloalkyl, 3-10 membered heterocycloalkyl, $C_5$-$C_{10}$ aryl or 5-12 membered heteroaryl;

$R^5$ and $R^{5a}$ are each independently absent, halogen, cyano, hydroxy, difluoromethyl, trifluoromethyl, $C_1$-$C_3$ alkyl, $C_1$-$C_3$ alkoxy, $C_3$-$C_5$ cycloalkyl or 4-6 membered heteroaryl, wherein the $C_1$-$C_3$ alkyl is optionally substituted by hydroxy, difluoromethyl, trifluoromethyl, $C_1$-$C_3$ alkoxy or $C_3$-$C_5$ cycloalkyl;

$R^6$ is

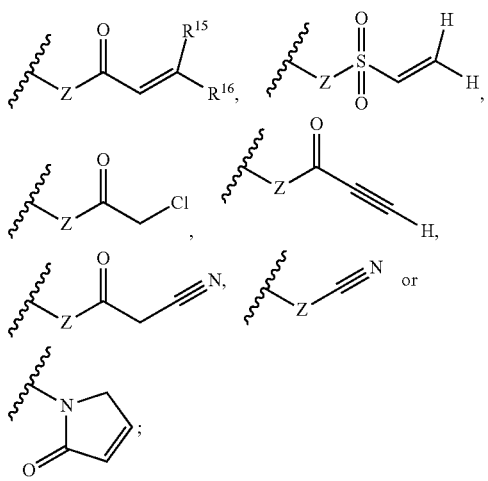

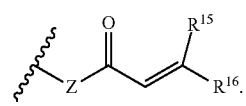

Z is absent when the attachment point of $R^6$ on ring A is a nitrogen atom, and Z is —$NR^{17}$— when ring A is absent or when the attachment point of $R^6$ on ring A is a carbon atom;

$R^7$ is hydrogen, halogen, cyano, $C_1$-$C_6$ alkyl, $C_2$-$C_6$ alkenyl, $C_2$-$C_6$ alkynyl or 4-6 membered heteroaryl, wherein the $C_1$-$C_6$ alkyl may be optionally substituted by hydroxy or $C_1$-$C_3$ alkoxy, and further wherein the 4-6 membered heteroaryl may be optionally substituted by $C_1$-$C_3$ alkyl;

$R^8$ is hydrogen or $C_1$-$C_3$ alkyl;

$R^9$ and $R^{10}$ are each independently hydrogen or $C_1$-$C_6$ alkyl; or $R^9$ and $R^{10}$ together with the nitrogen to which they are attached, may combine to form a 4-7 membered ring, when $R^9$ and $R^{10}$ are each $C_1$-$C_3$ alkyl, wherein the 4-7 membered ring is optionally substituted by one or more $R^{14}$ groups;

$R^{11}$ and $R^{12}$ are each independently hydrogen or $C_1$-$C_3$ alkyl;

each $R^{13}$ is independently halogen, cyano, hydroxy, $C_1$-$C_6$ alkoxy, —$N(R^9)(R^{10})$, —$CON(R^9)(R^{10})$ or 3-7 membered heterocycloalkyl, wherein the 3-7 membered heterocycloalkyl in $R^{13}$ is optionally substituted by one or more $R^{14}$ groups;

each $R^{14}$ is independently halogen, $C_1$-$C_3$ alkyl, hydroxy, $C_1$-$C_6$ alkoxy, —$NH_2$, —$NHCH_3$ or $N(CH_3)_2$;

$R^{15}$ and $R^{16}$ are each independently hydrogen or $C_1$-$C_6$ alkyl, wherein the $C_1$-$C_6$ alkyl of one of $R^{15}$ and $R^{16}$ is optionally substituted by —$N(R^9)(R^{10})$;

$R^{17}$ is hydrogen or $C_1$-$C_3$ alkyl; and m is 0, 1 or 2, provided that when ring A is absent, m is 2; or a pharmaceutically acceptable salt thereof.

2. The compound or salt of claim 1, wherein X is $CR^7$.

3. The compound or salt of claim 1, wherein Y is O.

4. The compound or salt of claim 1, wherein Y is $NR^8$.

5. The compound or salt of claim 2, wherein $R^7$ is hydrogen, halogen, cyano or 4-6 membered heteroaryl.

6. The compound or salt of claim 2, wherein $R^7$ is hydrogen.

7. The compound or salt of claim 5, wherein the halogen is fluorine or chlorine.

8. The compound or salt of claim 2, wherein $R^7$ is cyano.

9. The compound or salt of claim 2, wherein $R^7$ is 4-6 membered heteroaryl optionally substituted by $C_1$-$C_3$ alkyl.

10. The compound or salt of claim 1, wherein m is 0.

11. The compound or salt of claim 1, wherein m is 1.

12. The compound or salt of claim 1, wherein Q and T are N.

13. The compound or salt of claim 1, wherein T and V are N.

14. The compound or salt of claim 1, wherein $R^6$ is

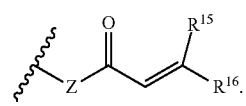

15. The compound or salt of claim 1, wherein ring A is phenyl.

16. The compound or salt of claim 1, having formula (Ia):

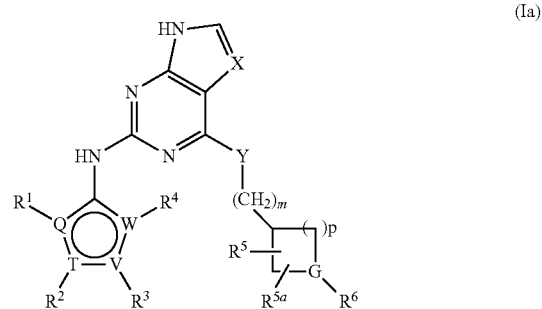

wherein
G is CH or N; and
p is 1 or 2.

17. The compound or salt of claim 16, wherein G is CH.
18. The compound or salt of claim 16, wherein G is N.
19. The compound or salt of claim 16, wherein p is 1.
20. The compound or salt of claim 16, wherein p is 2.
21. A compound, which is selected from the group consisting of:
  1-{(3R,4R)-3-[({5-chloro-2-[(1-methyl-1H-pyrazol-4-yl)amino]-7H-pyrrolo[2,3-d]pyrimidin-4-yl}oxy)methyl]-4-methoxypyrrolidin-1-yl}prop-2-en-1-one;
  N-[3-({5-(1-methyl-1H-pyrazol-4-yl)-2-[(1-methyl-1H-pyrazol-4-yl)amino]-7H-pyrrolo[2,3-d]pyrimidin-4-yl}oxy)phenyl]prop-2-enamide;
  N-[trans-3-({2-[(1,3-dimethyl-1H-pyrazol-4-yl)amino]-5-(pyridin-2-yl)-7H-pyrrolo[2,3-d]pyrimidin-4-yl}oxy)cyclobutyl]-N-methylprop-2-enamide;
  1-[(3S,4R)-3-({5-chloro-2-[(1-methyl-1H-pyrazol-4-yl)amino]-7H-pyrrolo[2,3-d]pyrimidin-4-yl}amino)-4-(1H-1,2,3-triazol-1-yl)pyrrolidin-1-yl]prop-2-en-1-one;
  1-[(3R,4S)-3-({5-chloro-2-[(1-methyl-1H-pyrazol-4-yl)amino]-7H-pyrrolo[2,3-d]pyrimidin-4-yl}amino)-4-(trifluoromethyl)pyrrolidin-1-yl]prop-2-en-1-one;
  N-methyl-N-[trans-3-({2-[(1-methyl-1H-pyrazol-4-yl)amino]-5-(pyridin-2-yl)-7H-pyrrolo[2,3-d]pyrimidin-4-yl}oxy)cyclobutyl]prop-2-enamide;
  1-{(3R,4R)-3-[({5-chloro-2-[(1-methyl-1H-pyrazol-4-yl)amino]-7H-pyrrolo[2,3-d]pyrimidin-4-yl}oxy)methyl]-4-fluoropyrrolidin-1-yl}prop-2-en-1-one; and
  1-{(3R,4R)-3-methoxy-4-[({2-[(1-methyl-1H-pyrazol-4-yl)amino]-5-(pyridin-2-yl)-7H-pyrrolo[2,3-d]pyrimidin-4-yl}oxy)methyl]pyrrolidin-1-yl}prop-2-en-1-one,
  or a pharmaceutically acceptable salt thereof.
22. A pharmaceutical composition comprising a compound of claim 1, or a pharmaceutically acceptable salt thereof, and a pharmaceutically acceptable carrier or diluent.
23. A pharmaceutical composition comprising a compound of claim 21, or a pharmaceutically acceptable salt thereof, and a pharmaceutically acceptable carrier or diluent.
24. A compound of formula (III):

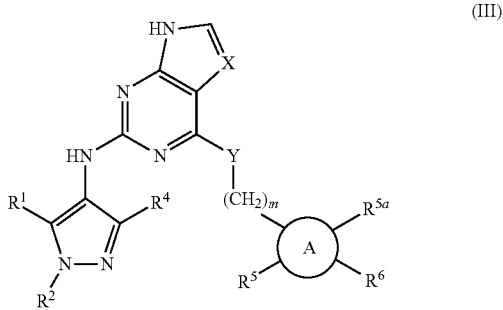

wherein
  X is N or $CR^7$;
  Y is absent, O, S or $NR^8$;
  $R^1$ and $R^4$ are each independently hydrogen, cyano, difluoromethyl, trifluoromethyl, $C_1$-$C_6$ alkyl, $C_2$-$C_6$ alkenyl, $C_2$-$C_6$ alkynyl, $C_1$-$C_6$ alkoxy, —$N(R^9)(R^{10})$, $C_3$-$C_5$ cycloalkyl, or 4-6 membered heterocycloalkyl, wherein the $C_1$-$C_6$ alkyl may be optionally substituted by halogen, hydroxy, $C_1$-$C_6$ alkoxy, or $N(R^{11})(R^{12})$;
  $R^2$ is $C_1$-$C_6$ alkyl, $C_2$-$C_6$ alkenyl, $C_1$-$C_6$ alkoxy, $C_3$-$C_7$ cycloalkyl or 3-7 membered heterocycloalkyl, wherein the $C_1$-$C_6$ alkyl and $C_1$-$C_6$ alkoxy in $R^2$ is optionally substituted by one or more $R^{13}$ groups, and further wherein the $C_3$-$C_7$ cycloalkyl and the 3-7 membered heterocycloalkyl in $R^2$ is optionally substituted by one or more $R^{14}$ groups; or
  $R^1$ and $R^2$ may combine to form a $C_5$-$C_7$ cycloalkyl ring or a 5-7 membered heterocycloalkyl ring, wherein the $C_5$-$C_7$ cycloalkyl ring and the 5-7 membered heterocycloalkyl ring are optionally substituted by one or more $R^{13}$ groups;
  ring A is absent, $C_3$-$C_{10}$ cycloalkyl, 3-10 membered heterocycloalkyl, $C_5$-$C_{10}$ aryl or 5-12 membered heteroaryl;
  $R^5$ and $R^{5a}$ are each independently absent, halogen, cyano, hydroxy, difluoromethyl, trifluoromethyl, $C_1$-$C_3$ alkyl, $C_1$-$C_3$ alkoxy, $C_3$-$C_5$ cycloalkyl or $C_3$-$C_5$ heteroaryl, wherein the $C_1$-$C_3$ alkyl is optionally substituted by hydroxy, difluoromethyl, trifluoromethyl, $C_1$-$C_3$ alkoxy or $C_3$-$C_5$ cycloalkyl;
  $R^6$ is

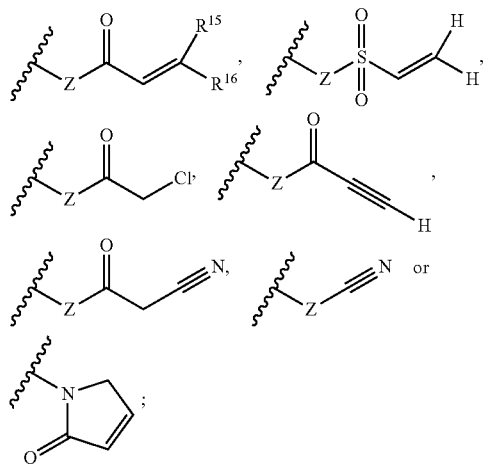

Z is absent when the attachment point of $R^6$ on ring A is a nitrogen atom, and Z is —$NR^{17}$— when ring A is absent or when the attachment point of $R^6$ on ring A is a carbon atom;
  $R^7$ is hydrogen, halogen, cyano, $C_1$-$C_6$ alkyl, $C_2$-$C_6$ alkenyl, $C_2$-$C_6$ alkynyl, or 4-6 membered heteroaryl, wherein the $C_1$-$C_6$ alkyl may be optionally substituted by hydroxy or $C_1$-$C_3$ alkoxy, and further wherein the 4-6 membered heteroaryl may be optionally substituted by $C_1$-$C_3$ alkyl;
  $R^8$ is hydrogen or $C_1$-$C_3$ alkyl;
  $R^9$ and $R^{10}$ are each independently hydrogen or $C_1$-$C_6$ alkyl; or $R^9$ and $R^{10}$ together with the nitrogen to which they are attached, may combine to form a 4-7 membered ring, when $R^9$ and $R^{10}$ are each $C_1$-$C_3$ alkyl, wherein the 4-7 membered ring is optionally substituted by one or more $R^{14}$ groups;
  $R^{11}$ and $R^{12}$ are each independently hydrogen or $C_1$-$C_3$ alkyl;
  each $R^{13}$ is independently halogen, cyano, hydroxy, $C_1$-$C_6$ alkoxy, —$N(R^9)(R^{10})$, —$CON(R^9)(R^{10})$, 3-7 membered heterocycloalkyl, wherein the 3-7 membered heterocycloalkyl in $R^{13}$ is optionally substituted by one or more $R^{14}$ groups;
  each $R^{14}$ is independently halogen, $C_1$-$C_3$ alkyl, hydroxy, $C_1$-$C_6$ alkoxy, —$NH_2$, —$NHCH_3$, or $N(CH_3)_2$;

$R^{15}$ and $R^{16}$ are each independently hydrogen or $C_1$-$C_6$ alkyl, wherein the $C_1$-$C_6$ alkyl of one of $R^{15}$ and $R^{16}$ is optionally substituted by —N($R^9$)($R^{10}$);

$R^{17}$ is hydrogen or $C_1$-$C_6$ alkyl; and m is 0, 1 or 2, provided that when ring A is absent, m is 2; or a pharmaceutically acceptable salt thereof.

25. The compound or salt of claim 24, wherein X is $CR^7$.
26. The compound or salt of claim 24, wherein Y is O.
27. The compound or salt of claim 25, wherein $R^7$ is hydrogen, halogen, cyano or 4-6 membered heteroaryl.
28. The compound or salt of claim 25, wherein $R^7$ is halogen.
29. The compound or salt of claim 28, wherein the halogen is chlorine.
30. The compound or salt of claim 24, wherein m is 0.
31. The compound or salt of claim 24, wherein m is 1.
32. The compound or salt of claim 24, wherein $R^1$ is hydrogen.
33. The compound or salt of claim 24, wherein $R^2$ is $C_1$-$C_4$ alkyl or $C_3$-$C_4$ cycloalkyl.
34. The compound or salt of claim 24, wherein $R^2$ is methyl.
35. The compound or salt of claim 24, wherein $R^4$ is hydrogen.
36. The compound or salt of claim 24, having formula (IIIb):

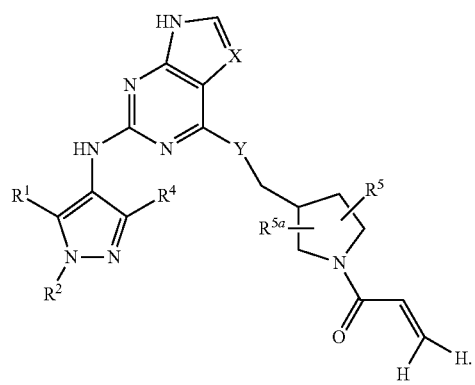

(IIIb)

37. The compound or salt of claim 36, wherein $R^5$ and $R^{5a}$ are each independently absent, hydroxy, difluoromethyl, trifluoromethyl, $C_1$-$C_3$ alkyl, $C_1$-$C_3$ alkoxy, cyclopropyl, —($CH_2$)—$OCH_3$ or —($CH_2$)-trifluoromethyl.
38. The compound or salt of claim 36, wherein $R^5$ and $R^{5a}$ are absent.
39. The compound or salt of claim 36, wherein $R^{5a}$ is absent.
40. A compound, which is

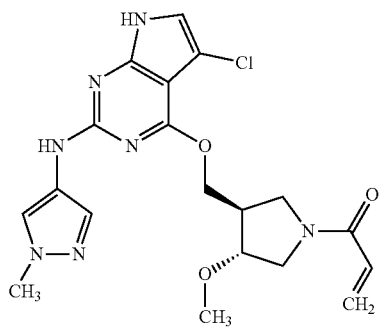 [SMILES: C=CC(=O)N1C[C@H](COc2nc(Nc3cnn(C)c3)nc3[nH]cc(Cl)c23)[C@@H](OC)C1]

or a pharmaceutically acceptable salt thereof.

41. A pharmaceutical composition comprising a compound, which is

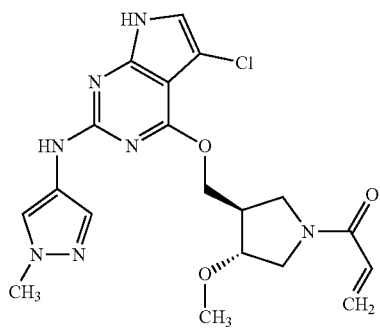 [SMILES: C=CC(=O)N1C[C@H](COc2nc(Nc3cnn(C)c3)nc3[nH]cc(Cl)c23)[C@@H](OC)C1]

or a pharmaceutically acceptable salt thereof, and a pharmaceutically acceptable carrier or diluent.

* * * * *